US007785886B2

(12) United States Patent
Hayden et al.

(10) Patent No.: US 7,785,886 B2
(45) Date of Patent: Aug. 31, 2010

(54) METHODS AND REAGENTS FOR MODULATING CHOLESTEROL LEVELS

(75) Inventors: Michael R. Hayden, Vancouver (CA); Angela R. Brooks-Wilson, Richmond (CA); Simon N. Pimstone, Vancouver (CA)

(73) Assignees: Xenon Pharmaceuticals, Inc., Burnaby, B.C. (CA); Univ. of British Columbia, Vancouver, B.C. (CA)

( * ) Notice: Subject to any disclaimer, the term of this patent is extended or adjusted under 35 U.S.C. 154(b) by 237 days.

(21) Appl. No.: 10/833,679

(22) Filed: Apr. 28, 2004

(65) Prior Publication Data
US 2004/0185508 A1 Sep. 23, 2004

Related U.S. Application Data

(63) Continuation of application No. 10/617,334, filed on Jul. 10, 2003, now abandoned, and a continuation of application No. 10/452,510, filed on Jun. 2, 2003, which is a continuation of application No. 09/526,193, filed on Mar. 15, 2000, now Pat. No. 6,617,122.

(60) Provisional application No. 60/124,702, filed on Mar. 15, 1999, provisional application No. 60/138,048, filed on Jun. 8, 1999, provisional application No. 60/139,600, filed on Jun. 17, 1999, provisional application No. 60/151,977, filed on Sep. 1, 1999.

(51) Int. Cl.
C07H 21/04 (2006.01)
C12N 15/12 (2006.01)
C12N 15/86 (2006.01)
A61K 39/235 (2006.01)

(52) U.S. Cl. ............ 435/455; 435/456; 514/44; 536/23.5; 424/204.1; 424/233.1

(58) Field of Classification Search .......... 424/204.1, 424/233.1; 435/455, 456; 514/44; 536/23.5
See application file for complete search history.

(56) References Cited

U.S. PATENT DOCUMENTS

| 5,744,310 | A | 4/1998 | Reed |
| 6,030,806 | A | 2/2000 | Landes et al. |
| 6,555,323 | B2 | 4/2003 | Bamberger et al. |
| 6,713,300 | B1 | 3/2004 | Allikmets et al. |
| 6,821,774 | B1 * | 11/2004 | Lawn et al. ............ 435/320.1 |
| 2004/0005666 | A1 | 1/2004 | Hayden et al. |
| 2004/0058869 | A1 * | 3/2004 | Hayden et al. ............ 514/12 |

FOREIGN PATENT DOCUMENTS

| WO | WO 97/17359 | 5/1997 |
| WO | WO 98/03548 | 1/1998 |
| WO | WO 98/24818 | 6/1998 |
| WO | WO 98/48784 | 11/1998 |
| WO | WO 98/51351 | 11/1998 |
| WO | WO 99/31133 | 6/1999 |
| WO | WO 00/24390 | 5/2000 |
| WO | WO 00/18912 | 6/2000 |
| WO | WO 00/34461 | 6/2000 |
| WO | WO 98/37764 | 9/2000 |
| WO | WO 00/71710 | 11/2000 |
| WO | WO 00/78970 | 12/2000 |
| WO | WO 00/78971 | 12/2000 |
| WO | WO 00/78972 | 12/2000 |
| WO | WO 01/32184 | 5/2001 |
| WO | WO 01/41704 | 6/2001 |
| WO | WO 01/66098 | 9/2001 |
| WO | WO 01/83746 | 11/2001 |

OTHER PUBLICATIONS

Fitzgerald et al., J Biol Chem 279:48477-48485, 2004.*
Kaminski et al, Biochimica et Biophysica Acta 1762: 510-524, 2006.*
Wollmer et al, Neurobiology of Aging 24: 421-426, 2003.*
Kolsch et al, International Journal of Molecular Medicine 17(5): 791-794, 2006. Abstract only.*
Pullinger et al, Biochem Biophys Res Comm 271:451-455, 2000.*
Santamariana-Fojo et al, PNAS 97:7987-7992, 2000.*
Witkowski et al, Biochemistry 38:11643-11650, 1999.*
Williams et al, Biochemistry 37:7096-7102, 1998.*
Guo et al, Proc Natl Acad Sci 101(25):9205-9210, 2004.*
Hult and Berglund, Curr Opin Biotechnol 14:395-400, 2003.*
Kronqvist et al, Eur. J. Biochem 262: 939-946, 1999.*
Remarque et al, Exp. Gerontology 36: 171-176, 2001.*
Reale et al, J. Neuroimmunology 148: 162-171, 2004.*
Orkin et al, National Institutes of Health Report, Dec. 7, 1995.*
Statement of Amy Patterson M.D., Subcommittee on Public Health, Feb. 2, 2000.*
Deonarain, Expert Opin. Ther. Pat. 8: 53-69, 1998.*
Verma and Somia, Nature 389: 239-242, 1997.*
Verma and Weitzman, Annu. Rev. Biochem. 74:711-738, 2005.*
Goncalves, BioEssays 27:506-517, 2005.*
Johnson-Saliba et al, Curr. Drug. Targets 2:371-99, 2001.*
Shoji et al, Current Pharmaceutical Design 10(7): 785-796, 2004.*
Eck et al, Goodman & Gilman's The Pharmacological Basis of Therapeutics, McGraw-Hill, New York, NY., pp. 77-101, 1996.*
Gorecki, Expert Opin. Emerging Drugs 6(2): 187-98, 2001.*
Xu et al, Advanced Drug Delivery Reviews 57:781-802, 2005.*
Nofer et al, Cell Mol Life Sci 62:2150-2160, 2005.*
Search Result for SEQ ID No. 1.*
Brown, "Hybridization Analysis of DNA Blots" in Current Protocols in Molecular Biology John Wiley & Sons, Inc., 2003.*
Neve et al, Trends in Neurosci. 21:15-19, 1998.*
Brinton et al, Pharm. Res. 15(3): 386-398, 1998.*
Frikke-Schmidt et al, JAMA 299(21):2524-2532, 2008.*
Allikmets et al., Gene, 215:111-122 (1998).

(Continued)

Primary Examiner—Kevin K. Hill
(74) Attorney, Agent, or Firm—Elliot M. Olstein; Alan J. Grant

(57) ABSTRACT

The invention features ABC1 nucleic acids and polypeptides for the diagnosis and treatment of abnormal cholesterol regulation. The invention also features methods for identifying compounds for modulating cholesterol levels in an animal (e.g., a human).

5 Claims, 76 Drawing Sheets

OTHER PUBLICATIONS

Allikmets et al., Hum. Mol. Gen. 5:1649-1655 (1996).
Bodzioch et al., Nat Genetics 22:347-351 (1999).
Borst, O., Semin. Cancer Biol. 8:131-134 (1997).
Brooks-Wilson et al., Nature Genetics 22:336-345 (1999).
Dean et al., Curr. Opin. Gen. Dev. 5:779-785 (1995).
Drobnik et al., Arterioscler. Thromb. Vasc. Biol. 15:1369-1377 (1995).
Kuivenhoven et al., Arterioscler. Thromb. Vasc. Biol. 17:560-568 (1997).
Langmann et al., BBRC 257:29-33 (1999).
Lawn et al., J. Clin. Invest. 104:R25-R31 (1999).
Luciani et al., Genomics 21:150-159 (1994).
Marcil et al., Arterioscler. Thromb. Vasc. Biol. 19:159-169 (1999).
Remaley et al., PNAS 96:12685-12690 (1999).
Rogler et al., Arterioscler. Thromb. Vasc. Biol. 15:683-690 (1995).
Rust et al., Nature Genetics 20:96-98 (1998).
Rust et al., Nature Genetics 22:352-355 (1999).
Savary et al., Genomics 41:275-278 (1997).
Schmitz et al., Pathobiology 67:236-240 (1999).
Wilson et al., Nature 368:32-38 (1994).
Becq et al J. Biol. Chem. 272:2695-1699 (1997).
Bellosta et al., Atherosclerosis 137:S101-109 (1998) (Abstract).
Hamon et al., Blood 90:2911-2915 (1997).
Hansen et al., Danish Medical Bulletin 45:370-382 (1998) (Abstract).
Kim-Schultze et al., Circulation 98:413-421 (1998) (Abstract).
Luciani et al., EMBO Journal 15:226-235 (1996).
Schreyer et al., Arterioscler. Thromb. Vasc. Biol. 14:2053-2059 (1994) (Abstract).
Bloom et al., Nucleic Acids Res. 26:384-386 (1998).
Rust, S., (Jul. 1, 1999) GenBank Accession No. AF165281.
Luciani, M.F. (1994) GenBank Accession No. P41233.
Luciani, M.F. (1994) GenBank Accession No. NM_005502.
Chimini, G., (Nov. 5, 1993) GenBank Accession No. X75926.
Luciani, M.F., (1994) GenBank Accession No. A54774.
Waterston, R. (Oct. 26, 1998) GenBank Accession No. AAC69223.
Langmann, T. (Nov. 11, 1998) GenBank Accession No. CAA10005.
Langmann, T. (Nov. 11, 1998) GenBank Accession No. AJ012376.
Broach et al., Nature 384 (Supp.): 14-16 (1996).
Burbaum et al., Curr. Opin. Chem. Biol. 1:72-78 (1997).
Mendez, J. Biol. Chem. 270:5891-5900 (1995).
Maguire et al., N Engl J Med, 358:2240-2248 (2008).
Nierman et al., J. Medicine, 63:14-19 (2005).
Rader, D.J., J. Medicine, 63, 2-3 (2005).
Ross et al., Human Gene Therapy, 15:906-919 (2004).
Ross et al., Human Gene Therapy, 17:1-13 (2006).
Wellington et al., J. Lipid Res., 44, 1470-1480 (2003).
Attie et al., GenBank Accession No. NP_989476 (2007).
Fischer et al., The FASEB Journal, vol. 10, pp. 126-136 (1996).
Lange et al., J. Biol Chem., vol. 264, pp. 3786-3793 (1989).
Mack and Blankenharn, Amer. J Pub. Health, vol. 81, pp. 1180-1184 (1991).
Olivier et al., Atherosclerosis, vol. 70, pp. 107-114 (1988).
Orso et al., Nature Genetics, vol. 24, pp. 192-196 (2000).
Schwartz et al., Biochem. Biophys. Res. Comm., vol. 274, pp. 794-802 (2000).
Smud and Sermukslis. Curr. Med. Res. & Opinion, vol. 10, pp. 612-624 (1987).
Staels et al., Circulation, vol. 98, pp. 2088-2093 (1998).
Steiner et al., Diabetelogia, vol. 39, pp. 1655-1661 (1996).
Arakawa et al., Arterioscler. Thromb. Vasc. Biol., vol. 25, pp. 1193-1197 (2005).
Broccardo et al., BBA, vol. 1461, pp. 395-404 (1999).
Carmeci et al., Genomics, vol. 45, pp. 607-617 (1997).
Hahmann et al., Am. J. Cardiol., vol. 67, pp. 957-961 (1991).
Herz and Gerard, PNAS, vol. 90, pp. 2812-2816 (1993).
Kamei et al., Psycho-Pharmacology, vol. 113, pp. 318-331 (1994).
Klein et al., BBA, vol. 1461, pp. 237-262 (1999).
Kozarsky et al., Nature, vol. 387, pp. 414417 (1997).
Timmins et al., J. Clin. Invest., vol. 115, pp. 1333-1342 (2005).
Toti et al., BBRC, vol. 241, pp. 548-552 (1997).
Vinals et al., Cardiovascular Res., vol. 66, pp. 141-149 (2005).
Wang et al., J. Lipid Res., vol. 48, pp. 1062-1068 (2007).
Fitzgerald et al., J. Biol. Chem., vol. 276, pp. 15137-15145 (May 4, 2001).
Wang et al., J. Biol. Chem., vol. 275, pp. 33053-33068 (Oct. 20, 2000).

* cited by examiner

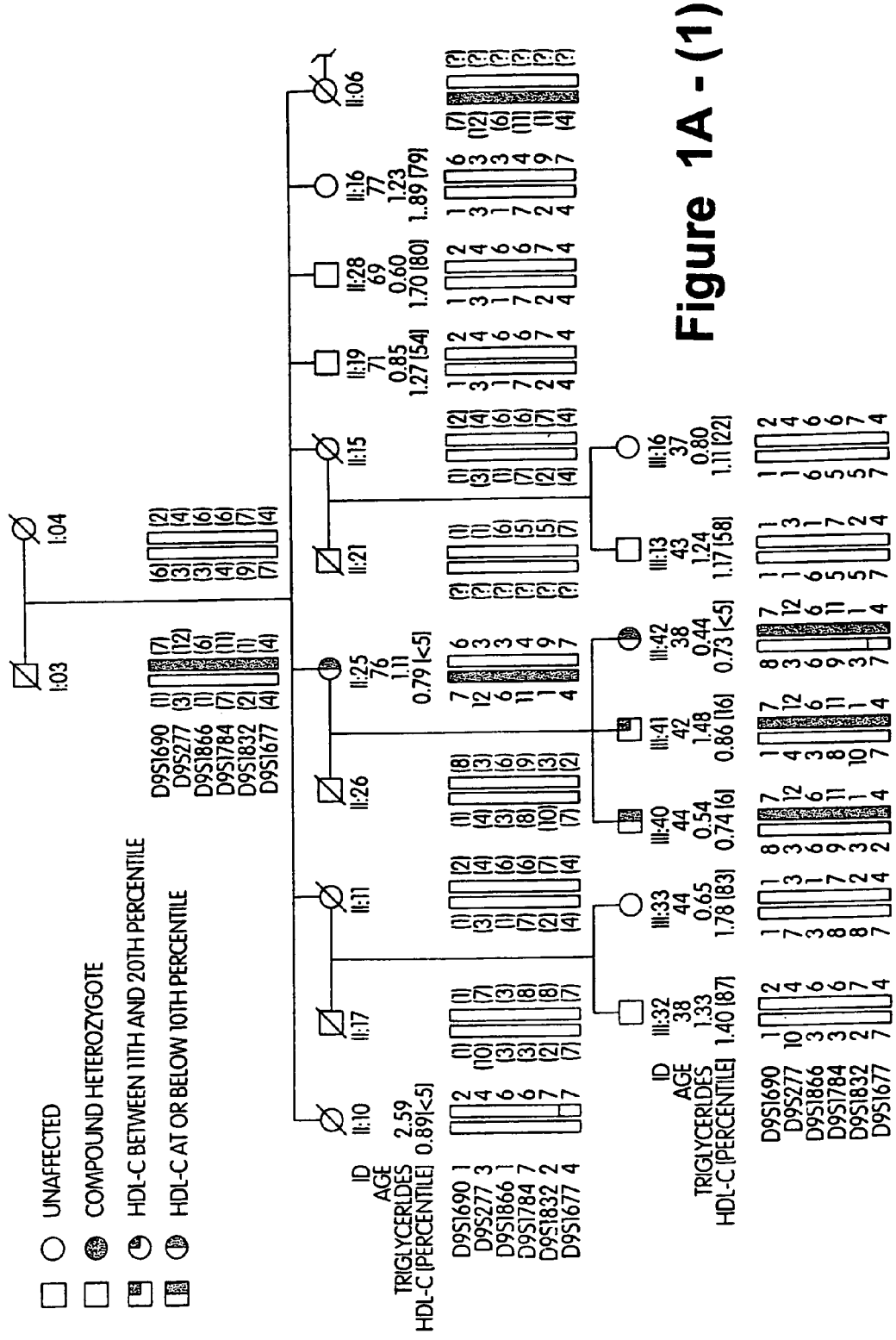

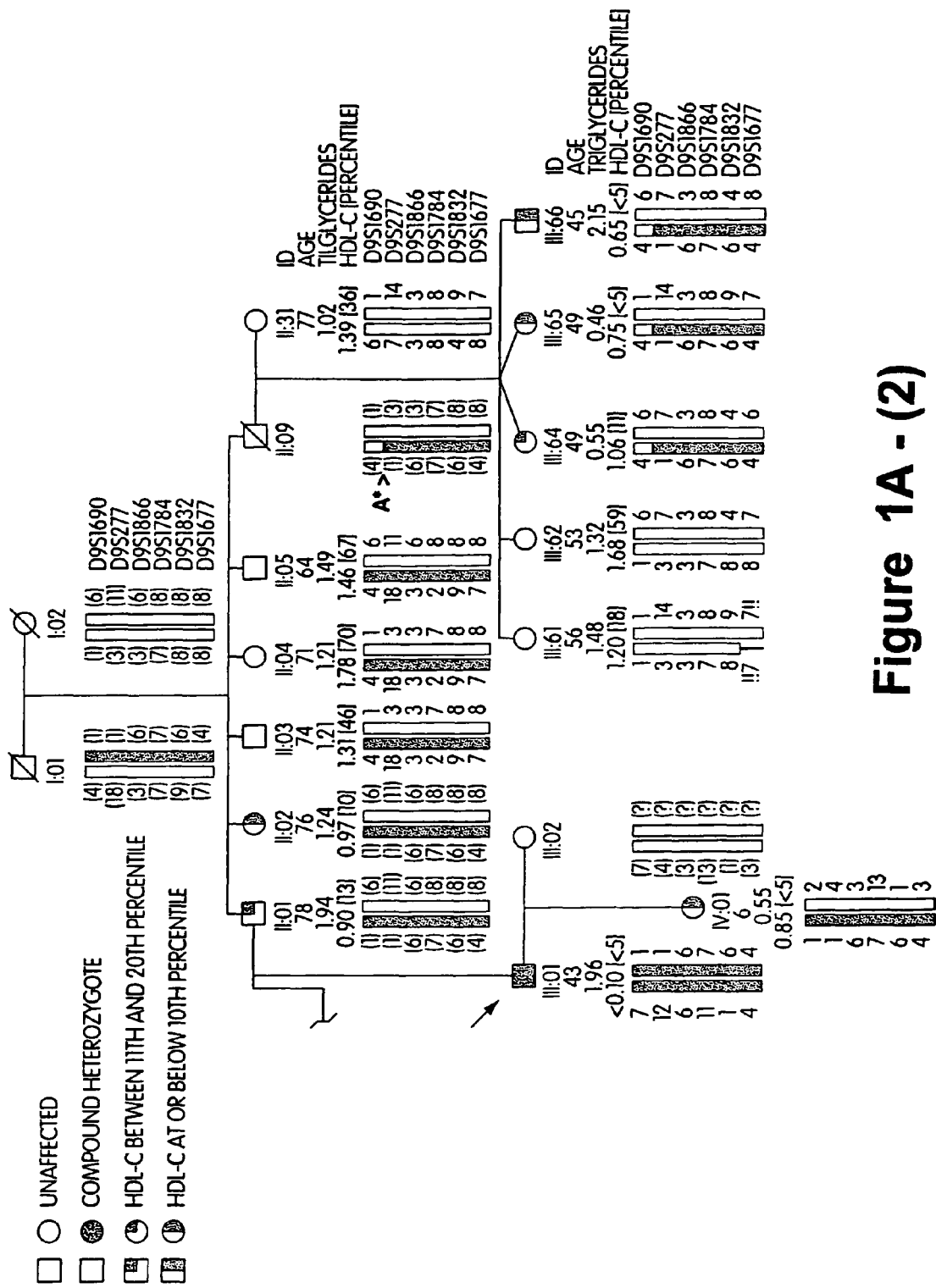
Figure 1A - (2)

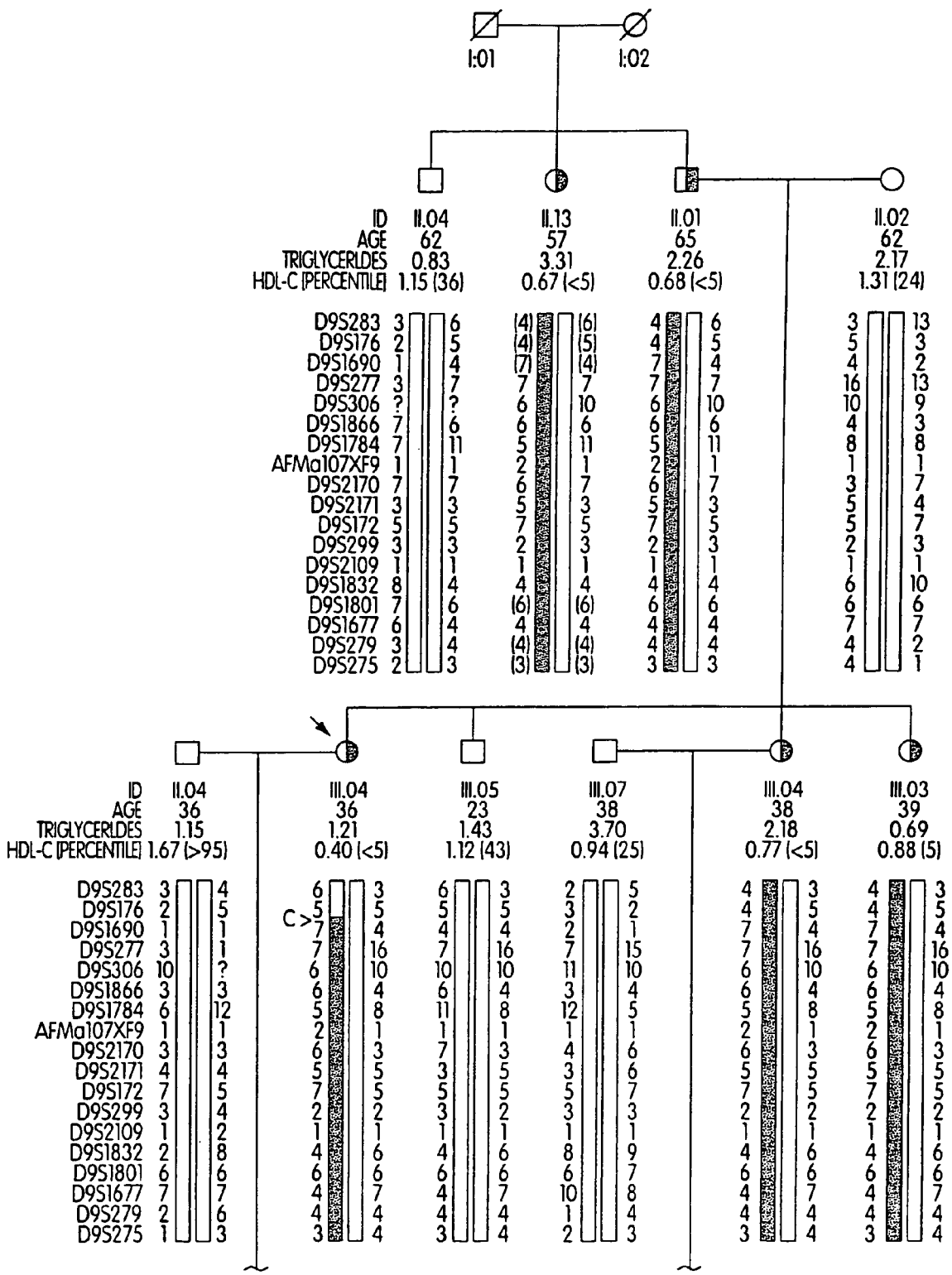
Figure 2A – (1)

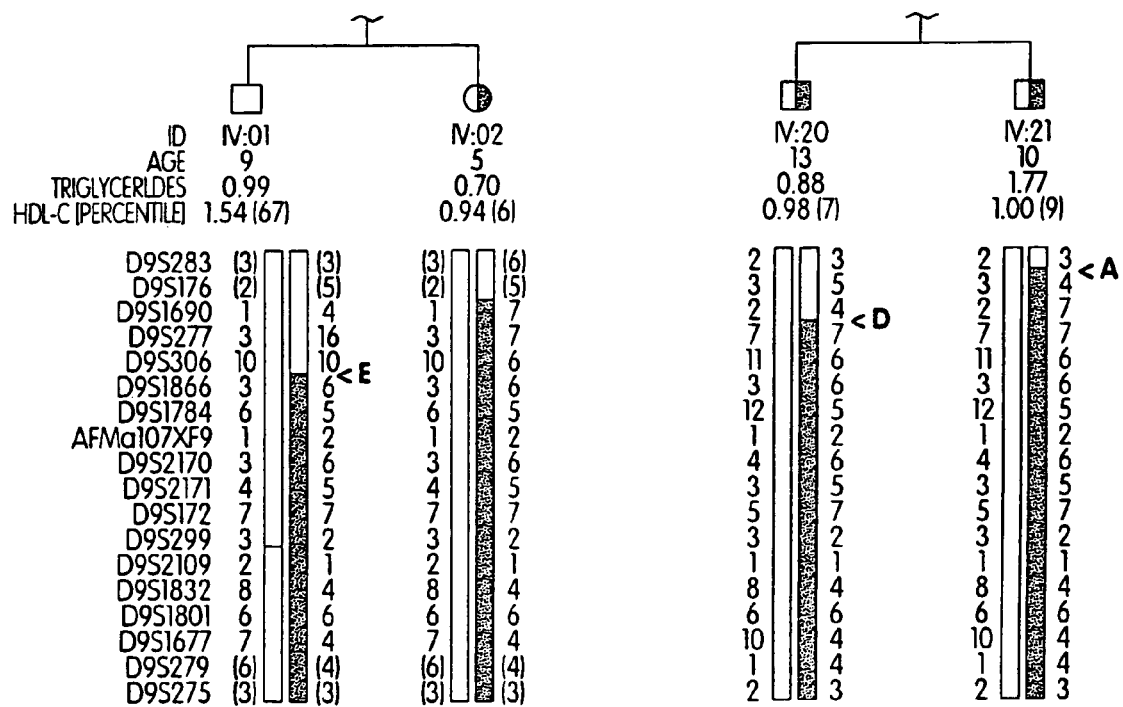
Figure 2A – (2)

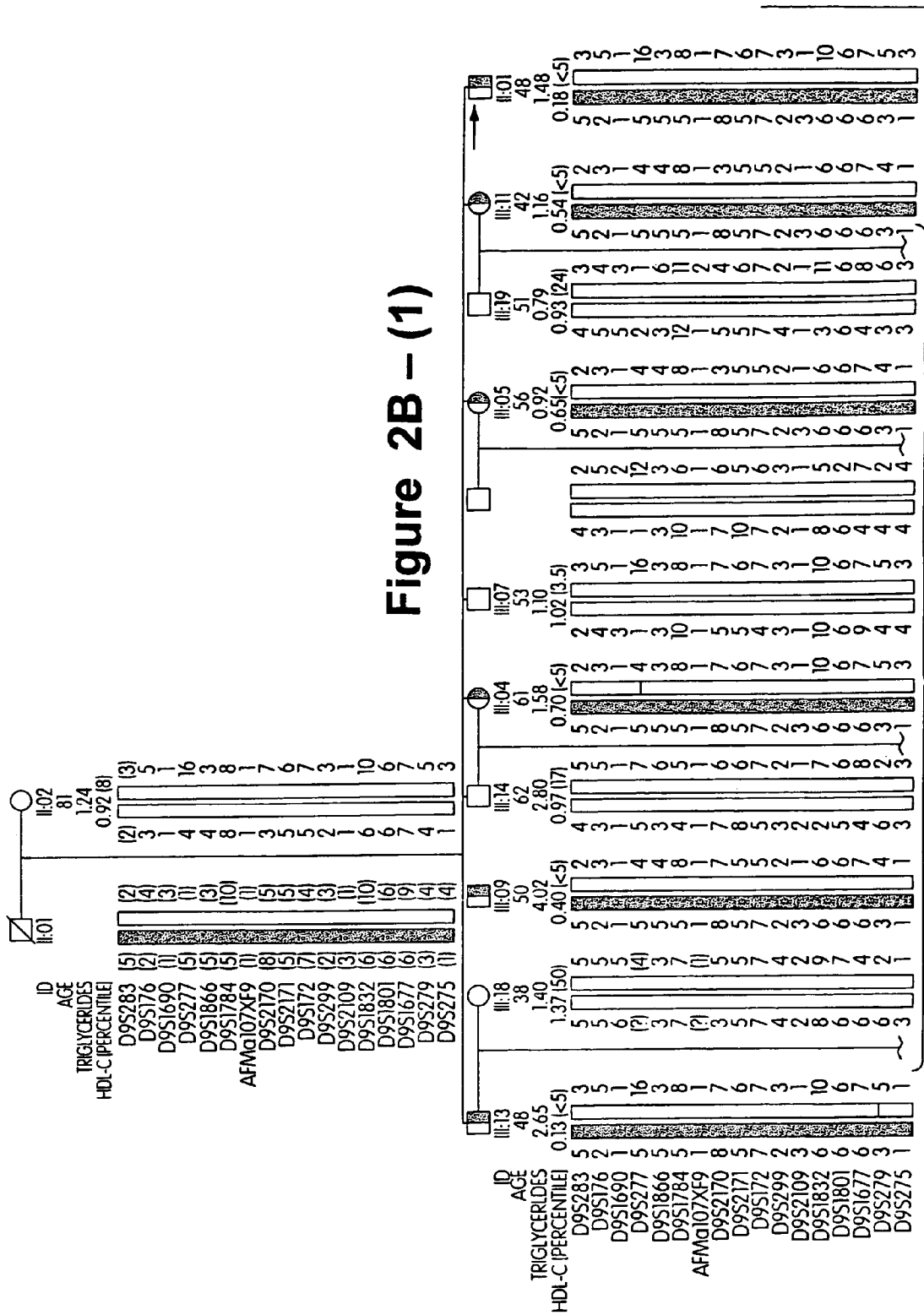
Figure 2B – (1)

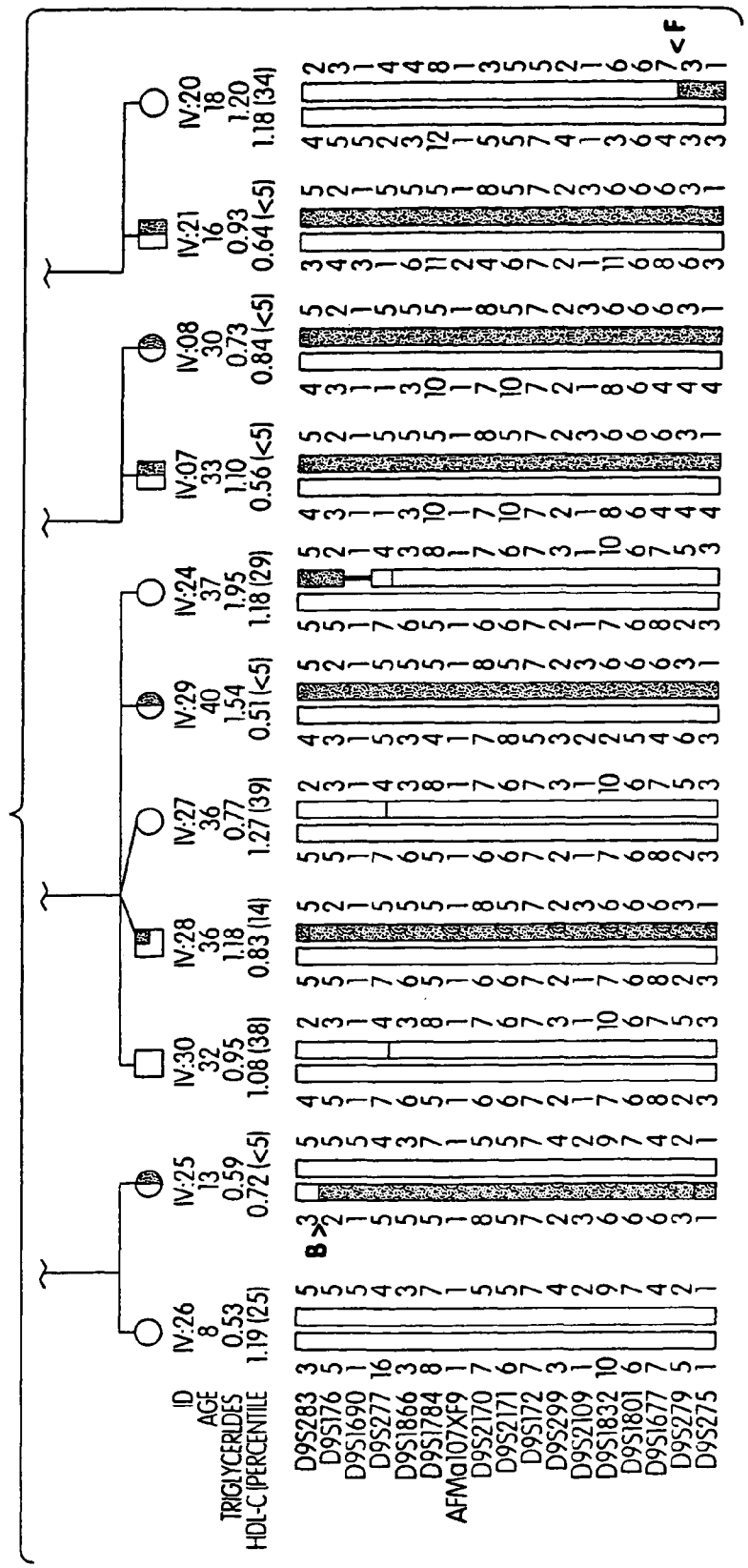
Figure 2B – (2)

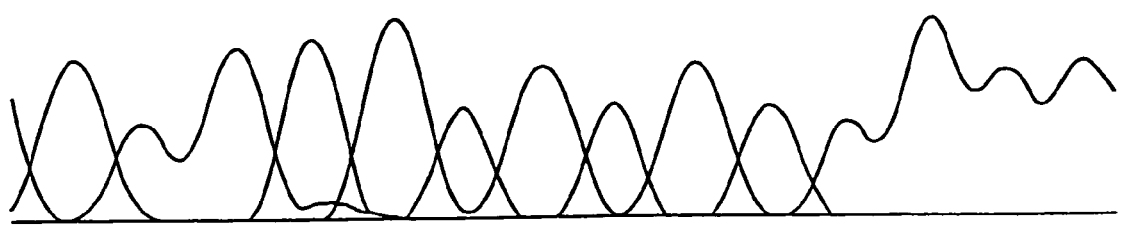
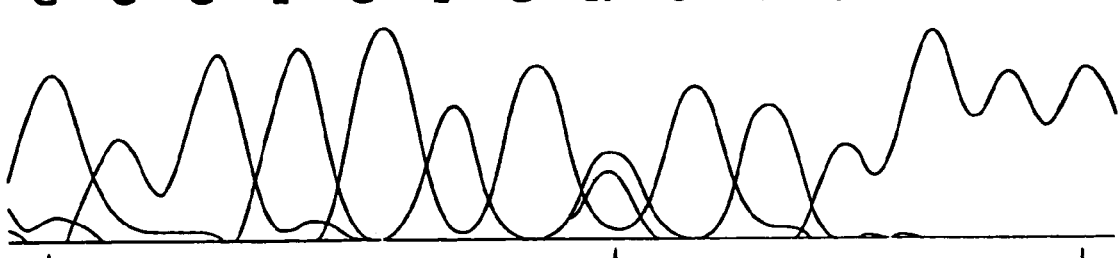
4496   T4503C (Cys1477Arg)   4509
Fig. 4A

EXON 20
TD-1

```
                    4485                4503                         4529
                    |                    |                             |
wt sequence   aagaagatgctgcctgtgTgtcccccagggggcagggggggctgcct
HUMAN_ABC1     K  K  M  L  P  V  C  P  P  G  A  G  G  L  P
MOUSE_ABC1     K  K  M  L  P  V  C  P  P  G  A  G  G  L  P
Patient        K  K  M  L  P  V  R  P  P  G  A  G  G  L  P
CAEEL_ABC      -  -  L  L  -  -  -  -  -  -  -  G  G  S  -
Patient       aagaagatgctgcctgtgCgtcccccagggggcagggggggctgcct
```

Fig. 4B

EXON 13
TD-2

```
                1842                      1864                      1886
                 |                         |                         |
wt sequence    tggggggggcttcgcctacttgcAggatgtggtggagcaggcaatc
HUMAN_ABC1      N   G   G   F   A   Y   L   Q   D   V   V   E   Q   A   I
MOUSE_ABC1      N   G   G   F   A   Y   L   Q   D   V   V   E   Q   A   I
Patient         N   G   G   F   A   Y   L   R   D   V   V   E   Q   A   I
CAEEL_ABC       -   -   -   F   M   T   V   Q   R   A   V   D   V   A   I
Patient        tggggggggcttcgcctacttgcGggatgtggtggagcaggcaatc
```

Fig. 5B

EXON 14
FHA-1

```
                    2136                2151                          2180
                      |                  |                              |
wt sequence         agtagcctcattcctCTTcttgtgagcgctggcctgctagtggtc
HUMAN_ABC1           S  S  L  I  P  L  V  S  A  G  L  L  V  V
MOUSE_ABC1           S  S  L  I  P  L  V  S  A  G  L  L  V  V
Patient              S  S  L  I  P  L  -  V  S  A  G  L  L  V  V
CAEEL_ABC            I  N  Y  A  K  L  T  F  A  V  I  V  L  T  I
Patient             agtagcctcattcct---cttgtgagcgctggcctgctagtggtc
                                    ↑
                              3 bp deletion
```

Fig. 6B

Exon 48 mutation:
Control
Family FHA - 2, patient III:01
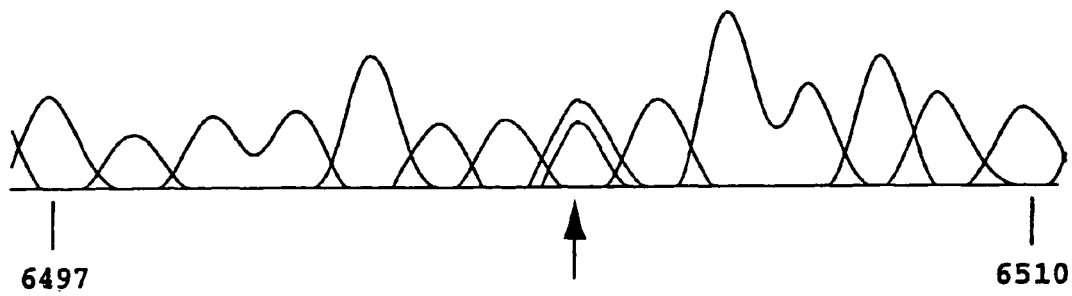
6497          C6504T (Arg2144STOP)          6510
Fig. 6F

SEQ ID NO: 1

MACWPQLRLLLWKNLTFRRRQTCQLLLEVAWPLFIFLILISVRLSYPPYEQHECHFPNKAMPSAGTLPWVQ
GIICNANNPCFRYPTPGEAPGVVGNFNKSIVARLFSDARRLLLYSQKDTSMKDMRKVLRTLQQIKKSSSNL
KLQDFLVDNETFSGFLYHNLSLPKSTVDKMLRADVILHKVFLQGYQLHLTSLCNGSKSEEMIQLGDQEVSE
LCGLPREKLAAAERVLRSNMDILKPILRTLNSTSPFPSKELAEATKTLLHSLGTLAQELFSMRSWSDMRQE
VMFLTNVNSSSSSTQIYQAVSRIVCGHPEGGGLKIKSLNWYEDNNYKALFCGNGTEEDAETFYDNSTTPYC
NDLMKNLESSPLSRIIWKALKPLLVGKILYTPDTPATRQVMAEVNKTFQELAVFHDLEGMWEELSPKIWTF
MENSQEMDLVRMLLDSRDNDHFWEQQLDGLDWTAQDIVAFLAKHPEDVQSSNGSVYTWREAFNETNQAIRT
ISRFMECVNLNKLEPIATEVWLINKSMELLDERKFWAGIVFTGITPGSIELPHHVKYKIRMDIDNVERTNK
IKDGYWDPGPRADPFEDMRYVWGGFAYLQDVVEQAIIRVLTGTEKKTGVYMQQMPYPCYVDDIFLRVMSRS
MPLFMTLAWIYSVAVIIKGIVYEKEARLKETMRIMGLDNSILWFSWFISSLIPLLVSAGLLVVILKLGNLL
PYSDPSVVFVFLSVFAVVTILQCFLISTLFSRANLAAACGGIIYFTLYLPYVLCVAWQDYVGFTLKIFASL
LSPVAFGFGCEYFALFEEQGIGVQWDNLFESPVEEDGFNLTTSVSMMLFDTFLYGVMTWYIEAVFPCQYGI
PRPWYFPCTKSYWFGEESDEKSHPGSNQKRISEICMEEEPTHLKLGVSIQNLVKVYRDGMKVAVDGLALNF
YEGQITSFLGHNGAGKTTTMSILTGLFPPTSGTAYILGKDIRSEMSTIRQNLGVCPQHNVLFDMLTVEEHI
WFYARLKGLSEKHVKAEMEQMALDVGLPSSKLKSKTSQLSGGMQRKLSVALAFVGGSKVVILDEPTAGVDP
YSRRGIWELLLKYRQGRTIILSTHHMDEADVLGDRIAIISHGKLCCVGSSLFLKNQLGTGYYLTLVKKDVE
SSLSSCRNSSSTVSYLKKEDSVSQSSSDAGLGSDHESDTLTIDVSAISNLIRKHVSEARLVEDIGHELTYV
LPYEAAKEGAFVELFHEIDDRLSDLGISSYGISETTLEEIFLKVAEESGVDAETSDGTLPARRNRRAFGDK
QSCLRPFTEDDAADPNDSDIDPESRETDLLSGMDGKGSYQVKGWKLTQQQFVALLWKRLLIARRSRKGFFA
QIVLPAVFVCIALVFSLIVPPFGKYPSLELQPWMYNEQYTFVSNDAPEDTGTLELLNALTKDPGFGTRCME
GNPIPDTPCQAGEEEWTTAPVPQTIMDLFQNGNWTMQNPSPACQCSSDKIKKMLPVCPPGAGGLPPPQRKQ
NTADILQDLTGRNISDYLVKTYVQIIAKSLKNKIWVNEFRYGGFSLGVSNTQALPPSQEVNDAIKQMKKHL
KLAKDSSADRFLNSLGRFMTGLDTRNNVKVWFNNKGWHAISSFLNVINNAILRANLQKGENPSHYGITAFN
HPLNLTKQQLSEVALMTTSVDVLVSICVIFAMSFVPASFVVFLIQERVSKAKHLQFISGVKPVIYWLSNFV
WDMCNYVVPATLVIIIPICFQQKSYVSSTNLPVLALLLLLYGWSITPLMYPASFVFKIPSTAYVVLTSVNL
FIGINGSVATFVLELFTDNKLNNINDILKSVFLIFPHFCLGRGLIDMVKNQAMADALERFGENRFVSPLSW
DLVGRNLFAMAVEGVVFFLITVLIQYRFFIRPRPVNAKLSPLNDEDEDVRRERQRILDGGGQNDILEIKEL
TKIYRRKRKPAVDRICVGIPPGECFGLLGVNGAGKSSTFKMLTGDTTVTRGDAFLNKNSILSNIHEVHQNM
GYCPQFDAITELLTGREHVEFFALLRGVPEKEVGKVGEWAIRKLGLVKYGEKYAGNYSGGNKRKLSTAMAL
IGGPPVVFLDEPTTGMDPKARRFLWNCALSVVKEGRSVVLTSHSMEECEALCTRMAIMVNGRFRCLGSVQH
LKNRFGDGYTIVVRIAGSNPDLKPVQDFFGLAFPGSVLKEKHRNMLQYQLPSSLSSLARIFSILSQSKKRL
HIEDYSVSQTTLDQVFVNFAKDQSDDDHLKDLSLHKNQTVVDVAVLTSFLQDEKVKESYV*

Fig. 9A

SEQ ID NO: 2

```
GTCCCTGCTGTGAGCTCTGGCCGCTGCCTTCCAGGGCTCCCGAGCCACACGCTGGCGGTG
CTGGCTGAGGGAACATGGCTTGTTGGCCTCAGCTGAGGTTGCTGCTGTGGAAGAACCTCA
CTTTCAGAAGAAGACAAACATGTCAGCTGTTACTGGAAGTGGCCTGGCCTCTATTTATCT
TCCTGATCCTGATCTCTGTTCGGCTGAGCTACCCACCCTATGAACAACATGAATGCCATT
TTCCAAATAAAGCCATGCCCTCTGCAGGAACACTTCCTTGGGTTCAGGGGATTATCTGTA
ATGCCAACAACCCCTGTTTCCGTTACCCGACTCCTGGGGAGGCTCCCGGAGTTGTTGGAA
ACTTTAACAAATCCATTGTGGCTCGCCTGTTCTCAGATGCTCGGAGGCTTCTTTTATACA
GCCAGAAAGACACCAGCATGAAGGACATGCGCAAAGTTCTGAGAACATTACAGCAGATCA
AGAAATCCAGCTCAAACTTGAAGCTTCAAGATTTCCTGGTGGACAATGAAACCTTCTCTG
GGTTCCTGTATCACAACCTCTCTCTCCCAAAGTCTACTGTGGACAAGATGCTGAGGGCTG
ATGTCATTCTCCACAAGGTATTTTTGCAAGGCTACCAGTTACATTTGACAAGTCTGTGCA
ATGGATCAAAATCAGAAGAGATGATTCAACTTGGTGACCAAGAAGTTTCTGAGCTTTGTG
GCCTACCAAGGGAGAAACTGGCTGCAGCAGAGCGAGTACTTCGTTCCAACATGGACATCC
TGAAGCCAATCCTGAGAACACTAAACTCTACATCTCCCTTCCCGAGCAAGGAGCTGGCTG
AAGCCACAAAAACATTGCTGCATAGTCTTGGGACTCTGCCCAGGAGCTGTTCAGCATGA
GAAGCTGGAGTGACATGCGACAGGAGGTGATGTTTCTGACCAATGTGAACAGCTCCAGCT
CCTCCACCCAAATCTACCAGGCTGTGTCTCGTATTGTCTGCGGGCATCCCGAGGGAGGGG
GGCTGAAGATCAAGTCTCTCAACTGGTATGAGGACAACAACTACAAAGCCCTCTTTGGAG
GCAATGGCACTGAGGAAGATGCTGAAACCTTCTATGACAACTCTACAACTCCTTACTGCA
ATGATTTGATGAAGAATTTGGAGTCTAGTCCTCTTTCCCGCATTATCTGGAAAGCTCTGA
AGCCGCTGCTCGTTGGGAAGATCCTGTATACACCTGACACTCCAGCCACAAGGCAGGTCA
TGGCTGAGGTGAACAAGACCTTCCAGGAACTGGCTGTGTTCCATGATCTGGAAGGCATGT
GGGAGGAACTCAGCCCCAAGATCTGGACCTTCATGGAGAACAGCCAAGAAATGGACCTTG
TCCGGATGCTGTTGGACAGCAGGGACAATGACCACTTTTGGGAACAGCAGTTGGATGGCT
TAGATTGGACAGCCCAAGACATCGTGGCGTTTTTGGCCAAGCACCCAGAGGATGTCCAGT
CCAGTAATGGTTCTGTGTACACCTGGAGAGAAGCTTTCAACGAGACTAACCAGGCAATCC
GGACCATATCTCGCTTCATGGAGTGTGTCAACCTGAACAAGCTAGAACCCATAGCAACAG
AAGTCTGGCTCATCAACAAGTCCATGGAGCTGCTGGATGAGAGGAAGTTCTGGGCTGGTA
TTGTGTTCACTGGAATTACTCCAGGCAGCATTGAGCTGCCCCATCATGTCAAGTACAAGA
TCCGAATGGACATTGACAATGTGGAGAGGACAAATAAAATCAAGGATGGGTACTGGGACC
CTGGTCCTCGAGCTGACCCCTTTGAGGACATGCGGTACGTCTGCGGGGGCTTCGCCTACT
TGCAGGATGTGGTGGAGCAGGCAATCATCAGGGTGCTGACGGGCACCGAGAAGAAAACTG
```

Fig. 9B

```
GTGTCTATATGCAACAGATGCCCTATCCCTGTTACGTTGATGACATCTTTCTGCCGGTGA
TGAGCCGGTCAATGCCCCTCTTCATGACGCTGGCCTGGATTTACTCAGTGGCTGTGATCA
TCAAGGGCATCGTGTATGAGAAGGAGGCACGGCTGAAAGAGACCATGCGGATCATGGGCC
TGGACAACAGCATCCTCTGGTTTAGCTGGTTCATTAGTAGCCTCATTCCTCTTCTTGTGA
GCGCTGGCCTGCTAGTGGTCATCCTGAAGTTAGGAAACCTGCTGCCCTACAGTGATCCCA
GCGTGGTGTTTGTCTTCCTGTCCGTGTTTGCTGTGGTGACAATCCTGCAGTGCTTCCTGA
TTAGCACACTCTTCTCCAGAGCCAACCTGGCAGCAGCCTGTGGGGCATCATCTACTTCA
CGCTGTACCTGCCCTACGTCCTGTGTGTGGCATGGCAGGACTACGTGGCTTCACACTCA
AGATCTTCGCTAGCCTGCTGTCTCCTGTGGCTTTTGGGTTTGGCTGTGAGTACTTTGCCC
TTTTTGAGGAGCAGGGCATTGGAGTGCAGTGGACAACCTGTTTGAGAGTCCTGTGGAGG
AAGATGGCTTCAATCTCACCACTTCGGTCTCCATGATGCTGTTTGACACCTTCCTCTATG
GGGTGATGACCTGGTACATTGAGGCTGTCTTTCCAGGCCAGTACGGAATTCCCAGGCCCT
GGTATTTTCCTTGCACCAAGTCCTACTGGTTTGGCGAGGAAAGTGATGAGAAGAGCCACC
CTGGTTCCAACCAGAAGAGAATATCAGAAATCTGCATGGAGGAGGAACCCACCCACTTGA
AGCTGGGCGTGTCCATTCAGAACCTGGTAAAAGTCTACCGAGATGGGATGAAGGTGGCTG
TCGATGGCCTGGCACTGAATTTTTATGAGGCCAGATCACCTCCTTCCTGGCCACAATG
GAGCGGGGAAGACGACCACCATGTCAATCCTGACCGGGTTGTTCCCCCCGACCTCGGGCA
CCGCCTACATCCTGGGAAAAGACATTCGCTCTGAGATGAGCACCATCCGGCAGAACCTGG
GGGTCTGTCCCCAGCATAACGTGCTGTTTGACATGCTGACTGTCGAAGAACACATCTGGT
TCTATGCCCGCTTGAAAGGGCTCTCTGAGAAGCACGTGAAGGCGGAGATGGAGCAGATGG
CCCTGGATGTTGGTTTGCCATCAAGCAAGCTGAAAAGCAAAACAAGCCAGCTGTCAGGTG
GAATGCAGAGAAAGCTATCTGTGGCCTTGGCCTTTGTCGGGGATCTAAGGTTGTCATTC
TGGATGAACCCACAGCTGGTGTGGACCCTTACTCCCGCAGGGGAATATGGGAGCTGCTGC
TGAAATACCGACAAGGCCGCACCATTATTCTCTCTACACACCACATGGATGAAGCGGACG
TCCTGGGGACAGGATTGCCATCATCTCCCATGGGAAGCTGTGCTGTGTGGCTCCTCCC
TGTTTCTGAAGAACCAGCTGGGAACAGGCTACTACCTGACCTTGGTCAAGAAAGATGTGG
AATCCTCCCTCAGTTCCTGCAGAAACAGTAGTAGCACTGTGTCATACCTGAAAAACGAGG
ACAGTGTTTCTCAGAGCAGTTCTGATGCTGGCCTGGGCAGCGACCATGAGAGTGACACGC
TGACCATCGATGTCTCTGCTATCTCCAACCTCATCAGGAAGCATGTGTCTGAAGCCCGGC
TGGTGGAAGACATAGGGCATGAGCTGACCTATGTGCTGCCATATGAAGCTGCTAAGGAGG
GAGCCTTTGTGGAACTCTTTCATGAGATTGATGACCGGCTCTCAGACCTGGGCATTTCTA
GTTATGGCATCTCAGAGACGACCCTGGAAGAAATATTCCTCAAGGTGGCCGAAGAGAGTG
GGGTGGATGCTGAGACCTCAGATGGTACCTTGCCAGCAAGACGAAACAGGCGGGCCTTCG
GGGACAAGCAGAGCTGTCTTCGCCCGTTCACTGAAGATGATGCTGCTGATCCAAATGATT
```

Fig. 9C

```
CTGACATAGACCCAGAATCCAGAGAGACAGACTTGCTCAGTGGGATGGATGGCAAAGCGT
CCTACCAGGTGAAAGGCTGGAAACTTACACAGCAACAGTTTGTGGCCCTTTTGTGGAAGA
GACTGCTAATTGCCAGACGGAGTCGGAAAGGATTTTTTGCTCAGATTGTCTTGCCAGCTG
TGTTTGTCTGCATTGCCCTTGTGTTCAGCCTGATCGTGCCACCCTTTGGCAAGTACCCCA
GCCTGGAACTTCAGCCCTGGATGTACAACGAACAGTACACATTTGTCAGCAATGATGCTC
CTGAGGACACGGGAACCCTGGAACTCTTAAACGCCCTCACCAAAGACCCTGGCTTCGGGA
CCCGCTGTATGGAAGGAAACCCAATCCCAGACACGCCCTGCCAGGCAGGCGAGGAAGAGT
GGACCACTGCCCCAGTTCCCCAGACCATCATGGACCTCTTCCAGAATGGGAACTGGACAA
TGCAGAACCCTTCACCTGCATGCCAGTGTAGCAGCGACAAAATCAAGAAGATGCTGCCTG
TGTGTCCCCAGGGGCAGGGGGCTGCCTCCTCCACAAAGAAAACAAAACACTGCAGATA
TCCTTCAGGACCTGACAGGAAGAAACATTTCGGATTATCTGGTGAAGACGTATGTGCAGA
TCATAGCCAAAAGCTTAAAGAACAAGATCTGGGTGAATGAGTTTAGGTATGGCGGCTTTT
CCCTGGGTGTCAGTAATACTCAAGCACTTCCTCCGAGTCAAGAAGTTAATGATGCCATCA
ACAAATGAAGAAACACCTAAAGCTGGCCAAGGACAGTTCTGCAGATCGATTTCTCAACA
GCTTGGGAAGATTTATGACAGGACTGGACACCAGAAATAATGTCAAGGTGTGGTTCAATA
ACAAGGGCTGGCATGCAATCAGCTCTTTCCTGAATGTCATCAACAATGCCATTCTCCGGG
CCAACCTGCAAAAGGGAGAGAACCCTAGCCATTATGGAATTACTGCTTTCAATCATCCCC
TGAATCTCACCAAGCAGCAGCTCTCAGAGGTGGCTCTGATGACCACATCAGTGGATGTCC
TTGTGTCCATCTGTGTCATCTTTGCAATGTCCTTCGTCCCAGCCAGCTTTGTCGTATTCC
TGATCCAGGAGCGGGTCAGCAAAGCAAAACACCTGCAGTTCATCAGTGGAGTGAAGCCTG
TCATCTACTGGCTCTCTAATTTTGTCTGGGATATGTGCAATTACGTTGTCCCTGCCACAC
TGGTCATTATCATCTTCATCTGCTTCCAGCAGAAGTCCTATGTGTCCTCCACCAATCTGC
CTGTGCTAGCCCTTCTACTTTTGCTGTATGGGTGGTCAATCACACCTCTCATGTACCCAG
CCTCCTTTGTGTTCAAGATCCCCAGCACAGCCTATGTGGTGCTCACCAGCGTGAACCTCT
TCATTGGCATTAATGGCAGCGTGGCCACCTTTGTGCTGGAGCTGTTCACCGACAATAAGC
TGAATAATATCAATGATATCCTGAAGTCCGTGTTCTTGATCTTCCCACATTTTTGCCTGG
GACGAGGGCTCATCGACATGGTGAAAAACCAGGCAATGGCTGATGCCCTGGAAAGGTTTG
GGGAGAATCGCTTTGTGTCACCATTATCTTGGGACTTGGTGGGACGAAACCTCTTCGCCA
TGGCCGTGGAAGGGGTGGTGTTCTTCCTCATTACTGTTCTGATCCAGTACAGATTCTTCA
TCAGGCCCAGACCTGTAAATGCAAAGCTATCTCCTCTGAATGATGAAGATGAAGATGTGA
GGCGGGAAAGACAGAGAATTCTTGATGGTGGACGCCAGAATGACATCTTAGAAATCAAGG
AGTTGACGAAGATATATAGAAGGAAGCGGAACCCTGCTGTTGACAGGATTTCCGTGGCCA
TTCCTCCTGGTGAGTGCTTTGGCCTCCTGGGAGTTAATGGCGCTGGAAAATCATCAACTT
TCAAGATGTTAACAGGAGATACCACTGTTACCAGAGGAGATGCTTTCCTTAACAAAAATA
```

Fig. 9D

```
GTATCTTATCAAACATCCATGAAGTACATCAGAACATGGGCTACTGCCCTCAGTTTGATG
CCATCACAGAGCTGTTGACTGGGAGAGAACACGTGGAGTTCTTTGCCCTTTTGAGAGGAG
TCCCAGAGAAAGAAGTTGGCAAGGTTGGTGAGTGGGCGATTCGGAAACTGGGCCTCGTGA
AGTATGGAGAAAAATATGCTGGTAACTATAGTGGAGGCAACAAACGCAAGCTCTCTACAG
CCATGGCTTTGATCGGCGGGCCTCCTGTGGTGTTTCTGGATGAACCCACCACAGGCATGG
ATCCCAAAGCCCGGCGGTTCTTGTGGAATTGTGCCCTAAGTGTTGTCAAGGAGGGGAGAT
CAGTAGTGCTTACATCTCATAGTATGGAAGAATGTGAAGCTCTTTGCACTAGGATGGCAA
TCATGGTCAATGGAAGGTTCAGGTGCCTTGGCAGTGTCCAGCATCTAAAAAATAGGTTTG
GAGATGGTTATACAATAGTTGTACGAATAGCAGGGTCCAACCCGGACCTGAAGCCTGTCC
AGGATTTCTTTGGACTTGCATTTCCTGGAAGTGTTCTAAAAGAGAAACACCGGAACATGC
TACAATACCAGCTTCCATCTTCATTATCTTCTCTGGCCAGGATATTCAGCATCCTCTCCC
AGAGCAAAAAGCGACTCCACATAGAAGACTACTCTGTTTCTCAGACAACACTTGACCAAG
TATTTGTGAACTTTGCCAAGGACCAAAGTGATGATGACCACTTAAAAGACCTCTCATTAC
ACAAAAACCAGACAGTAGTGGACGTTGCAGTTCTCACATCTTTTCTACAGGATGAGAAAG
TGAAAGAAAGCTATGTATGAAGAATCCTGTTCATACGGGGTGGCTGAAAGTAAAGAGGAA
CTAGACTTTCCTTTGCACCATGTGAAGTGTTGTGGAGAAAAGAGCCAGAAGTTGATGTGG
GAAGAAGTAAACTGGATACTGTACTGATACTATTCAATGCAATGCAATTCAATGCAATGA
AAACAAAATTCCATTACAGGGGCAGTGCCTTTGTAGCCTATGTCTTGTATGGCTCTCAAG
TGAAAGACTTGAATTTAGTTTTTTACCTATACCTATGTGAAACTCTATTATGGAACCCAA
TGGACATATGGGTTTGAACTCACACTTTTTTTTTTTTTTTGTTCCTGTGTATTCTCATT
GGGGTTGCAACAATAATTCATCAAGTAATCATGGCCAGCGATTATTGATCAAAATCAAAA
GGTAATGCACATCCTCATTCACTAAGCCATGCCATGCCCAGGAGACTGGTTTCCCGGTGA
CACATCCATTGCTGGCAATGAGTGTGCCAGAGTTATTAGTGCCAAGTTTTTCAGAAAGTT
TGAAGCACCATGGTGTGTCATGCTCACTTTTGTGAAAGCTGCTCTGCTCAGAGTCTATCA
ACATTGAATATCAGTTGACAGAATGGTGCCATGCGTGGCTAACATCCTGCTTTGATTCCC
TCTGATAAGCTGTTCTGGTGGCAGTAACATGCAACAAAAATGTGGGTGTCTCCAGCCACG
GGAAACTTGGTTCCATTGTTATATTGTCCTATGCTTCGAGCCATGGGTCTACAGCGTCAT
CCTTATGAGACTCTTAAATATACTTAGATCCTGGTAAGAGGCAAAGAATCAACAGCCAAA
CTGCTGGGGCTGCAACTGCTGAAGCCAGGCCATGGGATTAAAGAGATTGTGCGTTCAAAC
CTAGGGAAGCCTGTGCCCATTTGTCCTGACTGTCTGCTAACATGGTACACTGCATCTCAA
GATGTTTATCTGACACAAGTGTATTATTTCTGCTTTTTGAATTAATCTAGAAAATGAAA
```

Fig. 9E

| | Exon (bp) | Forward Primer | SEQ ID No. | Reverse Primer | SEQ ID No. | | intron(kb) | intron (kb) |
|---|---|---|---|---|---|---|---|---|
| exon 1 | 140 | GGCTGGATTAGCAGTCCTCA | 70 | ATCCCCAACTCAAACCACA | 119 | intron 1 | >6.413 | >6.4 |
| exon 2 | 94 | GGATTTCCCAGATCCCAGTG | 71 | AAGTCCAATTAGCCCACGTT | 120 | intron 2 | >4.241 | >4.2 |
| exon 3 | 142 | GACAGACTTGGCATGAAGCA | 72 | CCAGCCATTCAAATTCTCC | 121 | intron 3 | >1.248(1.6) | 1.6 |
| exon 4 | 119 | GCACTTGGCAGTCACTTCTG | 73 | GGGTGCAGTCAATTTCCAAT | 122 | intron 4 | >1.512 | >1.5 |
| exon 5 | 122 | CGTTTCTCCACTGTCCCATT | 74 | CCCCTTCACCACCATTACAA | 123 | intron 5 | >1.796(3) | 3 |
| exon 6 | 177 | ACTTCAAGGACCCAGCTCC | 75 | TGTCCAAGGAAAAGCCTCAC | 124 | intron 6 | >2.726 (10) | 10 |
| exon 7 | 93 | TCGGTTTCTTGTTGTTAAACTCA | 76 | AGGACCTCTTGCCAGACTCA | 125 | intron 7 | 4.975 | 5 |
| exon 8 | 241 | TCCCAAGGCTTTGAGATGAC | 77 | AGGAGATGACACAGGCCAAG | 126 | intron 8 | >2.311(.5) | 2.5 |
| exon 9 | 140 | GGCTCCAAAGCCTTGTAA | 78 | CGCACACCTCTGAAGCTACC | 127 | intron 9 | 0.332 | 0.3 |
| exon 10 | 117 | GCTGCTGTGATGGGGTATCT | 79 | ACCTCACTCACACCTGAACTTAT | 128 | intron 10 | 4.208 | 4.2 |
| exon 11 | 198 | TTTGTAAATTTTGTAGTGCTCCTCA | 80 | GCTCCTGCCTGAACTTAT | 129 | intron 11 | 0.747 | 0.7 |
| exon 12 | 206 | TAGTCAGCCCCTTGCCTCTA | 81 | CAAAATCATGACACCAAGTTGAG | 130 | intron 12 | 0.523 | 0.5 |
| exon 13 | 177 | AAAGGGGCTTGGTAAGGGTA | 82 | CATGCACATGCACACACATA | 131 | intron 13 | 1.787 | 1.8 |
| exon 14 | 223 | GATGTGGGCTGTCCCTCTAGC | 83 | CCTTAGCCGTGTTGAGCTA | 132 | intron 14 | 1.747 | 1.7 |
| exon 15 | 222 | CAAGTGAGTGCTTGGGATTG | 84 | TGCTTTTATTCAGGGACTCCA | 133 | intron 15 | 1.059 | 1.1 |
| exon 16 | 205 | GCAAATTCAAATTTCTCCAGG | 85 | CCCATGCACTGCAGAGATTC | 134 | intron 16 | 1.105 | 1.1 |
| exon 17 | 114 | TCAAGGAGGAAATGGACCTG | 86 | AAGGCAGGAGACATGCTT | 135 | intron 17 | 1.789 | 1.8 |
| exon 18 | 172 | CTGAAAGTTCAAGCGCAGTG | 87 | GGGATCAGCATGGTTTCCTA | 136 | intron 18 | 0.99 | 1 |
| exon 19 | 132 | TGCAGACTGAATGGAGCATC | 88 | GCTTAAGTTCCCACTCCTCCC | 137 | intron 19 | 1.307 | 1.3 |
| exon 20 | 143 | GCCAGGGGACACTGTATTCT | 89 | ATTTTCCTCCGCATGTGTGT | 138 | intron 20 | 0.204 | 0.2 |
| exon 21 | 138 | AGGTCCTCTGCCTTCACTCA | 90 | TCACAGAAGCCTAGCCATGA | 139 | intron 21 | 0.706 | 0.7 |
| exon 22 | 221 | CCAGTGCTTACCCCTGCTAA | 91 | AACAGAGCAGGAGAGATGGTG | 140 | intron 22 | >0.866(1.7) | 1.7 |
| exon 23 | 73 | CACACAACAGAGCTTCTTGGA | 92 | TCTGCACCTCTCCTCTCTG | 141 | intron 23 | 0.986 | 1 |
| exon 24 | 203 | ACCTGGAACAGAGTGTGGTGT | 93 | ACTGGGGCCAACATTAATCA | 142 | intron 24 | 1.668 | 1.7 |
| exon 25 | 49 | GGGCTAACATGCCACTCAGTA | 94 | CTTCCCCATCTGCAACAAAC | 143 | intron 25 | 0.196 | 0.2 |

| ERRORS IN PUBLIC SEQUENCE (differences between samples and Genbank entry AJ012376.1): | | | | |
|---|---|---|---|---|
| Exon/Intron | Nucleotides | Amino Acid Change | | sequence difference/context | SEQ ID NO: |
| 2 | T150C A152G | no change | Public sequence: Correct sequence: | TGTCAGCTGTTACTGGAAGTGG TGTCAGCTGCTGCTGGAAGTGG | 168 169 |
| 7 | C839T | no change | Public sequence: Correct sequence: | AGGAGCTGGCGAAGCCACAA AGGAGCTGGCTGAAGCCACAA | 170 171 |
| 33 | C4738T | T1495I | Public sequence: Correct sequence: | AATGATGCCACCAAACAAATG AATGATGCCATCAAACAAATG | 172 173 |
| 35 | C5017T | P1588L | Public sequence: Correct sequence: | GAGGTGGCTCGATGACCACA GAGGTGGCTCTGATGACCACA | 174 175 |
| 43 | G5995A | R1914K | Public sequence: Correct sequence: | TTCCTTAACAGAATAGTATC TTCCTTAACAAAATAGTATC | 176 177 |
| 48 | C6577T | P2108L | Public sequence: Correct sequence: | GGAAGTGTTCCAAAGAGAAA GGAAGTGTTCTAAAGAGAAA | 178 179 |
| 49 | G6899A | not applicable | Public sequence: Correct sequence: | AGTAAAGAGGACTAGACTTT AGTAAAGAGAACTAGACTTT | 180 181 |
| Mutations: | | | | | SEQ ID NO: |
| 13 | A1864G | Q597R | More common: Less common: | GCCTACTTGCAGGATGTGGTG GCCTACTTGCGGGATGTGGTG | 182 183 |
| 14 | delta CTT 2151-3 | deltaL693 | More common: Less common: | CCTCATTCCTCTCTGTGAGCG CCTCATTCCT/CTTGTGAGCG | 184 185 |
| 15 | G2385A | V771M | More common: Less common: | GCAGGACTACGTGGGCTTCAC GCAGGACTACATGGGCTTCAC | 186 187 |
| 18 | C2799T | R909Stop | More common: Less common: | AAAAGTCTACCGAGATGGGAT AAAAGTCTACTGAGATGGGAT | 188 189 |
| 18 | C2860T | T929I | More common: Less common: | GGCCAGATCACCTCCTTCCTG GGCCAGATCATCTCCTTCCTG | 190 191 |
| 22 | T3346C | M1091T | More common: Less common: | ACACACCACATGGATGAAGCG ACACACCACACGGATGAAGCG | 192 193 |

Figure 11A

| | (+1) G to C splice donor site | Altered transcript lenght | More common: Less common: | CCTGGAAGAAGTAAGTAAGT CCTGGAAGAACTAAGTAAGT | 194 195 |
|---|---|---|---|---|---|
| Intron 24 | | | | | |
| 30 | T4503C | C1477R | More common: Less common: | GCTGCCTGTGTGTCCCCCAGG GCTGCCTGTGCGTCCCCCAGG | 196 197 |
| 35 | GG 4958-57 to C | Frameshift at aa 1628 | More common: Less common: | TAGCCATTATGAATTACTGCT TAGCCATTATCAATTACTGCT | 198 199 |
| 41 | delta AAGATG 5752-7 | delta(E,D)1893-1894 | More common: Less common: | GATGAAGATGAAGATGTGAGGCGGGA GATGAAGATG/TGAGGCGGGA | 200 201 |
| 48 | C6504T | R2144Stop | More common: Less common: | AATAGTTGTACGAATAGCAGG AATAGTTGTAATGAATAGCAGG | 202 203 |

| Promoter Variants: Location | Position Relative to Xenon cDNA | Position Realitive to SEQ ID NO: 14 Containing Exon 1 | | | SEQ ID NO: |
|---|---|---|---|---|---|
| 1 | G57C | 8216 | More common: Less common: | ACACGCTGGGGGTGCTGCCTG ACACGCTGGGGGGTGCAGGCTG | 204 205 |
| 5 | (-)4 ins. G | 8158 | More common: Less common: | GACCAGCCACGGCGTCCCTG GACCAGCCACGGCGGGGTCCCTG | 206 207 |
| 5 | A (-)380 G | 7780 | More common: Less common: | CATTTTCTTAGAAAAGAGAGGT CATTTTCTTAGAAGAGAGAGGT | 208 209 |
| 5 | A (-)479 C | 7681 | More common: Less common: | GAAAATTAGTATGTAAGAAG GAAATTAGTCTGTAAGGAAG | 210 211 |
| 5 | A (-)1738 G | 7422 | More common: Less common: | CCTCCGCCTGCCCAGGTTCAGCGATT CCTCCGCCTGCCCGGGTTCAGCGATT | 212 213 |
| 5 | A (-)1045 G | 7115 | More common: Less common: | TATGTGCTGACCATGGGAGCTTGTT TATGTGCTGACCGTGGGAGCTTGTT | 214 215 |
| 5 | A (-)1113 G | 7047 | More common: Less common: | GTGACACCCAACGGAGTAGGG GTGACACCCGACGGAGTAGGG | 216 217 |
| 5 | (-)1181 ins. CCCT | 6979 | More common: Less common: | AGTAACCCT/TGTTCACGAGAA AGTAACCCTCCCTTGTTCACGAGAA | 218 219 |

Figure 11B

Polymorphisms:

| Exon/Intron | Nucleotides | Amino Acid Change | Sequence differences/context | | SEQ ID NO: |
|---|---|---|---|---|---|
| 5 | G548A | no change | More common: Less common: | CTGGGTTCCTGTATCACAACC CTGGGTTCCTATATCACAACC | 220 221 |
| 6 | G730A | R219K | More common: Less common: | GGCCTACCAAGGGAGAAACTG GGCCTACCAAAGGAGAAACTG | 222 223 |
| Intron 7 | G(+)2383 T | Not applicable | Allele 1: Allele 2: | TTTAAAGGGGTGATTAGAA TTTAAAGGGGTTGATTAGAA | 224 225 |
| Intron 7 | G(+)3035 T | Not applicable | Allele 1: Allele 2: | GAAGAATTTGTTTTTTGATT GAAGAATTTTTTTTTTGATT | 226 227 |
| 8 | C1010T | no change | More common: Less common: | GCGGGCATCCCGAGGAGGGG GCGGGCATCCTGAGGAGGGG | 228 229 |
| 8 | G1022A | no change | More common: Less common: | AGGAGGGGGCTGAAGATCA AGGAGGGGGACTGAAGATCA | 230 231 |
| Intron 9 | (-42 ins. G) | Not applicable | More common: Less common: | AGGAGCCAAAGCGCTCATTGT AGGAGCCAAAGCGCTCATTGT | 232 233 |
| Intron 13 | T(+)124 A | Not applicable | More common: Less common: | AAGCCACTGTTTTTAACCAGT AAGCCACTGTATTTAACCAGT | 234 235 |
| 15 | A2394C | T774P | More common: Less common: | CGTGGGCTTCACACTCAAGAT CGTGGGCTTCCCACTCAAGAT | 236 237 |
| 15 | G2402C | K776N | More common: Less common: | TCACACTCAAGATCTTCGCTG TCACACTCAACATCTTCGCTG | 238 239 |
| Intron 14 | C(+)16 T | Not applicable | Allele 1: Allele 2: | GCAGCCCTCACCCGCTCTCCC GCAGCCCTCACTCGCTCTCCC | 240 241 |
| 17 | A2723G | I883M | Allele 1: Allele 2: | AGAAGAGAATATCAGAAATCT AGAAGAGAATGTCAGAAATCT | 242 243 |
| Intron 17 | C(+)2000 G | Not applicable | Allele 1: Allele 2: | GCGCAGTGCCCTGTGTCCTTA GCGCAGTGCGCTGTGTCCTTA | 244 245 |

Figure 11C

| | | | | SEQ ID NO: |
|---|---|---|---|---|
| 21 | T3233G | no change | More common: GATCTAAGGTTGTCATTCTGG<br>Less common: GATCTAAGGTCGTCATTCTGG | 246<br>247 |
| Intron 21 | G(+)1118 T | Not applicable | Allele 1: CTCTTCTGTTAGGACAGAAGAGA<br>Allele 2: CTCTTCTGTTATCACAGAAGAGA | 248<br>249 |
| Intron 21 | A(+)1563 G | Not applicable | Allele 1: CATTCTAGGGATCATAGCCAT<br>Allele 2: CATTCTAGGGGTCATAGCCAT | 250<br>251 |
| Intron 24 | G(+)1321 T | Not applicable | Allele 1: AAGTACAGTGGAGGAAACAGCG<br>Allele 2: AAGTACAGTGTAGGAAACAGCG | 252<br>253 |
| Intron 29 | A(-)624 G | Not applicable | Allele 1: AATTCCTAAAAATAGAAAATGCA<br>Allele 2: ATACCTAAAAAGTAGAAAATGCA | 254<br>255 |
| Intron 31 | T(+)130 C | Not applicable | More common: GGCCCCTGCCTTATTATTACT<br>Less common: GGCCCCTGCCGTATTATTACT | 256<br>257 |
| Intron 33 | A(+)1732 G | Not applicable | Allele 1: TGAGAGAATTACTTGAACCCCG<br>Allele 2: TGAGAGAATTGCTTGAACCCGG | 258<br>259 |
| Intron 33 | C(+)1898 T | Not applicable | Allele 1: TTTGCTGAAACAATCACTGCA<br>Allele 2: TTTGCTGAAATAATCACTGAC | 260<br>261 |
| Intron 34 | C(+) 234 T | Not applicable | Allele 1: AACTCAGTTCCCTCATCTGTG<br>Allele 2: AACTCAGTTCTCTCATCTGTG | 262<br>263 |
| 34 | G4834A | R158TK | More common: CTGGACACCAGAAATAATGTC<br>Less common: CTGACACCAAAAATAATGTC | 264<br>265 |
| 37 | C 5266G | S1731C | Allele 1: TCCTATGTGTCCTCCACCAAT<br>Allele 2: TCCTATGTGTCCGTCCACCAAT | 266<br>267 |
| Intron 43 | T(+)118 C | Not applicable | More common: AAGAGTGGCTTGTATTTTGC<br>Less common: AAGAGTGGCCTGTATTTTGC | 268<br>269 |
| Intron 43 | C(+)11665 G | Not applicable | Allele 1: AACTGATTTGATTGGTATAGCTG<br>Allele 2: AACTGATTTGGTTGGTATAGCTG | 270<br>271 |
| 48 | C6522T | no change | More common: CAGGGTTCCAACCCCGGACCTGA<br>Less common: CAGGGTTCCAATCCCGGACCCTGA | 272<br>273 |
| Intron 10 | (+)14 ins. T | Not applicable | More common: GCGTCAGGGATGGGGACAG<br>Less common: GCGTCAGGGATTGGGGACAG | 284<br>285 |
| Exon 16 | G2547A | V825I | More common: CCACTCGGTCTCCAAG<br>Less common: CCACTCGGATCTCCAAG | 286<br>287 |

Polymorphism in an ABC1 BAC contig:
This polymorphism is within approximately 200kb of the ABC1 gene

| | | | | SEQ ID NO: |
|---|---|---|---|---|
| | A or G | Not applicable | Allele 1: TTGGAGGCCTAAGGCAGGAGAA<br>Allele 2: TTGGGAGGCTGAGGCAGGAGAA | 274<br>275 |

Figure 11D

Genomic contig containing ABC1 exon 1:
Underline = putitive promotor element

```
acctcttatagaatgatagaattcctctggaatgattggataacttcatttcatccttgactttttaccttggaggattt
cttacccctttttggcttctcaaatttgactattaaaatgttgcctttaaaaataggaacacagtttcagggggggagtac
cagcccatgacccttctgcaaggcccccctaactcaaggtagtttccctggaactgtggtttatggaatgtttcaggagt
gtgaggaggtataatttaaggctgtcctagcaaggatacccttaaggatagagggcccagtagcatctggaggccagaa
aagttaaactgaggcagtcagattagcttcaggctcaattaagctgatgggtcagcctgggagaaattgcaggatgact
ctcaatatcccctcccaccccacagcagccacgatctgtctgtctttaatcatgggtgcagtgaacctgttctttcca
ggtgtcttggccttcagtaaccttgttaggcttgtccctgaacgtggctaccgatccaaagacacatgatcagagaggc
aattagagaacagaccttttccaaagcaagcatgttctgttgggcttagaagtttcatgtcctaatattataggaccct
gtgcatctctctggagatgaggcacatgagtcatatctgtgattcttgcttttgtgtcaacatctcatgaataggcaat
cagagctttggcaccaatgtattttcagttcatatctgatgtagttaaatccacctcctgctttgtagtttactggcaa
gctgtttttgatataagacatctagaacactgtaaatatataacatttttatttgtctattatacctcaattacgaaaa
agacatctagaagcaacctcatcaagagagatactgaggccgggcatggtagctcacacttgcaatcccattactttgg
gaggctgaggcaggtagatcacttgaggtcaagagtttgaaaccagcctggccaacatgttgaaacctgtctctatta
aaaatacaaaaaagttagctgggcttggtggtgggcacctgtaatcccagctactccggaggctgaggcaggagaatca
cttgaacctgggaggcagaggttgcagtgagctgagatcacaccactgcactccaacctgggcaccagagtgagattac
atctaaaaaataaaataaagtaataaaaaagagagatattgatagctgttgttggaaatttcaacttccatctcacttc
tggtaacttttggaagtttgttgaacaaagtggaatacacgcacatacacacacacacatactctcttgtttgtttaa
ggtttaatgaaatagctgtcatataatcactgtttttgaaagaggagaattagttgctatctgtacatttttgggtatgt
gaactatttggatagaactctgagaaatgcattcagaacaacaaacaaaatcataggagaaatagctaagtgggaaggg
gcatataagagttgttgaaaaagttatttcttgagaaaccagctctaatgctaggcaagtcacttgctttgggggaggc
ctcagcttctctgtctataagattgcagcaggggtgtagtgggaatgagtcttcaacattccaagagatttatctact
aatacgacagtcaaatggagcatgactttgtggaagcctctcctcttccacccagaggggccaatttctctgtcccagt
gagatgttgacacttgtatgatccctgcttggagacttccctcttctggaacctgccctggctcaggcatgagggctga
ctgtcacccttcgataggagcccagcactaaagctcatgtgttggcagtgttcttgcgggaaggaaaaagaccagccag
cccatttgttactgcacaagcaaacagcttctggtagctgtacagatacatgcactttctttcctcactgtgtttccat
agacagatttagtgctgtagaagagtagagggcagtcacgggaaggagttcctgttttttcttttggctatgccaaatgg
ggaaaaatcctcctatcttgtcttttagtgtcatcctctctcccctttcttcttctttataattctcatctctcatc
tctcctggaaatgtgcatgtcaagttcaaaagggcacaatgttttggtgaggaagaggtgggagaacacgtgccaggtg
ctaactagggtcatcatttcccccttcacagccagcttcctgtgaatgtgtgtgtgtgtgtgtgtgtgtgtgtgtgt
gtgtgtgtgtgtatttcttttgccagcatcactgaatctgtctgctgtctggtattccaggttttggtttagggaaa
agtaaaagtaattttataatcccagctgtcatttaagccacccctttgtgggtagcatatggtccactctctcagttca
ttgtcctaaagatgcttcatcagaaaggaataacttccaccccgttactctctgtcccttactctgctttatttttct
tcgtcaatcctaccaccaccacccactgtttgaacaacccactattatttgtctgtttcccatccctggtagaatagga
gccccatgaatgaaggaactttgcttctgttgttcaccactgaatctctaaggtatggaacacacctggcatgtgatag
gcactcgataaatatttgttgtggctcatgggcaccttgcagagttaaggctgcagttgtttgtggaatttataagtgg
taatgaatatttatctactattcctcttccaaggcgatcacacaataatcaggctttacactatccagttcttaggtct
tccaagttatgacttgtgaggtatgttaattatgataatagaaggcagtttatttggttcagatttattgatgtgtaat
ttaccacagtaagacttccccttttacaaaagtatgatgagttttgacaaatggatacacatgtgtatctaccactgcca
tgctccttttcagtctgtcgtcccctccacccatgaccactggtcaccactgcagtgatttctgtccccttcatttcac
cttttccagaatgtcatataaatggaatcatgcagtatgtagttttttgtgtctggcttatttttcttagcattaggct
tttgggattcatccaggttgtcgcatgtaacagtagcttattccttttatggctgagtaagtgtcccagttttattta
tatatttatttatgaggaggtgtctcactctgtcacccaggctggagtgcggtagcgcgatctcagctcactgcaacct
ccgcctcccaggttcaagcaattctcctgcctcctgagtagctgggattacaggcacccaccgccacgcccaactaatt
tttatattttttagtagagatggggtttcaccatgttggccaggctgatctcaaactcttgacctcaggtgatccgccca
cctctggctcccaaagtgctaggattacaggcatgagccactgtgcccagcccagttttatttattcaccagttgatg
gtcttttcgacaactaattgtttccagtttttggctattctgtataaggcttctataaatattcacaaatacctaggat
gggatgactgggtcatataatagtactgtataaccttagcagaaactgtcaaactattttccaaagtggctcttccatt
ttacaattccacagtgtattgagtcccagtgtctccatacacatgctagcacttttaatatttaatttagtgggtatgt
aatgatatctcattgtggttttaatttgcatttctctgcagctaatgatgagtgtttctgcttatttgggaaggtttta
atttagcagtctgttgtattctgtagatattaataacttcaaaatatcagtggcatttgcagttaaaatttccttaaaa
aattggccaaaggtttccagcagtcacttctgccatgcccaaactgtatgaaacaaggctgaggtgtggagattgtcac
attttggcaaggagtgatccacttgggtgactgatgagacccagagagcgtacgcctcgggcttgagggtgaggacggg
cgggaagtcgactgcatggccctgctggccttggaggctgcccagtcctagctaaagctggcagttatgggaaacag
```

Figure 12A-(1)

```
acttagattctattacgtttttcaggatgtcccaggagtcacctgggaagctcagcagtcctttgtgactttcaagcat
atggtagaagctgctgaacacagagctccctctttggggataatttgcccaaatcatttaatcaggcttgagaaatgag
ttaccacaggtccaggagtgctgccacccttgaattctgacaccctatttctcctatccgtctcttaattaattaagca
gacatcccaagtgcttacgacaagccaggacccttttgcatactaaggaaaacagggatgaaggaaacagaaatggtc
tctgctctgactcagaaggtagaaatcctctttcccagccaagtcttcctagggagcacgtaggaagggctctgaaccc
acgtgtcagttgcaggggaggatatcaggaaaggacattgaagaagtggagacctaagtttgagacctaggcattagcc
aggctagcagtgcttgaaaaagtgtcttaggacaagagaactcaccagtgaagtcccagtggtaggagagcgtgcagca
tattctgagcctgtatacacatctccagggcattgcttagcaggtggggagtggcaagagagtaggctggagtcacaga
agggaggccaggtagaccttggtgagcactggactctatgttcaggtgctgaggagctggcaaaaggtttttaagtcggg
gagaggcatgttcagatatttggtctagctgagtaactttgggtgtctctgtgacaaatggttgggagaccagtgaggtg
gcagttgcggtcatctaggagcaggatcagagtggcctattgactgggatgactgtgaagtgggatcctttccagccag
taactggaaatgtgtatgagggcagaagtgagtgtactgcatttgaaacattgagaaatctagtacatagtactgtctc
tttatatcttttttttttttttttttgattttggtttgtttgttcactaacttggaaaactgatgtggaaatgtccct
ttggcttcagttacctgagcagaaggggccgggcattgccaaactctcctcttaggacagaattgctcccagtattgat
cattgtgttctgagttggggagcaaattgtgcaggaggccaggtcagtgccaaggtgggtgggaggaattggagcagg
aagcttgcctaagtgtgcccagcaaagccacggtagaactttctactgtggctctatgctacttcttagcaaccttctc
catgtgcttcctggagagtccttggagtcagaaccttttcttgaaacccagacacttttacttccaagaaaatgctgtc
caagaaaactcatccttcccttcttctcatgaacgttgtgtagaggtgtgtcttctcttcctttgagcttttccactca
gggtttaggggaggtgatattctatatttgggtttggctctgggtactgcaacactaggctattaagatttcatccta
ctgctttgcccctcctatctttccagaaacccacaatggatttgctagaaataatggaacgtcctgtttggacaggata
taaccatttctcagctagaggatattgttggaatgaagaaagataaatggggagaagggaactcacattgctttggcac
ttaaattaagccatgtactgtgttgggaaattatttatattatctcgttgaatccacagtagaacacagttgaacacca
tacaaggtaagtattgtcatccttattttaccatgaggaaattgatgcttagagagcataaagccttggccaggggcac
atagttgggaagccggggctaattcatgcctgggctcttctgatagtttccttttttaattgtcccgtcctcattgt
tacccttgggattcaagagattcatgtagcttctaaatcaacgaactgattcctggagagcagcttctgtatgagaaa
aatctagctaattatttatttcagtgtctctctgaatgcaagctctgtcctgagccacttagaaaacaatttgggatgac
aagcatgtgtctcacaatgctgctctggttgccagtgctgtgctgccagttgtcatctttgaacaaactgatgcagtgc
tggtttaactcttcctcttttttggagtaagaaactttggaggcctgtgtccttctagaagtttgctgagcaaatggtaa
ggaaaagaaataggtcctaaggcttgactatttcagagaatttcttgatttattggactgtcaatgaatgaattggaat
acatagtggtaggctgtcttttcttctcagacactgcaatttcctccaatctcttgacttttctagaagtttaatcca
agtccttgttgggtggtagataaaagggtattgttctactagagactgaccttggcatggagatctcatttggactcac
agatttctagtctagcgcttggttttgtatccataccctcgctactgcattcttagttccttctgctccttgttcctcat
gcccagtgtcccaccctaccccttgcccctactcctctagaggccacagtgattcactgagccatttcataagcacagct
aggagagttcatggctaccaagtgccagcagggccgaattttcacctgtgtgtcctcccttccatttttcatcttctgc
cccctcccagctttaactttaatataactacttgggactattccagcattaaataagggtaactgctggatgggtggc
tgggatacacagaatgtagtatcccttgttcacgagaagaccttcttgccctagcatggcaaacagtcctccaaggagg
cacctgtgacacccaacggagtaggggggcggtgtgttcaggtgcaggtggaacaaggccagaagtgtgcatatgtgct
gaccatgggagcttgtttgtcggtttcacagttgatgccctgagcctgccatagcagacttgtttctccatgggatgct
gttttctttccagagacacagcgctagggttgtcctccattacctgagagccaggtgtcggtagcattttcttggtgttt
actcacactcatctaaggcacgttgtggttttccagattaggaaactgctttattgatggtgcttttttttttttttttt
tgagacagagtctcgctctgtcgccatgctggagtgtagtggcacaatcttggctcactgcacctccgcctgccaggtt
cagcgattctcctgcctcagcctcccaagtagctgggactacaggtgcctgccaccatgcccagctaatttttgtattt
ttagtagagacggggtttcaccgtattggctaggatggtctcgatttcttgacctcgtgatccgcctgcctcggcctcc
caaagtgctgggattataggcttgagccaccacgcctggccgatggtgcttttatcatttgaaggactcagttgtata
acccactgaaaattagtatgtaaggaagttcagggaatagtataagtcactccaggcttgagcaaaatttacaaatgc
tgctgactttgtatgtaaggggaggcattttcttagaaaagagaggtaggtctctgggattccagtatgccatttccat
cctcagtgtttttggccacctgagagaggtctattttcagaaatgcattcttcattcccagatgataacatctatagaa
ctaaaatgattaggaccataacacgtagctcctagcctgctgtcggaacacctcccgagtccctctttgtgggtgaacc
cagaggctgggagctggtgactcatgatccattgagaagcagtcatgatgcagagctgtgtgttggaggtctcagctga
gagggctggattagcagtcctcattggtgtatggctttgcagcaataactgatggctgtttcccctcctgctttatctt
tcagttaatgaccagccacggcGTCCCTGCTGTGAGCTCTGGCCGCTGCCTTCCAGGGCTCCCGAGCCACACGCTGGGG
GTGCTGGCTGAGGGAACATGGCTTGTTGGCCCTCAGCTGAGGTTGCTGCTGTGGAAGAACCTCACTTTCAGAAGAAGACA
AACAgtaagcttgggttttcagcagcggggggttctctcatttttctttgtggttttgagttggggattggaggagg
```

Figure 12A-(2)

```
gagggagggaaggaagctgtgttggttttcacacagggattgatggaatctggctcttatggacacagaactgtgtggt
ccggatatggcatgtggcttatcatagagggcagatttgcagccaggtagaaatagtagctttggtttgtgctactgcc
caggcatgagttctgatccctaggacctggctccgaatcgccctgagcacccacttttccttttgctgcagccctg
ggaccacctggctctccaaaagcccctaatgggccctgtatttctggaagctgtgggtgaagtgagttagtggcccca
ctcttagagatcaatactgggtatcttggtgtcaatctggattctttccttcaggcctggaggaatataataactgaga
cttgttttatttctgcagaggggttctaagccattcacttcccagatgggccaataatgctttgagtaatctggagatca
tctttaatgcgcaggtgaatggaactcttccacagagggatgtgagggctgtagagcagagtgaactccctgaaactca
gacgtcagctctttgtctctctatctctgaacacccttccttagagatcccatctctaggatgcatttctctgtagtta
gtttctaagtctcttgttcctgttctgcctttatttttttttcctggattctaagccagtatccccacttggctgtctt
aatgtagcttaacatgtctgtaatcaaaatgatcatctttctgagattcaaagggctataagggactttggagagaatt
tcattcagttttcctcaaactagaataatgcttgcactgtctgtaaaagaacaaaagtgtcaaagcatcctttttgttca
ctaaatttccttttttattatagtgttacttaaatattaggaagttaaaagtaggtataaacttcttataggctgttat
tatacaactatatgacccatacatatttacaaattaagtgcagccaaaattgcaaaatcaataccattcaaattaatac
cttaaatgtggtgaggcagctgttgttcaactgaaaccaaattataagttgcatggcagtaaatgctatcatgctgatc
attttgagtttggccagtctatattatcatgtgctaatgattgaattctccacccatttttctacttgtatgaccttaa
tttgatggcacctgttccatcctcatgagtttgctacaattatactggtgccaacacaatcataaacacaaatataaac
ttgggctttgaaatcttgtgccagaacttggctttaaagtaagcatttaaaaaatccatatgtgtttattagactttgt
ttagatgactgttgaaatgaaaacaaagtgtttaaaatcctcttagagaacttaaatataatccctcagcaatatgtat
acagatcttcctttgagaaaaactgattgtgttcagcctctcatgttacaaatggggaacctgaattctgaggtctcta
gtgagagaacagggactggaatctgtggatcctatctgttttaataataattgtaaagtataatagataatattatatt
aaaaagagagnnnnnnacacttagaatgagcttccatgtgtgaggcactaactgattaggcattattaactagatttat
tccttttaaggccccgcgatgtactgttatttccacatgttgtagctggggaacgtgctactcagagaggttaagtaac
ttgtctgaggtccacaccactaacaaggagcacaggtagggttcaaatccagataatctgactttggagctggcactct
aactcaatgtgcctaatcgcttttcagtggtgtcattattttgcctattctccatctgagaatattgaagtttctgact
ccttccttgcctttctccctgcctcccgtggttatcccaggtcttggtgttccagtcctctatgtccgtccttactct
tattcctttgctacagtgtgatccagggctcctgcccttcttatcctggtagaggggggcccacttgctgggaaattgtc
tccgccatggtttatccatgttgtgtgtccattagtgagtagtgggaagaatcatatcatgttggcaatgaaagggggg
ctatggctctggggtagtctagtctgaactcttatttt
```

Figure 12A-(3)

SEQ ID NO: 15
Genomic contig containing ABC1 exon 2:

```
cttttttttttttttttttttttttttttttgaggtgaagtctcactctgttgcccaggctggagtgcaatggagcgatc
ttggctcaccccaacctctgtctcctgggttcaaacagttctcctgcctcagcctcccgagtagctgggattacaggctc
ccgccaccatgcccagctattttttgtattttcagtagagatggggtttcacccttttgaccaggctggtcttgaactc
ctgacctcatgatcaacccacctcagcctcccaaagtgctgggattacaggtgtgagccaccacgcccggcctcataagt
atttttctaaatttatttacagtcatgccatttaaaaggaaagttgtattcctgtctttgttaatatttataagtgatttt
attcagctacaagcttggaatggcatataattttgtattctgcttttttcacttaatattacatggctaatgatttctgt
gtttcataaacattattctgatgatggcatgatatattgttgagtacatgtaccataattgaatcatttccctattgcta
tgcaattaagttgtttccaatatttttgcaattataatgtttcaatgaatgaataactttatgcatatagcttttgatat
cttaagttcagtttcctaggatgaatttccaggaatagtaattgggcaaatgggataaacatgactcttgaatcgtatt
gttaacattgcttcccaaagggctcaactgatttatatttccgtgttcattatcttttaaaccagctcatttactcacc
aaacattttaaagccattatcatgtggtaggcttagtaagaagaaagtgacccttaaggggagaagcttatatataaatag
ggtccctggtgtaccaagtgctgatacagacacaaagtacctggggaaattgagatgagggagtcctggctcagctggga
gaaaagttcatttctatagagtcatggttttgttctttggcagaaagaaaattgctttcttccccaccccccacccccagc
tttattgaggtataattgacaaataaaaattgtatatctttaagatatgcaatgtgatatatatgtatatctcaacttaa
aaaataagctacagaataaaaaggtgtttgctattaaaaaaaaagaaaaggctgaatgtcattcccaagcttggaaattt
gagtatgttgcctctttgggattatttacagaaatattagcaagaccagccccatctttggtcttgagtactccactgtc
agcatgctttcttccagagagggatccatttgcctttatttttcattctgttgtgccgtctatgcaaactattcttgata
gttttatggtaacagtgttttttttgttccatgagataaatttatacatgctcattgtggaaaatttagaaaagacaggaa
agtattaaaaacatcmcytttttttttttttttttttttttttttttamgcagacagagtcttgctctgtcgcccaggcc
ggagtgcagtggcgtgatctcagctcacagcaacctccgcttcccaggtttaagtgattctcctgcctcagcctcccaag
tagctgggagtacaggcatgcaccaccacgcccggctaattttgtatttttagtagagatgggtttcaccatgttggcc
aggctggtctcaaactcctgacctcaggtgatccgcctgccttggcctcgcaaagttctgggattataggcaggagccac
tgcgccagccacacctacgttcttatcatcctagtacatccactgtcattatcttgctgtatttccttctgcccagtctc
actctgatcatgcagtggcgtgatcatgcagtgatctcggctcactgcaacctaggccttctgggttcgagtgattctcc
tgccttagcctcctgggttcaagtgattctcttgccttggcctcccaagtagctgggattacaggcatacaccccatgc
ccatctaattttgtattttagtagacacagcgtttcactaaaatttgtattttagtagagatggggtttcaccatg
ttggccaggctggtctccaactcctgacctcaggtgatccgcctgccttggcctcacaaagtgattacaggcatgagcca
ctgcatccatcgccaaaaagattttttaaaagagtttaatgtagaaccatatcaaaggtctttggaaataaaaaacagtt
ttttaaaaatatcagaaataaaacaacaaataaataaataaataaaaacacccaaaacaatctgaagcacgagcacctag
cagaaaggttcaattatgatctattcatagagtggaatatcaagtagacattacaggacatgttttaagattatatttta
tgtcatgggaaatgctctcccagtatgatgttaaatgaaaaaacagaatacaaaagtatatatgctgcatagtctcaata
ttgtagagaaaaatattatttatgtatgcatgaaaaaagacaaaagatgttaacagagatccattgttacttcagttta
ctagggattgtctctggaggtaggattaaggtgatttatatttacctttttaaacttttctgtatttttttatttttcaa
attttccataaaaatataaggacttgaagatcaagaaaaaatttctgctttggctcagtgcagtcgtcacgcctgtaatc
ccagcagtttgggagccctaggggagaggatcacttgaacccaagagtttgacgttccagtgagctatgatctccggatc
gtaccgcctggacgatggagcaagacccttgtctcaaaaaaaaaaatctttgcttttttttttttgtttgttttgagacgg
agtctctctctgttgcccagctggagtacagtggcacaatctcagctcaccgcaacctctgcctcctgggttcaagcga
ttctcttgcctcagcctcccaagtacctgggattccatgcacccaccactatgcccagctactttttgtatttcagta
gagacagggtttcaccatgttggccaggctggtctcgaattcctgacctcagctgatccaccggccttggcctcccaaag
tgctgggattacaggcatgagccactgtgcccagcccaatcttttgctttttttaaaaaaagaagacaaaagggatttt
ataccagtattatcttggctgtgtgactctgaagccacagttgtaagttataattactctgaaacacaaggccctgtgac
tcttttgggctctttggtgtttatcttgattacaacgttggaatatagaaatgaaaggaatgggagaggtgatagacttc
aggcagtgtaactagttgtctgaacactactggctcaattatattgtgtctagtgatttccatcttgtccgtctgctaat
ttatcgcctggtaactcactgaggcagggttttcctttggagaaacctcattgttttaaccagtgtatcatgcttgttta
gaagttcaatgatcttttaactcatcggagaagatgatgaccagacctggacagatggggaaggactttgcactctctc
tttacagtcctgagtgcacacaggtcaatatggaactatgtgtgaattttcattgtctttgagagccctcttctctgccc
catagggagcagctttgtgtgcaattagaggagcaagggttgtgtgtatttagcacagcaggttggcctggtcctctcct
ctcaacatagtcaccacatacctggcactatgctaaggctgggaatgcagacagatgggtgcctgctttcagagtgctca
atgtgctgaggaagccagcaacagaaacagatgatttcaggagctccaggaaaatgctacaggaggagtgtgcctgggtt
```

Figure 12B - (1)

```
actggagtagcacaggaggagggcttctagctcaggctgagattttagtaaaggaaattatgccacgatgaatcctgaag
aatgaatagaagtgaaccagataaagcacgataggaagcatcttcccttacctaagggaagacacagaggtatatggaat
ggtatgttaaaaggttgggactccaaacagttctgttaaagcttagagagtggtgggagagactggagaagttgattaat
tagtaaatgaagttgtctgtggatttcccagatcccagtggcattggatatccatattattttaaatttacagtgttct
atcttatttcccactcagTGTCAGCTGCTGCTGGAAGTGGCCTGGCCTCTATTTATCTTCCTGATCCTGATCTCTGTTCG
GCTGAGCTACCCACCCTATGAACAACATGAATgtaagtaactgtggatgttgcctgagactcaccaatggcagggaaaat
ccaggcaattaacgtgggctaaattggacttttccaaagatgctgtctttgggaaacatcacacatgctttggatcagaa
aacctaggcttctaatttgttgataaggcatgaactcaggagactgttttcagtcctagtgaatggtgataattgtaatt
ataacagtagacaacatctcttttacacattttaaatcatgaaaatagaataaccttactgataatttagaaagtggtg
attaaaagcacatttaagataatgccttaacacctagtctttccatatgcatgatgtcttaatcacacattgcaaatca
tggaacacagaatttt
```

Figure 12B - (2)

SEQ ID NO 16
Genomic contig containing ABC1 exon 3:
atcttacaatcacagtctttctcttagggctgggctcagtgggtggattgacactgcagaaatggccagatctaaaggat
caacatttacgtagctgggaaatgtagctgggacttcagtttcactgccctagtgattttcctaccactaagcagctca
gtccatacccctacgagacccacaagcttatgagatactgttcttccaggaaagcagtggggccagggccacctttaat
tgtgtttcttggcctggtcccatctttctcacaatatatagcaacagttatttacttgctgatttctaatgcacatcac
acatagtcatattaaacacacacacacacacacacacacacaccccctcaagaaacattttctgagacgtgatttcc
tgatttcatcaaaaaagaaaagagcgggccaggcacagtgggaagtcaaggtgggtggatcacttgaggtcaggagtttg
aaaccagcctggccaacacggtggaacctcgtctctactaaaaatacaaaaattagccaggcgtggtggcgcacacctgt
aatcccagctactggggaggctgaggcaggagaattgcttcaacctgcgaggctgaggttgcagtgagccgagattgcgc
cattgcactccagcctgggcaacagagtgagactctgtctcaaaaaaaaaaaaaaaaaaaagcataaactgaaattta
tatgcaatttatatgcctgtgagataattctgttttctcttttggaaccccaaagagattttttgattgatgagcaaat
acatttagatttattaagcattatgccaagcaccactgaagtataagtttcaagggcaaactcagttttttcatcta
ctagacgaatgatttctggaatgattacaagcaggcaagatggtgtagtggaaatagcaaatgtcttcggcatcagaca
agttgggtttgtttgtatcctgcctctgcccttcaccgaggttgtgatcttgggcagattgttgagttttaacctagat
tcctctgactccagatcataaattttcagaaaagttctgaaattcttgtatatactgatggtaaatgagacttttcctta
catctatgcacttctttgtttgttttgagatggtcttgctctgttgcccagactggagtgcagtagtgcaatctcc
gctcactacaatgtctgcctccaggttccagtgagcctcctgcctcagcctcccaaatagctgagactacaggcatgtg
ccaccacgtccggctaattttgtattttagtagagacagggttttgccatgttgaccacactggtctcgaactcctgg
cctcaggtgattcgcccgcctcagcctcccaaagtgctgggattacaggcatgagccaccatgcccggccatatccatgc
acttcttgcaaccttaccttcttttctcatcaccctccagggacctagttggaagagcagagttaaaagttaaggtgaaa
cttggagaggtgtcttgtccctaggaacaaaggactggtttgaaattctctgtaaatcttccccagttcaaaccagagtt
atcaaggtcttaaaaacttccctgggtcctgagagcccattatattatttacttgtcttcctgtacacccactgcctagt
cctgatcctacttttgtttgcaaataggatggggcacaacgtacaaggaagggcctttgccacccctgctaagggataac
ctgaaataccttcaccatcactgccctgtgctgcttttcacctatgccagtctgtctacagtgccagtgtctcctggcat
tgaaaggggagaatcttttggtcctttgagtatttggttgggttacataaatctccctgaatgaagagcagctgacttag
gcaaggggccttgtttggttttccttgaactattaacaggaagatagggagattaactgtgtaaatgttcaataggccag
agtccctgcagagggtggccacagtgatcagatcttatcacatccttgctttgggtgttgcctctctggttggagtatgg
atagaaaagaaagaaagacccatatattgaaatgcaaagtgcagcaagtcctgactttggattaacttctcagcccatttg
catgaaaataaaaagatgaataaaacaaggttcccactttggagggaggtggtagctgtgagatggaaggagtgttcctg
ctgggcaacagcagagtaagtgctggggtagattcactcccacagtgcctggaaaatcctcataggctcatttgttgagt
ctttgtcctacaccaggcactctgcaaaaacgctttgcctgcaaggtctcatgcgatgctcaccacagctctgtgaagtt
aattgtacttttatcaccatttacagatgagaaaactgagggtatgggtcaatgacttggctaaagtcactgcttagc
aagctgcagggactggatgtgaattccaattggtttgactccaaagcctgtgaagctacttgttcttcaccacctagagc
tgtggttcttgataactgtgaactcttttggggtcacaaatagccctgagaatatgatagaagcaggagctctggcctt
ctgtccatacctgaacaggtccttgggttaagagcccctcgtccagggcctattaatcttgatcctcataagcagcatcc
atgtattacggccgcaaaccaaactgtgccagaccgaatcctaggaccaagcccaaatatgtccatcatccttttggta
agaagctcattgtaagaaagaaagaggagagcaagaggatgacctagtgcatgggcctcattgttttaattagtgacaa
aacaacaataataacaacaaaaccccgaagcttcacagatgacatcagaccccaagcctgtgtgtttttcaggtgccct
tgaggagctttgtagctggcagaggaggtgaaactgacaaatgtttggcagatggaggagagtaccagaggggtttgaga
tgagctaaattccaatctaaccgcagtgttgaggaagaggcttggattgggaccatggagatgggggttctactcccagt
cacgccagctgactttgcgagtgttctttgtcagtcactttatcttatttttatttttatttttttgaaatggagtt
tcgctcttgtcgcccaggctggagtgaaatggcgcgatcttggctcactgcaacctccccctcctgagttcaagcgattc
tcctgcctcagcctccagagtacctgggattacaggcgcctgccaccaagcccatcgaattttgtatgcttagtagaga

Figure 12C - (1)

```
cagggtttcgccatgttggccagggtggtcttgaactcctgacctcaggtgatccgcccaccttggcctcccaaagtgct
gggattacaggcgcgagccactgtgcccagcccacttcatcttaccgtagttacctccttagagtatgaaaaaataggct
tagggcatccccaagtcccctctatgtctgagagctgaggctggctgtcaaagaggaactaaggatgccagggactttct
gcttaggacccctctcatcacttctccaacgctggtatcatgaacccattctacagatgatgtccactagattaagaat
ggcatgtgaggccaagtttccacctgagagtcagtttttattcagaagagacaggtctctgggatgtggggaatgggacgg
acagacttggcatgaagcattgtataaatggagcctcaaaatcgcttcagggaattaatgtttctccctgtgttttcta
ctcctcgatttcaacagGCCATTTTCCAAATAAAGCCATGCCCTCTGCAGGAACACTTCCTTGGGTTCAGGGGATTATCT
GTAATGCCAACAACCCCTGTTTCCGTTACCCGACTCCTGGGGAGGCTCCCGGAGTTGTTGGAAACTTTAACAAATCCATg
taagtatcagatcaggttttctttccaaacttgtcagttaatccttttccttcctttcttgtcctctggagaatttgaa
tggctggatttaagtgaagttgtttttgtaaatgcttgtgtgatagagtctgcagaatgagggaagggagaatttggag
aatttggggtatttggggtatccatcacctcgagtatttatcatttctgtatgttgtgaacatttcaagtcctgtctgct
agctattttggaatatactatatgttgttaatgatatcatgcagcagacgtgcatctgaatgggctggctctaggagcta
gagggtaggggctggcacaaagatgcatgctggaagggtccttgcccataagaagcttacagccaaggctaggggagttc
tgtcttctctgcatcaggtcacctctctcacctctgtcactgccccatcagactacaatgtctgcaggtctttctcccct
gagtgtgagctccctgagcaaagcaggatgctgcccctt cccttt gtattccttgctccttgcttcagtgcctgtacata
agtatgggcataataagtgtcccccaaatgagacattgaggattcttcaaatgcacaggaccgtgatgtgagttaggacg
gagtaaggacgatgggatgtggctcatgacaatcctgaggaagctgcagctgcggcacgcagggccacactgtcatgttc
atggaccctagactggctttgtagcctccatgggccccttccatacac
```

Figure 12C - (2)

SEQ ID NO 17
Genomic contig containing ABC1 exon 4:

tcatgactgccattggtataaagatgaatataatccagaccagattcatgattattcatacattttagtgtattaactt
ttaattctgctttaaaataaattaaaacattctaatatgcccttaagagtatcccagcccaggccactgagcctactgt
ggttcatggataagtttgcccctgggggcatgtgtgtgcatgcatgtgtgtgcacatgcatgatgagccgggccttgaag
ggtggtaagatttgggtgtgtagaccaatggagaaaggcatttggggcagtgatgatgggtgggggagggaacatggtga
tgaatggagctggtgtggggagccatgggagtgggttagggccagcctgtggaggacctgggagccaggctgagttcta
tgcacttggcagtcacttctgtaaagcagcagaggcagttggcctagctaaagcctttcgccttttcttgcaccctttac
agTGTGGCTCGCCTGTTCTCAGATGCTCGGAGGCTTCTTTTATACAGCCAGAAAGACACCAGCATGAAGGACATGCGCAA
AGTTCTGAGAACATTACAGCAGATCAAGAAATCCAGCTCAAgtaagtaaaaaccttctctgcatccgtttataattggaa
attgacctgcaccagggaaagagagtagcccaggtgtctggggcttgttcccattagatcttccccaaggggtttttctc
cttggtggctggcctgtggggcccctctccaggaggcattggtgaagaaactaggggagctggttgccacagacagtgat
gtactaatcttctctgggaagacagaagaaaagtccccagggaagaatactacagacttggccttagggacagctagggg
tgcagattgctgccaactgcattttttctgaagttggccatatggttgcagtgaatggatttatagacagagtatttctg
tgcatataagagcaattacagttgtaagttgatatggataagtgaaagttaagcacttctttctaaaaagagaatgcaat
tcatttttcccctaatcatttcaattagtctgatgggcatttgaacttgttgtctttaaaaagtgaaatctttacctctga
tctggtaagtatccaggcaatttcttgtgtgccacccaggaggtatctggggagtgggcattttctgactgaggcattgg
ctgccatagcatcagagcagccttccaggcagtggcctggcaaggggacagaggctggtgggagcagctggctgagtgca
gccagtaatggcatgt

Figure 12D

SEQ ID NO 18
Genomic contig containing ABC1 exon 5:

agctctccaggtgattctgatgcatacttaagtttgagaaccattgcttgttttgcattaaacaggagattagtctctgc
agcttgtgggaataaagctttaaatctctccaatttagctctgtgaaaaggcagtggggagacaggaatgaacggacta
gtgccacaaagctcaggtggggtgggtgagatcatttagaagagaaagaccgggcatggtggctcacgcctgtactgtca
gcactttgggaggccaaggcaggttggatcacaaggtcaggagtttgagaccagcctgcctatcatggtgaaacccgtc
tgtactaaagataaaaaaaaaaaaatttgccagtcatggtgatgcatacctgtaatcccagctactcgggaggctgaggc
aggagaatctcttgaacccgggaggcgggggttgcagtgagctgagattccaccattgcactccaacctaggtgacaggg
tgagactccgtctcaaaataaaaaaaaaaaaagaaaaggaaaggctgtgtgtgtgtgtatgtgtgtgtgtgtgtgtgtgt
gtgtgtgtaacagcaccatcacactgtttgagttgaggagcacatgctgagtgtggctcaacatgttaccagaaagcaat
atttcatgcctctcctgatatggcgatgctccctatctcattcctgtgtgtgtttagccaggcaactgttgatcatca
atattatgataacgtttctccactgtcccattgtgcccacttttttttttttttgagttacttactaaataaaaataaa
acactatttctcaatagACTTGAAGCTTCAAGATTTCCTGGTGGACAATGAAACCTTCTCTGGGTTCCTGTATCACAACC
TCTCTCTCCCAAAGTCTACTGTGGACAAGATGCTGAGGGCTGATGTCATTCTCCACAAGgtaagctgatgcctccagctt
cctcagtagggctgatggcaattacgttgtgcagctactggaaagaaatgaataaacccttgtccttgtaatggtggtga
aggggagggaggtagtttgaatacaacttcacttaattttacttccctattcaggcaggaattgccaaaccatccaggag
tggaatatgcaacctggcgtcatgggccagctggttaaaataaaattgatttctggcttatcacttggcatttgtgatga
tttcctcctacaagggatacatttaagttgagttaaacttaaaaaatattcacagttctgaggcaataaccgtggttaa
gggttattgatctggaggagctctgtctaaaaaattgaggacaggagactttagacaagggtgtatttggagactttaa
gaattttataaaataagggctggacgcagtggcactgagttgagaactgttgcttgctttgcattaaataggagatcagt
ccctgcagcttgtgggaataaggctttaaatctctccaatttagctctgtgagatggcactggggaaacagaaatgaac
ggactagtgtcacaaagctcaggtgggatggacgagatcacttcaaaggtctgtaatcccacgtctataatcccagcact
ttgggaggccaaggcgggaaaatcacttgaggtcaggagttcgagaccatcctggccaacaatgcaaagcctgtctctac
taaaaatatgaaaattagctcagcgtggtggcatgctcctgtagtcccagctactcgtgaggctgagacaggagaatcgt
ttgaacctgggaggcggaggttgcagtgagccaatatcacgccattgcactccagcctggctgacagagtgagactccat
ctcaaaaaaaaaaaaaaaaaagaatttataaaatcaggaaataatattagtgtttatgttgaattttaactttagaat
catagaaaacttcctctggcatcattattagacagctcttgtgcagtgggtagcaccagacccagcttgcatggttattg
atttttcagagacactttttgagcttattctctggcagaaaggggaactgcttcctcccctatctcgtgtctgcatacta
gcttgtctttacaagaagcagaagtagtggaaatgtttattcttgaaaataagcttttttgcttcacatgatctagaattt
ttaaaattagaaaaatgtgcttactgcg

Figure 12E

SEQ ID NO 19
Genomic contig containing ABC1 exon 6:

agtaaaatggagaattccaaattctgaaattgttagaacatagttctgtgtcttagttaaatatcgacacttacagataa
atagcataaatgctttctccccatatttcagcccagtcctacttaaagacaacataaattgcaaaatagtgaggatgttg
ttcatctaataaaagtggttccaggaattcagactctggattcctgtttgccaaatcatgtgtcccactcttaagaaaac
gagttggactntggattttctttgcaagagggacaagagtgtgggagatactgagttaatgcaacttgcaggttttaag
tgtcctgtcattgtgccttgtgctttgatacattctgagtttcagtaaagagacctgatgcattggactgttgcaatgga
acctgttaagatcttcaaagctgtattgatatgaagttctccaaaagacttcaaggacccagcttccaatcttcataa
tcctcttgtgcttgtctctctttgcatgaaatgcttccagGTATTTTTGCAAGGCTACCAGTTACATTTGACAAGTCTGT
GCAATGGATCAAAATCAGAAGAGATGATTCAACTTGGTGACCAAGAAGTTTCTGAGCTTTGTGGCCTACCAAGGGAGAAA
CTGGCTGCAGCAGAGCGAGTACTTCGTTCCAACATGGACATCCTGAAGCCAATCCTGgtgagtagacttgctcactggag
aaacttcaagcactaatgctttcggaatgtgaggcttttccttggacagcatgactttgttttgtagaaaagtacggctg
gctgggagtttgtgatataatttagttcagtggtattctaagtgttcttagtgttctttcagacttttgggccatctccc
aaagggtgaatgggaagaataagctgggtgtggctgagtttaagccaaaagttttttgtgcttgtttcaatcagagaaga
cctgcttttcatgttttactattataatactaagcaagagctcatttgaaaacagagttcttcatatttaaaaaaaaa
aagtcttgaaaccattgatgggaagatggatatctatttatgtttaaaaacccatcataaagatgacattgtgggctgtc
acagttggaaggccctggaattagatgagaccacactatttagcttacttagtaataacattg

Figure 12F

SEQ ID NO 20
Genomic contig containing ABC1 exon 8:
ccgtttggcaaatgctcagtaaaagaaaagggttagaaggggagaaaggcattttatcccaagccttcaggaatcaggat
gaggatgtcttcaccttgtggtggggagtaattatacaattagagacagcacattggagtgtggctgatatgctgtgtga
tgatagctctagctctctgcctagcagaggaaggacatttcaatagaagaaaaagtttaagaccttgccgagaaacagag
aaaggatgtttgtcttttaagaagttgaaaaccctgtttgcagacaaaagccctccagttttggcagtaaactttcatg
caagggaagaaaaaggcaggggatgacattgttgacaattgtgaggaattaccatgtgccaggcactgtgcgaggggctt
tgtacatatcctctagttttagtgcttataaaaactctgtgatatgtgcacagcattttaaactttgctgcatagtcgag
aaaatggaaggatggggaatttgagtcatttgcccagggttctatagctaccccaggttcccatgactggagaattgggg
cacagggtggcgggggagagtgagtgacaagaatcctaacaatcttatttccattgagtccttataaaagaagtggatta
actaccacgtttttaagttttcttaaatttaggttatgtggatctggcgtttcttgttttgtcctgggtttgttttgtt
tttgctatgctgtcttgaacatctgtcatcttgtaggcctaacgtaaacacaaaaacactttacctcctatagctttca
attaagatctctcagtttgtgtttgtaatagttttccaggcaagttctccctaggttcggcttctagtgtgttaaccttt
agttataaagtgaacccaaagagagaaagtagaaacaaaacacctcacctgttttgctcatgaattactctctatggaa
ggaacaatcatgaacacctctgcgtatcacagaggcctatctgagtctgacgtttaagggagaccgcgtaggtcccttg
aggactgtgaatgtgggagtcctgggactctggtgaagaacccgttccagaagagatgaatgagctggacaagttctttc
atagaacctttaggcaggtttttcttagaaatgcacattgaggattatgcttggatattgtgatgatcagaatgatactca
atcccttctgcatttggaattctctttgaaagaaaacatcccaggcagctatttctcagagatagtgagtcccagccact
tctagacattttcttgtgtagtctacattataatttcacagcagtctctgatatgacaaatgtcaaaatagcccaacctt
ctctaaacttcagagatgtctgatatgatattgaataaaacaatgctcatagaaacatcaagaaaggtggattttccctg
gatacttttttcctgcttgacaaataacagtgaagaaactgatctcacgtcttttctctttggaagcctgaacactcag
aacccaacttgaggctcctcagctatagcaattctgacttcacagtctgtaaattattgttcttttttttctttagctta
tgctttctgccctaatttatcttttccctgttctaatgaattattgtcctatatctgctgtgcagttaggtgacatataa
cagcaattaaatatatgaattggtacatataaagatttgactaaaactcgatgtaaaaataagtgttctacattcaattt
ccagtgttagaaacagtgctgacttgaacagagtgacagaattccatctttccctattttttgacagctttaaactttata
ttttcttcctttcttgtgagccgtcattaacttgtttctcaaagccattcccgtattacccatcttgcagacgcagacag
atttgggaatttgcggtcagagttgtattggacacatccccccagcccacatgagatccttttaatctattgcatattaa
ctagttttaagtacaatattcctacttcatttaaaaccattaatcaaagaatgagtttgaaaatgaacaaaatgcaaact
tacagttagaaataattgtagtgtctttagttttggttaggagtcggtttcttgtttgttaaactcaagattgtgaacag
ttttaattcacttgtttatttccaatagagatttcaggtttacatttgaattcagaaacaaagttttcttctcattaca
gAGAACACTAAACTCTACATCTCCCTTCCCGAGCAAGGAGCTGGCCGAAGCCACAAAAACATTGCTGCATAGTCTTGGGA
CTCTGGCCCAGGAGgtaagttgtgtctttccagtaccaggaagcggatcatccactgtatcagtatttcattcctgagt
ctggcaagaggtcctttgagttgaatatcacatgggatgtaatatcaattttcaaagtataagtgatgtaaacaataat
gtttgatttccttatttagaaatgaagaaacctaaaactcatagatgtctcagagctaattggttagtggctaacagc
tggatatctagtttagaaccttctccattttttcttttgccctaggtaatcatacatttgtaaagaggagaattatct
ctgccactgcccatgcactgcttttgtctgaccagcaatttctccatattgcttcttcagtagcaaggccaatcatttta
ccaacacacatgcttgctaactaacaggaataacgtggtacccctaattcagcccttttcccttgaaagcatctggcttct
gaggttcaactatgggaatatggtctcttaatgaacattaagttgagtttgccttttaggtccacatgttgacaaatgta
tcagagtaatctctgtcctaggatcagagggcctgtaggcacttgcaaaagcagttagctctgactcccagccagtgcac
actccacctttctgactcccagccttgtctcaaattaggcttggaagcgaggaactgtctggtgtccccagcataggaa
gctgagccaggggggcagtgctcacaaacaatacagactttaacgtgtaggatattggaaaataataatttgtggggaaat
tgtctcagacttggtccacccttattttttagctgcttctctaatccgttttctttttttggtgcttgtatctaacctac
ccatttttggtgcttgcatcattttttcaaatatcaaaaacgaacttatgtttctaacaatgaaagtattgcatgtt
cattgtggaaaatgctgaagacttggaaaatacaaaaatgctgagatcaaacactattgatacgttagtgtatttcttcc
tgtcctgttctactttctttctttgaattctgctcacgtgtttctgactgatgaggtctgactttgggttccttttcca
gaggagaagccttctttcagcttgccatttgttaccctggttatgaaggctggtaacctttttactaggtagagaagct

```
ggaccaactggggttcttccaggggggagaatgagaaagagaaactgttttgcaagtccgtagctatttctctagggccct
gttagctgacattgacatgccttgcattgctctgcagatccctcgcagccctctgtcccttgttcatttctggccttag
agaaagcaaagcagggtctgtaacaggggaggctgcctctaaactcagggtttggttacagctgttttcacttacatcac
tggccctggtttttttttttttctggcattaaaaaaaaaaattggaagcaggtgatgttcccattgctgatgtggtgga
aactctccaagtgaacaatatacgttttcttggcagctgtttcttgtgccctgcttgctcctggtccaggacaagcaag
gaccatctgcctcttcaatagaacacctccagatccctttgatcaaaagttactcattgtctgacttgctatttctgtg
agataaatgggagaagatcaataaatgcacttgtttgtccagtcagcgtgtggaaagttgataattttgaccaaagcaca
accctgaaggaaaagaaaagggagtgaatgtcttctgagaagctgcctaggttcagacagtgtcacccatttccctgt
atgctccacatgacaaacctgagtgggtctcatcatgtccatttgcagatggcaccaaggctcagaaaggttaggcaac
ttttccagtcacccaatgagttaattgacaaaactgggattcaaacccagaactgttggattccaaagcctgtgttgttg
cctgcttcgtgaaaaactccagtagcgactggaatagaaaggagaaccttccaagaaagaaaatacgcactagcagaacc
tggaaattgggaggaaatgaggacttgaggaataagatgaatgaaagctgacctgagtttcacatctgggtgatgggaag
ggaggacagggaggcagcatctcagatgtccacccagcaccgaccagctgcctggcattgctaggtgttgaggactcagc
agtgaacacgctaacttctctgctttcttggggcacgtatagggtgagagacagaaacaaacaggtcagtgtacaatgcc
acaggagggatatatgcagtgaagaaaaagcagggtaaggggcatagagcatgagaaggtgcttttttttaaaggggktga
ttaggaaagctctctctaaggtgacagttggacctgaaggagatgatagcatgtctgtggtgagggaaggaaactccgaa
caggaagaatggcagatacaaagacattgatgctagagcatgcctaaggaatgtgtttaaggaccagggaaagtgagcaa
gtggtgggggggaggagaggagctcagagcaggaggaggtgagtgccatacaggcctggcaagactttggattcctgctgg
gtgagatgagaatccagcggagggcttgagggagggggacatgatgtgatctagagtttagactgtttacactctggttgt
tgggttgagaagagactgggatggggggaaaggggaggacaaaggacattgtgctggattgagaaagcagtaagtcagtttc
attcattcactcaaccgatgatgttcaaataccaccatcatccgtgggctaaaggatgaagagccatccctccctgagag
tcaggaagcacttcccagataaagtttggagtgtgagctgaggtgtaggagaaagagtaagagtttacccctgaaacggg
tgctgggaagagtcaatagtttggaataactcaataatttatggtgcttctttagaaagatttgctggctttatgtggga
agaaatttktttttttgattggggagtggtgggttggtggtgaggctgcctgtggaaagagaagtgagtgttttgactca
ctgttatttaaaaatctctagggctgttccaataagcaacaaaaggcaaaatggcctggttctctgtcccctttctgtct
gtatgcctcgtacaggttatgaaaagaaaaagttgggaaaagctgtccacctcacctaattgtgttcttgtggagtgtgc
tagatgcccctctctggagaaaaaaaatccttgtggcctctgacccacctctggagagcctagttcccttctggaggca
gaaggcaaagcttaggacctagagagtgctggaccacgccactcacaggaaccagcaggctgtgaggttgaaagctaggc
atatggagctttccaggctgggtgcagggcctcgtggcccttcccctccctctgtgctctatagctcagtcttcccagg
cggtgtgaacacgcagtgacatttccaggaatacagggatttattaatgatttcttgtgaaatgtttggaaatacaaagt
actctataaatatttcataatagcattggggctgagaactccacaaagtgccggaatacatttgcatgtaagacagaacg
ctgcctgggtcattgatgcctgttgagtggcagtcacagacactgcctaggggtttctgactcacgctgttgggactgttc
tatgcagggcaccctcttgtgtggcataggatttgtgcctcaccacacactgttgtagctttgctgtcttgatgatgagt
agagggcagtgtccaggccatggtataagcatctactgccccccagggttaccaaaaccaagccaagttgtgtctcagcg
agctccgtgaagcatggagaagttgagtactcagagacatgacgtgacttttcaaaggctgtaagctgacgagggacata
gctagggttcagacttgagttttttcttttttcttttttcttttttttttaagactgagtcttgcttttgtcgccca
ggctggattgcagtggtgcttggctcactgcaacctctgcctcccgggttcaagcaattctcctgcctcagcctcccag
tagctgggattacaggcacctgccaccatgcctggccaacatttttgtatttttagtagagatggggtttcaccatgt
tggccaggctggtcttgaactcctgacctcaggtgatccacccgcctcgacctcccaaagtactgggattacaggtgtga
gccactgcacccggcccagactcgagttttcatcttaatgcttttcattgcctgacactttactgagaccaagatagg
gaacttcacatacagtaccttttctcccaaggcggaagagggctgttcaatttctacactagagttcggggagttttaga
aatgagtcagttatcgaggatgagagcagttcctgataggctcaaccacaatgagatgtagctgttcagagaaagcattc
ttttatctataaactggaagataatcccggtgaaacgaagcccagccccaggggcttcactaactccaggctgtgcttct
caaactttagtgagcataggaatcacctgggcatcttgtgaagctgtagatttgaattctgcaggtcggcagaggggtct
```

Figure 12G - (2)

```
cagaatccgcatttccaacaatgtctccagtaatgctgatgctgctcgtccctggaccacagattgggtagccaggttct
ggcaagctcatcccaaggctttgagatgacatcagacaaaatatgttctgggacatggcttttgagaggtcaagaaaata
agatgtttctttctcttctcatccccaacccttgcactgcccttttctcccttccccctaccctcctttctgtccccatcc
ctgacgccagCTGTTCAGCATGAGAAGCTGGAGTGACATGCGACAGGAGGTGATGTTTCTGACCAATGTGAACAGCTCCA
GCTCCTCCACCCAAATCTACCAGGCTGTGTCTCGTATTGTCTGCGGGCATCCCGAGGGAGGGGGGCTGAAGATCAAGTCT
CTCAACTGGTATGAGGACAACAACTACAAAGCCCTCTTTGGAGGCAATGGCACTGAGGAAGATGCTGAAACCTTCTATGA
CAACTCTACAAgtgagtgtccatgcagaccccagccctgtccccaacccccatccctcccttagttctggccttggcctgt
gtcatctcctccctctgtagcagcgttagatgtctacatgcccatttgcccaccagactgagctcttcctagaggagaga
ggcttctcttgaatagctacctgtccccagttctctgaatgcagcctggcacatctcaggtgcacagtagtgtttatcaa
tggaatgaatgattgacagccaaccttctggttttctgggggatgtggaagggtggcttccagggtgatcaagaatgaga
taatggcagaaggacaaatcctgcaagatctcacttatatatggaatatatgtaaggtagaaagtgtcagtttcacatga
tgaataagttcctgggatcttgatgtacatcgtgatgactatagttagtaacactgtatagtatacttgaaatttgctaa
gagagtagatccgaagtgttcacactacacaaaaaaggcaactatgaggtgatggatttattaacagcttgattgtggtg
atccttttacaaagtatacatatattaaaacatcacattgtataccttaaatatatacaatttttatttgtcagttgtaa
ctcaaaaaagctagaaaagcatttttaaaaaggatgatgtactggtcttaatattaccattgagataagctttataataa
cataaaaagaaataacagtaatgataatagcaacaacaacaacaacaaagaactaacatttaagtagaatttcttgtgca
ctgtgcattctgtttaagttatctcattttaccctcatgataacctgcagggaagattctttaaccccacatttcatagg
ctcagagaggttaagtgccttggttagagccacatcagagttaatccacaagagccaggattcaagcccaaatctgcctg
gatctgtgctctctaagataactgttagtggtggcgtgtgtgttctcacactcagacatttgatctgcccttttgtttccc
attcttagctgcaaggcagtgttaaagaaccctgtgtctccatatccactccccacacttaagcacttttgtgggcccgt
gtgccgtatgcctcgtggcagcagggatccaatgtcacagttttaggcagtggcatccttttccttgaaaacttgatgca
ggggaacctttctccatttccaaccacaggtgtgtctttcagacactgagtgaggcaggttttgtactttattgtaacac
aagaaccttttcttctctggagtaaagcactccagacattcgcaagttgctttacaagcctttaaaaggatggtattgtag
gcaactttaattaaatcccatctcctcctctcccccagcttgcaagttgacccaaggaagccttcatttccatgacagac
ttaattgtgagggcatcctca
```

Figure 12G - (3)

SEQ ID NO 21
Genomic contig containing ABC1 exon 9 through 22:
actgtgttagcaaggatggtctcgatctcctgacctcgtgatccgcctgtatcggcctcccaaagtgctgggattacagg
cgtgaaccactgcgccctgttgagaatttttttttttttttttgggagaaagagtttcgctcttgttgcccgggctagag
tgcagtgacacaatctcggctcactgcaacctctgcctcctgggttcaagcaattctcctgcctcagcctcatgcgtcac
cacgcccagctaattttgtattttagtagagacagggtttctccatgttggtcaggctggtctcgaactcccaacctca
ggtggtcgcccgccttggcctcccaaagtgctgggattgcaggcatgagccactgcgcccagccccaaattttggtttt
tgcttgaaaactgaggtctgaattcagccttctggttgcccctcaagagtcagtttaaatgttggtcatgttagttgtca
gtgaaaacaatggtgaggctggcatgagagtgtgaatctggatgggagggcttgtgcttcatgaaaacattttttccagat
cagctcagtcgtgagttatccgtcattgacgttataataagctctgattatttatcaagcatcattctttatagatatct
cagtttaatctgagataatcttctccacatctctccacatagatgttatgaattttacttttacagaggagccaactgag
gctcagataagttacttattatatgactagtagtggtagagctggggtttcaactaagaactctctggctccaaagccct
tgtaagtttctatcagtatatgaccatgcatatgagcatttgtctctcctcttcttcatagCTCCTTACTGCAATGATTT
GATGAAGAATTTGGAGTCTAGTCCTCTTTCCCGCATTATCTGGAAAGCTCTGAAGCCGCTGCTCGTTGGGAAGATCCTGT
ATACACCTGACACTCCAGCCACAAGGCAGGTCATGGCTGAGgtaagctgccccagcccaagactccctccccagaatct
ccccagaactgggggcaaaaaactcaaggtagcttcagaggtgtgcgctaagtatactcacggctcttctggaattccca
gagtgaaaacctcaagtctgatgcagaccagagctgggccagctcccagtcgtgggtatagaatcatagttacaagcag
gcatttcttggggatggggaggactggcacagggctgctgtgatggggtatcttttcagggaggagccaaacgctcattg
tctgtgcttctcctcctttttctgcggtccctggctccccacctgactccagGTGAACAAGACCTTCCAGGAACTGGCTG
TGTTCCATGATCTGGAAGGCATGTGGGAGGAACTCAGCCCCAAGATCTGGACCTTCATGGAGAACAGCCAAGAAATGGAC
CTTGTCCGGgtgagtgtccctcccattattaccatgtgcctgcttgatactggagaggtgagtttctggtcactttccca
ggtgtgagtgaggtgagaattctttcagtttatctagctgggggaatgtagtgagcatagctaaagtcacagggcaccac
ctctccagaagtacaggccatggtgcagagataacgctgtgcatatcagcatccatgccactcacggtcaaatagcagtt
ttctgcaaaacttagtgagggctggtgtttggaagtggagttgagtaattgcagtaccctatttttccttttttgctgcagc
ctctcagccagccacagcatctccctgtgtcttggtaggttttggaaagaagtgtgggagcaaaagcatgatgttacatg
tagactggcctgagatactcattctcagggcactgtgtgaatgatgagctgctgttactgtgtggagggggaaatgcactt
agtgcttcagagccacttgaaagggataagtgctctagagacaattgggttcaaatgtggagcaggctgagcaagaacag
aatgtctcctttgcctgagcctgagtgctgttaatcacatcttcctgccttgggctgagttagagaatcattagactatt
tcctgtttccatggtgagggaggcctcttcctttttgtctctgctcccttaagaagcaggtgaggattttgccaggtttc
ttgttttgaaccttattgactttaagggcggctgggttttagagactgtacctacctaggggggaacacttccgaagttta
ggactattccctgatccgctgggaggcaggttactgaggaagtccctttaaaaacaaaggagtttatactgagaaaagca
taaacagtgatttgtatggattcacactgactaatatagctcatgccattaaagtggggtctcttctctaaggagggtt
atatgatctagccccgtagacctaagtgtggtttcagacctgttcttcctggtcctctccttggaatccatatttctact
agttggacttttctgtttgtctggctctcagaggattataggaggccctgtgaagtgactcagtgaattttgatttgtg
ggcaagtagatggttccctagtctgaaattgactttgccttaggtgcttcaattcttcataagctcccagttcttaaagg
acaagatccttgtaaacatggcaatggcattcattaggaatctagctgggaaaatccagtgtgtatgcttggaaatgagg
gatctggggctggagagaaaggcatgggcatgccttggagggacttgtgtgtcaagctgaggacctttactttaagctct
aggggaccaggcaaggggagatgtagatacgttactctgatggggtggatgaattgaagaaggatgaggcaagaatgaag
gcagagaccagggaggaggctctccaagtggccaaggcataaagcaagaaatgaggcctggtgactgcttagtggcagag
cagtgaaagagagggaggcatcaaagtgagtctcgatttctagctgggtgggtggtagcgatgtccagtaggccagtggc
tactgaggtctgcagtggaggagggtggttgggctggagacagatgatgagggagtcatcagcctgtgggtggaagaaaa
gggaacctcttccaactgttttctttgcttcttccctctctttctcttttttttttttttttggacagagtcttgctctgt
cacccaggctgaaatgcagtggcatgatcttggctcaccacagcctccgcctcctgggttcaagcaattctcctgtctca
gcctccagagtagctgggattacaggcacatatcactgtgcccggctaattttgtatttttcagtggagatgggatttca
ccatgttggtcgggctggaatgaactcctgacctcaagtgatccacctgcctcagcctcccaaagtgttgggattacagg
catgagccaccgcgcccggcctttcttccctctcttaaagagtgtttatttaattccacaaacatgagcttgtcacccc
tgtagcctggcatctcctacacgaggtgatggctgaggcttctgcttctgctggggtagctctgatcttctgctttctc

Figure 12H - (1)

```
tggcactgtctacccatgttgcctcaccccacaggtcccagggcacctctctcgggcaagtcttggaaccctctgacact
gatttgctctcttttctgagctgcttttagccacccatcctcgggacctgttttctctctgcctccacccctgcgggcag
tcttaggtctcctgcccctcacgagcaccccagagaggccacgtgctcagtgatctcagtgggcgcatctttctagtctt
gctattcttttggccatgttgttcagaaaccatactgggcagggccgacttcaccctaaaggctgcgtctcttcactct
gctttgtttgttccaaataaagtggcttcagaattgctaacctagcctctgtgaacttgtgaggtacaatttgtgtc
tgttatgttaacaaaaatacatacataccttcctggtgatggtataaattgctattctctattggaaagcaatttggaat
gaaaatttaaagaaccatttaaaatatgctatcctgcgtacctccattccacccaccccagggatgtagcctactgaa
ataattttaaagaagtcaccatatgagagaaatgttattgctatattgttattgtgagaaattggaaatagactaaatg
ttcagcactataggaataattaatgaaattacatatactctatacaatcattatgctgccattgaaataataaatacaaa
ggcgcaaggggggaaaagcttataatgttagtgaaactaagactgattttttataaagcagcagttttcagacccttgg
agactccaattcggtagaaccagagcttcatcttctctgtcgaagctgtgacaggagttgcaaatgcctctccttttgc
tgagtttgcagctgctgtttttccggcagcacatctgtgcaggcctctgcctcggcccctctggatctgctgattgagca
gcggattgatctgtccttctctttcgtgttgacccatgtgaggaaccaactggcaagggaacaagaaatggaaataggcc
tcctttgcatcatgacctgtacatcctgcaattggaaaagattgtactttagttggtttaaccagcagcattatttttct
aaactaagcagtaagaaggaattaggttttatgtgggatcaacagactgggtctcaaaagaggaaggtgatagaacacag
tggggaggggggaggtgcactagaaacagagggcctatgctttcattctggctttgctacttaatagctgtgtgacccaat
cttagagacttaacctctctgaacttccatttctcatgtataaaatgggaaatattaaaggatactcactgggctggtg
gcttgtgcctgtaatcccagcacttggggaggttgaggtgggaggatcacttgagcccaggtgttcaagaccagcccagg
caacatggcaagactctgtctctatgaaaaaattaaaaattagccaggtgtggtggtgtgcacctgtagtcttagctact
tggtaggctgagatggaggatcacttgggcttgggaggtcaaggctgcggtgagctgtgattccatcactgcactccag
cccgggcggcagagcgagacactgaatccaaacgacaacaacaacaaaggcaaaaaataaaagtgccctctttatgga
gttgtgtaaggtgaagcatatacactattcaacatagtaactatataaggaagtattgttgttgttactgtagttaata
ccattaagtgagatgtttcgtatagtggaaagcacatggactctgaattcagactggtctgactttgagtctcagctcca
catctagtaatactatgaccaagccctggttaaaatcatgttttttttcttcagcctcagtcttctcacatataaaata
gggacactgtcatttacctcagttttctgtgaggataaaacaacgacagtgtatatgcaagtatttgtaaatttgtag
tgctcctcaagatttagttggtgtttactacttgtactttctcactggaatggcagATGCTGTTGGACAGCAGGGACAAT
GACCACTTTTGGGAACAGCAGTTGGATGGCTTAGATTGGACAGCCCAAGACATCGTGGCGTTTTTGGCCAAGCACCCAGA
GGATGTCCAGTCCAGTAATGGTTCTGTGTACACCTGGAGAGAAGCTTTCAACGAGACTAACCAGGCAATCCGGACCATAT
CTCGCTTCATGGAGgtgaatctgttgctgggatcatttagaaaagacttaacggcttctttctctgagacgttacaataa
ggttcaggcaggaggcaagtttagaaataatgtatagtctcatttacaaaactatccctcaagcctaacacaggatttga
taacaaaaggcacttaataaatgttagttgagtggttgaatgagtaaataaactctagctttagtaaattaactctagct
tattctatataggctcaagagaatatttctacccattttcttctaggttttcctatctcagtgactaatggtagcaaagc
attcccttaaaaaggcattatttgtgaaacttayctaaaatcgaattcgggtccaattaaattttgaaattttatatta
aaaattatattagtagggatgggtaagaggtgttttggtctggttggttggttagttgctatgactcagaattgctaaga
aaacagaaaagtaagataagatcattgttttaacctcttttcctccacaaaatcaataaataacatatccctaaattact
cttagaatttctcttaaattgcagtgaaaaaccaaaatccttcattcttggttgaaggttggaaaactacgttagagagg
attagagagagaggatgagcaatcgtgtagtcagcccttgcctcctagtgtaggatttgtctcagccactgcttgttgtc
ctggctgccaacgttctcatgaaggctgttcttctatcagTGTGTCAACCTGAACAAGCTAGAACCCATAGCAACAGAAG
TCTGGCTCATCAACAAGTCCATGGAGCTGCTGGATGAGAGGAAGTTCTGGGCTGGTATTGTGTTCACTGGAATTACTCCM
RGCAGCATTGAGCTGCCCCATCATGTCAAGTACAAGATCCGAATGGACATTGACAATGTGGAGAGGACAAATAAAATCAA
GGATGGgtaagtggaatcccatcacaccagcctggtcttggggaggtccagagcacctattatattaggacaagaggtac
tttatttaactaaaaatttggtagaaatttcaacaacaacaaaaaaactcaacttggtgtcatgatttggtgaaattg
gtacatgacttgctggaaggttttcataggtcataaaataacagtatcttttgatttagcatttctactcaagggaatt
aattccaggaatttggtggcaggcacctgtaatcccagctactcgggaggctgaggcaggagaattgcttgaacccagg
aggcagaggttgcagtgagctaagatcgcatcattgcactccgcctgggcaataagagtgaaactccatctcaaaaaaa
```

Figure 12H - (2)

```
aaaaaagatacaaaaatagaaaaaggggcttggtaagggtagtagggttttgggcaatttttttttttttttttttttttt
attgtatggttctaaaggaatggttgattacctgtggtttggttttagGTACTGGGACCCTGGTCCTCGAGCTGACCCCT
TTGAGGACATGCGGTACGTCTGGGGGGGCTTCGCCTACTTGCAGGATGTGGTGGAGCAGGCAATCATCAGGGTGCTGACG
GGCACCGAGAAGAAAACTGGTGTCTATATGCAACAGATGCCCTATCCCTGTTACGTTGATGACATgtaagttacctgcaa
gccactgttttaaccagtttatactgtgccagatgggggtgtatatatgtgtgtgcatgtgcatgcatgtgtgaatgat
ctggaaataagatgccagatgtaagttgtcaacagttgcagccacatgacagacatagatatatgtgcacacactagtaa
acctctttccttctcatccatggttgccacttttatcttttttattttttttttttttgagatggagtctcgctctga
cgcccaggctggagtgcagtggctcgatctcggctcactgcaacctttgcctcccgggttcaagctattcctgcctca
gcctccacagtagctgggactacaggctcatgctgccacgcccggctgacttttgtatttagtagagacgaggtttca
ccatgttacccaggctagacttcaactcctgagctcaggcaatccaccctccttggcctcccaaagtgctgggattacag
gtgtgagccactgcacccagcccaccactttaatttttttacactctaccctttggtcaaaatttgctcaatctgcaagc
ttaaaatgtgtcatgacaaacacatgcaagcacatactcacacatagatgcagaaacagcgtctaaacttataaaagcac
agtttatgtaaatgtgtgcacttcttctccctaggtggtaaaccacatttcaaaacaacccaaataaaactgaacaaagc
ttcttcctcttagacttttagaaaatctttcagtgctgagtcactaagctgccaagttctcattgtgggaactatgcct
ttggatgtaatgatttcttctaagacaatgggcggaggtgtagttattgcagacatctgaaatatgtaatgtttcttcca
gattctggaaattctcttattctctgtggttggtggtggtggtgggatgtgtgtgtgtgtgtgtgtgtgtgtgtgtgtgt
gtgtgtagggatcaggatgcgggaggagctgggttctgcttgtattggttctctgttttgcattgaatagtgtgtttcct
tgtatggctatctatagcttttcaaggtcaccagaaattatcctgttttcaccttctaaacaattagctggaattttc
aaaggaagacttttacaaagaccctaagctaaggtttactctagaaaggatgtcttaagacagggcacaggagttcaga
ggcattaagagctggtgcctgttgtcatgtagtgagtatgtgcctacatggtaaagctttgacgtgaacctcaagttcag
ggtccaaaatctgtgtgccttttactttgcacatctgcatttctattctagcttggaatctgaaacattgacaagagc
tgcctgaaatgtatgtctgtggtgtgattagagttacgataagcaagtcaatagtgagatgaccttggagatgttgaact
tttgtgagagaatgagttgtttttttgttttggttttagtacttaacataatctacctttagtttaagtatcgctcac
agttacctagttactgaagcaagcccccaaagaaatttggtttggcaacactttgttagcctcgttttctctctacatt
gcattgctcgtgaagcattggatcatacgtacatttcagagtctagagggcctgtccttctgtggcccagatgtggtgct
ccctctagcatgcaggctcagaggccttggcccatcaccctggctcacgtgtgtctttctttctccccttgtccttcctt
ggggcctccagCTTTCTGCGGGTGATGAGCCGGTCAATGCCCCTCTTCATGACGCTGGCCTGGATTTACTCAGTGGCTGT
GATCATCAAGGGCATCGTGTATGAGAAGGAGGCACGGCTGAAAGAGACCATGCGGATCATGGGCCTGGACAACAGCATCC
TCTGGTTTAGCTGGTTCATTAGTAGCCTCATTCCTCTTCTTGTGAGCGCTGGCCTGCTAGTGGTCATCCTGAAGgtaagg
cagcctcactcgctcttccctgccaggaaactccgaaatagctcaacacgggctaagggaggagaagaagaaaaaaaatc
caagcctctggtagagaaggggtcatacctgtcatttcctgcaatttcatccatttatagttggggaaagtgaggcccag
agaggggcagtgacttgcccaaggtcaacccagccgggtagcagctaagtaggatgagagtgcagggttcatgctttcca
gataaccacatgctcaactgtgccatgctgtctcattggtagtggttcatggcagcatctgaaagctatttatttctta
gatatattgggtggcgattcttcctaagtttctaagaacaataatcagaaggatatatattgttgcaggttagactgtct
ggaagcagaggctgaaatagagtttgatgtatgggtatttatgagggctcaataccctatggaagagatatggaagatgca
ggattgggcagagggaggagttgaactgtgatatagggccaaccccgtggggcactctagagaatatgcagcttgttgga
gttgttcttcatcgagctgaaacatccagcccttgtgctccccaaggcctccctcctgacaccacctacctcagccct
ctcaatcaatcactggatgtgggctgccctgggaaggtcgtgccccagggcctacatggctctctgctgctgtgacaaac
ccagagttgctgatgcctgaggccgtctactgacagctgggcaacaaggcttccctgaatggggactctgggcagtgcag
ttttgtgtctgaaccatacattaatatatttatatccgaattttctttctgcaagcatttcatataaagacacatcag
gtaaaaataaatgttttgaagcaaaaggagtacaaagagataagaactaactaatttaatactagttaccatctgttac
aaatagttcctactgattgccaaggactgtttaaacacatcacatgggcttcttcttctatcctcactaacccttttaac
agacaaggaaatgaggctcaggaaggtcaaggactttattgaggttccacagtaggatacagttcttgctaaaagcaacc
cctcccctcatgctctgttatctaactgcaaggggaaggtcagtggcagaggtagtggtcccatggttggtgcataagagc
tgctctgagacaactgcatgctggtgggtcctgcagacatgtacccatcagccggagataggctcaaaatatccacaaga
```

Figure 12H - (3)

```
gtttggatgattgtgggaatgcagaatccatggtgatcaagagggaaagtcaagttgcctggccatttccttggctttt
agacagaaaagttacgtgggatattatctcccacagctcttctgtggtgccaccagtcatagtccttatataaggagaaa
ccagttgaaattacctattgaagaaacaaagagcaaactcgcccactgaaatgcgtagaaagccctggactctgttgtat
tcataactctgccattattttctgcgtagttttgggtaagtcacttatcttctttaggatggtaatgatcagttgcctc
atcagaaagatgaacagcattacgcctctgcattgtctctaacatgagtaggaataaaccctgtctttttctgtagatc
atacaagtgagtgcttgggattgttgaggcagcacatttgatgtgtctcttccttcccagTTAGGAAACCTGCTGCCCTA
CAGTGATCCCAGCGTGGTGTTTGTCTTCCTGTCCGTGTTTGCTGTGGTGACAATCCTGCAGTGCTTCCTGATTAGCACAC
TCTTCTCCAGAGCCAACCTGGCAGCAGCCTGTGGGGCATCATCTACTTCACGCTGTACCTGCCCTACGTCCTGTGTGTG
GCATGGCAGGACTACGTGGGCTTCACACTCAAGATCTTCGCTgtgagtacctctggcctttcttcagtggctgtaggcat
ttgaccttcctttggagtccctgaataaaagcagcaagttgagaacagaagatgattgtcttttccaatgggacatgaac
cttagctctagattctaagctctttaagggtaagggcaagcattgtgttttattaaattgtttacctttagtcttctcag
tgaatcctggttgaattgaattgaatggaatttttccgagagccagactgcatcttgaactgggctggggataaatggca
ttgaggaatggcttcaggcaacagatgccatctctgccctttatctcccagctctgttggctatgttaagctcatgacaa
accaaggccacaaatagaactgaaaactcttgatgtcagagatgacctctcttgtcttccttgtgtccagtatggtgttt
tgcttgagtaatgttttctgaactaagcacaactgaggagcaggtgcctcatcccacaaattcctgacttggacacttcc
ttccctcgtacagagcaggggatatcttggagagtgtgtgagcccctacaagtgcaagttgtcagatgtccccaggtca
cttatcaggaaagctaagagtgactcataggatgctcctgttgcctcagtctgggcttcataggcatcagcagccccaaa
caggcacctctgatcctgagccatccttggctgagcagggagcctcagaagactgtgggtatgcgcatgtgtgtggggga
acaggattgctgagccttggggcatctttggaaacataaagttttaaaagttttatgcttcactgtatatgcatttctga
aatgtttgtatataatgagtggttacaaatggaatcattttatatgttacttggtagcccaccactccctaaagggactc
tataggtaaatactacttctgcaccttatgattgatccattttgcaaattcaaatttctccaggtataatttacactaga
agagatagaaaatgagactgaccaggaaatggataggtgactttgcctgtttctcacagAGCCTGCTGTCTCCTGTGGC
TTTTGGGTTTGGCTGTGAGTACTTTGCCCTTTTTGAGGAGCAGGGCATTGGAGTGCAGTGGGACAACCTGTTTGAGAGTC
CTGTGGAGGAAGATGGCTTCAATCTCACCACTTCGGTCTCCATGATGCTGTTTGACACCTTCCTCTATGGGGTGATGACC
TGGTACATTGAGGCTGTCTTTCCAGtacactgctttgggcatctgtttggaaaatatgacttctagctgatgtcctttc
tttgtgctagaatctctgcagtgcatgggcttccctgggaagtggtttgggctatagatctatagtaaacagatagtcca
aggacaggcagctgatgctgaaagtacaattgtcactacttgtacagcacttgttcttgaaaactgtgtgccaggcagc
atgcaaaatgttttatacacattgcttcatttaattctcacaaggctactctgaagtagttactataataaccagcaatt
ttcaaatgagagaactgtgactcaaagacgttaagtaaccagctttggtcacacaactgttaaatgttggtacgtggagg
tgaatccacttcggttacactgggtcaataagcccaggcgaatcctcccaatgctcacccaattctgtatttctgtgtcc
tcagaggggtacaactaggagaggttctgtttcctgagtacaggttgttaataattaaatatactagctctaaggcctg
cctgtgatttaattagcattcaataaaaattcatgttgaattttctttagtacttctttcttaatataatacatcttct
tgaccaagtccaagaggaacctgcgttggacagttttcatatgagatcaaattctgagagagcaagatttaaccctttt
ggttcaccttctgatcctcccctaaggaggtatacatgaaatatttattactcctgcctgaacttctttcattgaatatg
caattttgcagcatgcagattctggatttaaattctgagtcttaacttactggctgagggaccttggataggctccttat
ccctcagtttcctcatctctaaaatggggatggcacctgccccgtgggttgttggaaggacttacagaggtgcagaatgt
acgttgtacatagcaggtttcagcaaatgttagctccctcttccccacatccattcaaatctgttccttctccaaagga
tgtgtcaaggaggaaatggacctggctgggaaaccctcagaatactgggatgatgctgagcttggctcatacctgtgctt
tgctttcagGCCAGTACGGAATTCCCAGGCCCTGGTATTTTCCTTGCACCAAGTCCTACTGGTTTGGCGAGGAAAGTGAT
GAGAAGAGCCACCCTGGTTCCAACCAGAAGAGAATGTCAGAAAgtaagtgctgttgacctcctgctctttcttaaccta
gtgctgctgcctctgctaactgttggggcaagcgatgtctcctgcctttctaaaagactgtgaaaccactccaggggca
gagaaatcacatgcagtgtcccttccaaatcctcccatgccatttatgtccaatgctgttgacctattgggagttcacg
gtctcgatccctgagggacattttctttgttgtcttggcttctagaagagtatcttttacttgccccctcccaaacacac
atttcatggtctcctaacaagctagaagaaagaggtaaagacaagcgtgattgtggaaccatagcctcgctgcctgcctg
tgacatggtgacctgtgtatcagcctgtgtgggctgagaccaagtggctaccacagagctcagcctatgcttcataatgt
```

Figure 12H - (4)

```
aatcattacccagatccctaatcctctcttggctcttaactgcagacagagatgtccacagctcatcaaaggctctgctt
ctggggttcttgtgcttagagtggcttcctaaatatttaataggtccctttctgccagtctcttctgtgcccatcccct
gattgcccttggtaaaagtatgatgcccccttagtgtagcacgcttgcctgctgttcctaatcatcttctcctacctcctc
tttacacctagctcctgtttcagtcacctagaaatgctcacagtcgctggaatatgtcatgttcttccacacctccatgc
ctttgtaggtactgtttgctctcacaggagaactttctctctaacttgcctatcttctcaactcctcctttctctccaag
atctagttccggatcccctcccctgagcatccctccttggttctcaggtagtcagtcactctctgccctgaacttccatg
gcacgtgaaagaaaatcttttatttttaaaacaattacagactcacaagaagtaatacaaattacatgaggggggttccct
taaaacctttcatccagtttccccaatggtagcagcatgtgtaactgtagaatagtatcaaaaccatgaaattgacatagg
tacaattcacaaaccttcttcagatttcactagctttatgtgcgctcatttgtgtgtgtgtgcgtatttagttctatg
caatttatcatgtgtgaattcatgtaattactagctcagtcaagctgcagaaatatctcattgtcacaaagctccttca
tgctacccttaatggccacagccacctcccttcttcctcagttcctgacacctgtcaaccactaatgcgttcctcgttt
ttacagttttattatttctagaatgttacataaatggaaccatacagtaggtatccttttgatactggcttttttttttt
tttcactcagcagtattcccttagatctatccaagttgtgtgtgtcaacagttcattcctcttcactgctgagtagtgtt
ccctggggaggggtgtatcacagttccatggcattttttagatgtatttttttaaacagctttcagcatcctctatttaatt
gttcatcaagtccttttttcccaatagactctgaatgctcctttatcatcgtattcccatcaccaacatcagtacccaaat
aggccctaaataaacatttatagcctcctgcctgcctgagaaaccagggtggacatggagagaaggcacttctgaaagtt
caagcgcagtgcsctgtgtccttacactccactcctcagtgctttctgtgggttcatttctgtcttctctcctgtcacag
TCTGCATGGAGGAGGAACCCACCCACTTGAAGCTGGGCGTGTCCATTCAGAACCTGGTAAAAGTCTACCGAGATGGGATG
AAGGTGGCTGTCGATGCCTGGCACTGAATTTTTATGAGGGCCAGATCACCTCCTTCCTGGGCCACAATGGAGCGGGGAA
GACGACCACCATgtaagaagagggtgtggttcccgcagaatcagccacaggagggttctgcagtagagttagaaatttat
accttaggaaaccatgctgatccctgggccaagggaaggagcacatgaggagttgccgaatgtgaacatgttatctaatc
atgagtgtctttccacgtgctagtttgctagatgttatttcttcagcctaaaacaagctggggcctcagatgacctttcc
catgtagttcacagaattctgcagtggtcttggaacctgcagccacgaaaagatagattacatatgttggagggagttgg
taattcccaggaactctgtctctaagcagatgtgagaagcacctgtgagacgcaatcaagctgggcagctggcttgattg
ccttccctgcgacctcaaggaccttacagtgggtagtatcaggaggggtcaggggctgtaaagcaccagcgttagcctca
gtggcttccagcacgattcctcaaccattctaaccattccaaagggtatatctttgggggggtgacattcttttcctgttt
tcttttttaatctttttttaaaacatagaattaatatattatgagcttttcagaagatttttaaaaggcagtcagaaatcc
tactacctaacacaaaaattgttttttatctttgaataatatgttcttgtttgtccattttccatgcatgcgatgttaggc
atacaaaatacatttttttaaagaatactttcattgcaaattggaaacttcgtttaaaaaatgctcatactaaaattggca
tttctaacccataggcccacttgtagttatttaccgaagcaaaaggacagctttgctttgtgtgggtctggtagggttca
ttagaaaggaatgggggcggtgggagggttggtgttctgttctctctgcagactgaatggagcatctagagttaagggta
ggtcaaccctgacttctgtacttctaaatttttgtcctcagGTCAATCCTGACCGGGTTGTTCCCCCCGACCTCGGGCAC
CGCCTACATCCTGGGAAAAGACATTCGCTCTGAGATGAGCACCATCCGGCAGAACCTGGGGGTCTGTCCCCAGCATAACG
TGCTGTTTGACATgtgagtaccagcagcacgttaagaataggccttttctggatgtgtgtgtgtcatgccatcatgggag
gagtgggacttaagcatttttactttgctgtgttttttgttttttcttttttttcttttttattttttttgagatggagtctcg
ctctgtagccaggctggactgtagtggcgcgatctcggctcactgcaaccttggcctcccaggttcaagcgattctcctg
cctcagcctcccgagtagctgggactctaggcacacaccaccatgcccagctaattttttgtgtttttagtagagacgggg
tttcaccatgttggccaggatggtctcaatgtcttgacctcgtgatccgcccacctcggtctcccaaagtgctgggaaca
caggcatgagccactgtgtctggccacattttactttctttgaatatggcaggctcacctccgtgaacaccttgagacct
agttgttctttgattttaggagaagtgggaggtgaatggttgagctgtagaggtgacatcagcccagccagtggatgggg
gcttgggaaacattgcttcccattattgtcatgctggagggcctttagcccatcctctcccccgccaccctccttatt
gaggcctggagcagacttcccagacctggtagtgcttcagggcctggtatgatggacctatattgctgcttaagacat
ttgctcccactcaggttgtcccatcagccataaggcccccagggagcccgtgtgatggagcagagagagacctgagctct
gcaatcttgggcaaggcttttcccttatgtttcttcttatctaaagtgaacagctggggctcatgtgctccctcctcatc
taaagtgaacacatggggctcatgtgcagggtcctccccgctttcagagcctgaggtcccctgaggctcaggaaggctgc
```

Figure 12H - (5)

```
tccaggtgagtgccgagctgacttcttggtggacgtgctgtggggacagcccattaaagaccacatcttggggccctgaa
attgaaagttgtaactgcctggtgcatggtggccaggcctgctggaaacaggttggaagcgatctgtcacctttcacttt
gatttcctgagcagctcatgtggttgctcactgttgttctaccttgaatcttgaagattattttcagaaattgataaag
ttattttaaaaagcacggggagagaaaaatatgcccattctcatctgttctgggccaggggacactgtattctggggtat
ccagtagggcccagagctgacctgcctccctgtccccagGCTGACTGTCGAAGAACACATCTGGTTCTATGCCCGCTTGA
AAGGGCTCTCTGAGAAGCACGTGAAGGCGGAGATGGAGCAGATGGCCCTGGATGTTGGTTTGCCATCAAGCAAGCTGAAA
AGCAAAACAAGCCAGCTGTCAGgtgcggcccagagctaccttccctatccctctccctcctcctccggctacacacatg
cggaggaaaatcagcactgccccagggtcccaggctgggtgcggttggtaacagaaacttgtccctggctgtgcccctag
gtcctctgccttcactcactgtctgggctggtcctggagtttgtcttgctctgttttttgtagGTGGAATGCAGAGAA
AGCTATCTGTGGCCTTGGCCTTTGTCGGGGATCTAAGGTTGTCATTCTGGATGAACCCACAGCTGGTGTGGACCCTTAC
TCCCGCAGGGGAATATGGGAGCTGCTGCTGAAATACCGACAAGgtgcctgatgtgtatttattctgagtaaatggactga
gagagagcggggggcttttgagaagtgtggctgtatctcatggctaggcttctgtgaagccatgggatactcttctgtta
kcacagaagagataaagggcattgagactgagattcctgagaggagatgctgtgtctttattcatctttttgtccccaac
atggtgcactaaatttatggttagttgaaagggtggatgcttaaatgaatggaagcggagaggggcaggaagacgattgg
gctctctggttagagatctgatgtggtacagtatgaggagcacaggcaggcttggagccaactctggcttggccctgaga
cattgggaaagtcacaacttgcctcaccttctttgccgataataatagtggtgcgttacctcatagaggattaaattaaa
tgagaatgcacacaaaccacctagcacaatgcctggcatatagcaagttcccaaataaaatgcgtactgttcttacctct
gtgaggatgtggtacctatatatacaaagctttgccattctaggggtcatagccatacagggtgaaaggtggcttccagg
tctcttccagtgcttaccccctgctaatatctctctagtccctgtcactgtgacaaatcagaactgagaggcctcacctgt
cccacatccttgtgtttgtgcctggcagGCCGCACCATTATTCTCTCTACACACCACATGGATGAAGCGGACGTCCTGGG
GGACAGGATTGCCATCATCTCCCATGGGAAGCTGTGCTGTGTGGGCTCCTCCCTGTTTCTGAAGAACCAGCTGGGAACAG
GCTACTACCTGACCTTGGTCAAGAAAGATGTGGAATCCTCCCTCAGTTCCTGCAGAAACAGTAGTAGCACTGTGTCATAC
CTGAAAAAGgtgagctgcagtcttggagctgggctggtgttgggtctgggcagccaggacttgctggctgtgaatgattt
ctccatctccaccccttttgccatgttgaaaccaccatctccctgctctgttgccccctttgaaatcatatcatacttaag
gcatggaaagctaaggggccctctgctcccattgtgctagttctgttgaatcccgttttccttttcctatgaggcacana
gagtgatggagaaggtccttagaggacattattatgtcaaagaaaagagacttgtcaagaggtaagagccttggctacaa
atgacctggtcgttcctgctcattacttttcaatctcattgaccttaacttttaaactataaaacagccaatatttatta
ggcactgatttcatgccagagacactctgggcattgaaagaaagtaatgataatagttaattttatatagcgttgttacc
atttcaacctttttttttttttaacctctatcatctcaattaaag
```

Figure 12H - (6)

SEQ ID NO: 22
Genomic contig containing ABC1 exon 23 to 28:

gtgaacacacattaaagcatgagaagcatgaactagacatgtagccaggtaaaggccttgctgagatggttggcaaaggc
ctcattgcagcattcattggcaggccacagttcttttggcagctctgcttcctgacctttcaccctcaggaagcgaggct
gttcacacggcacacacatgccagacagggtcctctgaagccacggctgccagtgcatgtgtcccagggaaagcttttc
ctttagttctcacacaacagagcttcttggaagccctccccggcgaaggtgctggtggctctgccttgctccgtccctga
cccgttctcacctccttctttgccatcagGAGGACAGTGTTTCTCAGAGCAGTTCTGATGCTGGCCTGGGCAGCGACCAT
GAGAGTGACACGCTGACCATCGgtaaggactctggggtttcttattcaggtggtgcctgagcttcccccagctgggcaga
gtggaggcagaggaggagaggtgcagaggctggtggcgctgactcaaggtttgctgctgggctggggctgggtggctgcg
ggggtgggagcagcttggtggcgggttggcctaatgcttgctggggtgcctggggctcggtttgggagctagcagggcag
tgtcccagagagctgagatgattggggtttggggaatcccttaggggagtggacactgaataccagggatgaggagctga
gggccaagccaggagggtgggatttgagcttagtacataagaagagtgagagcccaggagatgaggaacagccttccaga
ttttcttgggtagcgtgtgtaggaggccagtgtcaccagtagcatatgtggaacagaagtcttgacccttgctatctct
gcctagtcctaatggctggcttttcccaggaaggcttctgcttccatggactgttagattaacccttatttaggtaaat
gagggaacctactttataagcataggaaagggtgaagaatcttttaagattcctttactcaagttttcttttgaagaatc
ccagagcttaggcaatagacaccagactttgagcctcagttatccattcacccatccacccacccacccacccatccttc
catcctcccatcctcccattcacccatccacccatccagctgtccacccattctacactgagtacctataatgtgcctgg
ctttggtgatacaaaggtgaataagacatagtcctttccttttgcccccaaccctcagaccagagatgaacatgtggaatg
acctaaacacctggaacaggtgtggtgtatgagcggcaggcctctgatgagagggtgggggatggccagccctcactccg
aagcccctctgagttgattgagccatctttgcattctggtcctgcagATGTCTCTGCTATCTCCAACCTCATCAGGAAGC
ATGTGTCTGAAGCCCGGCTGGTGGAAGACATAGGGCATGAGCTGACCTATGTGCTGCCATATGAAGCTGCTAAGGAGGGA
GCCTTTGTGGAACTCTTTCATGAGATTGATGACCGGCTCTCAGACCTGGGCATTTCTAGTTATGGCATCTCAGAGACGAC
CCTGGAAGAAgtaagttaagtggctgactgtcggaatatatagcaaggccaaatgtcctaaggccagaccagtagcctgc
attgggagcaggattatcatggagttagtcattgagttttaggtcatcgacatctgattaatgttggccccagtgagcc
atttaagatggtagtgggagatagcaggaaagaagtgttttcctctgtaccacagtacatgcctgagatttgtgtgttga
aaccagtggtacctaacacatttacatcccaaccttaaactcctatgcacttatttacccttaatgagcctcttactt
aagtacagtgkgaggaacagcggcatcaggatcacttgggaacttgttagaaattcagcaacttgggcccagctcagacc
tactgaatcagaatcaggagcaattctctggtgtgactgtgtcacagccaggtatcaactggattctcatacataggaaa
tgacaaacgtttatggatggatagtctacttgtgccaggtgctgagatttgtttttttgtttttgatttttttttaatca
ctgtgacctcatttaattctcaaaaaaagatgaaaaaatgaacactcaggaatgctgacatgagattcagaatcaggggt
ttgggcttcaaagtccatcctctctttatccatgtaatgcctcccttagagatacaacatcacagaccttgaaggctg
aaggggatataaaagctgtctggccaagtggtctccaagcttgacagtgcagcagaatcacctggggatattattaaaaa
taaacatactaaggtttggcttcagggcctgtgaatcagaatttctggaggtgaggccttgaagtctgtatttctattgc
atactttggacacagtggtctatagactagagtttggaaatgattgcgctcattcagattctcttctgatgtttgaattg
ctgccatcatatttctagtgctctatttcctcctgctcattctgtcttggataacttatcatagtactagcctactcaaa
gatttagagccacagtcctgaaagaagccacttgactcattccctgtaggttcagaataaatttcttctgcgcagtgtct
gtcatagcttttttaaattttttttttatttttgatgagactggagttttgctcttattgcccaagctggagtgcagtgg
tgcgatttggctcactgcaacctccacctcccaggttcaagcgattctcctgcctcagcctcccaagtagctgagatta
caagcatgtgctaccacgcccagctaattttgtatttttagtagagatgggttttatccatgttggtcaggctggtctcg
agctccagacctcaggtgatctgcccgcctcggcctcccaaagtgctgggattataggcctgagccacagcgctcagcca
taactttaatttgaaaatgattgtctagcttgatagctctcaccactgaggaaatgttctctggcaaaaacggcttctct
cccaggtaactctgagaaagtgttattaagaaatgtggcttctactttctctgtcttacggggctaacatgccactcagt
aatataataatcgtggcagtggtgactactctcgtaatgttggtgcttataatgttctcatctctctcatttccagATA
TTCCTCAAGGTGGCCGAAGAGAGTGGGGTGGATGCTGAGACCTCAGgtaactgccttgagggagaatggcacacttaaga
tagtgccttctgctggctttctcagtgcacgagtattgttcctttcccttgaattgttctattgcattctcatttgtag
agtgtaggtttgttgcagatggggaaggtttgttttgttgtaaataaaataaagtatgggattcttttccttgtgccttca

Figure 12 I - (1)

```
gATGGTACCTTGCCAGCAAGACGAAACAGGCGGGCCTTCGGGACAAGCAGAGCTGTCTTCGCCCGTTCACTGAAGATGA
TGCTGCTGATCCAAATGATTCTGACATAGACCCAGgtctgttagggcaagatcaaacagtgtcctactgtttgaatgtga
aattctctctcatgctctcacctgttttctttggatggcctttagccaaggtgatagatccctacagagtccaaagagaa
gtgaggaaatggtaaaagccacttgttctttgcagcatcgtgcatgtgatcaaacctgaaagagcctatccatatcactt
cctttaaagacataaagatggtgcctcaatcctctgaacccatgtatttattatcttttctgcggggtcctagtttcttg
tatacattaggtgtttaattgttgaacaaatattcattcgagtagatgagtgattttgaaagagtcagaaaggggaattt
gctgttagagttaattgtaccctaagacttagatatttgaggctgggcatggtggctcatgccagtaatcccagcgcttt
gagaggctgaggtgggtagatcacctgaggtcaggagtttgagaccagtctgaccaacaaggtgaaacccgtctctact
aaatacaaaaaattagccgagtgtggtggcacatgcctgtcatcccagctacttgggaggctgaggcaggagaatcgctt
gaacccaggaggcagaggttgcagtcagccacggttgcgccattgcactccagactgggcaacaagagtgaaaactccat
ctcaaaaagaaaaaaaagaattagatattttggatgagtgtgtctttgtgtgtttaactgagatggagaggagagcta
agacatcaaacaaatattgttaagatgtaaaagcacatcagttaggtatcattagtttaggacaaggatttctagaaaat
ttttaggaacagaaaactttccagttctctcaccccctgctcaaagagtgtatggctcttacattatatataactgcctga
cttcatacagtatcagtacttagatcatttgaaatgtgtccacgttttaccaaaatataataggggtgagaagctgagatg
ctaattgccattgtgtattctcaaatatgtcaagctacgtacatggcctgtttcatagagtagtctataagaaattgatg
acttgattcatccgaatggctggctgtaacacctggttacgcatgaacacctcttttcagttgtctcaagacacctttct
tttctgtacttatcagacaaggactgaaaggcagagactgctactgttagacattttgagtcaagcttttccttggacat
agcttgtcatgaaagccctttacttctgagaaacttctagcttcagacacatgccttcaagatagttgttgaagacacc
agaagaaggagcatggcaatgccgaaaacacctaagataataggtgaccttcagtgttggcttcttgcagAATCCAGAGA
GACAGACTTGCTCAGTGGGATGGATGGCAAAGGGTCCTACCAGGTGAAAGGCTGGAAACTTACACAGCAACAGTTTGTGG
CCCTTTTGTGGAAGAGACTGCTAATTGCCAGACGGAGTCGGAAAGGATTTTTTGCTCAGgtgagacgtgctgttttcgcc
agagactctggcttcatggtgggctgcaggctctgtgaccagtgaaggcaggatagcatcctggtcaagatatggatgc
cggagccagatttatctgtatttcaatcccagttctattccttgccagttgtgtatccgctggcaagttacttctctatg
cctcaatctcctcatctgtaaaatggggataataatattacctgcaatacagggttgttacgaaaataaaaatgaatagg
tgcttagaatgggcctgacattagtaagtgcttagttttgtgtgtgtatatgttatttttattttggaggagaacataa
aaaggacaaagtgtagaaaaactggttgggtgtattcagctgtcataacatgagagttgttatgcccagatgcacttgac
atgtgaatttattagaaacatgattttctctgagttgatgtttaactcaaactgatagaaaagataggtcagaatatag
ttggccaacagagaagacttgttagactattgtctgcatgtcagtgtttgcatgctaacttgcttagttagaaaggttaa
atttttttcactctataaaatcaagaaatatagagaaaaggtctgcagagagtcttttcatttgatgatgtggatattgtta
agagcgggagtttggagcatacagagctcaagttgaatcctgactttgctactattggctatatgaccttgggcaagct
gcttagtctctctgatcctcagttaccttgttgttgatgatgaccattgataacacaaccataaataatgacaacata
gagatagttctcattatagtagttgttatacagaattattcactcaatgttaattttctgcattgaaatcccagaacatt
agaattgggggcattatttgaatcttttaaggttataaggaatacatttctcagcaataaatggaaggagttttgggttaa
cttataaagtatacccaagtcattttttttcagagaagatatggtagaaagtcttaggaggttgaagaaggaattggata
tttattctttctgagactatcatggggagataatgactatggttgtccatgattggagccgttgctgtagagttggtttta
ttatagtgtaggatttgaatgggccatgtgttctcagacctcagaataaaaagagaaaactgaggccagtggggagcgtg
acttcacatgggtacacttgtgctagagacagaaccaggattcaggacttctggctcctggtcctgggttcatggcccaa
tgtagtctttctcagtcttcaggaggaggaagggcaggacccagtgttctgagtcaccctgaatgtgagcactatttact
tcgtgaacttcttggcttagtgcctctgccaggtggccataacctctggccttgtgttgccagagaaaaggtttagtttt
caggctccattgcttcccagctgccaagaatgccttggtgcagcacagtcataggccctgcattcctcattgccgtgctg
gttggtcggggaggtgggctggactcgtagggatttgccccttggccttgtttctaacacttgccgtttcctgctgtccc
cctgccccctccactgcctgggtaaagATTGTCTTGCCAGCTGTGTTTGTCTGCATTGCCCTTGTGTTCAGCCTGATCGT
GCCACCCTTTGGCAAGTACCCCAGCCTGGAACTTCAGCCCTGGATGTACAACGAACAGTACACATTTGTCAGgtatgttt
gtcttctacatcccaggagggggtaagattcgagcagaccaaagatgtttacgagggccaagggaatggacttcagaatt
acacggtggaat
```

SEQ ID NO: 23
Genomic contig containing ABC1 exon 29:

gggaagcatttaaaaaaaaaaaagtatatatatatatatatatatatatgtaatgtgaattggcctcttttctctaa
gcccacattttcttcttacatagttcaggttttactttattttttcctttccggctgctgaccctgtattgcccgtagttg
tggaacatagcatgtgtttgtgacctgtgcctgttatttttgtgctttctagttgtgcatgcaaagagtacaaagttttc
ttgccctttcttggaaaatcctgcttgtctgtgccaaagggataattgtgaaagcacttttgaaatacttaatgagttga
ttttcttcaaattaaaaaaaatatataaatgtatatgtgtatgtacatgtgtgtacacatacacacctttatacatacag
cccatttaaaacaagctccactttggagtgctctacgtcaccctgatgccgaatacagggccagagtctgagatccttct
gggtggtttctgtgttttgttcatttctgttttaagagcctgtcacagagaaatgcttcctaaaatgtttaatttataaa
aacatttttatctctcgattactggttttaatgaattactaagctggctgcctctcatgtacccacagCAATGATGCTCC
TGAGGACACGGGAACCCTGGAACTCTTAAACGCCCTCACCAAAGACCCTGGCTTCGGGACCCGCTGTATGGAAGGAAACC
CAATCCCgtgagtgccactttagccataagcagggcttcttgtgcttgttgcctggtttgatttctaatatgctgcattt
atcaactgcatgccacattgtgaccgccagcatttgcccttttgaattattattatgtttatttacaaaaagcgaaggta
gtaaccgaactaaattatctaggaacaaacgtttggagagtcttctaacaccgyscaaagcacgtcattacagacatttg
tttactgatttagaaccttaatatttaattaaatacgcacttttacacttactgatgaaatgcttttcctttctttctct
cccagcccctgtacttaagtgcttcaataggctctcattatatatgatttttaggttttgcttatcagcttcttcgcttt
tataatctgaaaagatggcatatgaatttttataaaaagggacactttcttcttctcaaattgtatattttattgtact
ttccttcaaaaccccctttttaaaaagtaagcagtggataaataaattcagtgaagcatccatatgacccttaagtgagtg
taggggaagggaggtcaccagatcactgtgagtgaagatggtggagaggtgaggatcttatgaggccgtgctcaaggctg
gtagaggtgggttagtgtttccaggtttaggcagaatctcagctgaggtcatgaaacaacagtgatctctgaaaaattat
ggcaaggtgggaaggtgctggagaattggagaggggcaaacttgactttcaagtttcaatgggaagataggtgactctg
cacaccacagaacagtgagcatgataacctgtttatacaaggttctagagcagatttctaaatggatagctactgtgtgc
ttgtttgttcttaattagtattggatagttactaaatacttgttagtacttagtacataatgggtggtaaatcctagcag
ctaatattggttcccaaataaccagatgacaaggatagagaaggacacagacacggcctatctggatttcatggtgcctt
tgattttccacatgaaggttgtgtagggaagatagaagcatgagatgagatgataatatagttatctggattcatcactg
gccagctgaaccatatgaactcatggattgatgctagcttaggaaggctctgtaggagccagaactgggctgagagccag
cccatagagacaaaagaggcccggccctgacatcagagggttcaaacatgatgtctgagccccacctacagtctgccgga
ggtggttggaaggaagagcctttatccttacaattcttactgaaattcaaattttttaggttttgcaaaaaaatggtggac
ctgaaggaaatttgacaggagcatgtctcagctgtatttaaatttgtctcagccaatccccttttgaatgttcagagtgt
aagcttcaggagggcagcgcgtcttagtgtgacttttctggtcagttcaggtgctttaaggagacaattagagatcaatc
tggaaaacttcatttgaattttttaatacataagaaaacaataagaaatagttaaaaatatatatttatataatatatata
tgtgtgtgtgtgtgtgtgtgtgtgtgtgtatatatatatatatttttatttatttattttttttttgagatggagtctcg
ctctgttgcccaggctggagtgcagtggctcaatcttggctcactgccacctctgcctcccaggttcaagtgattctcct
acctcagcctcctgagtagctgggattacaagcatgtgccaccacactggctaa

Figure 12J

SEQ ID NO: 24
Genomic contig containing ABC1 exon 30 and 31:

tcttgccagtctctactcatttttcagcacatcgagcataagatccagactctttcccaggcctctctcatctggctcct
ctcctcctcctttatcattactcttcttcgtagcttatcctactccagccatgctgtcttcctattattcctaaaaarta
gaaatgcatttcttcctagggcctttgtacctgcacttgccatcgcttttgctcagaatgttcttttttgccaagcttttg
cccagcttgttctccatcattgttatgttttggctgaaatgtcttctcttagtaggttcattctccccagtcactgtctt
tttatttttgctttatttttgggccatctaaggttatcttattagtgtatttgttgttcgtctcctccatgggcatacacct
ccatgaaggcaggtattttcaccttaggccctcgaatatactggacagcatctggcacgtagtagatgctcaacgaatgt
ttgttgtgtgagcaaatggttggttgattggattgaactgagttcagtatgtaaatatttagggcctctttgcattctat
tttacttatgtataaaatgatacataatgatgatataaatgatgtcacagtgtacaaggctgttgtgggatcaagcaatc
aaatgagatcatgcttgtcttttccaaatggtgagggaatagatgcatgtttgtggttgttacggaatgatcctgtgctc
ctgaggcaacagaaaggccaggccatctctggtaatcctactcttgctgtcttccctttgcagAGACACGCCCTGCCAGG
CAGGGGAGGAAGAGTGGACCACTGCCCCAGTTCCCCAGACCATCATGGACCTCTTCCAGAATGGGAACTGGACAATGCAG
AACCCTTCACCTGCATGCCAGTGTAGCAGCGACAAAATCAAGAAGATGCTGCCTGTGTGTCCCCCAGGGGCAGGGGGGCT
GCCTCCTCCACAAgtgagtcactttcaggggggtgattgggcagaaggggtgcaggatgggctggtagcttccgcttggaa
gcaggaatgagtgagatatcatgttgggagggtctgtttcagtctttttttgttttttgttttttttttctgaggcggagtc
ttgctctgtcgcccaggctggagtgctgtggcatgatcttgcctcactgcaacctccacctcccaggttcaagcgattct
cctgcctcagcctcctgagtagctgggattacaggcacgcaccaccatgtctggctaatttttgtgtttttagtagagat
agggtttcgccgtgttggctaggctggtctggaattcctgacctcaggtgatccacccgcctcggcctcccaaagtgctg
ggattacaggcgtgagccactacgcccagccctgtttcagtctttaactcgcttcttgtcataagaaaaagcatgtgagt
tttgaggggagaaggtttggaccacactgtgcccatgcctgtcccacagcagtaaagtcacaggacagactgtggcaggc
ctggcttccaatcttggctctgcaacaaatgagctggtagcctttgacaggcctgggcctgtttcttcacctctgaatta
gggaggctggaccagaaaactcctgtggatcttgtcaactctggtattcttagagactctgtttgggaaggagtcctgag
ccatttttttttcttgagaatttcaggaagaggagtgcttatgatagctctctgctgcttttatcagcaaccaaattgc
aggatgaggacaagcaattctaaatgagtacaggaactaaaagaaggcttggttaccactcttgaaaataatagctagtc
caggtgcgggtggctcacacctgtaatctcagtattttgggatgccgaggtggactgatcacctaaggtcaggagttcg
aaaccagcttggccaatgtggcgaaaccctgtctctactaaaaattcaaaaattagccaggcatggtggcacatgcctgt
aatcccagttacttgggaggctgaagcaggagaattgcttgaacctgggaggtggaggtcgcagggagccaaaattgcgc
cactgtactccagcctgagcaacacagcaaaactccatatcaaaaataaaatgaataaaataacagctaatctagtcat
cagtataactccagtgaacagaagatttattaggcatagtgaatgatggtgcttcctaaaaatctcttgactacaaagaa
tctcatttcaatgtttattgtttagatgttcagaataaattcttgggaaagaccttggcttggtgtaagtgaattaccag
tgccgagggcagggtgaaccaagtctcagtgctggttgactgagggcagtgtctgggacctgtagtcaggtttccggtca
cactgtggacatggtcactgttgtccttgatttgttttctgtttcaattcttgtctataaagacccgtatgcttggtttt
catgtgatgacagAGAAAACAAAACACTGCAGATATCCTTCAGGACCTGACAGGAAGAAACATTTCGGATTATCTGGTGA
AGACGTATGTGCAGATCATAGCCAAAAGgtgacttttttactaaacttggccctgccttattattactaattagaggaat
taaagacctacaaataacagactgaaacagtgggggaaatgccagattatggcctgattctgtctattggaagtttagga
tattatcccaaactagaaaagatgacgagagggactgtgaacattcagttgtcagcttcaaggctgaggcagcctggtct
agaatgaaaatagaaatggattcaacgtcaaattttgccac

Figure 12K

SEQ ID NO: 25
Genomic contig containing ABC1 exon 32:_ gcatgctggagtgatagtgaccatgagtttctaagaaagaagcataatttctccatatgtcatccacaattgaaatatta
ttgttaattgaaaaagcttctaggccaggcacggtggctcatgcctgtaatcccagcactttaggagccaaggcgggtgg
atcacttgaggtcaggagtttgagaccagcctggccaacatggggaaaccctgtctctactaaaaatacaaaataagctg
ggcgtggtggtgcgtgcctgtaatcccagctacttgggaggctgaggcaggagaactgcttgaatctgggaggcggaggt
tgcagtgagctgagttcatgccattgcattccagcctgggcaacaagagcgaaaccatctcccaaaagaaaaaaaaaaga
aagaaaaagcttctagtttggttacatcttggtctataaggtggtttgtaaattggtttaacccaaggcctggttctcat
ataagtaatagggtatttatgatggagagaaggctggaagaggcctgaacacaggcttctttctctagcacaaccctac
aaggccagctgattctagggttatttctgtccgttccttatatcctcaggtggatatttactcctttgcatcattagga
ataggctcagtgctttctttgaactgatttttgtttctttgtctctgcagCTTAAAGAACAAGATCTGGGTGAATGAGT
TTAGgtaagttgctgtctttctggcacgtttagctcaggggaggatggtgttgtaggtgtgcttggattgaagaaagcc
ttggggattgtttgtcactcacacacttgtgggtgccatctcactgtgagga

Figure 12L

SEQ ID NO: 26
Genomic contig containing ABC1 exon 33 to 36:

gctttatagagtttctgcctagagcatcatggctcagtgcccagcagccctccagaggcctctgaatatttgatatact
gatttccttgaggagaatcagaaatctcctgcaggtgtctagggatttcaagtaagtagtgttgtgaggggaatacctac
ttgtactttcccccaaaccagattcccgaggcttcttaaggactcaaggacaatttctaggcatttagcacgggactaa
aaaggtcttagaggaaataagaagcgccaaaaccatctctttgcactgtatttcaacccatttgtccttctgggttttga
aggaacaggtgggactggggacagaagagttcttgaagccagtttgtccatcatggaaaatgagataggtgatgtggcta
cgtcagggggcccgaaggctccttgttactgatttccgtcttttctctctgccttttccccaagggccaggacccctgga
tctctgggcagagcagacgcaggcccctataatagccctcatgctagaaaggagccggagcctgtgtataaggccagcgc
agcctactctggacagtgcaggttcccactctcccaactccccatctgcttgcctccagacccacattcacacacgagc
cactgggttggaggagcatctgtgagatgaaacaccattctttcctcaatgtctcagctatctaactgtgtgtgtaatca
ggccaggtcctccctgctgggcagaaaccatgggagttaagagattgccaacatttattagaggaagctgacgtgtaact
tctgaggcaaaatttagccctcctttgaacaggaatttgactcagtgaaccttgtacacactcgcactgagtctgctgct
gatgatactgtgcaccccactgtctgggttttaatgtcaggctgttctttagGTATGGCGGCTTTTCCCTGGGTGTCAG
TAATACTCAAGCACTTCCTCCGAGTCAAGAAGTTAATGATGCCATCAAACAAATGAAGAAACACCTAAAGCTGGCCAAGg
taaaatatctatcgtaagatgtatcagaaaaatgggcatgtagctgctgggatataggagtagttggcaggttaaacgga
tcacctggcagctcattgttctgaatatgttggcatacagagccgtctttggcatttagcgatttgagccagacaaaact
gaattacttagttgtacgtttaaaagtgtaggtcaaaaacaaatccagaggccaggagctgtggctcatgcctgtaatcc
tagcactttgggaggctgaagcgggtggatcacttgaggtcaggagttcgagaccagcctggcctacatgacaaaacccc
gtatctactaaaaatacaaaaaaattagctgggcttggtggcacacacctgtaatcccagctacttgggaggctgaggca
ggagaattgcttgaacctgtaggaagaggttgtagtgagccaagatcgcaccgttgcactccagcctgggcaacaagag
caaaactccatctcaaaaaacaaattaaatccagagatttaaaagctctcagaggctgggcgcggtggcttacacctgtt
atcccagcattttgggatgccgaggcgggcaaagcacaaggtcaggagtttgagaccagcctggccaacatagtgaaacc
ctgtctctgctaaaaacatagaaaaattagccgggcatggtggcgtgcgcctgtaatcccagctactcgggaggctgagg
tgagagaattccttgaacccgggaggcggaggttgcagtgagcccagattgcaccactgcactccagcctgggcgacaga
gcaagactccatctcaaaaaagctctcagaacaaccaggtttacaaatttggtcagttggtaaataaactgggtttcaa
acatactttgctgaaayaatcactgactaaataggaaatgaatctttttttttttttttttttaagctggcaagctggtctg
taggacctgataagtactcacttcatttctctgtgtctcaggtttcccatttttaggtgagaattaaggggctctgataa
aacagaccctaggattgtggacagcagtgatagtcctagagtccacaagtctgcttttgagtgatgggcccatgtatctg
gcacatctgcaggcagagcgtggttctggctcttcagatgatgccggtggagcactttgaggagtcctcaccccaccgtg
ataaccagacattaaaatcttgggctttgcatcccaggatttctctgtgattccttctagacttgtggcatcatggcag
catcactgctgtagatttctagtcacttggttctcaggagccgtttatttaatggcttcacatttaatttcagtgaacaa
ggtagtggcattgctcttcacagggccgtcctgttgtccacaggttccagattgactgttgccccttatctatgtgaaca
gtcacaactgaggcaggtttctgttgtttacagGACAGTTCTGCAGATCGATTTCTCAACAGCTTGGAAGATTTATGAC
AGGACTGGACACCAGAAATAATGTCAAGgtaaaccgctgtctttgttctagtagcttttttgatgaacaataatccttatg
tttcctggagtactttcaactcatggtaaagttggcaggggcattcacaacagaaaagagcaaactattaactttaccag
tgaggcagtacggtgtagtgtagtgattcagagaatttgctttgccaccagacataccaggtaaccttgactaagttact
taacctatctaaacctcagttycctcatctgtgaaatggagacagtaatcatagctatttccaaactgttgtgagaattc
aatgagttaaaggtataaggtcctcaccacagcgcctgcccacatagtcagtgatcactatgtcctgaacactgtaatta
cttcgccatattctctgatcatagtgttttgccttggtatgtgactagaatttctttctgaggtttatgggcatggttgg
tgggtatgcacctgcctgcaggagcccggtttgggggcattaccttgtacctggtatgttttctttcagGTGTGGTTCAA
TAACAAGGGCTGGCATGCAATCAGCTCTTTCCTGAATGTCATCAACAATGCCATTCTCCGGGCCAACCTGCAAAAGCGAG
AGAACCCTAGCCATTATGGAATTACTGCTTTCAATCATCCCCTGAATCTCACCAAGCAGCAGCTCTCAGAGGTGGCTCTg
taagtgtggctgtgtctgtatagatggagtggggcaagggagagggttatggagaaggggagaaaaatgtgaatctcatt
gtaggggaacagctgcagagaccgttatattatgataaatctggattgatccaggctctgggcagaagtgataagtttac
gaattggctggtttgggcttcttgaactgcagaagagaaaatgacactgatatgtaaaaatcgtaacatttagtgaattca

Figure 12M – (1)

```
tataaagtgagttcaaaaattgttaattaaattataatttaattataagtgtttaatcagtttgatttgtttaaaaacca
ctgttttaaatttggtggaatatgttttattagcttgtatctttaattcctaaattaagctgtgtgtgtgtgtgtgtgt
gtgtgtgtgtgtgtgtgtgtgtgtgtgtgaagtttaaagccaggatgagctagtttaaagtatgcagcctttggagtc
atacagatctgggtttgaatctggtctctaaactttatagatgtatgatattaaatgaggcagttcatgtaaattgccaa
gcccagcactcagcacagagttgatatttcacacacattagataccttcctgtatgtggagcatggcagttcctgtttc
tgctttactcctacaggatactaatataggacactaggatctttataccaagaccccatgtaatgggcttatgagaccat
tcttcttataaaaatctgacagaattttttgtatgtgttagatcaataggctgcatactgttattttcaagttgatttaca
gccagaaatattaatttatttgagtagttacagagtaatatttctgctctcatttagttttcaagccccactagtcctt
gtgtgtgaaaatttacaacttactgctcttacaaggtcatgaacagtggaccaaagtgaatgccattaaccactctgact
tccttcattagttttattgtgacagtggactcttttgacctcagtaataccagtttggcatttacattgtcatattttta
gacttaaaaaatgatcatcttaaccctgaataaaatgtgtctggtgaacagatgtttttccttggctgtgcctcagatatc
tctgtgtgtgtgtacgtgtgtgtttgtctgtgtgtccatgtcctcactgattgagccctaactgcatcaaagacccctca
gatttttcacacgcttttctctccagGATGACCACATCAGTGGATGTCCTTGTGTCCATCTGTGTCATCTTTGCAATGTC
CTTCGTCCCAGCCAGCTTTGTCGTATTCCTGATCCAGGAGCGGGTCAGCAAAGCAAAACACCTGCAGTTCATCAGTGGAG
TGAAGCCTGTCATCTACTGGCTCTCTAATTTTGTCTGGGATATGgtaaggacacaggcctgctgtatctttctgatgtct
gtcagggccatggattgatatggataagaaagaaagagctctggctatcatcaggaaatgttccagctactctaaagatg
tatgaaaaagaaatagccagaggcaggtgatcactttcatgacaccaaacacagcattgggtaccagagttcatgtcaca
ccagagggaaaattctgtacacaatgatgaaaattaataccactaccacttaagttcctatgtgacaactttcccaagaa
tcagagagatacaagtcaaaactccaagtcaatgcctctaacttctctgatgggttttaacctccagagtcagaatgttc
tttgccttactaggaaagccatctgtcatttagaaaactctgtacattatcagcagcttatccatccattgcaaatat
tgtttttgtgccascacaatatattgcttctatttggaccaatatgggggatttgaaggaattctgaagttctaattat
atttcaactctactttacaatatctccctgaaatatatctccctgtaacttctattaattataagctacacagagcaaat
ctaattcttctcccaccgaacaagtccctggatatttaaaaataactctcatactctcatttaacctgagtattacccag
ataagatgatatatgagaatacaccttgtaacctccgaagcactgtacaaatgtgagcaatgatggtggagatgatgatg
agatctttgctgtttataccaagcccctagactgtgtcactcttctgatccggttgtccttgtatggccatgctgtata
ttgtgaatgtcccgttttcaaaagcaaagccaagaattaaccttgtgttcaggctgtggtctgaatggttatgggtccag
agggagttgatctttagctcacacttctattactgcagcacaaagattttgcattttggaaggagcaccgtcttactggc
aacttagtggtaaaccaaaacctccatttcacacaaatgattgtgaaattcgggtctccttcattctatacaaattcatt
tgattttttttgaaactaaactttatatttatccatattaaattacatgggttttattttttgttttatcttgattcagtaa
ttactcctttcagtaaacacagactgagtgctgtgtgtctgacttatgccaggcataggtgattcagagatgaaaggtca
agtccctgaacccatctcttgtcttcctgggtattatctgtccctccctgctttagagctcctgaaatttgctagaagca
tgtcttcatctaagttgttgataaacacatcaagtaggattggactgaggcagagccctgtagtctgaagctgcagttct
tctagcggctgacaagccccactatcacttccctgctggtgctttgctctgccagctgtgaattctcataattgtcctat
cgtcaagtctttatttctgcatttttactgcttgatacactgtcaggacagacttttaaaattattctcagtgcgatgaaac
aattctgacattcatgttatgagcagttacctcataaatagattacatg
```

Figure 12M – (2)

SEQ ID NO: 27
Genomic contig containing ABC1 exon 37 to 41:

aaattactctgactgggaatccatcgttcagtaagtttactgagtgtgacaccttggcttgactgttggaaagacagaaa
gggcatgtagtttataaaatcagccaaggggaaaatgcttgtcaaaatgtattgtcgggtattttgattaatagtttatg
tggcttcattaattcagagttactctccaatatgtttatctgccctttcttgtctgataatggtgaaaacttgtgtgatg
cattgtatatttgatttagggggtgaactggatgtctttgttttcacttttagTGCAATTACGTTGTCCCTGCCACACTGG
TCATTATCATCTTCATCTGCTTCCAGCAGAAGTCCTATGTGTCCTCCACCAATCTGCCTGTGCTAGCCCTTCTACTTTTG
CTGTATGGgtaagtcacctctgagtgagggagctgcacagtggataaggcatttggtgcccagtgtcagaaggagggcag
ggactctcagtagacacttatctttttgtgtctcaacagGTGGTCAATCACACCTCTCATGTACCCAGCCTCCTTTGTGT
TCAAGATCCCCAGCACAGCCTATGTGGTGCTCACCAGCGTGAACCTCTTCATTGGCATTAATGGCAGCGTGGCCACCTTT
GTGCTGGAGCTGTTCACCGACAATgtgagtcatgcagagagaacactcctgctgggatgagcatctctgggagccagagg
acagtgtttaattgtgatcttattccacttgtcagtggtattgacactgctgactgccttgtcctgtcttcagagtctgt
cttccctgagaaggcaaagcacctttctttcttgctgtgccttacatttgctggtcaagcctttcagtttcttttgaca
gttttttttacttcttctttttcaatgttgctcttaccaagagtagctcctctgccttccactttacacatgagagct
gggcgacgcattcagtcctaaggcttttaccatcacctctcttggtgtttttattgtcatctctaagatcaatgccttta
gccttgatcataaccttgaactctaatctcaaattctcacttgcctagtggattgctccatttagatagtatatagatac
cccaacctggatatgtcctagttttctttccccttggaacttaatgcttttcttgccatccctgtcacactcagtggcac
taccatccactcggttgcccaagctggctcttagagttatcctagatgcttgctttgctgttgcagatttcccacattca
actggttatgttgtcagttcttccaggtatggacctctaaaataaggcttcctctccattccggttgtcattgcctttgt
ccaaacacagcacacaaggccttttacagttgcacaactcttcctgtccatacccaccacaccctttcccagctgtaagc
ttcagatgagttgcctccaaccaccatgctcctgtaggcctggcttgaaatgcccttcttctgtcacagggtctggtagt
atatcccttgcccttcaagatttagctaaaatgtgaagcttccttacctgctgggaggtgttctctcttttctctgtgc
tctcagagtccttagtccatgcctccagtacaacgtacatccacttacatggtaatttcctgtttacatacttttcctac
tcggagtggagtctgtttcttaataattttgcctctcccatgccctagcacagtgcatccagcgtatagcccccttattca
gttggtagatatttggccactgttgccttgtgggatcataagttctgatgtatttgagaagaatttctaaaattctgaca
aaatcctgaaactcaaatattgacccagacatgagcaatttgcttttcaaatgctaagggatttttaatggatttgcttt
aattaaatctagcctgtttctaagcttttattcattatttctccatactcagagcatttctccagatttttctaaagaatag
aattttattgctacatatcatcagctatgcctgctgctattaattggtatctgaattaaaaggtctggtttgtccctag
agaatcaaattttttcttcactcccatatttcagaacttgatacattttaggataaaccatgaatgacacccgttttctt
ctccctcacctcccttccctcccatttttttttttttttttttttagAAGCTGAATAATATCAATGATATCCTGAAGTC
CGTGTTCTTGATCTTCCCACATTTTTGCCTGGGACGAGGCTCATCGACATGGTGAAAAACCAGGCAATGGCTGATGCCC
TGGAAAGGTTTGgtgagtgaagcagtggctgtaggatgctttaatggagatggcactctgcataggccttggtaccctga
actttgttttggaaagaagcaggtgactaagcacaggatgttccccacccccatgcccagtgacagggctcatgccaac
acagctggttgtggcatgggttttgtgacacaaccatttgtctgtgtctctgatagcattgagaaaagtgaaagggcagt
tttgaaggtaaggaaaatagtgttatttgcttggatccactggctcatgccactgtctgggttggttagaagcactggaa
aagtcaaaccataactttgagaattaggtgatcagggaatcagaaggaaagatgcaaactttggctcttttaggcgaatc
atgtgcctgcagatgaggtcatttattatcttttacacagtctataaaattataatgtattacatcttttctaccttta
gaatggttaaaaatatttctccggtagccatatgattattattcatccattagataatatagtcaaatgggccatgttat
ttactgttcatagaagaggggcttttttgcaacttgggctacaaaggagatatgtaaggaatttaaggaatggttacatgg
aactagatttaattgaatctagtggtttaattgattcactaggatatatgctactgaaaggggaatctgcttaaagtgct
ttctgatatttattattactaaaacttagaatttattaaaaatactgactgtgaaaattacttgggtcgtttgccttttt
aaaaggattttggcatgtctcattaaaaaaagaaatactagatatcttcagtgaagttacaaatcgaatacacattggc
tctgaaattctgattgatactgggtcataaaaagttttcccaaatcagacttggaaagtgatcactctcttgttactctt
ttttccttgtcatgggtgatagccatttgtgtttattggaagatcggtgaatttttaaggaacataggcccaaatttgagg
aagggccatggttttgatccctccattctgaccggatctctgcattgtgtctactagGGGAGAATCGCTTTGTGTCACC
ATTATCTTGGGACTTGGTGGGACGAAACCTCTTCGCCATGGCCGTGGAAGCGGTGGTGTTCTTCCTCATTACTGTTCTGA

Figure 12N – (1)

TCCAGTACAGATTCTTCATCAGGCCCAGgtgagcttttcttagaacccgtggagcacctggttgagggtcacagaggag
gcgcacagggaaacactcaccaatgggggttgcattgaactgaactcaaaatatgtgataaaactgattttcctgatgtg
ggcatcccgcagcccctccctgcccatcctggagactgtggcaagtaggtttataatactacgttagagactgaatct
ttgtcctgaaaaatagtttgaaaggttcattttcttgttttttcccccaagACCTGTAAATGCAAAGCTATCTCCTCTG
AATGATGAAGATGAAGATGTGAGGCGGGAAAGACAGAGAATTCTTGATGGTGGAGGCCAGAATGACATCTTAGAAATCAA
GGAGTTGACGAAGgtgagagagtacaggttacaatagctcatcttcagttttttttcagctttatgtgctgtaacccagca
gtttgctgacttgcttaataaaagggcatgtgttcccaaaatgtacatctataccaaggttctgtcaatttatttaaa
aacaccatggagacttcttaaagaattcttactgagaattcttttgtgatatgaattcccattctcgaatactttggttt
tatatgcttacatttatgtgttagttattaaaacatactaatattgtatatctagtcaaactgagtagagagataatggt
gatt

Figure 12N – (2)

SEQ ID NO: 28
Genomic contig containing ABC1 exon 42 to 45:

```
ttttaaaatacctgcaatacatatatatgttgaatagatgaaaaattatgtagatgataatgaatgatacggttctaaaa
agacaggttaaaaagtaagttcactttttattttgagcttcagaatcattcagaagccagtcgccacaaacgcagaccaag
gctcttggcacatcaaatatgcctatggcttagggttattgacaagtcttatgttgcagtgtatgtggtttatagtcctg
ccttccacagttgcttgggagagctgtgagtcactgaggcttatgaatgtttacattttgtttgttgcagATATATAGAA
GGAAGCGGAAGCCTGCTGTTGACAGGATTTGCGTGGGCATTCCTCCTGGTGACGtaaagacactttgtctatattgcgtt
tgtccctattagttcagactatctctacccaatcaagcaacgatgctcgttaagaggtaaaagtggattttaaaggcttc
tgtatttatgccaggatggagcaattagtcatcgagaagagagggaccctgtatgtcaagagaatgatttcagagaatcc
aatacaatttaagaaaaagcatggggctgggcgcagtgattcactcctgtaatcccagcactttgggaggccgaggtggg
cggactcacgaggtcaggagattgagaccatcctggccaacatggtgaaacccatctctactataaatacaaaaattag
ctgggcatagtagtgcattcctgtagtcccagctactcgggaggctgaggcaggagaattgcttgaacctaggaggggga
ggttgcccagattgcgctgctgcactccagcctggtgacagagtgagactcatgtcaacaacaaaaacagaaaaagcacg
cacatctaaaacatgcttttgtgatccatttgggatggtgatgacattcaaatagttttttaaaaatagatttctcctt
tctggtttccgtttgtgttcttttatgcccttttgccagagtaggtggtgcaatttggctagctggctttcattactgtt
tttcacacattaactttggcctcaacttgacaactcaaataatatttataaatacagccacacttaaaatggtcccatta
tgaaatacatatttaaatatctatacgatgtgttaaaaccaagaaaatatttgattcttctctgatatttaagaattgaa
ggtttgaggtagttacgtgttaggggcatttatattcatgtttttagagtttgcttatacaacttaatctttccttttca
gTGCTTTGGGCTCCTGGGAGTTAATGGGGCTGGAAAATCATCAACTTTCAAGATGTTAACAGGAGATACCACTGTTACCA
GAGGAGATGCTTTCCTTAACAAAAATAGgtgagaaaagaagtggcttgtattttgctgcaaagactttgttttaattta
tttaaagaaataggttgttatttttgattacagtggtattttagagttcataaaaatgttgaaatatagtaaagggtaa
agaagcacataaaatcatccatgatttcaatatctagagataatcacaatttacatttcctttcagtctcattctcttct
tttaacagctttattcaggtataatttacatacaatataatttgcttgttttttaagagtataatttagtgattttggt
aaattgagagttttgcaaccatcaccacaatccagttttagaacttttccatcaccccacatctgtcttatatacacata
taaatgtgccatacaattgagatcatactgtatgtagaatttaaaattagttttttattgttaatgagtgtattatgaata
tttcccagtgggttacatttcctaagatgtggaatttacattgctacataaaatcccctatgtacatgtacctataat
ttatttaataaattccttataaatgttggacacattagtttccatttttcactatgtaaatatgtccctgtatacatctt
ttattatttcctcaggaacaattcctacaaagtaaattgccctctctaaagagcatacaaattgactgagccaccgttag
gccatttctgagactgcacaggtcacaaagcaatctgatctttgggaatacagctacattttataggcttcttagataa
tgttactctaagtactttaaatatgtggggcttctctgggctttttttttttttgagacggagtttcactcttactgccca
ggctggagagcaatggcgcgaccttggctcactgcaacctccgcctcccaggttcaagcgattctcctgcctcagcctcc
tgagtagctgagattacaggtgcccgccacaatgcctgcctaattttttgtattttcagtagagatggggtttcaccat
gttggccagactggtctcgagctcctgacctcaggtgatccacctgcctcagcctcccaaagttctgggattacaggcat
gagccactgcgcccggcttctctggacttattatgtggagagatagtacaaggcagtggctttcagagttttttgaccat
gaccgttgtgggaaatacattttatatctcaacctagtatgtacacacagacatgtagacacatgtataacctaaagttt
cataaagcagtacctactgttactaattgtagtgcactctgctatttcttattctacctttatactgcgtcattaaaaaag
tgctggtcatgacccactaaatttatttcccaaaccactaatgaacaatgactcacaatttgaacacactggacagggg
atagccaataaaattgaaaagagcaaggaaattaatgtattcatgatctcctctcctgtctcttacattttttgcagtagc
aatgtaaaggaatcctaagagaacagacattctgggaatagcaggcctagcgctgcacaactgctttcctaggcttgctc
ctagtaccaagctcctgacgcatatagcagtggcagtaataaccagcccatagtaaggtttgtcacagggactggttgta
agaactgatttgrttggtatagctgtgagggcctggcacggtgtccacgtgtgcctcaatcctaattctgaaaaaggctg
accctgggggtgctaattagatacacagagaggaatgaatgctgccagaaggccaagttcatggcaatgccgctgtggct
gaggtgcagtcatcagtctggaacgtgaacactgaacttctctcacatgtgattcttcacttgactggcttcatagaacc
ccaaagccaccccaccaccacataaattgtgtctctaggttctgtgttgctcacactcaaaatttctgggccttctcatt
tggtgcatgtgaatggtgcatatgagtgaagtctaggatggggccttagcgttaaagccctggggtagtgtgactgagat
tgttggtaaagaatgtgcagtggttggcatgacctcagaaattctgaaatgggactgcacctgcagactgaagtgttcag
```

Figure 12O – (1)

```
agagccagggaggtgcaaggactggggagggtagaggcaggaaccctgcctgccaggaagagctagcatcctgggggcag
aaaggctgtgctttcaagtagcagcagatgtattggtatctttgtaatggagaagcatactttacaggaacattaggcca
gattgtctaaccagagtatctctacctgcttaaaatctaagtagttttcttgtcctttgcagTATCTTATCAAACATCCA
TGAAGTACATCAGAACATGGGCTACTGCCCTCAGTTTGATGCCATCACAGAGCTGTTGACTGGGAGAGAACACGTGGAGT
TCTTTGCCCTTTTGAGAGGAGTCCCAGAGAAAGAAGTTGGCAAGtactgtgggcacctgaaagccagcctgtctcctttt
ggcatcctgacaatatataccttatggcttttccacacgcattgacttcaggctgttttcctcatgaatgcagcagcac
aaaatgctggttctttgtatctgctttcagggtggaaacctgtaacggtggtggggcagggctgggtgggcagagaggga
gtgctgctcccaccacacgagtcccttctccctgctttggctcctcaccagttgtcaggttatgattatagaatctagtc
ctactcagtgaaagaactttcatacatgtatgtgtaggacagcatgataaaattcccaagccagaccaaagtcaaggtgc
tttttatcactgtagGTTGGTGAGTGGGCGATTCGGAAACTGGCCTCGTGAAGTATGGAGAAAAATATGCTGGTAACTA
TAGTGGAGGCAACAAACGCAAGCTCTCTACAGCCATGGCTTTGATCGGCGGGCCTCCTGTGGTGTTTCTGgtgagtataa
ctgtggatggaaaactgttgttctggcctgagtggaaaacatgactgttcaaaagtcctatatgtccagggctgttgtat
gattggcttgtcttcccccagggacagcagagcaaccttggaaaagcagagggaagcttctcccttggcacacactgggg
tggctgtaccatgcctgcagatgctcccaaatagaggcactccaagcactttgtttcttagcgtgattgaggctggatat
gtgatttgatctttctctggaacattctttctaatcatctttgtgttcattccctgaaaatgaagagtgtggacacagct
ttaaaatcccaaggtagcaactaggtcatagttccttacacacggatagatgaaaaacagatcagactgggaagtggcc
cttgaccttttttcttctgtagataagagcattgatgttattacgggaagaagcctttgaggcttttatgtattccacct
cggtctggaatttgtttctgtaaggctaacagttgcaatatactagggtaatctgagtgagctggaattaaaaaaaaaaa
ggaatttcaccccaatcttatactgacttcaatagaggtttcagacaaaaagttgttttgtat
```

Figure 12O – (2)

SEQ ID NO: 29
Genomic contig containing ABC1 exon 46 to 49:

ngccnngttnaaaangaaaatttnnnnnaaattnaannttannggngnnntttccccagaaaaaacnaaaangatttccn
cccnggggggnccccnantcnaaaaggccccncttntttgnggngagggaaagntttttttggaattttttaattttttgg
tcccccaaaacctattattgagaatttaattacataaaaaagtactcagaatatttgagtttcctgcatcaataagacat
ttataataatgaccttgtttacaaatgaatttgaaagttactctaattctttgattcatcaagaaataactagaatggca
agttaaaatttaagctgtttcaaagatgcttctgcatttaaaaacaaatttatctttgattttttttcccccccagcaaat
aagacttattttattctaattacagGATGAACCCACCACAGGCATGGATCCCAAAGCCCGGCGGTTCTTGTGGAATTGTG
CCCTAAGTGTTGTCAAGGAGGGGAGATCAGTAGTGCTTACATCTCATAGgtccgtagtaaagtcttgggttcctcactgt
gggatgttttaactttccaagtagaatatgcgatcatttgtaaaaattagaaaatacagaaaagcaaagagtaaaacaa
ttattacctgaaattatatatgcatattcttacaaaaatgcaagcccagtataaatactgctcttttcacttaatatat
tgtaaacattattccaagtcagtgcatttaggtgtcatttcttatagctggatagtattccattaggatatactcttatt
taactattccccttttgtagacatttggattatttccaacttgttcacaattgtaaacaccactacactgaacagcatc
atccctatatccacatgtacttgtaacagaatacaattccctaggaagctggaatgctggaagtcatggtgatgttctca
tggttacagagaatctctctaaaactaaaacctctttctgttttaccgcagTATGGAAGAATGTGAAGCTCTTTGCACTA
GGATGGCAATCATGGTCAATGGAAGGTTCAGGTGCCTTGGCAGTGTCCAGCATCTAAAAAATAGgtaataaagataattt
ctttgggatagtgcctagtgagaaggcttgatatttattcttttgtgagtatataaatggtgcctctaaaataaagggaa
ataaaactgagcaaaacagtatagtggaaagaatgagggctttgaagtccgaactgcattcaaattctgtctttaccatt
tactggttctgtgactcttgggcaagttacttaactactgtaagagttagtttccctggaagatctacctcctagctttg
tgctatagatgaaatgaaaaaaatttacatgtgccagtactggtgagagcgcaagctttggagtcaaacacaaatgggtt
tgcatcctggccctaccaattatgagctctgagccatgggcaagtgactaactccctgggcctcagtttctctgtaacat
ctgtcagacttcatgggtccaggtgaggattaaaggagatcatgtatttacagcacatggcatggtgcttcacataaaat
aagtatttagtaaatgataactggttccttctctcagaaacttatttctgggcctgccaggggccgccctttttcatggc
acaagttgggttcccagggttcagtattcttttaaatagtttctggagatcctccatttgggtattttttcctgctttc
agGTTTGGAGATGGTTATACAATAGTTGTACGAATAGCAGGGTCCAACCCGGACCTGAAGCCTGTCCAGGATTTCTTTGG
ACTTGCATTTCCTGGAAGTGTTCYAAAAGAGAAACACCGGAACATGCTACAATACCAGCTTCCATCTTCATTATCTTCTC
TGGCCAGGATATTCAGCATCCTCTCCCAGAGCAAAAAGCGACTCCACATAGAAGACTACTCTGTTTCTCAGACAACACTT
GACCAAgtaagctttgagtgtcaaaacagatttacttctcagggtgtggattcctgccccgacactcccgcccataggtc
caagagcagtttgtatcttgaattggtgcttgaattcctgatctactattcctagctatgcttttactaaacctctctg
aacctgaaaagggagatgatgcctatgtactctataggattattgtgagaatttactgtaataataaccataaaaactac
catttagtgagcacctaccatgggccaggcatttttacttggtgcctaatcctatttaaattagataaaaaagtaccaaat
aggtcctgacacttaagaagtactcagtaaatattttcttccctcttccctttaatcaagaccgtatgtgccaaagtaaa
tggatgactgagcagttggtgatgtaggggtgggggcgatatagaaagtcagttttggccgggcgtggtggctcatgc
ctgtaatcccagcactttgggaggctgaggagcaggcagatcatgaggtcaggagatccagataatcctggccaacaggg
tgaaaccccgtctctactaaaaatacaaaaattagctgggcatggtggtgcgcacttgtagtcccagctacttgcgaggc
tgaggcaggagaattgctcgaacccaggaggtggaggttacagtgagccaaggtctcgccactgcactccagcctgggga
cagagcaagacccatttcaagggggggaaaaaaagtctattttaagttgttattgctttttcaagtattcttccctcc
ttcacacacagttttctagttaatccatttatgtaattctgtatgctcctacttgacctaatttcaacatctggaaaaat
agaactagaataaagaatgagcaagttgagtggtatttataaaggtccatcttaatcttttaacagGTATTTGTGAACTT
TGCCAAGGACCAAAGTGATGATGACCACTTAAAAGACCTCTCATTACACAAAAACCAGACAGTAGTGGACGTTGCAGTTC
TCACATCTTTTCTACAGGATGAGAAAGTGAAAGAAAGCTATGTATGAAGAATCCTGTTCATACGGGTGGCTGAAAGTAA
AGAGGAACTAGACTTTCCTTTGCACCATGTGAAGTGTTGTGGAGAAAAGAGCCAGAAGTTGATGTGGGAAGAAGTAAACT
GGATACTGTACTGATACTATTCAATGCAATGCAATTCAATGcaatgaaaacaaaattccattacaggggcagtgcctttg
tagcctatgtcttgtatggctctcaagtgaaagacttgaatttagttttttacctatacctatgtgaaactctattatgg
aacccaatggacatatgggtttgaactcacactttttttttttttttttgttcctgtgtattctcattggggttgcaacaa
taattcatcaagtaatcatggccagcgattattgatcaaaatcaaaaggtaatgcacatcctcattcactaagccatgcc

Figure 12P – (1)

```
atgcccaggagactggtttcccggtgacacatccattgctggcaatgagtgtgccagagttattagtgccaagtttttca
gaaagtttgaagcaccatggtgtgtcatgctcacttttgtgaaagctgctctgctcagagtctatcaacattgaatatca
gttgacagaatggtgccatgcgtggctaacatcctgctttgattccctctgataagctgttctggtggcagtaacatgca
acaaaaatgtgggtgtctccaggcacgggaaacttggttccattgttatattgtcctatgcttcgagccatgggtctaca
gggtcatccttatgagactcttaaatatacttagatcctggtaagaggcaaagaatcaacagccaaactgctgggctgc
aactgctgaagccagggcatgggattaaagagattgtgcgttcaaacctagggaagcctgtgcccatttgtcctgactgt
ctgctaacatggtacactgcatctcaagatgtttatctgacacaagtgtattatttctggctttttgaattaatctagaa
aatgaaaagatggagttgtattttgacaaaaatgtttgtacttttaatgttatttggaattttaagttctatcagtgac
ttctgaatccttagaatggcctctttgtagaaccctgtggtatagaggagtatggccactgcccactattttattttct
tatgtaagtttgcatatcagtcatgactagtgcctagaaagcaatgtgatggtcaggatctcatgacattatatttgagt
ttctttcagatcatttaggatactcttaatctcacttcatcaatcaaatatttttgagtgtatgctgtagctgaaagag
tatgtacgtacgtataagactagagagatattaagtctcagtacacttcctgtgccatgttattcagctcactggtttac
aaatataggttgtcttgtggttgtaggagcccactgtaacaatactgggcagccttttttttttttttttttaattgcaac
aatgcaaaagccaagaaagtttaagggtcacaagtctaaacaatgaattcttcaacagggaaaacagctagcttgaaaac
ttgctgaaaaacacaacttgtgtttatggcatttagtaccttcaaataattggctttgcagatattggatacccattaa
atctgacagtctcaaattttcatctcttcaatcactagtcaagaaaaaatataaaaacaacaaatacttccatatggag
cattttcagagttttctaacccagtcttatttttctagtcagtaaacatttgtaaaaatactgtttcactaatacttac
tgttaactgtcttgagagaaaagaaaaatatgagagaactattgtttggggaagttcaagtgatctttcaatatcattac
taacttcttccacttttttccagaatttgaatattaacgctaaaggtgtaagacttcagatttcaaattaatctttctata
ttttttaaatttacagaatattatataacccactgctgaaaaagaaacaaatgattgtttagaagttaaaggtcaatat
tgattttaaaatattaag
```

Figure 12P – (2)

| No. | Name | Location in SEQ ID No. 14 | Sequence | Sequence Strand Length | |
|---|---|---|---|---|---|
| 1 | PPRE | 58-69 | AGGTAAAGTCA | 12 | Complement |
| 2 | PPRE | 1997-2009 | AGAGTAGAGGCA | 13 | Lead |
| 3 | PPRE | 2150-2161 | ATGTCAAGTTCA | 12 | Lead |
| 4 | PPRE | 2156-2169 | AGTTCAAAAGGGCA | 14 | Lead |
| 5 | PPRE | 4126-1139 | AGGCCAGCAGGGCC | 14 | Complement |
| 6 | PPRE | 5075-5087 | AGGGCAGAAGTGA | 13 | Lead |
| 7 | PPRE | 6604-6615 | ATGCCAAGTCA | 12 | Complement |
| 8 | PPRE | 6731-6743 | GGGGCAAGGGTA | 13 | Complement |
| 9 | PPRE | 7220-7233 | AGGTAATGAGGACA | 14 | Complement |
| 10 | PPRE | 7554-7568 | GGATCACGAGGTCA | 15 | Complement |
| 1 | SRE | 159-166 | CAGCCCAT | 8 | Lead |
| 2 | SRE | 1133-1140 | CAGCTCAC | 8 | Complement |
| 3 | SRE | 1145-1152 | CACACCAC | 8 | Lead |
| 4 | SRE | 1809-1816 | CAGCCCTC | 8 | Complement |
| 5 | SRE | 1894-1901 | CAGCCCAT | 8 | Lead |
| 6 | SRE | 2563-2570 | CAACCCAC | 8 | Lead |
| 7 | SRE | 3303-3310 | CAGCTCAC | 8 | Lead |
| 8 | SRE | 3470-3477 | CCGCCCAC | 8 | Lead |
| 9 | SRE | 4784-4791 | CTCCCCAC | 8 | Complement |
| 10 | SRE | 4802-4809 | CAGCCCAC | 8 | Complement |
| 11 | SRE | 4970-4977 | CACCTCAC | 8 | Complement |
| 12 | SRE | 6487-6494 | CAGCCTAC | 8 | Complement |
| 13 | SRE | 6565-6572 | CACCCAAC | 8 | Lead |
| 14 | SRE | 6727-6734 | CACCCTCA | 8 | Lead |
| 15 | SRE | 7041-7048 | CACCCAAC | 8 | Complement |
| 16 | SRE | 8059-8066 | CAGCCCTC | 8 | Lead |
| 1 | ROR (retinoic acid receptor related) | 166-172 | AGGGTCA | 7 | Complement |
| 2 | ROR (retinoic acid receptor related) | 166-173 | AAGGGTCA | 8 | Complement |
| 3 | ROR (retinoic acid receptor related) | 263-370 | ATGGGTCA | 7 | Lead |
| 4 | ROR (retinoic acid receptor related) | 264-370 | TGGGTCA | 7 | Lead |
| 5 | ROR (retinoic acid receptor related) | 2218-2225 | TAGGGTCA | 8 | Lead |
| 6 | ROR (retinoic acid receptor related) | 2219-2225 | AGGGTCA | 7 | Lead |
| 7 | ROR (retinoic acid receptor related) | 3643-2649 | TGGGTCA | 7 | Lead |
| 8 | ROR (retinoic acid receptor related) | 6604-6610 | AAGGGTCA | 7 | Complement |
| 1 | SREBP-1 or "E box" | 473-479 | ACACCTG | 7 | Complement |
| 2 | SREBP-1 or "E box" | 536-541 | ACACATG | 7 | Lead |
| 3 | SREBP-1 or "E box" | 537-543 | TCATGTG | 7 | Complement |
| 4 | SREBP-1 or "E box" | 655-661 | TCATGTG | 7 | Complement |
| 5 | SREBP-1 or "E box" | 925-931 | ACACTTG | 7 | Lead |
| 6 | SREBP-1 or "E box" | 967-973 | TCAAGTG | 7 | Lead |
| 7 | SREBP-1 or "E box" | 968-974 | ACAGGTG | 7 | Complement |
| 8 | SREBP-1 or "E box" | 1053-1069 | TCACTTG | 7 | Complement |
| 9 | SREBP-1 or "E box" | 1104-1110 | TCAAGTG | 7 | Lead |
| 10 | SREBP-1 or "E box" | 1105-1111 | TCACTTG | 7 | Complement |
| 11 | SREBP-1 or "E box" | 1561-1567 | TCACTTG | 7 | Lead |

Figure 16A

| | | | | |
|---|---|---|---|---|
| 12 | SREBP-1 or "E box" | 1670-1676 | TCAAATG | Lead |
| 13 | SREBP-1 or "E box" | 1748-1754 | ACAACTG | Lead |
| 14 | SREBP-1 or "E box" | 1749-1755 | ACAAGTG | Complement |
| 15 | SREBP-1 or "E box" | 1852-1858 | TCATGTG | Lead |
| 16 | SREBP-1 or "E box" | 1853-1859 | ACACATG | Complement |
| 17 | SREBP-1 or "E box" | 1899-1905 | ACAAATG | Lead |
| 18 | SREBP-1 or "E box" | 2199-2205 | ACAGCTG | Complement |
| 19 | SREBP-1 or "E box" | 2393-2399 | ACACCTG | Lead |
| 20 | SREBP-1 or "E box" | 2669-2705 | ACACATG | Complement |
| 21 | SREBP-1 or "E box" | 2677-2683 | TCACATG | Lead |
| 22 | SREBP-1 or "E box" | 2740-2746 | ACAACTG | Lead |
| 23 | SREBP-1 or "E box" | 2969-5975 | ACAAATG | Complement |
| 24 | SREBP-1 or "E box" | 2979-2985 | ACACATG | Complement |
| 25 | SREBP-1 or "E box" | 2980-2986 | ACATGTG | Lead |
| 26 | SREBP-1 or "E box" | 2981-2987 | ACACATG | Lead |
| 27 | SREBP-1 or "E box" | 2982-2988 | TCAGGTG | Lead |
| 28 | SREBP-1 or "E box" | 3461-3467 | TCAACTG | Complement |
| 29 | SREBP-1 or "E box" | 3462-2468 | TCAACTG | Lead |
| 30 | SREBP-1 or "E box" | 3547-3553 | ACACATG | Complement |
| 31 | SREBP-1 or "E box" | 3752-3758 | ACACCTG | Lead |
| 32 | SREBP-1 or "E box" | 4226-4232 | TCAGTTG | Complement |
| 33 | SREBP-1 or "E box" | 4582-4588 | TCAGGTG | Lead |
| 34 | SREBP-1 or "E box" | 4588-4594 | ACAAATG | Lead |
| 35 | SREBP-1 or "E box" | 4861-4867 | TCAAACTG | Complement |
| 36 | SREBP-1 or "E box" | 4951-4957 | ACAGTTG | Complement |
| 37 | SREBP-1 or "E box" | 5096-5102 | ACACATG | Lead |
| 38 | SREBP-1 or "E box" | 5912-5918 | ACAGTTG | Lead |
| 39 | SREBP-1 or "E box" | 5913-5919 | TCATTTG | Lead |
| 40 | SREBP-1 or "E box" | 6245-6251 | ACAGGTG | Lead |
| 41 | SREBP-1 or "E box" | 6288-6294 | ACACATG | Complement |
| 42 | SREBP-1 or "E box" | 6623-6629 | ACAACTG | Complement |
| 43 | SREBP-1 or "E box" | 6836-6842 | ACAGGTG | Lead |
| 44 | SREBP-1 or "E box" | 6837-6843 | TCAGGTG | Lead |
| 45 | SREBP-1 or "E box" | 7032-7038 | ACACATG | Complement |
| 46 | SREBP-1 or "E box" | 7069-7075 | ACAGTTG | Complement |
| 47 | SREBP-1 or "E box" | 7101-7107 | TCAAACTG | Lead |
| 48 | SREBP-1 or "E box" | 7138-7144 | ACAGTTG | Complement |
| 49 | SREBP-1 or "E box" | 7139-7145 | TCAACTG | Lead |
| 50 | SREBP-1 or "E box" | 7240-7246 | ACACCTG | Lead |
| 51 | SREBP-1 or "E box" | 7467-7473 | ACAGGTG | Complement |
| 52 | SREBP-1 or "E box" | 7640-7646 | ACACATG | Lead |
| 53 | SREBP-1 or "E box" | 7641-7647 | TCATTTG | Complement |
| 54 | SREBP-1 or "E box" | 7653-7659 | TCAAATG | Lead |
| 55 | SREBP-1 or "E box" | 7654-7660 | ACAGTTG | Complement |
| 56 | SREBP-1 or "E box" | 7735-7741 | TCAACTG | Lead |
| 57 | SREBP-1 or "E box" | 7838-7844 | ACACCTG | Lead |
| 58 | SREBP-1 or "E box" | 7880-7886 | ACAGGTG | Complement |
| 59 | SREBP-1 or "E box" | 8052-8057 | TCATCTG | Lead |
| 60 | SREBP-1 or "E box" | 8052-8058 | TCAGCTG | Complement |

Figure 16B

SEQUENCE LISTING

```
<160> NUMBER OF SEQ ID NOS: 287

<210> SEQ ID NO 1
<211> LENGTH: 2261
<212> TYPE: PRT
<213> ORGANISM: Homo sapiens

<400> SEQUENCE: 1

Met Ala Cys Trp Pro Gln Leu Arg Leu Leu Trp Lys Asn Leu Thr
 1               5                  10                  15

Phe Arg Arg Arg Gln Thr Cys Gln Leu Leu Leu Glu Val Ala Trp Pro
                20                  25                  30

Leu Phe Ile Phe Leu Ile Leu Ile Ser Val Arg Leu Ser Tyr Pro Pro
                35                  40                  45

Tyr Glu Gln His Glu Cys His Phe Pro Asn Lys Ala Met Pro Ser Ala
    50                  55                  60

Gly Thr Leu Pro Trp Val Gln Gly Ile Ile Cys Asn Ala Asn Asn Pro
65                  70                  75                  80

Cys Phe Arg Tyr Pro Thr Pro Gly Glu Ala Pro Gly Val Val Gly Asn
                85                  90                  95

Phe Asn Lys Ser Ile Val Ala Arg Leu Phe Ser Asp Ala Arg Arg Leu
               100                 105                 110

Leu Leu Tyr Ser Gln Lys Asp Thr Ser Met Lys Asp Met Arg Lys Val
               115                 120                 125

Leu Arg Thr Leu Gln Gln Ile Lys Lys Ser Ser Ser Asn Leu Lys Leu
           130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
                180                 185                 190

Ser Leu Cys Asn Gly Ser Lys Ser Glu Glu Met Ile Gln Leu Gly Asp
            195                 200                 205

Gln Glu Val Ser Glu Leu Cys Gly Leu Pro Arg Glu Lys Leu Ala Ala
        210                 215                 220

Ala Glu Arg Val Leu Arg Ser Asn Met Asp Ile Leu Lys Pro Ile Leu
225                 230                 235                 240

Arg Thr Leu Asn Ser Thr Ser Pro Phe Pro Ser Lys Glu Leu Ala Glu
```

-continued

```
                245                 250                 255
Ala Thr Lys Thr Leu Leu His Ser Leu Gly Thr Leu Ala Gln Glu Leu
                260                 265                 270

Phe Ser Met Arg Ser Trp Ser Asp Met Arg Gln Glu Val Met Phe Leu
            275                 280                 285

Thr Asn Val Asn Ser Ser Ser Ser Thr Gln Ile Tyr Gln Ala Val
        290                 295                 300

Ser Arg Ile Val Cys Gly His Pro Glu Gly Gly Leu Lys Ile Lys
305                 310                 315                 320

Ser Leu Asn Trp Tyr Glu Asp Asn Asn Tyr Lys Ala Leu Phe Gly Gly
                325                 330                 335

Asn Gly Thr Glu Glu Asp Ala Glu Thr Phe Tyr Asp Asn Ser Thr Thr
                340                 345                 350

Pro Tyr Cys Asn Asp Leu Met Lys Asn Leu Glu Ser Ser Pro Leu Ser
            355                 360                 365

Arg Ile Ile Trp Lys Ala Lys Pro Leu Leu Val Gly Lys Ile Leu
    370                 375                 380

Tyr Thr Pro Asp Thr Pro Ala Thr Arg Gln Val Met Ala Glu Val Asn
385                 390                 395                 400

Lys Thr Phe Gln Glu Leu Ala Val Phe His Asp Leu Glu Gly Met Trp
                405                 410                 415

Glu Glu Leu Ser Pro Lys Ile Trp Thr Phe Met Glu Asn Ser Gln Glu
                420                 425                 430

Met Asp Leu Val Arg Met Leu Leu Asp Ser Arg Asp Asn Asp His Phe
            435                 440                 445

Trp Glu Gln Gln Leu Asp Gly Leu Asp Trp Thr Ala Gln Asp Ile Val
    450                 455                 460

Ala Phe Leu Ala Lys His Pro Glu Asp Val Gln Ser Ser Asn Gly Ser
465                 470                 475                 480

Val Tyr Thr Trp Arg Glu Ala Phe Asn Glu Thr Asn Gln Ala Ile Arg
                485                 490                 495

Thr Ile Ser Arg Phe Met Glu Cys Val Asn Leu Asn Lys Leu Glu Pro
            500                 505                 510

Ile Ala Thr Glu Val Trp Leu Ile Asn Lys Ser Met Glu Leu Leu Asp
    515                 520                 525

Glu Arg Lys Phe Trp Ala Gly Ile Val Phe Thr Gly Ile Thr Pro Gly
            530                 535                 540

Ser Ile Glu Leu Pro His His Val Lys Tyr Lys Ile Arg Met Asp Ile
545                 550                 555                 560

Asp Asn Val Glu Arg Thr Asn Lys Ile Lys Asp Gly Tyr Trp Asp Pro
                565                 570                 575

Gly Pro Arg Ala Asp Pro Phe Glu Asp Met Arg Tyr Val Trp Gly Gly
            580                 585                 590

Phe Ala Tyr Leu Gln Asp Val Val Glu Gln Ala Ile Ile Arg Val Leu
        595                 600                 605

Thr Gly Thr Glu Lys Lys Thr Gly Val Tyr Met Gln Gln Met Pro Tyr
    610                 615                 620

Pro Cys Tyr Val Asp Asp Ile Phe Leu Arg Val Met Ser Arg Ser Met
625                 630                 635                 640

Pro Leu Phe Met Thr Leu Ala Trp Ile Tyr Ser Val Ala Val Ile Ile
            645                 650                 655

Lys Gly Ile Val Tyr Glu Lys Glu Ala Arg Leu Lys Glu Thr Met Arg
                660                 665                 670
```

-continued

```
Ile Met Gly Leu Asp Asn Ser Ile Leu Trp Phe Ser Trp Phe Ile Ser
            675                 680                 685

Ser Leu Ile Pro Leu Leu Val Ser Ala Gly Leu Leu Val Ile Leu
        690                 695                 700

Lys Leu Gly Asn Leu Leu Pro Tyr Ser Asp Pro Ser Val Val Phe Val
705                 710                 715                 720

Phe Leu Ser Val Phe Ala Val Val Thr Ile Leu Gln Cys Phe Leu Ile
                725                 730                 735

Ser Thr Leu Phe Ser Arg Ala Asn Leu Ala Ala Ala Cys Gly Gly Ile
            740                 745                 750

Ile Tyr Phe Thr Leu Tyr Leu Pro Tyr Val Leu Cys Val Ala Trp Gln
        755                 760                 765

Asp Tyr Val Gly Phe Thr Leu Lys Ile Phe Ala Ser Leu Leu Ser Pro
770                 775                 780

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
                805                 810                 815

Asp Gly Phe Asn Leu Thr Thr Ser Val Ser Met Met Leu Phe Asp Thr
            820                 825                 830

Phe Leu Tyr Gly Val Met Thr Trp Tyr Ile Glu Ala Val Phe Pro Gly
        835                 840                 845

Gln Tyr Gly Ile Pro Arg Pro Trp Tyr Phe Pro Cys Thr Lys Ser Tyr
850                 855                 860

Trp Phe Gly Glu Glu Ser Asp Glu Lys Ser His Pro Gly Ser Asn Gln
865                 870                 875                 880

Lys Arg Ile Ser Glu Ile Cys Met Glu Glu Pro Thr His Leu Lys
                885                 890                 895

Leu Gly Val Ser Ile Gln Asn Leu Val Lys Val Tyr Arg Asp Gly Met
            900                 905                 910

Lys Val Ala Val Asp Gly Leu Ala Leu Asn Phe Tyr Glu Gly Gln Ile
        915                 920                 925

Thr Ser Phe Leu Gly His Asn Gly Ala Gly Lys Thr Thr Met Ser
930                 935                 940

Ile Leu Thr Gly Leu Phe Pro Pro Thr Ser Gly Thr Ala Tyr Ile Leu
945                 950                 955                 960

Gly Lys Asp Ile Arg Ser Glu Met Ser Thr Ile Arg Gln Asn Leu Gly
                965                 970                 975

Val Cys Pro Gln His Asn Val Leu Phe Asp Met Leu Thr Val Glu Glu
            980                 985                 990

His Ile Trp Phe Tyr Ala Arg Leu Lys Gly Leu Ser Glu Lys His Val
        995                 1000                1005

Lys Ala Glu Met Glu Gln Met Ala Leu Asp Val Gly Leu Pro Ser Ser
        1010                1015                1020

Lys Leu Lys Ser Lys Thr Ser Gln Leu Ser Gly Gly Met Gln Arg Lys
1025                1030                1035                1040

Leu Ser Val Ala Leu Ala Phe Val Gly Gly Ser Lys Val Val Ile Leu
                1045                1050                1055

Asp Glu Pro Thr Ala Gly Val Asp Pro Tyr Ser Arg Arg Gly Ile Trp
            1060                1065                1070

Glu Leu Leu Leu Lys Tyr Arg Gln Gly Arg Thr Ile Ile Leu Ser Thr
        1075                1080                1085
```

```
His His Met Asp Glu Ala Asp Val Leu Gly Asp Arg Ile Ala Ile Ile
        1090                1095                1100

Ser His Gly Lys Leu Cys Cys Val Gly Ser Ser Leu Phe Leu Lys Asn
1105                1110                1115                1120

Gln Leu Gly Thr Gly Tyr Tyr Leu Thr Leu Val Lys Lys Asp Val Glu
            1125                1130                1135

Ser Ser Leu Ser Ser Cys Arg Asn Ser Ser Ser Thr Val Ser Tyr Leu
            1140                1145                1150

Lys Lys Glu Asp Ser Val Ser Gln Ser Ser Ser Asp Ala Gly Leu Gly
            1155                1160                1165

Ser Asp His Glu Ser Asp Thr Leu Thr Ile Asp Val Ser Ala Ile Ser
        1170                1175                1180

Asn Leu Ile Arg Lys His Val Ser Glu Ala Arg Leu Val Glu Asp Ile
1185                1190                1195                1200

Gly His Glu Leu Thr Tyr Val Leu Pro Tyr Glu Ala Ala Lys Glu Gly
            1205                1210                1215

Ala Phe Val Glu Leu Phe His Glu Ile Asp Asp Arg Leu Ser Asp Leu
            1220                1225                1230

Gly Ile Ser Ser Tyr Gly Ile Ser Glu Thr Thr Leu Glu Glu Ile Phe
        1235                1240                1245

Leu Lys Val Ala Glu Glu Ser Gly Val Asp Ala Glu Thr Ser Asp Gly
        1250                1255                1260

Thr Leu Pro Ala Arg Arg Asn Arg Arg Ala Phe Gly Asp Lys Gln Ser
1265                1270                1275                1280

Cys Leu Arg Pro Phe Thr Glu Asp Asp Ala Ala Asp Pro Asn Asp Ser
            1285                1290                1295

Asp Ile Asp Pro Glu Ser Arg Gly Thr Asp Leu Leu Ser Gly Met Asp
        1300                1305                1310

Gly Lys Gly Ser Tyr Gln Val Lys Gly Trp Lys Leu Thr Gln Gln Gln
            1315                1320                1325

Phe Val Ala Leu Leu Trp Lys Arg Leu Leu Ile Ala Arg Arg Ser Arg
        1330                1335                1340

Lys Gly Phe Phe Ala Gln Ile Val Leu Pro Ala Val Phe Val Cys Ile
1345                1350                1355                1360

Ala Leu Val Phe Ser Leu Ile Val Pro Pro Phe Gly Lys Tyr Pro Ser
            1365                1370                1375

Leu Glu Leu Gln Pro Trp Met Tyr Asn Glu Gln Tyr Thr Phe Val Ser
            1380                1385                1390

Asn Asp Ala Pro Glu Asp Thr Gly Thr Leu Glu Leu Leu Asn Ala Leu
            1395                1400                1405

Thr Lys Asp Pro Gly Phe Gly Thr Arg Cys Met Glu Gly Asn Pro Ile
        1410                1415                1420

Pro Asp Thr Pro Cys Gln Ala Gly Glu Glu Glu Trp Thr Thr Ala Pro
1425                1430                1435                1440

Val Pro Gln Thr Ile Met Asp Leu Phe Gln Asn Gly Asn Trp Thr Met
            1445                1450                1455

Gln Asn Pro Ser Pro Ala Cys Gln Cys Ser Ser Asp Lys Ile Lys Lys
            1460                1465                1470

Met Leu Pro Val Cys Pro Pro Gly Ala Gly Gly Leu Pro Pro Pro Gln
        1475                1480                1485

Arg Lys Gln Asn Thr Ala Asp Ile Leu Gln Asp Leu Thr Gly Arg Asn
        1490                1495                1500

Ile Ser Asp Tyr Leu Val Lys Thr Tyr Val Gln Ile Ile Ala Lys Ser
```

-continued

```
             1505                1510                1515                1520
Leu Lys Asn Lys Ile Trp Val Asn Glu Phe Arg Tyr Gly Gly Phe Ser
                1525                1530                1535
Leu Gly Val Ser Asn Thr Gln Ala Leu Pro Pro Ser Gln Glu Val Asn
                1540                1545                1550
Asp Ala Ile Lys Gln Met Lys Lys His Leu Lys Leu Ala Lys Asp Ser
                1555                1560                1565
Ser Ala Asp Arg Phe Leu Asn Ser Leu Gly Arg Phe Met Thr Gly Leu
                1570            1575                1580
Asp Thr Arg Asn Asn Val Lys Val Trp Phe Asn Asn Lys Gly Trp His
1585                1590                1595                1600
Ala Ile Ser Ser Phe Leu Asn Val Ile Asn Asn Ala Ile Leu Arg Ala
                1605                1610                1615
Asn Leu Gln Lys Gly Glu Asn Pro Ser His Tyr Gly Ile Thr Ala Phe
                1620                1625                1630
Asn His Pro Leu Asn Leu Thr Lys Gln Gln Leu Ser Glu Val Ala Leu
                1635                1640                1645
Met Thr Thr Ser Val Asp Val Leu Val Ser Ile Cys Val Ile Phe Ala
                1650                1655                1660
Met Ser Phe Val Pro Ala Ser Phe Val Val Phe Leu Ile Gln Glu Arg
1665                1670                1675                1680
Val Ser Lys Ala Lys His Leu Gln Phe Ile Ser Gly Val Lys Pro Val
                1685                1690                1695
Ile Tyr Trp Leu Ser Asn Phe Val Trp Asp Met Cys Asn Tyr Val Val
                1700                1705                1710
Pro Ala Thr Leu Val Ile Ile Ile Phe Ile Cys Phe Gln Gln Lys Ser
                1715                1720                1725
Tyr Val Ser Ser Thr Asn Leu Pro Val Leu Ala Leu Leu Leu Leu Leu
                1730                1735                1740
Tyr Gly Trp Ser Ile Thr Pro Leu Met Tyr Pro Ala Ser Phe Val Phe
1745                1750                1755                1760
Lys Ile Pro Ser Thr Ala Tyr Val Val Leu Thr Ser Val Asn Leu Phe
                1765                1770                1775
Ile Gly Ile Asn Gly Ser Val Ala Thr Phe Val Leu Glu Leu Phe Thr
                1780                1785                1790
Asp Asn Lys Leu Asn Asn Ile Asn Asp Ile Leu Lys Ser Val Phe Leu
                1795                1800                1805
Ile Phe Pro His Phe Cys Leu Gly Arg Gly Leu Ile Asp Met Val Lys
                1810                1815                1820
Asn Gln Ala Met Ala Asp Ala Leu Glu Arg Phe Gly Glu Asn Arg Phe
1825                1830                1835                1840
Val Ser Pro Leu Ser Trp Asp Leu Val Gly Arg Asn Leu Phe Ala Met
                1845                1850                1855
Ala Val Glu Gly Val Val Phe Phe Leu Ile Thr Val Leu Ile Gln Tyr
                1860                1865                1870
Arg Phe Phe Ile Arg Pro Arg Pro Val Asn Ala Lys Leu Ser Pro Leu
                1875                1880                1885
Asn Asp Glu Asp Glu Asp Val Arg Arg Glu Arg Gln Arg Ile Leu Asp
                1890                1895                1900
Gly Gly Gly Gln Asn Asp Ile Leu Glu Ile Lys Glu Leu Thr Lys Ile
1905                1910                1915                1920
Tyr Arg Arg Lys Arg Lys Pro Ala Val Asp Arg Ile Cys Val Gly Ile
                1925                1930                1935
```

Pro Pro Gly Glu Cys Phe Gly Leu Leu Gly Val Asn Gly Ala Gly Lys
         1940                1945                1950

Ser Ser Thr Phe Lys Met Leu Thr Gly Asp Thr Thr Val Thr Arg Gly
        1955                1960                1965

Asp Ala Phe Leu Asn Lys Asn Ser Ile Leu Ser Asn Ile His Glu Val
    1970                1975                1980

His Gln Asn Met Gly Tyr Cys Pro Gln Phe Asp Ala Ile Thr Glu Leu
1985                1990                1995                2000

Leu Thr Gly Arg Glu His Val Glu Phe Phe Ala Leu Leu Arg Gly Val
            2005                2010                2015

Pro Glu Lys Glu Val Gly Lys Val Gly Glu Trp Ala Ile Arg Lys Leu
            2020                2025                2030

Gly Leu Val Lys Tyr Gly Glu Lys Tyr Ala Gly Asn Tyr Ser Gly Gly
            2035                2040                2045

Asn Lys Arg Lys Leu Ser Thr Ala Met Ala Leu Ile Gly Gly Pro Pro
    2050                2055                2060

Val Val Phe Leu Asp Glu Pro Thr Thr Gly Met Asp Pro Lys Ala Arg
2065                2070                2075                2080

Arg Phe Leu Trp Asn Cys Ala Leu Ser Val Val Lys Glu Gly Arg Ser
            2085                2090                2095

Val Val Leu Thr Ser His Ser Met Glu Glu Cys Glu Ala Leu Cys Thr
            2100                2105                2110

Arg Met Ala Ile Met Val Asn Gly Arg Phe Arg Cys Leu Gly Ser Val
            2115                2120                2125

Gln His Leu Lys Asn Arg Phe Gly Asp Gly Tyr Thr Ile Val Val Arg
    2130                2135                2140

Ile Ala Gly Ser Asn Pro Asp Leu Lys Pro Val Gln Asp Phe Phe Gly
2145                2150                2155                2160

Leu Ala Phe Pro Gly Ser Val Leu Lys Glu Lys His Arg Asn Met Leu
            2165                2170                2175

Gln Tyr Gln Leu Pro Ser Ser Leu Ser Ser Leu Ala Arg Ile Phe Ser
    2180                2185                2190

Ile Leu Ser Gln Ser Lys Lys Arg Leu His Ile Glu Asp Tyr Ser Val
    2195                2200                2205

Ser Gln Thr Thr Leu Asp Gln Val Phe Val Asn Phe Ala Lys Asp Gln
    2210                2215                2220

Ser Asp Asp Asp His Leu Lys Asp Leu Ser Leu His Lys Asn Gln Thr
2225                2230                2235                2240

Val Val Asp Val Ala Val Leu Thr Ser Phe Leu Gln Asp Glu Lys Val
            2245                2250                2255

Lys Glu Ser Tyr Val
        2260

<210> SEQ ID NO 2
<211> LENGTH: 7860
<212> TYPE: DNA
<213> ORGANISM: Homo sapiens

<400> SEQUENCE: 2
gtccctgctg tgagctctgg ccgctgcctt ccagggctcc cgagccacac gctgggggtg      60
ctggctgagg gaacatggct tgttggcctc agctgaggtt gctgctgtgg aagaacctca     120
ctttcagaag aagacaaaca tgtcagctgt tactggaagt ggcctggcct ctatttatct     180
tcctgatcct gatctctgtt cggctgagct acccacccta tgaacaacat gaatgccatt     240

```
ttccaaataa agccatgccc tctgcaggaa cacttccttg ggttcagggg attatctgta    300
atgccaacaa ccctgtttc cgttacccga ctcctggga ggctcccgga gttgttggaa     360
actttaacaa atccattgtg gctcgcctgt tctcagatgc tcggaggctt cttttataca   420
gccagaaaga caccagcatg aaggacatgc gcaaagttct gagaacatta cagcagatca   480
agaaatccag ctcaaacttg aagcttcaag atttcctggt ggacaatgaa accttctctg   540
ggttcctgta tcacaacctc tctctcccaa agtctactgt ggacaagatg ctgagggctg   600
atgtcattct ccacaaggta ttttgcaag gctaccagtt acatttgaca agtctgtgca    660
atggatcaaa atcagaagag atgattcaac ttggtgacca agaagtttct gagctttgtg   720
gcctaccaag ggagaaactg gctgcagcag agcgagtact tcgttccaac atggacatcc   780
tgaagccaat cctgagaaca ctaaaactcta catctcctt cccgagcaag gagctggctg   840
aagccacaaa aacattgctg catagtcttg ggactctggc ccaggagctg ttcagcatga   900
gaagctggag tgacatgcga caggaggtga tgtttctgac caatgtgaac agctccagct   960
cctccaccca aatctaccag gctgtgtctc gtattgtctg cgggcatccc gagggagggg  1020
ggctgaagat caagtctctc aactggtatg aggacaacaa ctacaaagcc ctctttggag  1080
gcaatggcac tgaggaagat gctgaaacct tctatgacaa ctctacaact ccttactgca  1140
atgatttgat gaagaatttg gagtctagtc ctctttcccg cattatctgg aaagctctga  1200
agccgctgct cgttgggaag atcctgtata cacctgacac tccagccaca aggcaggtca  1260
tggctgaggt gaacaagacc ttccaggaac tggctgtgtt ccatgatctg gaaggcatgt  1320
gggaggaact cagccccaag atctggacct tcatggagaa cagccaagaa atggaccttg  1380
tccgatgct gttggacagc agggacaatg accactttg gaacagcag ttggatggct     1440
tagattggac agcccaagac atcgtggcgt ttttggccaa gcacccagag gatgtccagt  1500
ccagtaatgg ttctgtgtac acctggagag aagctttcaa cgagactaac caggcaatcc  1560
ggaccatatc tcgcttcatg gagtgtgtca acctgaacaa gctagaaccc atagcaacag  1620
aagtctggct catcaacaag tccatggagc tgctggatga gaggaagttc tgggctggta  1680
ttgtgttcac tggaattact ccaggcagca ttgagctgcc ccatcatgtc aagtacaaga  1740
tccgaatgga cattgacaat gtggagagga caaataaaat caaggatggg tactgggacc  1800
ctggtcctcg agctgacccc tttgaggaca tgcggtacgt ctgggggggc ttcgcctact  1860
tgcaggatgt ggtggagcag gcaatcatca gggtgctgac gggcaccgag aagaaaactg  1920
gtgtctatat gcaacagatg ccctatccct gttacgttga tgacatctt ctgcgggtga   1980
tgagccggtc aatgccctc ttcatgacgc tggcctggat ttactcagtg ctgtgatca    2040
tcaagggcat cgtgtatgag aaggaggcac ggctgaaaga gaccatgcgg atcatgggcc  2100
tggacaacag catcctctgg tttagctggt tcattagtag cctcattcct cttcttgtga  2160
gcgctggcct gctagtggtc atcctgaagt taggaaacct gctgcctac agtgatccca   2220
gcgtggtgtt tgtcttcctg tccgtgtttg ctgtggtgac aatcctgcag tgcttcctga  2280
ttagcacact cttctccaga gccaacctgg cagcagcctg tggggcatc atctacttca   2340
cgctgtacct gccctacgtc ctgtgtgtgg catggcagga ctacgtgggc ttcacactca  2400
agatcttcgc tagcctgctg tctcctgtgg cttttgggtt tggctgtgag tactttgccc  2460
ttttgagga gcagggcatt ggagtgcagt gggacaacct gtttgagagt cctgtggagg   2520
aagatggctt caatctcacc acttcggtct ccatgatgct gtttgacacc ttcctctatg  2580
```

```
gggtgatgac ctggtacatt gaggctgtct ttccaggcca gtacggaatt cccaggccct    2640
ggtattttcc ttgcaccaag tcctactggt ttggcgagga aagtgatgag aagagccacc    2700
ctggttccaa ccagaagaga atatcagaaa tctgcatgga ggaggaaccc acccacttga    2760
agctgggcgt gtccattcag aacctggtaa aagtctaccg agatgggatg aaggtggctg    2820
tcgatggcct ggcactgaat ttttatgagg ccagatcac ctccttcctg gccacaatg      2880 gagcggggaa gacgaccacc atgtcaatcc tgaccgggtt gttcccccg acctcgggca     2940 ccgcctacat cctgggaaaa gacattcgct ctgagatgag caccatccgg cagaacctgg    3000
gggtctgtcc ccagcataac gtgctgtttg acatgctgac tgtcgaagaa cacatctggt    3060
tctatgcccg cttgaaaggg ctctctgaga agcacgtgaa ggcggagatg gagcagatgg    3120
ccctggatgt tggtttgcca tcaagcaagc tgaaaagcaa acaagccag ctgtcaggtg      3180 gaatgcagag aaagctatct gtggccttgg cctttgtcgg gggatctaag gttgtcattc    3240
tggatgaacc cacagctggt gtggacccct actcccgcag gggaatatgg gagctgctgc    3300
tgaaataccg acaaggccgc accattattc tctctacaca ccacatggat gaagcggacg    3360
tcctggggga caggattgcc atcatctccc atgggaagct gtgctgtgtg ggctcctccc    3420
tgtttctgaa gaaccagctg gaacaggct actacctgac cttggtcaag aaagatgtgg      3480
aatcctccct cagttcctgc agaaacagta gtagcactgt gtcatacctg aaaaaggagg    3540
acagtgtttc tcagagcagt tctgatgctg gcctgggcag cgaccatgag agtgacacgc    3600
tgaccatcga tgtctctgct atctccaacc tcatcaggaa gcatgtgtct gaagcccggc    3660
tggtggaaga catagggcat gagctgacct atgtgctgcc atatgaagct gctaaggagg    3720
gagcctttgt ggaactcttt catgagattg atgaccggct ctcagacctg gcatttctcta   3780 gttatggcat ctcagagacg accctggaag aaatattcct caaggtggcc gaagagagtg    3840
gggtggatgc tgagacctca gatggtacct tgccagcaag acgaaacagg cgggccttcg    3900
gggacaagca gagctgtctt cgcccgttca ctgaagatga tgctgctgat ccaaatgatt    3960
ctgacataga cccagaatcc agagagacag acttgctcag tgggatggat ggcaaagggt    4020
cctaccaggt gaaaggctgg aaacttacac agcaacagtt tgtggccctt ttgtggaaga    4080
gactgctaat tgccgacgg agtcggaaag gattttttgc tcagattgtc ttgccagctg      4140
tgtttgtctg cattgccctt gtgttcagcc tgatcgtgcc accctttggc aagtacccca    4200
gcctggaact tcagccctgg atgtacaacg aacagtacac atttgtcagc aatgatgctc    4260
ctgaggacac gggaaccctg gaactcttaa acgccctcac caaagaccct ggcttcggga    4320
cccgctgtat ggaaggaaac ccaatcccag acacgccctg ccaggcaggg gaggaagagt    4380
ggaccactgc cccagttccc cagaccatca tggacctctt ccagaatggg aactggacaa    4440
tgcagaaccc ttcacctgca tgccagtgta gcagcgacaa aatcaagaag atgctgcctg    4500
tgtgtccccc aggggcaggg gggctgcctc ctccacaaag aaaacaaaac actgcagata    4560
tccttcagga cctgacagga agaaacattt cggattatct ggtgaagacg tatgtgcaga    4620
tcatagccaa aagcttaaag aacaagatct gggtgaatga gtttaggtat ggcggcttt      4680 ccctgggtgt cagtaatact caagcacttc ctccgagtca agaagttaat gatgccatca    4740
aacaaatgaa gaaacaccta agctggcca aggacagttc tgcagatcga tttctcaaca    4800
gcttgggaag atttatgaca ggactggaca ccagaaataa tgtcaaggtg tggttcaata    4860
acaagggctg gcatgcaatc agctctttcc tgaatgtcat caacaatgcc attctccggg    4920
ccaacctgca aaagggagag aaccctagcc attatggaat tactgctttc aatcatcccc    4980
```

```
tgaatctcac caagcagcag ctctcagagg tggctctgat gaccacatca gtggatgtcc    5040
ttgtgtccat ctgtgtcatc tttgcaatgt ccttcgtccc agccagcttt gtcgtattcc    5100
tgatccagga gcgggtcagc aaagcaaaac acctgcagtt catcagtgga gtgaagcctg    5160
tcatctactg gctctctaat tttgtctggg atatgtgcaa ttacgttgtc cctgccacac    5220
tggtcattat catcttcatc tgcttccagc agaagtccta tgtgtcctcc accaatctgc    5280
ctgtgctagc ccttctactt tgctgtatg ggtggtcaat cacacctctc atgtacccag    5340
cctcctttgt gttcaagatc cccagcacag cctatgtggt gctcaccagc gtgaacctct    5400
tcattggcat taatggcagc gtggccacct tgtgctgga gctgttcacc gacaataagc    5460
tgaataatat caatgatatc ctgaagtccg tgttcttgat cttccacat ttttgcctgg     5520
gacgagggct catcgacatg gtgaaaaacc aggcaatggc tgatgccctg aaaggtttg     5580
gggagaatcg ctttgtgtca ccattatctt gggacttggt gggacgaaac ctcttcgcca    5640
tggccgtgga aggggtggtg ttcttcctca ttactgttct gatccagtac agattcttca    5700
tcaggcccag acctgtaaat gcaaagctat ctcctctgaa tgatgaagat gaagatgtga    5760
ggcgggaaag acagagaatt cttgatggtg gaggccagaa tgacatctta gaaatcaagg    5820
agttgacgaa gatatataga aggaagcgga agcctgctgt tgacaggatt tgcgtgggca    5880
ttcctcctgg tgagtgcttt gggctcctgg gagttaatgg ggctggaaaa tcatcaactt    5940
tcaagatgtt aacaggagat accactgtta ccagaggaga tgctttcctt aacaaaaata    6000
gtatcttatc aaacatccat gaagtacatc agaaacatggg ctactgccct cagtttgatg    6060
ccatcacaga gctgttgact gggagagaac acgtggagtt ctttgccctt ttgagaggag    6120
tcccagagaa agaagttggc aaggttggtg agtgggcgat tcggaaactg ggcctcgtga    6180
agtatggaga aaaatatgct ggtaactata gtggaggcaa caaacgcaag ctctctacag    6240
ccatggcttt gatcggcggg cctcctgtgg tgtttctgga tgaacccacc acaggcatgg    6300
atcccaaagc ccggcggttc ttgtggaatt gtgccctaag tgttgtcaag gaggggagat    6360
cagtagtgct tacatctcat agtatggaag aatgtgaagc tctttgcact aggatggcaa    6420
tcatggtcaa tggaaggttc aggtgccttg gcagtgtcca gcatctaaaa ataggttg      6480
gagatggtta tacaatagtt gtacgaatag cagggtccaa cccggacctg aagcctgtcc    6540
aggatttctt tggacttgca tttcctggaa gtgttctaaa agagaaacac cggaacatgc    6600
tacaatacca gcttccatct tcattatctt ctctggccag gatattcagc atcctctccc    6660
agagcaaaaa gcgactccac atagaagact actctgtttc tcagacaaca cttgaccaag    6720
tatttgtgaa ctttgccaag gaccaaagtg atgatgacca cttaaaagac ctctcattac    6780
acaaaaacca gacagtagtg gacgttgcag ttctcacatc ttttctacag gatgagaaag    6840
tgaaagaaag ctatgtatga agaatcctgt tcatacgggg tggctgaaag taaagaggaa    6900
ctagactttc ctttgcacca tgtgaagtgt tgtggagaaa agagccagaa gttgatgtgg    6960
gaagaagtaa actggatact gtactgatac tattcaatgc aatgcaattc aatgcaatga    7020
aaacaaaatt ccattacagg ggcagtgcct ttgtagccta tgtcttgtat ggctctcaag    7080
tgaaagactt gaatttagtt ttttaccttat acctatgtga aactctatta tggaacccaa    7140
tggacatatg ggttgaact cacactttt ttttttttt tgttcctgtg tattctcatt        7200
ggggttgcaa caataattca tcaagtaatc atggccagcg attattgatc aaaatcaaaa    7260
ggtaatgcac atcctcattc actaagccat gccatgccca ggagactggt ttcccggtga    7320
```

-continued

```
cacatccatt gctggcaatg agtgtgccag agttattagt gccaagtttt tcagaaagtt    7380
tgaagcacca tggtgtgtca tgctcacttt tgtgaaagct gctctgctca gagtctatca    7440
acattgaata tcagttgaca gaatggtgcc atgcgtggct aacatcctgc tttgattccc    7500
tctgataagc tgttctggtg gcagtaacat gcaacaaaaa tgtgggtgtc tccaggcacg    7560
ggaaacttgg ttccattgtt atattgtcct atgcttcgag ccatgggtct acagggtcat    7620
ccttatgaga ctcttaaata tacttagatc ctggtaagag gcaaagaatc aacagccaaa    7680
ctgctggggc tgcaactgct gaagccaggg catgggatta agagattgt gcgttcaaac     7740 ctagggaagc ctgtgcccat ttgtcctgac tgtctgctaa catggtacac tgcatctcaa    7800
gatgtttatc tgacacaagt gtattatttc tggctttttg aattaatcta gaaaatgaaa    7860
```

<210> SEQ ID NO 3
<211> LENGTH: 22
<212> TYPE: DNA
<213> ORGANISM: Homo sapiens

<400> SEQUENCE: 3
gcagagggca tggctttatt tg                                              22

<210> SEQ ID NO 4
<211> LENGTH: 24
<212> TYPE: DNA
<213> ORGANISM: Homo sapiens

<400> SEQUENCE: 4
ctgccaggca ggggaggaag agtg                                            24

<210> SEQ ID NO 5
<211> LENGTH: 23
<212> TYPE: DNA
<213> ORGANISM: Homo sapiens

<400> SEQUENCE: 5
gaaagtgact cacttgtgga gga                                             23

<210> SEQ ID NO 6
<211> LENGTH: 20
<212> TYPE: DNA
<213> ORGANISM: Homo sapiens

<400> SEQUENCE: 6
aaagggcttt ggtaagggta                                                 20

<210> SEQ ID NO 7
<211> LENGTH: 20
<212> TYPE: DNA
<213> ORGANISM: Homo sapiens

<400> SEQUENCE: 7
catgcacatg cacacacata                                                 20

<210> SEQ ID NO 8
<211> LENGTH: 27
<212> TYPE: DNA
<213> ORGANISM: Homo sapiens

<400> SEQUENCE: 8
ctttctgcgg gtgatgagcc ggtcaat                                         27

```
<210> SEQ ID NO 9
<211> LENGTH: 20
<212> TYPE: DNA
<213> ORGANISM: Homo sapiens

<400> SEQUENCE: 9
ccttagcccg tgttgagcta                                                   20

<210> SEQ ID NO 10
<211> LENGTH: 26
<212> TYPE: DNA
<213> ORGANISM: Homo sapiens

<400> SEQUENCE: 10
cctgtaaatg caaagctatc tcctct                                            26

<210> SEQ ID NO 11
<211> LENGTH: 26
<212> TYPE: DNA
<213> ORGANISM: Homo sapiens

<400> SEQUENCE: 11
cgtcaactcc ttgatttcta agatgt                                            26

<210> SEQ ID NO 12
<211> LENGTH: 20
<212> TYPE: DNA
<213> ORGANISM: Homo sapiens

<400> SEQUENCE: 12
gggttcccag ggttcagtat                                                   20

<210> SEQ ID NO 13
<211> LENGTH: 21
<212> TYPE: DNA
<213> ORGANISM: Homo sapiens

<400> SEQUENCE: 13
gatcaggaat tcaagcacca a                                                 21

<210> SEQ ID NO 14
<211> LENGTH: 10545
<212> TYPE: DNA
<213> ORGANISM: Homo sapiens
<220> FEATURE:
<221> NAME/KEY: misc_feature
<222> LOCATION: (1)...(10545)
<223> OTHER INFORMATION: n = a, t, c, or g

<400> SEQUENCE: 14
acctcttata gaatgataga attcctctgg aatgattgga taacttcatt tcatccttga        60
cttttacctt ggaggatttc ttaccccttt tggcttctca aatttgacta ttaaaatgtt       120
gcctttaaaa ataggaacac agtttcaggg gggagtacca gcccatgacc cttctgcaag       180 gcccctaac tcaaggtagt ttccctggaa ctgtggttta tggaatgttt caggagtgtg        240
aggaggtata atttaaggct gtcctagcaa ggataccctt aaggatagag ggcccagtag       300
catctggagg ccagaaaagt taaactgagg cagtcagatt agcttcaggc tcaattaagc       360
tgatgggtca gcctgggaga aattgcagga tgactctcaa tatcccctcc caccccaca        420 gcagccacga tctgtctgtc tttaatcatg ggtgcagtga acctgttctt tccaggtgtc       480
ttggccttca gtaaccttgt tagggcttgtc cctgaacgtg gctaccgatc caaagacaca      540
```

```
tgatcagaga ggcaattaga gaacagacct tttccaaagc aagcatgttc tgttgggctt    600
agaagtttca tgtcctaata ttataggacc ctgtgcatct ctctggagat gaggcacatg    660
agtcatatct gtgattcttg cttttgtgtc aacatctcat gaataggcaa tcagagcttt    720
ggcaccaatg tattttcagt tcatatctga tgtagttaaa tccacctcct gctttgtagt    780
ttactggcaa gctgttttg atataagaca tctagaacac tgtaaatata taacattttt    840
atttgtctat tatacctcaa ttacgaaaaa gacatctaga agcaacctca tcaagagaga    900
tactgaggcc gggcatggta gctcacactt gcaatcccat tactttggga ggctgaggca    960
ggtagatcac ttgaggtcaa gagtttgaaa ccagcctggc aacatgttg aaaccctgtc    1020 tctattaaaa atacaaaaaa gttagctggg cttggtggtg gcacctgta atcccagcta    1080 ctccggaggc tgaggcagga gaatcacttg aacctgggag gcagaggttg cagtgagctg    1140
agatcacacc actgcactcc aacctgggca ccagagtgag attacatcta aaaaataaaa    1200
taaagtaata aaaagagag atattgatag ctgttgttgg aaatttcaac ttccatctca    1260
cttctggtaa cttttttggaa gtttgttgaa caaagtggaa tacacgcaca tacacacaca    1320
cacatactct cttgtttgtt taaggtttaa tgaaatagct gtcatataat cactgttttt    1380
gaaagaggag aattagttgc tatctgtaca ttttgggtat gtgaactatt tggatagaac    1440
tctgagaaat gcattcagaa caacaaacaa aatcatagga gaaatagcta agtgggaagg    1500
ggcataaaag agttgttgaa aaagttattt cttgagaaac cagctctaat gctaggcaag    1560
tcacttgctt tgggggaggc ctcagcttct ctgtctataa gattgcagca ggggtgtagt    1620
gggaatgagt cttcaacatt ccaagagatt ttatctacta atacgacagt caaatggagc    1680
atgactttgt ggaagcctct cctcttccac ccagaggggc caatttctct gtcccagtga    1740
gatgttgaca cttgtatgat ccctgcttgg agacttccct cttctggaac ctgccctggc    1800
tcaggcatga gggctgactg tcacccttcg ataggagccc agcactaaag ctcatgtgtt    1860
ggcagtgttc ttgcgggaag gaaaaagacc agccagccca tttgttactg cacaagcaaa    1920
cagcttctgg tagctgtaca gatacatgca ctttcttttcc tcactgtgtt tccatagaca    1980
gatttagtgc tgtagaagag tagagggcag tcacgggaag gagttcctgt ttttcttttg    2040
gctatgccaa atggggaaaa atcctcctat cttgtctttt tagtgtcatc ctctctcccc    2100
ttttcttctt ctttataatt ctcatctctc atctctcctg gaaatgtgca tgtcaagttc    2160
aaaagggcac aatgttttgg tgaggaagag gtgggagaac acgtgccagg tgctaactag    2220
ggtcatcatt tccccttca cagccagctt cctgtgaatg tgtgtgtgtg tgtgtgtgtg    2280
tgtgtgtgtg tgtgtgtgtg tgtgtatttc ttttgccagc atcactgaat ctgtctgctg    2340
tctggtattc caggttttgg tttagggaaa agtaaaagta atttttataat cccagctgtc    2400 atttaagcca ccccttttgtg ggtagcatat ggtccactct ctcagttcat tgtcctaaag    2460
atgcttcatc agaaaggaat aacttccacc ccgttactct ctgtcccctt actctgcttt    2520 attttcttc gtcaatccta ccaccaccac ccactgtttg aacaacccac tattatttgt    2580
ctgtttccca tccctggtag aataggagcc ccatgaatga aggaaactttg cttctgttgt    2640 tcaccactga atctctaagg tatggaacac acctggcatg tgataggcac tcgataaata    2700
tttgttgtgg ctcatgggca ccttgcagag ttaaggctgc agttgtttgt ggaatttata    2760
agtggtaatg aatatttatc tactattcct cttccaaggc gatcacacaa taatcaggct    2820
ttacactatc cagttcttag gtcttccaag ttatgacttg tgaggtatgt taattatgat    2880
aatagaaggc agtttatttg gttcagattt attgatgtgt aatttaccac agtaagactt    2940
```

```
cccctttaca aaagtatgat gagttttgac aaatggatac acatgtgtat ctaccactgc   3000
catgctcctt ttcagtctgt cgtcccctcc acccatgacc actggtcacc actgcagtga   3060
tttctgtccc cttcatttca cctttttcag aatgtcatat aaatggaatc atgcagtatg   3120
tagttttttg tgtctggctt attttttctta gcattaggct tttgggattc atccaggttg   3180
tcgcatgtaa cagtagctta ttcctttta tggctgagta agtgtcccag ttttatttat   3240
atatttattt atgaggaggt gtctcactct gtcacccagg ctggagtgcg gtagcgcgat   3300
ctcagctcac tgcaacctcc gcctcccagg ttcaagcaat tctcctgcct cctgagtagc   3360
tgggattaca ggcacccacc gccacgccca actaattttt atattttttag tagagatggg   3420 gtttcaccat gttggccagg ctgatctcaa actcttgacc tcaggtgatc cgcccacctc   3480
tggctcccaa agtgctagga ttacaggcat gagccactgt gcccagcccc agttttattt   3540
attcaccagt tgatggtctt ttcgacaact aattgtttcc agttttggc tattctgtat   3600 aaggcttcta taaatattca caaataccta ggatgggatg actgggtcat ataatagtac   3660
tgtataacct tagcagaaac tgtcaaacta tttttccaaag tggctcttcc attttacaat   3720
tccacagtgt attgagtccc agtgtctcca tacacatgct agcacttta atatttaatt   3780 tagtgggtat gtaatgatat ctcattgtgg ttttaatttg catttctctg cagctaatga   3840
tgagtgtttc tgcttatttg ggaaggtttt aatttagcag tctgttgtat tctgtagata   3900
ttaataactt caaatatca gtggcatttg cagttaaaat ttccttaaaa aattggccaa   3960
aggtttccag cagtcacttc tgccatgccc aaactgtatg aaacaaggct gaggtgtgga   4020
gattgtcaca ttttggcaag gagtgatcca cttgggtgac tgatgagacc cagagagcgt   4080
acgcctcggg cttgagggtg aggacgggcg ggaagtcgac tgcatggccc tgctggcctt   4140
gggaggctgc ccagtcctta gctaaagctg gcagttatgg gaaacagact tagattctat   4200 tacgttttc aggatgtccc aggagtcacc tgggaagctc agcagtcctt tgtgactttc   4260
aagcatatgg tagaagctgc tgaacacaga gctccctctt tggggataat tgcccaaat   4320 catttaatca ggcttgagaa atgagttacc acaggtccag gagtgctgcc acccttgaat   4380
tctgacaccc tatttctcct atccgtctct taattaatta agcagacatc cccaagtgct   4440
tacgacaagc caggacccctt ttgcatacta aggaaaacag ggatgaagga aacagaaatg   4500
gtctctgctc tgactcagaa ggtagaaatc ctctttccca gccaagtctt cctagggagc   4560
acgtaggaag ggctctgaac ccacgtgtca gttgcagggg aggatatcag gaaaggacat   4620
tgaagaagtg gagacctaag tttgagacct aggcattagc caggctagca gtgcttgaaa   4680
aagtgtctta ggacaagaga actcaccagt gaagtcccag tggtaggaga gcgtgcagca   4740
tattctgagc ctgtatacac atctccaggg cattgcttag caggtgggga gtggcaagag   4800
agtaggctgg agtcacagaa gggaggccag gtagaccttg gtgagcactg gactctatgt   4860
tcaggtgctg aggagctggc aaaaggtttt aagtcgggga gaggcatgtt cagatatttg   4920
gtctagctga gtaactttgg gtgctctgtg acaaatggtt gggagaccag tgaggtggca   4980
gttgcggtca tctaggagca ggatcagagt ggcctattga ctgggatgac tgtgaagtgg   5040 gatccttttcc agccagtaac tggaaatgtg tatgagggca gaagtgagtg tactgcattt   5100
gaaacattga gaaatctagt acatagtact gtctctttta tatcttttttt ttttttttt   5160 ttgattttgg tttgtttgtt cactaacttg gaaaactgat gtggaaatgt ccctttggct   5220
tcagttacct gagcagaagg ggccgggcat tgccaaactc tcctcttagg acagaattgc   5280
```

```
tcccagtatt gatcattgtg ttctgagttg ggggagcaaa ttgtgcagga ggccaggtca    5340
gtgccaaggt gggtgggagg aattggagca ggaagcttgc ctaagtgtgc ccagcaaagc    5400
cacggtagaa ctttctactg tggctctatg ctacttctta gcaaccttct ccatgtgctt    5460
cctggagagt ccttggagtc agaacctttt tcttgaaacc cagacacttt acttccaaga    5520
aaatgctgtc caagaaaact catccttccc ttcttctcat gaacgttgtg tagaggtgtg    5580
tcttctcttc ctttgagctt ttccactcag ggtttagggg aggtgatatt ctatatttgg    5640
gtttggctct gggtactgca acactaggct attaagattt catccttact gctttgcccc    5700
tcctatcttt ccagaaaccc acaatggatt tgctagaaat aatggaacgt cctgtttgga    5760
caggatataa ccatttctca gctagaggat attgttggaa tgaagaaaga taaatgggga    5820
gaagggaact cacattgctt tggcacttaa attaagccat gtactgtgtt gggaaattat    5880
ttatattatc tcgttgaatc cacagtagaa cacagttgaa caccatacaa ggtaagtatt    5940
gtcatcctta ttttaccatg aggaaattga tgcttagaga gcataaagcc ttggccaggg    6000
gcacatagtt gggaagccgg ggctaattca tgcctgggct ctttctgata gttttccttt    6060
tttaattgtc ccctcctcat tgttaccttg gggatttcaa gagattcatg tagcttctaa    6120
atcaacgaac tgattcctgg agagcagctt ctgtatgaga aaaatctagc taattattta    6180
tttcagtgtc tctggaatgc aagctctgtc ctgagccact tagaaaacaa tttgggatga    6240
caagcatgtg tctcacaatg ctgctctggt tgccagtgct gtgctgccag ttgtcatctt    6300
tgaacaaact gatgcagtgc tggtttaact cttcctcttt ttggagtaag aaactttgga    6360
ggcctgtgtc cttctagaag tttgctgagc aaatggtaag gaaaagaaat aggtcctaag    6420
gcttgactat ttcagagaat ttcttgattt attggactgt caatgaatga attggaatac    6480
atagtggtag gctgtctttt cttctcagac actgcaattt cctccaatct cttgactttt    6540
ctagaagttt taatccaagt ccttgttggg tggtagataa aagggtattg ttctactaga    6600
gactgacctt ggcatggaga tctcatttgg actcacagat ttctagtcta gcgcttggtt    6660
ttgtatccat acctcgctac tgcattctta gttccttctg ctccttgttc tcatgcccca    6720
gtgtcccacc ctacccttgc ccctactcct ctagaggcca cagtgattca ctgagccatt    6780
tcataagcac agctaggaga gttcatggct accaagtgcc agcagggccg aattttcacc    6840
tgtgtgtcct cccttccatt tttcatcttc tgcccccctcc ccagctttaa ctttaatata    6900
actacttggg actattccag cattaaataa gggtaactgc tggatgggtg gctgggatac    6960
acagaatgta gtatcccttg ttcacgagaa gaccttcttg ccctagcatg gcaaacagtc    7020
ctccaaggag gcacctgtga cacccaacgg agtaggggggg cggtgtgttc aggtgcaggt    7080
ggaacaaggc cagaagtgtg catatgtgct gaccatggga gcttgtttgt cggtttcaca    7140
gttgatgccc tgagcctgcc atagcagact tgtttctcca tgggatgctg ttttcttttcc    7200
agagacacag cgctagggtt gtcctcatta cctgagagcc aggtgtcggt agcattttct    7260
tggtgtttac tcacactcat ctaaggcacg ttgtggtttt ccagattagg aaactgcttt    7320
attgatggtg ctttttttttt tttttttga gacagagtct cgctctgtcg ccatgctgga    7380
gtgtagtggc acaatcttgg ctcactgcac ctccgcctgc caggttcagc gattctcctg    7440
cctcagcctc ccaagtagct gggactacag gtgcctgcca ccatgcccag ctaatttttg    7500
tattttagt agagacgggg tttcaccgta ttggctagga tggtctcgat ttcttgacct    7560
cgtgatccgc ctgcctcggc ctcccaaagt gctgggatta taggcttgag ccaccacgcc    7620
tggccgatgg tgcttttttat catttgaagg actcagttgt ataacccact gaaaattagt    7680
```

```
atgtaaggaa gttcagggaa tagtataagt cactccaggc ttgaggcaaa atttacaaat   7740
gctgctgact ttgtatgtaa ggggaggcat tttcttagaa aagagaggta ggtctctggg   7800
attccagtat gccatttcca tcctcagtgt ttttggccac ctgagagagg tctattttca   7860
gaaatgcatt cttcattccc agatgataac atctatagaa ctaaaatgat taggaccata   7920
acacgtagct cctagcctgc tgtcggaaca cctcccgagt ccctctttgt gggtgaaccc   7980
agaggctggg agctggtgac tcatgatcca ttgagaagca gtcatgatgc agagctgtgt   8040
gttggaggtc tcagctgaga gggctggatt agcagtcctc attggtgtat ggctttgcag   8100
caataactga tggctgtttc ccctcctgct ttatctttca gttaatgacc agccacggcg   8160
tccctgctgt gagctctggc cgctgccttc cagggctccc gagccacacg ctggggtgc    8220 tggctgaggg aacatggctt gttggcctca gctgaggttg ctgctgtgga agaacctcac   8280
tttcagaaga agacaaacag taagcttggg ttttttcagca gcggggggtt ctctcatttt   8340
ttctttgtgg ttttgagttg gggattggag gagggaggga gggaaggaag ctgtgttggt   8400
tttcacacag ggattgatgg aatctggctc ttatggacac agaactgtgt ggtccggata   8460
tggcatgtgg cttatcatag agggcagatt tgcagccagg tagaaatagt agctttggtt   8520
tgtgctactg cccaggcatg agttctgatc cctaggacct ggctccgaat cgcccctgag   8580
caccccactt tttcctttg ctgcagccct gggaccacct ggctctccaa aagcccctaa    8640
tgggcccctg tatttctgga agctgtgggt gaagtgagtt agtggcccca ctcttagaga   8700
tcaatactgg gtatcttggt gtcaatctgg attctttcct tcaggcctgg aggaatataa   8760
taactgagac ttgttttatt tctgcagagg gttctaagcc attcacttcc cagatgggcc   8820
aataatgctt tgagtaatct ggagatcatc tttaatgcgc aggtgaatgg aactcttcca   8880
cagagggatg tgagggctgt agagcagagt gaactccctg aaactcagac gtcagctctt   8940
tgtctctcta tctctgaaca cccttcctta gagatcccat ctctaggatg catttctctg   9000
tagttagttt ctaagtctct tgttcctgtt ctgcctttat tttttttcc tggattctaa    9060 gccagtatcc ccacttggct gtcttaatgt agcttaacat gtctgtaatc aaaatgatca   9120
tctttctgag attcaaaggg ctataaggga cttggagag aatttcattc agttttcctc    9180
aaactagaat aatgcttgca ctgtctgtaa aagaacaaaa gtgtcaaagc atcccttttgt  9240 tcactaaatt tcctttttta ttatagtgtt acttaaatat taggaagtta aaagtaggta   9300
taaacttctt ataggctgtt attatacaac tatatgaccc atacatattt acaaattaag   9360
tgcagccaaa attgcaaaat caataccatt caaattaata ccttaaatgt ggtgaggcag   9420
ctgttgttca actgaaacca aattataagt tgcatggcag taaatgctat catgctgatc   9480
attttgagtt tggccagtct atattatcat gtgctaatga ttgaattctc cacccatttt   9540
tctacttgta tgaccttaat ttgatggcac ctgttccatc ctcatgagtt tgctacaatt   9600
atactggtgc caacacaatc ataaacacaa atataaactt gggctttgaa atcttgtgcc   9660
agaacttggc tttaaagtaa gcatttaaaa aatccatatg tgtttattag actttgttta   9720
gatgactgtt gaaatgaaaa caaagtgttt aaaatcctct tagagaactt aaatataatc   9780
cctcagcaat atgtatacag atcttccttt gagaaaaact gattgtgttc agcctctcat   9840
gttacaaatg gggaacctga attctgaggt ctctagtgag agaacaggga ctggaatctg   9900
tggatcctat ctgttttaat aataattgta aagtataata gataatatta tattaaaaag   9960
agagnnnnnn acacttagaa tgagcttcca tgtgtgaggc actaactgat taggcattat  10020
```

```
taactagatt tattccttt  aaggccccgc gatgtactgt tatttccaca tgttgtagct    10080
ggggaacgtg ctactcagag aggttaagta acttgtctga ggtccacacc actaacaagg    10140
agcacaggta gggttcaaat ccagataatc tgactttgga gctggcactc taactcaatg    10200
tgcctaatcg cttttcagtg gtgtcattat tttgcctatt ctccatctga aatattgaa    10260 gtttctgact ccttccttgc ctttctccct gcctcccgtg ttatcccca ggtcttggtg    10320 ttccagtcct ctatgtccgt ccttactctt attcctttgc tacagtgtga tccagggctc    10380
ctgcccttct tatcctggta gagggggccc acttgctggg aaattgtctc cgccatggtt    10440
tatccatgtt gtgtgtccat tagtgagtag tgggaagaat catatcatgt tggcaatgaa    10500 agggggggcta tggctctggg gtagtctagt ctgaactctt atttt                   10545
```

<210> SEQ ID NO 15
<211> LENGTH: 4736
<212> TYPE: DNA
<213> ORGANISM: Homo sapiens

<400> SEQUENCE: 15

```
ctttttttt tttttttt tttttttttt tgaggtgaag tctcactctg ttgcccaggc      60
tggagtgcaa tggagcgatc ttggctcacc ccaacctctg tctcctgggt tcaaacagtt    120
ctcctgcctc agcctcccga gtagctggga ttacaggctc cgccaccat gcccagctat    180 ttttttgtat tttcagtaga gatggggttt caccctttg accaggctgg tcttgaactc    240
ctgacctcat gatcaaccca cctcagcctc ccaaagtgct gggattacag gtgtgagcca    300
ccacgcccgg cctcataagt attttctaaa tttatttaca gtcatgccat ttaaaggaa    360 agttgtattc ctgtctttgt taatatttat aagtgatttt attcagctac aagcttggaa    420
tggcatataa ttttgtattc tgcttttttc acttaatatt acatggctaa tgatttctgt    480
gtttcataaa cattattctg atgatggcat gatatattgt tgagtacatg taccataatt    540
gaatcatttc cctattgcta tgcaattaag ttgtttccaa tattttgcaa ttataatgtt    600
tcaatgaatg aataacttta tgcatatagc tttttgatat cttaagttca gtttcctagg    660
atgaatttcc aggaatagta attgggcaaa tgggataaac atgactcttg aatacgtatt    720
gttaacattg ctttcccaaa gggctcaact gatttatatt tccgtgttca ttatctttta    780
aaccagctca tttactcacc aaacatttt aaagccatta tcatgtggta ggcttagtaa    840
gaagaaagtg accctaaggg agaagcttat atataaatag ggtccctggt gtaccaagtg    900
ctgatacaga cacaaagtac ctggggaaat tgagatgagg gagtcctggc tcagctggga    960
gaaaagttca ttttcataga gtcatggttt tgttctttgg cagaaagaaa attgcttttct   1020 tccccacccc caccccagc tttattgagg tataattgac aaataaaaat tgtatatctt   1080
taagatatgc aatgtgatat atatgtatat ctcaacttaa aaataagct acagaataaa   1140 aaggtgtttg ctattaaaaa aaagaaaag gctgaatgtc attcccaagc ttggaaattt   1200
gagtatgttg cctctttggg attatttaca gaaatattag caagaccagc cccatctttg   1260
gtcttgagta ctccactgtc agcatgcttt cttccagaga gggatccatt tgcctttatt   1320
tttcattctg ttgtgccgtc tatgcaaact attcttgata gttttatggt aacagtgttt   1380
ttttgttcca tgagataaat ttatacagc tcattgtgga aaatttagaa aagacaggaa   1440
agtattaaaa acatcmcytt tttttttttt tttttttttt tttttttamg cagacagagt   1500
cttgctctgt cgcccaggcc ggagtgcagt ggcgtgatct cagctcacag caacctccgc   1560
ttcccaggtt taagtgattc tcctgcctca gcctcccaag tagctgggag tacaggcatg   1620
```

```
caccaccacg cccggctaat tttgtatttt tagtagagat ggggtttcac catgttggcc    1680
aggctggtct caaactcctg acctcaggtg atccgcctgc cttggcctcg caaagttctg    1740
ggattatagg caggagccac tgcgccagcc acacctacgt tcttatcatc ctagtacatc    1800
cactgtcatt atcttgctgt atttccttct gcccagtctc actctgatca tgcagtggcg    1860
tgatcatgca gtgatctcgg ctcactgcaa cctaggcctt ctgggttcga gtgattctcc    1920
tgccttagcc tcctgggttc aagtgattct cttgccttgg cctcccaagt agctgggatt    1980
acaggcatac accccatgc ccatctaatt tttgtatttt tagtagacac agcgtttcac    2040
taaaattttg tattttagt agagatgggg tttcaccatg ttggccaggc tggtctccaa     2100
ctcctgacct caggtgatcc gcctgccttg gcctcacaaa gtgattacag gcatgagcca    2160
ctgcatccat cgccaaaaag atttttaaa agagtttaat gtagaaccat atcaaaggtc    2220
tttggaaata aaaacagtt ttttaaaaat atcagaaata aaacaacaaa taaataaata     2280
aataaaaaca cccaaaacaa tctgaagcac gagcacctag cagaaaggtt caattatgat    2340
ctattcatag agtggaatat caagtagaca ttacaggaca tgttttaaga ttatatttta    2400
tgtcatggga aatgctctcc cagtatgatg ttaaatgaaa aaacagaata caaaagtata    2460
tatgctgcat agtctcaata ttgtagagaa aaaatattat ttatgtatgc atgaaaaaag    2520
acaaaagatg ttaacagaga tccattgtta cttcagtta ctaggattg tctctgggag      2580
gtaggattaa ggtgatttat atttaccttt ttaaacttt ctgtatttt ttattttcaa      2640
attttccata aaaataag acttgaaga tcaagaaaaa atttctgctt tggctcagtg        2700
cagtcgtcac gcctgtaatc ccagcagttt gggagcccta ggggagagga tcacttgaac    2760
ccaagagttt gacgttccag tgagctatga tctccggatc gtaccgcctg gacgatggag    2820
caagaccctg tctcaaaaaa aaaaatcttt gctttttttt tttgtttgtt tttgagacgg    2880
agtctctctc tgttgcccca gctggagtac agtggcacaa tctcagctca ccgcaacctc    2940
tgcctcctgg gttcaagcga ttctcttgcc tcagcctccc aagtacctgg gattccatgc    3000
acccaccact atgcccagct actttttgt attttcagta gagacagggt ttcaccatgt      3060
tggccaggct ggtctcgaat tcctgacctc agctgatcca ccggccttgg cctcccaaag    3120
tgctgggatt acaggcatga gccactgtgc ccagcccaat cttttgcttt ttttaaaaa     3180
agaagacaaa aagggatttt ataccagtat tatcttggct gtgtgactct gaagccacag    3240
ttgtaagtta taattactct gaaacacaag gccctgtgac tcttttgggc tctttggtgt    3300
ttatcttgat tacaacgttg gaatatagaa atgaaaggaa tgggagaggt gatagacttc    3360
aggcagtgta actagttgtc tgaacactac tggctcaatt atattgtgtc tagtgatttc    3420
catcttgtcc gtctgctaat ttatcgcctg gtaactcact gaggcagggt tttcctttgg    3480
agaaacctca ttgttttaac cagtgtatca tgcttgttta aagttcaat gatctttta     3540
actcatcgga gaagatgatg accagacctg gacagatggg aaggactttt gcactctctc    3600
tttacagtcc tgagtgcaca caggtcaata tggaactatg tgtgaatttt cattgtcttt    3660
gagagccctc ttctctgccc catagggagc agctttgtgt gcaattagag gagcaagggt    3720
tgtgtgtatt tagcacagca ggttggcctg gtcctctcct ctcaacatag tcaccacata    3780
cctggcacta tgctaaggct gggaatgcag acagatgggc gcctgctttc agagtgctca    3840
atgtgctgag gaagccagca acagaaacag atgatttcag gagctccagg aaaatgctac    3900
aggaggagtg tgcctgggtt actggagtag cacaggagga gggcttctag ctcaggctga    3960
```

```
gattttagta aaggaaatta tgccacgatg aatcctgaag aatgaataga agtgaaccag    4020
ataaagcacg ataggaagca tcttccctta cctaagggaa gacacagagg tatatggaat    4080
ggtatgttaa aaggttggga ctccaaacag ttctgttaaa gcttagagag tggtgggaga    4140
gactggagaa gttgattaat tagtaaatga agttgtctgt ggatttccca gatcccagtg    4200
gcattggata tccatattat ttttaaattt acagtgttct atcttatttc ccactcagtg    4260
tcagctgctg ctggaagtgg cctggcctct atttatcttc ctgatcctga tctctgttcg    4320
gctgagctac ccaccctatg aacaacatga atgtaagtaa ctgtggatgt tgcctgagac    4380
tcaccaatgg cagggaaaat ccaggcaatt aacgtgggct aaattggact tttccaaaga    4440
tgctgtcttt gggaaacatc acacatgctt tggatcagaa aacctaggct tctaatttgt    4500
tgataaggca tgaactcagg agactgtttt cagtcctagt gaatggtgat aattgtaatt    4560
ataacagtag acaacatctc ttttacacat ttaaatcat gaaaatagaa taaccttact    4620
gataatttta gaaagtggtg attaaaagca catttaagat aatgccttaa cacctagtct    4680
tttccatatg catgatgtct taatcacaca ttgcaaatca tggaacacag aatttt        4736

<210> SEQ ID NO 16
<211> LENGTH: 4768
<212> TYPE: DNA
<213> ORGANISM: Homo sapiens

<400> SEQUENCE: 16
atcttacaat cacagtcttt ctcttagggc tgggctcagt gggtggattg acactgcaga      60
aatggccaga tctaaaggat caacatttac gtagctggga aatgtagctg ggacttcagt     120
ttcactgccc tagtgatttt tcctaccact aagcagctca gtccataccc ctacgagacc     180
cacaagctta tgagatactg ttcttccagg aaagcagtgg ggccagggcc acctttaat      240 tgtgtttctt ggcctggtcc catctttctc acaatatata gcaacagtta tttacttgct     300
gattttctaa tgcacatcac acatagtcat attaaacaca cacacacaca cacacacaca    360
cacacacccc tcaagaaaca ttttctgaga cgtgatttcc tgatttcatc aaaaaagaaa    420
agagcgggcc aggcacagtg ggaagtcaag gtgggtggat cacttgaggt caggagtttg    480
aaaccagcct ggccaacacg gtggaacctc gtctctacta aaaatacaaa aattagccag    540
gcgtggtggc gcacacctgt aatcccagct actggggagg ctgaggcagg agaattgctt    600
caacctgcga ggctgaggtt gcagtgagcc gagattgcgc cattgcactc cagcctgggc    660
aacagagtga gactctgtct caaaaaaaaa aaaaaaaaa aaagcataaa ctgaaattta    720
tatgcaattt atatgcctgt gagataattc tgttttctct tttggaaccc caaagagatt    780
tttttgattg atgagcaaat acattttaga ttttatttaa gcattatgcc aagcaccact    840
gaagtataag tttcaagggc aaactcagtt ttttcatcta ctagacgaat gattttctgg    900
aatgattaca agcaggcaag atggtgtagt ggaaatagca aatgtcttcg gcatcagaca    960
agttggggtt tgtttgtatc ctgcctctgc ccttcaccga ggttgtgatc ttgggcagat   1020
tgttgagttt taacctagat tcctctgact ccagatcata aattttcaga aaagttctga   1080
aattcttgta tatactgatg gtaaatgaga cttttcctta catctatgca cttctttgtt   1140 tgtttgttt gagatggtct tgctctgttg cccagactgg agtgcagtag tgcaatctcc   1200
gctcactaca atgtctgcct cccaggttcc agtgagcctc ctgcctcagc tcccaaata   1260 gctgagacta caggcatgtg ccaccacgtc cggctaattt ttgtatttt agtagagaca   1320 gggttttgcc atgttgacca cactggtctc gaactcctgg cctcaggtga ttcgcccgcc   1380
```

-continued

```
tcagcctccc aaagtgctgg gattacaggc atgagccacc atgcccggcc atatccatgc    1440
acttcttgca accttacctt cttttctcat caccctccag ggacctagtt ggaagagcag    1500
agttaaaagt taaggtgaaa cttggagagg tgtcttgtcc ctaggaacaa aggactggtt    1560
tgaaattctc tgtaaatctt ccccagttca aaccagagtt atcaaggtct taaaaacttc    1620
cctgggtcct gagagcccat tatattattt acttgtcttc ctgtacaccc actgcctagt    1680
cctgatccta cttttgtttg caaataggat ggggcacaac gtacaaggaa gggcctttgc    1740
caccctgct aagggataac ctgaaatacc ttcaccatca ctgccctgtg ctgcttttca    1800
cctatgccag tctgtctaca gtgccagtgt ctcctggcat tgaaagggga gaatcttttg    1860
gtcctttgag tatttggttg ggttacataa atctccctga atgaagagca gctgacttag    1920
gcaaggggcc ttgtttggtt ttccttgaac tattaacagg aagatagggaa gattaactgt    1980
gtaaatgttc ataggccag agtccctgca gagggtggcc acagtgatca gatcttatca    2040
catccttgct ttgggtgttg cctctctggt tggagtatgg atagaaaaga aagaaagacc    2100
ctatattgaa atgcaaagtg cagcaagtcc tgactttgga ttaacttctc agcccatttg    2160
catgaaaata aaagatgaa taaaacaagg ttcccacttt ggagggaggt ggtagctgtg    2220
agatggaagg agtgttcctg ctgggcaaca gcagagtaag tgctggggta gattcactcc    2280
cacagtgcct ggaaaatcct cataggctca tttgttgagt ctttgtccta caccaggcac    2340
tctgcaaaaa cgctttgcct gcaaggtctc atgcgatgct caccacagct ctgtgaagtt    2400
aattgtactt ttatcaccat tttacagatg agaaaactga gggtatgggg tcaatgactt    2460
ggctaaagtc actgcttagc aagctgcagg gactggatgt gaattccaat tggtttgact    2520
ccaaagcctg tgaagctact tgttcttcac cacctagagc tgtggttctt gataactgtg    2580
aactcttttg gggtcacaaa tagccctgag aatatgatag aagcaggagc tctggccttt    2640
ctgtccatac ctgaacaggt ccttgggtta agagcccctc gtccagggcc tattaatctt    2700
gatcctcata agcagcatcc atgtattacg gccgcaaacc aaactgtgcc agaccgaatc    2760
ctaggaccaa gcccaaatat gtcccatcat ccttttggta agaagctcat tgtaagaaag    2820
aaagaggaga gcaagaggat gacctagtgc atggggcctc attgtttaa ttagtgacaa    2880
aacaacaata ataacaacaa aaccccgaa gcttcacaga tgacatcaga ccccaagcct    2940
gtgtgttttt caggtgccct tgaggagctt tgtagctggc agaggaggtg aaactgacaa    3000
atgtttggca gatggaggag agtaccagag gggtttgaga tgagctaaat tccaatctaa    3060
ccgcagtgtt gaggaagagg cttggattgg gaccatggag atggggttc tactcccagt    3120
cacgccagct gactttgcga gtgttctttg tcagtcactt tatcttattt tatttatttt    3180
tatttttttg aaatggagtt tcgctcttgt cgcccaggct ggagtgaaat ggcgcgatct    3240
tggctcactg caacctcccc ctcctgagtt caagcgattc tcctgcctca gcctccagag    3300
tacctgggat tacaggcgcc tgccaccaag cccatcgaat ttttgtatgc ttagtagaga    3360
cagggtttcg ccatgttggc cagggtggtc ttgaactcct gacctcaggt gatccgccca    3420
ccttggcctc ccaaagtgct gggattacag gcgcgagcca ctgtgcccag cccacttcat    3480
cttaccgtag ttacctcctt agagtatgaa aaaataggct tagggcatcc ccaagtcccc    3540
tctatgtctg agagctgagg ctggctgtca agaggaact aaggatgcca gggactttct    3600
gcttaggacc cctctcatca cttctccaac gctggtatca tgaacccat tctacagatg    3660
atgtccacta gattaagaat ggcatgtgag gccaagtttc cacctgagag tcagttttat    3720
```

-continued

| | | | | |
|---|---|---|---|---|
| tcagaagaga | caggtctctg | ggatgtgggg | aatgggacgg | acagacttgg catgaagcat | 3780 |
| tgtataaatg | gagcctcaaa | atcgcttcag | ggaattaatg | tttctccctg tgttttccta | 3840 |
| ctcctcgatt | tcaacaggcc | attttccaaa | taaagccatg | ccctctgcag gaacacttcc | 3900 |
| ttgggttcag | gggattatct | gtaatgccaa | caaccctgt | ttccgttacc cgactcctgg | 3960 |
| ggaggctccc | ggagttgttg | gaaactttaa | caaatccatg | taagtatcag atcaggtttt | 4020 |
| cttttccaaac | ttgtcagtta | atcctttttcc | ttcctttctt | gtcctctgga gaattttgaa | 4080 |
| tggctggatt | taagtgaagt | tgttttttgta | aatgcttgtg | tgatagagtc tgcagaatga | 4140 |
| gggaagggag | aattttggag | aatttggggt | atttggggta | tccatcacct cgagtattta | 4200 |
| tcatttctgt | atgttgtgaa | catttcaagt | cctgtctgct | agctattttg gaatatacta | 4260 |
| tatgttgtta | atgatatcat | gcagcagacg | tgcatctgaa | tgggctggct ctaggagcta | 4320 |
| gagggtaggg | gctggcacaa | agatgcatgc | tggaagggtc | cttgcccata agaagcttac | 4380 |
| agccaaggct | aggggagttc | tgtcttctct | gcatcaggtc | acctctctca cctctgtcac | 4440 |
| tgccccatca | gactacaatg | tctgcaggtc | tttctcccct | gagtgtgagc tccctgagca | 4500 |
| aagcaggatg | ctgccccttc | cctttgtatt | ccttgctcct | tgcttcagtg cctgtacata | 4560 |
| agtatgggca | taataagtgt | cccccaaatg | agacattgag | gattcttcaa atgcacagga | 4620 |
| ccgtgatgtg | agttaggacg | gagtaaggac | gatgggatgt | ggctcatgac aatcctgagg | 4680 |
| aagctgcagc | tgcggcacgc | agggccacac | tgtcatgttc | atggaccctca gactggcttt | 4740 |
| gtagcctcca | tgggcccctt | ccatacac | | | 4768 |

<210> SEQ ID NO 17
<211> LENGTH: 1295
<212> TYPE: DNA
<213> ORGANISM: Homo sapiens

<400> SEQUENCE: 17

| | | | | |
|---|---|---|---|---|
| tcatgactgc | cattggtata | aagatgaata | taatccagac | cagattcatg attattcata | 60 |
| catttttagt | gtattaactt | ttaattctgc | ttttaaaata | aattaaaaca ttctaatatg | 120 |
| cccttaagag | tatcccagcc | caggccactg | agcctactgt | ggttcatgga taagtttgcc | 180 |
| cctgggggca | tgtgtgtgca | tgcatgtgtg | tgcacatgca | tgatgagccg ggccttgaag | 240 |
| ggtggtaaga | tttgggtgtg | tagaccaatg | gagaaaggca | tttggggcag tgatgatggg | 300 |
| tgggggaggg | aacatggtga | tgaatggagc | tgggtgtggg | gagccatggg agtgggttag | 360 |
| ggccagcctg | tggaggacct | gggagccagg | ctgagttcta | tgcacttggc agtcacttct | 420 |
| gtaaagcagc | agaggcagtt | ggcctagcta | aagcctttcg | ccttttcttg caccctttac | 480 |
| agtgtggctc | gcctgttctc | agatgctcgg | aggcttcttt | tatacagcca gaaagacacc | 540 |
| agcatgaagg | acatgcgcaa | agttctgaga | acattacagc | agatcaagaa atccagctca | 600 |
| agtaagtaaa | aaccttctct | gcatccgttt | ataattggaa | attgacctgc accagggaaa | 660 |
| agagtagccc | aggtgtctgg | ggcttgttcc | cattagatct | tccccaaggg gttttttctcc | 720 |
| ttggtggctg | gcctgtgggg | cccctctcca | ggaggcattg | tgaagaaaac tagggagct | 780 |
| ggttgccaca | gacagtgatg | tactaatctt | ctctgggaag | acagaagaaa agtccccagg | 840 |
| gaagaatact | acagacttgg | ccttagggac | agctaggggt | gcagattgct gccaactgca | 900 |
| tttttttctga | agttggccat | atggttgcag | tgaatggatt | tatagacaga gtatttctgt | 960 |
| gcatataaga | gcaattacag | ttgtaagttg | atatggataa | gtgaaagtta agcacttctt | 1020 |
| tctaaaaaga | gaatgcaatt | catttttcccc | taatcatttc | aattagtctg atgggcattt | 1080 |

```
gaacttgttg tctttaaaaa gtgaaatctt tacctctgat ctggtaagta tccaggcaat   1140
ttcttgtgtg ccacccagga ggtatctggg gagtgggcat tttctgactg aggcattggc   1200
tgccatagca tcagagcagc cttccaggca gtggcctggc aagggacag aggctggtgg    1260 gagcagctgg ctgagtgcag ccagtaatgg catgt                              1295

<210> SEQ ID NO 18
<211> LENGTH: 2188
<212> TYPE: DNA
<213> ORGANISM: Homo sapiens

<400> SEQUENCE: 18
agctctccag gtgattctga tgcatactta agtttgagaa ccattgcttg ttttgcatta     60
aacaggagat tagtctctgc agcttgtggg aataaagctt taaatctctc caattttagc   120
tctgtgaaaa ggcagtgggg agacaggaat gaacggacta gtgccacaaa gctcaggtgg   180
ggtgggtgag atcatttaga agagaaagac cgggcatggt ggctcacgcc tgtactgtca   240
gcactttggg aggccaaggc aggttggatc acaaggtcag gagtttgaga ccagcctgcc   300
tatcatggtg aaaccctgtc tgtactaaag ataaaaaaaa aaaatttgc cagtcatggt    360 gatgcatacc tgtaatccca gctactcggg aggctgaggc aggagaatct cttgaacccg   420
ggaggcgggg gttgcagtga gctgagattc accattgca ctccaaccta ggtgacaggg    480
tgagactccg tctcaaaata aaaaaaaaaa aagaaaagga aaggctgtgt gtgtgtgtat   540
gtgtgtgtgt gtgtgtgtgt gtgtgtgtaa cagcaccatc acactgtttg agttgaggag   600
cacatgctga gtgtggctca acatgttacc agaaagcaat attttcatgc ctctcctgat   660
atggcgatgc tcccctatct cattcctgtg tgtgtttagc caggcaactg ttgatcatca   720
atattatgat aacgtttctc cactgtccca ttgtgcccac tttttttttt ttttgagtt    780 acttactaaa taaaaataaa acactatttc tcaatagact tgaagcttca agatttcctg   840
gtggacaatg aaaccttctc tgggttcctg tatcacaacc tctctctccc aaagtctact   900
gtggacaaga tgctgagggc tgatgtcatt ctccacaagg taagctgatg cctccagctt   960
cctcagtagg gctgatggca attacgttgt gcagctactg gaaagaaatg aataaaccct  1020
tgtccttgta atggtggtga aggggaggga ggtagtttga atacaacttc acttaatttt  1080
acttccctat tcaggcagga attgccaaac catccaggag tggaatatgc aacctggcgt  1140
catgggccag ctggttaaaa taaaattgat ttctggctta tcacttggca tttgtgatga  1200
tttcctccta caagggatac atttttaagtt gagttaaact taaaaaatat tcacagttct  1260
gaggcaataa ccgtggttaa gggttattga tctggaggag ctctgtctaa aaaattgagg  1320
acaggagact ttagacaagg gtgtatttgg agactttaa gaattttata aaataagggc   1380
tggacgcagt ggcactgagt tgagaactgt tgcttgcttt gcattaaata ggagatcagt  1440
ccctgcagct tgtgggaata aggctttaaa tctctccaat tttagctctg tgagatggca  1500
ctggggaaac agaaatgaac ggactagtgt cacaaagctc aggtgggatg gacgagatca  1560
cttcaaaggt ctgtaatccc acgtctataa tcccagcact ttgggaggcc aaggcgggaa  1620
aatcacttga ggtcaggagt tcgagaccat cctggccaac aatgcaaagc tgtctctac   1680 taaaaatatg aaaattagct cagcgtggtg gcatgctcct gtagtcccag ctactcgtga  1740
ggctgagaca ggagaatcgt ttgaacctgg gaggcggagg ttgcagtgag ccaatatcac  1800
gccattgcac tccagcctgg ctgacagagt gagactccat ctcaaaaaaa aaaaaaaaaa  1860
```

| aagaattttta taaaatcagg aaataatatt agtgttatg ttgaatttta actttagaat | 1920 |
| catagaaaac ttcctctggc atcattatta gacagctctt gtgcagtggg tagcaccaga | 1980 |
| cccagcttgc atggttattg attttcaga gacacttttt gagcttattc tctggcagaa | 2040 |
| aggggaactg cttcctcccc tatctcgtgt ctgcatacta gcttgtcttt acaagaagca | 2100 |
| gaagtagtgg aaatgtttat tcttgaaaat aagcttttg cttcacatga tctagaattt | 2160 |
| ttaaaattag aaaaatgtgc ttactgcg | 2188 |

<210> SEQ ID NO 19
<211> LENGTH: 1183
<212> TYPE: DNA
<213> ORGANISM: Homo sapiens
<220> FEATURE:
<221> NAME/KEY: misc_feature
<222> LOCATION: (1)...(1183)
<223> OTHER INFORMATION: n = a, t, c, or g

<400> SEQUENCE: 19

| agtaaaatgg agaattccaa attctgaaat tgttagaaca tagttctgtg tcttagttaa | 60 |
| atatcgacac ttacagataa atagcataaa tgctttctcc ccatatttca gcccagtcct | 120 |
| acttaaagac aacataaatt gcaaaatagt gaggatgttg ttcatctaat aaaagtggtt | 180 |
| ccaggaattc agactctgga ttcctgtttg ccaaatcatg tgtcccactc ttaagaaaac | 240 |
| gagttggact ntggattttt cttttgcaaga gggacaagag tgtgggagat actgagttaa | 300 |
| tgcaacttgc aggttttaag tgtcctgtca ttgtgcctcg tgctttgata cattctgagt | 360 |
| ttcagtaaag agacctgatg cattggactg ttgcaatgga acctgttta agatcttcaa | 420 |
| agctgtattg atatgaagtt ctccaaaaga cttcaaggac ccagcttcca atcttcataa | 480 |
| tcctcttgtg cttgtctctc tttgcatgaa atgcttccag gtattttgc aaggctacca | 540 |
| gttacatttg acaagtctgt gcaatggatc aaaatcagaa gagatgattc aacttggtga | 600 |
| ccaagaagtt tctgagcttt gtggcctacc aagggagaaa ctggctgcag cagagcgagt | 660 |
| acttcgttcc aacatggaca tcctgaagcc aatcctggtg agtagacttg ctcactggag | 720 |
| aaacttcaag cactaatgct ttcggaatgt gaggcttttc cttggacagc atgactttgt | 780 |
| tttgtagaaa agtacggctg gctgggagtt tgtgatataa tttagttcag tggtattcta | 840 |
| agtgttctta gtgttctttc agacttttgg gccatctccc aaagggtgaa tgggaagaat | 900 |
| aagctgggtg tggctgagtt taagccaaaa gtttttttgtg cttgtttcaa tcagagaaga | 960 |
| cctgcttttt catgtttta ctattataat actaagcaag agctcatttg aaaacagagt | 1020 |
| tcttcatatt taaaaaaaaa aagtcttgaa accattgatg ggaagatgga tatctattta | 1080 |
| tgtttaaaaa cccatcataa agatgacatt gtgggctgtc acagttggaa ggccctggaa | 1140 |
| ttagatgaga ccacactatt tagcttactt agtaataaca ttg | 1183 |

<210> SEQ ID NO 20
<211> LENGTH: 8981
<212> TYPE: DNA
<213> ORGANISM: Homo sapiens

<400> SEQUENCE: 20

| ccgtttggca aatgctcagt aaaagaaaag ggttagaagg ggagaaaggc attttatccc | 60 |
| aagccttcag gaatcaggat gaggatgtct tcaccttgtg gtggggagta attatacaat | 120 |
| tagagacagc acattggagt gtggctgata tgctgtgtga tgatagctct agctctctgc | 180 |
| ctagcagagg aaggacattt caatagaaga aaaagtttaa gaccttgccg agaaacagag | 240 |

-continued

```
aaaggatgtt tgtctttta agaagttgaa aaccctgttt gcagacaaaa gccctccagt    300
tttggcagta aactttcatg caagggaaga aaaaggcagg ggatgacatt gttgacaatt   360
gtgaggaatt accatgtgcc aggcactgtg cgagggctt tgtacatatc ctctagtttt    420
agtgcttata aaaactctgt gatatgtgca cagcatttta aactttgctg catagtcgag   480
aaaatggaag gatggggaat ttgagtcatt tgcccaggt tctatagcta ccccaggttc    540
ccatgactgg agaattgggg cacagggtgg cgggggagag tgagtgacaa gaatcctaac   600
aatcttattt ccattgagtc cttataaaag aagtggatta actaccacgt ttttaagttt   660
ttcttaaatt taggttatgt ggatctggcg tttcttgttt tgtcctgggt ttgttttgtt   720
tttgctatgc tgtcttgaac atctgtcatc ttgtaggcct aacggtaaac acaaaaacac   780
tttacctcct atagctttca attaagatct ctcagtttgt gtttgtaata gttttccagg   840
caagttctcc ctaggttcgg cttcagtgt gttaaccttt agttataaag tgaacccaaa    900
gagagaaagt agaaacaaaa cacctcacct gttttgctc atgaattact ctctatggaa    960
ggaacaatca tgaacacctc tgcgtatcac agaggcctat ctgagtctga cgttaagg    1020 agaccgcgta ggtccctttg aggactgtga atgtgggagt cctgggactc tggtgaagaa   1080
cccgttccag aagagatgaa tgagctggac aagttcttc atagaacctt taggcaggtt    1140
ttcttagaaa tgcacattga ggattatgct tggatattgt gatgatcaga atgatactca    1200
atcccttctg catttggaat tctctttgaa agaaaacatc ccaggcagct atttctcaga    1260
gatagtgagt cccagccact tctagacatt ttcttgtgta gtctacatta taatttcaca   1320
gcagtctctg atatgacaaa tgtcaaaata gcccaacctt ctctaaactt cagagatgtc   1380
tgatatgata ttgaataaaa caatgctcat agaaacatca agaaaggtgg attttccctg   1440 gatactttt tcctgcttga caaataacag tgaagaaact gatctcacgt cttttctct     1500 ttggaagcct gaacactcag aacccaactt gaggctcctc agctatagca attctgactt    1560
cacagtctgt aaattattgt tctttttttt ctttagctta tgctttctgc cctaatttat    1620
cttttccctg ttcaatgaa ttattgtcct atatctgctg tgcagttagg tgacatataa     1680
cagcaattaa atatatgaat tggtacatat aaagatttga ctaaaactcg atgtaaaaat   1740
aagtgttcta cattcaattt ccagtgttag aaacagtgct gacttgaaca gagtgacaga   1800
attccatctt tccctatttt tgacagcttt aaactttata ttttcttcct ttcttgtgag   1860
ccgtcattaa cttgtttctc aaagccattc ccgtattacc catcttgcag acgcagacag   1920
atttgggaat ttgcggtcag agttgtattg gacacatccc cccagcccac atgagatcct    1980
tttaatctat tgcatattaa ctagttttaa gtacaatatt cctacttcat ttaaaaccat    2040
taatcaaaga atgagtttga aaatgaacaa atgcaaact tacagttaga ataattgta     2100 gtgtctttag ttttggttag gagtcggttt cttgtttgtt aaactcaaga ttgtgaacag    2160
ttttaattca cttgtttatt ccaatagag atttcaggtt tacatttgaa ttcagaaaca    2220
aagttttctt tctcattaca gagaacacta aactctacat ctcccttccc gagcaaggag    2280
ctggccgaag ccacaaaaac attgctgcat agtcttggga ctctggccca ggaggtaagt   2340
tgtgtctttc cagtaccagg aagcggatca tccactgtat cagtattttc attcctgagt    2400
ctggcaagag gtccttttga gttgaatatc acatgggatg taatatcaat tttcaaagta    2460
taagtgatgt aaacaataat gttttgattt ccttatttta gaaatgaaga aacctaaaac    2520
tcatagatgt ctcagagcta attggttagt ggctaacagc tggatatcta gtttagaacc    2580
```

```
ttctccattt tttcttttg cccctaggta atcatacatt tgtaaagagg agaattatct    2640
ctgccactgc ccatgcactg cttttgtctg accagcaatt tctccatatt gcttcttcag    2700
tagcaaggcc aatcatttta ccaacacaca tgcttgctaa ctaacaggaa taacgtggta    2760
cccctaattc agccctttcc cttgaaagca tctggcttct gaggttcaac tatgggaata    2820
tggtctctta tgaacatta  agttgagttt gccttttagg tccacatgtt gacaaatgta    2880
tcagagtaat ctctgtccta ggatcagagg gcctgtaggc acttgcaaaa gcagttagct    2940
ctgactccca gccagtgcac actccacctt tctgactccc agccttgtct caaattaggc    3000
ttggaagcga ggaactgtct ggtgtccccc agcataggaa gctgagccag ggggcagtgc    3060
tcacaaacaa tacagacttt aacgtgtagg atattggaaa ataataattt gtggggaaat    3120
tgtctcagac ttggtccacc cttattttta gctgcttctc taatccgttt ttctttttt    3180
ggtgcttgta tctaacctac ccatttttg  gtgcttgcat cattttttca aatatcaaaa    3240
acgaacttta tgttttctaa caatgaaagt attgcatgtt cattgtggaa aatgctgaag    3300
acttggaaaa tacaaaaatg ctgagatcaa acactattga tacgttagtg tatttcttcc    3360
tgtcctgttc tactttcttt ctttgaattc tgctcacgtg tttctgactg atgaggtctg    3420
acttttgggt tccttttcca gaggagaagc cttctttcag cttgccattt gttaccctgg    3480
ttatgaaggc tggtaacctt ttttactagg tagagaagct ggaccaactg gggttcttcc    3540
agggggagaa tgagaaagag aaactgtttt gcaagtccgt agctatttct ctagggccct    3600
gttagctgac attgacatgc cttgcattgc tctgcagatc ccctcgcagc cctctgtccc    3660
ttgttcattt ctggccttag agaaagcaaa gcagggtctg taacagggga ggctgcctct    3720
aaactcaggg tttggttaca gctgttttca cttacatcac tggccctggt tttttttttt    3780
tttctggcat taaaaaaaaa aattggaagc aggtgatgtt cccattgctg atgtggtgga    3840
aactctccaa gtgaacaata tacgttttc  ttggcagctg tttcttgtgc cctgcttgct    3900
cctggtccag gacaagcaag gaccatctgc ctctttcaat agaacacctc cagatccctt    3960
tgatcaaaag ttactcattg tctgacttgc tatttctgtg agataaatgg gagaagatca    4020
ataaatgcac ttgtttgtcc agtcagcgtg tggaaagttg ataattttga ccaaagcaca    4080
accctgaaag gaaagaaaaa agggagtgaa tgtcttctga gaagctgcct aggttcagac    4140
agtgtcaccc atttccctgt atgctccaca tgacaaacct gagtgggtct catcatgtcc    4200
attttgcaga tggcaccaag gctcagaaag gttaggcaac ttttccagtc acccaatgag    4260
ttaattgaca aaactgggat tcaaacccag aactgttgga ttccaaagcc tgtgttgttg    4320
cctgcttcgt gaaaaactcc agtagcgact ggaatagaaa ggagaacctt ccaagaaaga    4380
aaatacgcac tagcagaacc tggaaattgg gaggaaatga ggacttgagg aataagatga    4440
atgaaagctg acctgagttt cacatctggg tgatgggaag ggaggacagg gaggcagcat    4500
ctcagatgtc cacccagcac cgaccagctg cctggcattg ctaggtgttg aggactcagc    4560
agtgaacacg ctaacttctc tgctttcttg gggcacgtat agggtgagag acagaaacaa    4620
acaggtcagt gtacaatgcc acaggaggga tatatgcagt gaagaaaaag cagggtaagg    4680
ggcatagagc atgagaaggt gcttttttta aagggktga  ttaggaaagc tctctctaag    4740
gtgacagttg gacctgaagg agatgatagc atgtctgtgg tgaggaagg  aaactccgaa    4800
caggaagaat ggcagataca aagacattga tgctagagca tgcctaagga atgtgtttaa    4860
ggaccaggga aagtgagcaa gtggtggggg gaggagagga gctcagagca ggaggaggtg    4920
agtgccatac aggcctggca agactttgga ttcctgctgg gtgagatgag aatccagcgg    4980
```

```
agggcttgag ggaggggaca tgatgtgatc tagagtttag actgtttaca ctctggttgt    5040
tgggttgaga agagactggg atgggggaaa gggaggacaa aggacattgt gctggattga    5100
gaaagcagta agtcagtttc attcattcac tcaaccgatg atgttcaaat accaccatca    5160
tccgtgggct aaaggatgaa gagccatccc tccctgagag tcaggaagca cttcccagat    5220
aaagtttgga gtgtgagctg aggtgtagga gaaagagtaa gagtttaccc ctgaaacggg    5280
tgctgggaag agtcaatagt ttggaataac tcaataattt atggtgcttc tttagaaaga    5340
tttgctggct ttatgtggga agaaatttkt ttttttgatt ggggagtggt gggttggtgg    5400
tgaggctgcc tgtggaaaga gaagtgagtg ttttgactca ctgttattta aaaatctcta    5460
gggctgttcc aataagcaac aaaaggcaaa atggcctggt tctctgtccc ctttctgtct    5520
gtatgcctcg tacaggttat gaaaagaaaa agttgggaaa agctgtccac ctcacctaat    5580
tgtgttcttg tggagtgtgc tagatgcccc ctctctggag aaaaaaaatc cttgtggcct    5640
ctgacccacc tctggagagc ctagttccct tctggaggca gaaggcaaag cttaggacct    5700
agagagtgct ggaccacgcc actcacagga accagcaggc tgtgaggttg aaagctaggc    5760
atatggagct ttccaggctg ggtgcagggc ctcgtggccc ttcccctccc ctctgtgctc    5820
tatagctcag tcttcccagg cggtgtgaac acgcagtgac atttccagga atacagggat    5880
ttattaatga tttcttgtga aatgtttgga aatacaaagt actctataaa tatttcataa    5940
tagcattggg gctgagaact ccacaaagtg ccggaataca tttgcatgta agacagaacg    6000
ctgcctgggt cattgatgcc tgttgagtgg cagtcacaga cactgcctag ggtttctgac    6060
tcacgctgtt gggactgttc tatgcagggc accctcttgt gtggcatagg atttgtgcct    6120
caccacacac tgttgtagct ttgctgtctt gatgatgagt agagggcagt gtccaggcca    6180
tggtataagc atctactgcc ccccagggtt accaaaacca agccaagttg tgtctcagcg    6240
agctccgtga agcatggaga agttgagtac tcagagacat gacgtgactt ttcaaaggct    6300
gtaagctgac gagggacata gctagggttc agacttgagt ttttcttttt ctttttcttt    6360
ttctttttt tttaagactg agtcttgctt ttgtcgccca ggctggattg cagtggtgct    6420
tggctcactg caacctctgc ctcccgggtt caagcaattc tcctgcctca gcctccccag    6480
tagctgggat tacaggcacc tgccaccatg cctggccaac attttttgtat tttttagta    6540
gagatggggt ttcaccatgt tggccaggct ggtcttgaac tcctgacctc aggtgatcca    6600
cccgcctcga cctcccaaag tactgggatt acaggtgtga gccactgcac ccggcccaga    6660
ctcgagtttt tcatcttaat gcttttttcat tgcctgacac tttactgaga ccaagatagg    6720
gaacttcaca tacagtacct ttttctcccaa ggcggaagag ggctgttcaa tttctacact    6780
agagttcggg gagttttaga aatgagtcag ttatcgagga tgagagcagt tcctgatagg    6840
ctcaaccaca atgagatgta gctgttcaga gaaagcattc ttttatctat aaactggaag    6900
ataatcccgg tgaaacgaag cccagcccca ggggcttcac taactccagg ctgtgcttct    6960
caaactttag tgagcatagg aatcacctgg gcatcttgtg aagctgtaga tttgaattct    7020
gcaggtcggc agaggggtct cagaatccgc atttccaaca atgtctccag taatgctgat    7080
gctgctcgtc cctggaccac agattgggta gccaggttct ggcaagctca tcccaaggct    7140
ttgagatgac atcagacaaa atatgttctg ggacatggct tttgagaggt caagaaaata    7200
agatgtttct ttctcttctc atccccaacc cttgcactgc cttttctccc cttcccctac    7260
cctcctttct gtccccatcc ctgacgccag ctgttcagca tgaagctg gagtgacatg    7320
```

-continued

| | |
|---|---|
| cgacaggagg tgatgtttct gaccaatgtg aacagctcca gctcctccac ccaaatctac | 7380 |
| caggctgtgt ctcgtattgt ctgcgggcat cccgagggag gggggctgaa gatcaagtct | 7440 |
| ctcaactggt atgaggacaa caactacaaa gccctctttg gaggcaatgg cactgaggaa | 7500 |
| gatgctgaaa ccttctatga caactctaca agtgagtgtc catgcagacc ccagccctgt | 7560 |
| ccccaaccccc atccctccct tagttctggc cttggcctgt gtcatctcct ccctctgtag | 7620 |
| cagcgttaga tgtctacatg cccatttgcc caccagactg agctcttcct agaggagaga | 7680 |
| ggcttctctt gaatagctac ctgtccccag ttctctgaat gcagcctggc acatctcagg | 7740 |
| tgcacagtag tgtttatcaa tggaatgaat gattgacagc caaccttctg gttttctggg | 7800 |
| ggatgtggaa gggtggcttc cagggtgatc aagaatgaga taatggcaga aggacaaatc | 7860 |
| ctgcaagatc tcacttatat atggaatata tgtaaggtag aaagtgtcag tttcacatga | 7920 |
| tgaataagtt cctgggatct tgatgtacat cgtgatgact atagttagta acactgtata | 7980 |
| gtatacttga aatttgctaa gagagtagat ccgaagtgtt cacactacac aaaaaaggca | 8040 |
| actatgaggt gatggattta ttaacagctt gattgtggtg atccttttac aaagtataca | 8100 |
| tatattaaaa catcacattg tataccttaa atatatacaa tttttatttg tcagttgtaa | 8160 |
| ctcaaaaaag ctagaaaagc attttttaaaa aggatgatgt actggtctta atattaccat | 8220 |
| tgagataagc tttataataa cataaaaaga aataacagta atgataatag caacaacaac | 8280 |
| aacaacaaag aactaacatt taagtagaat ttcttgtgca ctgtgcattc tgtttaagtt | 8340 |
| atctcatttt accctcatga taacctgcag ggaagattct ttaacccccac atttcatagg | 8400 |
| ctcagagagg ttaagtgcct tggttagagc cacatcagag ttaatccaca agagccagga | 8460 |
| ttcaagccca aatctgcctg gatctgtgct ctctaagata actgttagtg gtggcgtgtg | 8520 |
| tgttctcaca ctcagacatt tgatctgccc tttgtttccc attcttagct gcaaggcagt | 8580 |
| gttaaagaac cctgtgtctc catatccact ccccacactt aagcactttt gtgggcccgt | 8640 |
| gtgccgtatg cctcgtggca gcagggatcc aatgtcacag ttttaggcag tggcatcctt | 8700 |
| ttccttgaaa acttgatgca ggggaacctt tctccatttc caaccacagg tgtgtctttc | 8760 |
| agacactgag tgaggcaggt tttgtacttt attgtaacac aagaaccttt tcttctctgg | 8820 |
| agtaaagcac tccagacatt cgcaagttgc tttacaagcc ttaaaaggat ggtattgtag | 8880 |
| gcaactttaa ttaaatccca tctcctcctc tccccagct tgcaagttga cccaaggaag | 8940 |
| ccttcatttc catgacagac ttaattgtga gggcatcctc a | 8981 |

<210> SEQ ID NO 21
<211> LENGTH: 20284
<212> TYPE: DNA
<213> ORGANISM: Homo sapiens
<220> FEATURE:
<221> NAME/KEY: misc_feature
<222> LOCATION: (1)...(20284)
<223> OTHER INFORMATION: n = a, t, c, or g

<400> SEQUENCE: 21

| | |
|---|---|
| actgtgttag caaggatggt ctcgatctcc tgacctcgtg atccgcctgt atcggcctcc | 60 |
| caaagtgctg ggattacagg cgtgaaccac tgcgccctgt tgagaatttt ttttttttt | 120 |
| tttgggagaa agagtttcgc tcttgttgcc cgggctagag tgcagtgaca caatctcggc | 180 |
| tcactgcaac ctctgcctcc tgggttcaag caattctcct gcctcagcct catgcgtcac | 240 |
| cacgcccagc taattttgta ttttttagtag agacaggggt tctccatgtt ggtcaggctg | 300 |
| gtctcgaact cccaacctca ggtggttcgc ccgccttggc ctcccaaagt gctgggattg | 360 |

```
caggcatgag ccactgcgcc cagccccaaa ttttggtttt tgcttgaaaa ctgaggtctg      420
aattcagcct tctggttgcc cctcaagagt cagtttaaat gttggtcatg ttagttgtca      480
gtgaaaacaa tggtgaggct ggcatgagag tgtgaatctg gatgggaggg cttgtgcttc      540
atgaaaacat ttttccagat cagctcagtc gtgagttatc cgtcattgac gttataataa      600
gctctgatta tttatcaagc atcattcttt atagatatct cagtttaatc tgagataatc      660
ttctccacat ctctccacat agatgttatg aattttactt ttacagagga gccaactgag      720
gctcagataa gttacttatt atatgactag tagtggtaga gctggggttt caactaagaa      780
ctctctggct ccaaagccct tgtaagtttc tatcagtata tgaccatgca tatgagcatt      840
tgtctctcct cttcttcata gctccttact gcaatgattt tgatgaagaat ttggagtcta    900
gtcctctttc ccgcattatc tggaaagctc tgaagccgct gctcgttggg aagatcctgt      960
atacacctga cactccagcc acaaggcagg tcatggctga ggtaagctgc ccccagccca     1020
agactccctc cccagaatct cccagaact  ggggggcaaaa aactcaaggt agcttcagag    1080
gtgtgcgcta agtatactca cggctcttct ggaattccca gagtgaaaac ctcaagtctg     1140
atgcagacca gagctgggcc agctccccag tcgtgggtat agaatcatag ttacaagcag     1200
gcatttcttg gggatgggga ggactggcac agggctgctg tgatggggta tcttttcagg     1260
gaggagccaa acgctcattg tctgtgcttc tcctccttt  tctgcggtcc ctggctcccc     1320
acctgactcc aggtgaacaa gaccttccag gaactgctg  tgttccatga tctggaaggc     1380
atgtgggagg aactcagccc caagatctgg accttcatgg agaacagcca agaaatggac     1440
cttgtccggg tgagtgtccc tcccattatt accatgtgcc tgcttgatac tggagaggtg     1500
agtttctggt cactttccca ggtgtgagtg aggtgagaat tctttcagtt tatctagctg     1560
ggggaatgta gtgagcatag ctaaagtcac agggcaccac ctctccagaa gtacaggcca     1620
tggtgcagag ataacgctgt gcatatcagc atccatgcca ctcacggtca aatagcagtt     1680
ttctgcaaaa cttagtgagg ctggtgttt  ggaagtggag ttgagtaatt gcagtaccct     1740
attttccttt ttgctgcagc ctctcagcca gccacagcat ctccctgtgt cttggtaggt     1800
tttggaaaga agtgtgggag caaaagcatg atgttacatg tagactggcc tgagatactc     1860
attctcaggg cactgtgtga atgatgagct gctgttactg tgtggagggg aaatgcactt     1920
agtgcttcag agccacttga aagggataag tgctctagag acaattgggt tcaaatgtgg     1980
agcaggctga gcaagaacag aatgtctcct ttgcctgagc ctgagtgctg ttaatcacat     2040
cttcctgcct tgggctgagt tagagaatca ttagactatt tcctgtttcc atggtgaggg     2100
aggcctcttc cttttgtctc tgctcccctt aagaagcagg tgaggatttt gccaggtttc     2160
ttgttttgaa ccttattgac tttaagggcg gctgggtttt agagactgta cctacctagg     2220
gggaacactt ccgaagttta ggactattcc ctgatccgct gggaggcagg ttactgagga     2280
agtcccttta aaaacaaagg agtttatact gagaaaagca taaacagtga tttgtatgga     2340
ttcacactga ctaatatagc tcatgccatt aaagtgggt  ctcttctcta aggagggtt     2400
atatgatcta gccccgtaga cctaagtgtg gtttcagacc tgttcttcct ggtcctctcc     2460
ttggaatcca tatttctact agttggactt tttctgtttg tctggctctc agaggattat     2520
aggaggccct gtgaagtgac tcagtgaatt ttgatttgtg ggcaagtaga tggttcccta     2580
gtctgaaatt gactttgcct taggtgcttc aattcttcat aagctcccag ttcttaaagg     2640
acaagatcct tgtaaacatg gcaatggcat tcattaggaa tctagctggg aaaatccagt     2700
```

```
gtgtatgctt ggaaatgagg gatctggggc tggagagaaa ggcatgggca tgccttggag    2760
ggacttgtgt gtcaagctga ggacctttac tttaagctct aggggaccag gcaaggggag    2820
atgtagatac gttactctga tggggtggat gaattgaaga aggatgaggc aagaatgaag    2880
gcagagacca gggaggaggc tctccaagtg gccaaggcat aaagcaagaa atgaggcctg    2940
gtgactgctt agtggcagag cagtgaaaga gagggaggca tcaaagtgag tctcgatttc    3000
tagctgggtg ggtggtagcg atgtccagta ggccagtggc tactgaggtc tgcagtggag    3060
gagggtggtt gggctggaga cagatgatga gggagtcatc agcctgtggg tggaagaaaa    3120
gggaacctct tccaactgtt ttctttgctt cttccctctc tttctctttt ttttttttt    3180 tggacagagt cttgctctgt cacccaggct gaaatgcagt ggcatgatct tggctcacca    3240
cagcctccgc ctcctgggtt caagcaattc tcctgtctca gcctccagag tagctgggat    3300
tacaggcaca tatcactgtg cccggctaat ttttgtattt tcagtggaga tgggatttca    3360
ccatgttggt cgggctggaa tgaactcctg acctcaagtg atccacctgc ctcagcctcc    3420
caaagtgttg ggattacagg catgagccac cgcgcccggc ctttcttccc tctcttaaag    3480
agtgtttatt taattccaca aacatgagct tgtcaccccc tgtagcctgg catctcctac    3540
acgaggtgat ggctgaggct tctgcttctg ctggggtagc tctgatcttt ctgctttctc    3600
tggcactgtc tacccatgtt gcctcacccc acaggtccca gggcacctct ctcgggcaag    3660
tcttggaacc ctctgacact gatttgctct cttttctgag ctgcttttag ccacccatcc    3720 tcggacctg ttttctctct gcctccaccc ctgcgggcag tcttaggtct cctgcccctc    3780
acgagcaccc cagagaggcc acgtgctcag tgatctcagt gggcgcatct ttctagtctt    3840
gctattcttt ttggccatgt tgttcagaaa ccatactggg cagggccgac ttcaccctaa    3900
aggctgcgtc tcttcactct gcttttgttt gttccaaata aagtggcttc agaattgcta    3960
accctagcct ctgtgaactt gtgaggtaca attttgtgtc tgttatgtta acaaaaatac    4020
atacatacct tcctggtgat ggtataaatt gctattctct attggaaagc aatttggaat    4080
gaaaatttaa agaaccattt taaaatatgc tatcctgcgt acctccattc cacccacccc    4140
cagggatgta gcctactgaa ataattttaa agaagtcacc atatgagaga aaatgttatt    4200
gctatattgt tattgtgaga aattggaaat agactaaatg ttcagcacta taggaataat    4260
taatgaaatt acatatactc tatacaatca ttatgctgcc attgaaataa taaatacaaa    4320
ggcgcaaggg gggaaaagct tataatgtta gtgaaactaa gactgatttt tttataaagc    4380
agcagttttc agacccttgg agactccaat tcggtagaac cagagcttca tcttctctgt    4440
cgaagctgtg acaggagttg caaatgcctc tccttttgc tgagtttgca gctgctgttt    4500
ttccggcagc acatctgtgc aggcctctgc ctcggcccct ctggatctgc tgattgagca    4560
gcggattgat ctgtccttct ctttcgtgtt gacccatgtg aggaaccaac tggcaaggga    4620
acaagaaatg gaaataggcc tcctttgcat catgacctgt acatcctgca attggaaaag    4680
attgtacttt agttggttta accagcagca ttattttttct aaactaagca gtaagaagga    4740
attaggtttt atgtgggatc aacagactgg gtctcaaaag aggaaggtga tagaacacag    4800
tggggagggg gaggtgcact agaaacagag ggcctatgct ttcattctgg ctttgctact    4860
taatagctgt gtgacccaat cttagagact taacctctct gaacttccat tttctcatgt    4920
ataaaatggg aaatattaaa ggatactcac tgggctggtg gcttgtgcct gtaatcccag    4980
cacttgggga ggttgaggtg ggaggatcac ttgagcccag gtgttcaaga ccagcccagg    5040
caacatggca agactctgtc tctatgaaaa aattaaaaat tagccaggtg tggtggtgtg    5100
```

```
cacctgtagt cttagctact tggtaggctg agatgggagg atcacttggg cttgggaggt    5160
caaggctgcg gtgagctgtg attccatcac tgcactccag cccgggcggc agagcgagac    5220
actgaatcca aacgacaaca acaacaaaag gcaaaaaaat aaaagtgccc tctttatgga    5280
gttgtgtaag gtgaagcata tacactattc aacatagtaa ctatataaag gaagtattgt    5340
tgttgttact gtagttaata ccattaagtg agatgtttcg tatagtggaa agcacatgga    5400
ctctgaattc agactggtct gactttgagt ctcagctcca catctagtaa tactatgacc    5460
aagccctggt taaaatcatg ttttttttc ttcagcctca gtcttctcac atataaaata    5520
gggacactgt catttacctc agttttctgt gaggataaaa caacgacagt gtatatgcaa    5580
gtattttgta aattttgtag tgctcctcaa gatttagttg gtgtttacta cttgtactt    5640 ctcactggaa tggcagatgc tgttggacag cagggacaat gaccactttt gggaacagca    5700
gttggatggc ttagattgga cagcccaaga catcgtggcg tttttggcca agcacccaga    5760
ggatgtccag tccagtaatg gttctgtgta cacctggaga gaagctttca acgagactaa    5820
ccaggcaatc cggaccatat ctcgcttcat ggaggtgaat ctgttgctgg gatcatttag    5880
aaaagactta acggcttctt tctctgagac gttacaataa ggttcaggca ggaggcaagt    5940
ttagaaataa tgtatagtct catttacaaa actatccctc aagcctaaca caggatttga    6000
taacaaaagg cacttaataa atgttagttg agtggttgaa tgagtaaata aactctagct    6060
ttagtaaatt aactctagct tattctatat aggctcaaga gaatattttct acccatttc    6120 ttctaggttt tcctatctca gtgactaatg gtagcaaagc attcccttaa aaaggcatta    6180
tttgtgaaac ttayctaaaa tcgaattcgg gtccaattaa attttgaaa ttttatatta    6240 aaaattatat tagtagggat gggtaagagg tgttttggtc tggttggttg gttagttgct    6300
atgactcaga attgctaaga aaacagaaaa gtaagataag atcattgttt taacctcttt    6360
tcctccacaa aatcaataaa taacatatcc ctaaattact cttagaattt ctcttaaatt    6420
gcagtgaaaa accaaaatcc ttcattcttg gttgaaggtt ggaaaactac gttagagagg    6480
attagagaga gaggatgagc aatcgtgtag tcagcccttg cctcctagtg taggatttgt    6540
ctcagccact gcttgttgtc ctggctgcca acgttctcat gaaggctgtt cttctatcag    6600
tgtgtcaacc tgaacaagct agaacccata gcaacgaag tctggctcat caacaagtcc    6660
atggagctgc tggatgagag gaagttctgg gctggtattg tgttcactgg aattactccm    6720
rgcagcattg agctgccccca tcatgtcaag tacaagatcc gaatgacat tgacaatgtg    6780 gagaggacaa ataaaatcaa ggatgggtaa gtggaatccc atcacaccag cctggtcttg    6840
gggaggtcca gagcacctat tatattagga caagaggtac tttattttaa ctaaaaattt    6900
ggtagaaatt tcaacaacaa caaaaaaact caacttggtg tcatgatttt ggtgaaattg    6960
gtacatgact tgctggaagg ttttcatag gtcataaaat aacagtatct tttgatttag    7020
catttctact caagggaatt aattccagga attttggtgg caggcacctg taatcccagc    7080
tactcgggag gctgaggcag gagaattgct tgaacccagg aggcagaggt tgcagtgagc    7140
taagatcgca tcattgcact cccgcctggg caataagagt gaaactccat ctcaaaaaaa    7200
aaaaagatac aaaatagaa aaggggctt ggtaagggta gtagggtttt gggcaatttt    7260
tttttttttt tttttttta ttgtatggtt ctaaaggaat ggttgattac ctgtggttg    7320 gttttaggta ctgggaccct ggtcctcgag ctgacccctt tgaggacatg cggtacgtct    7380
gggggggctt cgcctacttg caggatgtgg tggagcaggc aatcatcagg gtgctgacgg    7440
```

```
gcaccgagaa gaaaactggt gtctatatgc aacagatgcc ctatccctgt tacgttgatg   7500
acatgtaagt tacctgcaag ccactgtttt taaccagttt atactgtgcc agatgggggt   7560
gtatatatgt gtgtgcatgt gcatgcatgt gtgaatgatc tggaaataag atgccagatg   7620
taagttgtca acagttgcag ccacatgaca gacatagata tatgtgcaca cactagtaaa   7680
cctctttcct tctcatccat ggttgccact tttatctttt tattttttatt ttttttttg   7740 agatggagtc tcgctctgac gcccaggctg gagtgcagtg gctcgatctc ggctcactgc   7800
aacctttgcc tcccgggttc aagctattct cctgcctcag cctccacagt agctgggact   7860
acaggctcat gctgccacgc ccggctgact ttttgtattt tagtagagac gaggtttcac   7920
catgttaccc aggctagact tcaactcctg agctcaggca atccaccctc cttggcctcc   7980
caaagtgctg ggattacagg tgtgagccac tgcacccagc ccaccacttt aattttttac   8040
actctaccct tttggtcaaa atttgctcaa tctgcaagct taaaatgtgt catgacaaac   8100
acatgcaagc acatactcac acatagatgc agaaacagcg tctaaactta taaaagcaca   8160
gtttatgtaa atgtgtgcac ttcttctccc taggtggtaa accacatttc aaaacaaccc   8220
aaataaaact gaacaaagct tcttcctctt agacttttta gaaaatcttt cagtgctgag   8280
tcactaagct gccaagttct cattgtggga actatgcctt tggatgtaat gatttcttct   8340
aagacaatgg gcggaggtgt agttattgca gacatctgaa atatgtaatg tttcttccag   8400
attctggaaa ttctcttatt ctctgtggtt ggtggtggtg gtgggatgtg tgtgtgtgtg   8460
tgtgtgtgtg tgtgtgtgtg tgtgtaggga tcaggatgcg ggaggagctg ggttctgctt   8520
gtattggttc tctgttttgc attgaatagt gtgtttcctt gtatggctat ctatagcttt   8580
tcaaggtcac cagaaattat cctgttttc accttctaaa caattagctg gaattttca   8640 aaggaagact tttacaaaga cccctaagct aaggtttact ctagaaagga tgtcttaaga   8700
cagggcacag gagttcagag gcattaagag ctggtgcctg ttgtcatgta gtgagtatgt   8760
gcctacatgg taaagctttg acgtgaacct caagttcagg gtccaaaatc tgtgtgcctt   8820
tttactttgc acatctgcat tttctattct agcttggaat ctgaaacatt gacaagagct   8880
gcctgaaatg tatgtctgtg gtgtgattag agttacgata agcaagtcaa tagtgagatg   8940
accttggaga tgttgaactt ttgtgagaga atgagttgtt ttttgtttt ggttttagt   9000 actttaacat aatctacctt tagtttaagt atcgctcaca gttacctagt tactgaagca   9060
agcccccaaa gaaatttggt ttggcaacac tttgttagcc tcgttttct ctctacattg   9120 cattgctcgt gaagcattgg atcatacgta catttcagag tctagagggc ctgtccttct   9180
gtggcccaga tgtggtgctc cctctagcat gcaggctcag aggccttggc ccatcaccct   9240
ggctcacgtg tgtctttctt tctccccttg tccttccttg gggcctccag cttctgcgg    9300 gtgatgagcc ggtcaatgcc cctcttcatg acgctggcct ggatttactc agtggctgtg   9360
atcatcaagg gcatcgtgta tgagaaggag gcacggctga agagaccat gcggatcatg    9420 ggcctggaca acagcatcct ctggtttagc tggttcatta gtagcctcat tcctcttctt   9480
gtgagcgctg gcctgctagt ggtcatcctg aaggtaaggc agcctcactc gctcttccct   9540
gccaggaaac tccgaaatag ctcaacacgg gctaagggag gagaagaaga aaaaaaatcc   9600
aagcctctgg tagagaaggg gtcatacctg tcatttcctg caatttcatc catttatagt   9660
tggggaaagt gaggcccaga gaggggcagt gacttgccca aggtcaaccc agccgggtag   9720
cagctaagta ggatgagagt gcagggttca tgctttccag ataaccacat gctcaactgt   9780
gccatgctgt ctcattggta gtggttcatg gcagcatctg aaagctattt attttcttag   9840
```

```
atatattggg tggcgattct tcctaagttt ctaagaacaa taatcagaag gatatatatt   9900
gttgcaggtt agactgtctg gaagcagagg ctgaaataga gtttgatgta tgggtattta   9960
tgagggctca atacctatgg aagagatatg gaagatgcag gattgggcag agggaggagt  10020
tgaactgtga tatagggcca accccgtggg gcactctaga gaatatgcag cttgttggag  10080
ttgttcttca tcgagctgaa acatccagcc ctttgtgctc ccccaaggcc tccctcctga  10140
caccacctac ctcagccctc tcaatcaatc actggatgtg ggctgccctg ggaaggtcgt  10200
gccccagggc ctacatggct ctctgctgct gtgacaaacc cagagttgct gatgcctgag  10260
gccgtctact gacagctggg caacaaggct tccctgaatg gggactctgg gcagtgcagt  10320
tttgtgtctg aaccatacat taatatattt atatccgaat tttctttctc tgcaagcatt  10380
tcatataaag acacatcagg taaaaataaa tgttttgaa gcaaaggag tacaaagaga    10440
taagaactaa ctaatttaat actagttacc atctgttaca aatagttcct actgattgcc  10500
aaggactgtt taaacacatc acatgggctt cttcttctat cctcactaac ccttttaaca  10560
gacaaggaaa tgaggctcag gaaggtcaag gactttattg aggttccaca gtaggataca  10620
gttcttgcta aaagcaaccc ctccctcatg ctctgttatc taactgcaag gggaaggtca  10680
gtggcagagg tagtggtccc atggttggtg cataagagct gctctgagac aactgcatgc  10740
tggtgggtcc tgcagacatg tacccatcag ccggagatag gctcaaaata tccacaagag  10800
tttggatgat tgtgggaatg cagaatccat ggtgatcaag agggaaagtc aagttgcctg  10860
gccattttcc ttggcttta gacagaaaag ttacgtggga tattatctcc cacagctctt   10920
ctgtggtgcc accagtcata gtccttatat aaggagaaac cagttgaaat tacctattga  10980
agaaacaaag agcaaactcg cccactgaaa tgcgtagaaa gccctggact ctgttgtatt  11040
cataactctg ccattatttt tctgcgtagt tttgggtaag tcacttatct tctttaggat  11100
ggtaatgatc agttgcctca tcagaaagat gaacagcatt acgcctctgc attgtctcta  11160
acatgagtag gaataaaccc tgtctttttt ctgtagatca tacaagtgag tgcttgggat  11220
tgttgaggca gcacatttga tgtgtctctt ccttcccagt taggaaacct gctgccctac  11280
agtgatccca gcgtggtgtt tgtcttcctg tccgtgtttg ctgtggtgac aatcctgcag  11340
tgcttcctga ttagcacact cttctccaga gccaacctgg cagcagcctg tggggcatc   11400
atctacttca cgctgtacct gccctacgtc ctgtgtgtgg catggcagga ctacgtgggc  11460
ttcacactca agatcttcgc tgtgagtacc tctggccttt cttcagtggc tgtaggcatt  11520
tgaccttcct ttggagtccc tgaataaaag cagcaagttg agaacagaag atgattgtct  11580
tttccaatgg gacatgaacc ttagctctag attctaagct ctttaagggt aagggcaagc  11640
attgtgtttt attaaattgt ttacctttag tcttctcagt gaatcctggt tgaattgaat  11700
tgaatggaat ttttccgaga gccagactgc atcttgaact gggctgggga taaatggcat  11760
tgaggaatgg cttcaggcaa cagatgccat ctctgccctt tatctcccag ctctgttggc  11820
tatgttaagc tcatgacaaa ccaaggccac aaatagaact gaaaactctt gatgtcagag  11880
atgacctctc ttgtcttcct tgtgtccagt atggtgtttt gcttgagtaa tgttttctga  11940
actaagcaca actgaggagc aggtgcctca tcccacaaat tcctgacttg gacacttcct  12000
tccctcgtac agagcagggg gatatcttgg agagtgtgtg agcccctaca agtgcaagtt  12060
gtcagatgtc cccaggtcac ttatcaggaa agctaagagt gactcatagg atgctcctgt  12120
tgcctcagtc tgggcttcat aggcatcagc agccccaaac aggcacctct gatcctgagc  12180
```

```
catccttggc tgagcaggga gcctcagaag actgtgggta tgcgcatgtg tgtgggggaa    12240
caggattgct gagccttggg gcatctttgg aaacataaag ttttaaaagt tttatgcttc    12300
actgtatatg catttctgaa atgtttgtat ataatgagtg gttacaaatg gaatcatttt    12360
atatgttact tggtagccca ccactcccta aagggactct ataggtaaat actacttctg    12420
caccttatga ttgatccatt ttgcaaattc aaatttctcc aggtataatt tacactagaa    12480
gagatagaaa aatgagactg accaggaaat ggataggtga ctttgcctgt ttctcacaga    12540
gcctgctgtc tcctgtggct tttgggtttg gctgtgagta ctttgcccct tttgaggagc    12600
agggcattgg agtgcagtgg gacaacctgt ttgagagtcc tgtggaggaa gatggcttca    12660
atctcaccac ttcggtctcc atgatgctgt ttgacacctt cctctatggg gtgatgacct    12720
ggtacattga ggctgtcttt ccaggtacac tgctttgggc atctgtttgg aaaatatgac    12780
ttctagctga tgtcctttct ttgtgctaga atctctgcag tgcatgggct tccctgggaa    12840
gtggtttggg ctatagatct atagtaaaca gatagtccaa ggacaggcag ctgatgctga    12900
aagtacaatt gtcactactt gtacagcact tgtttcttga aaactgtgtg ccaggcagca    12960
tgcaaaatgt tttatacaca ttgcttcatt taattctcac aaggctactc tgaagtagtt    13020
actataataa ccagcaattt tcaaatgaga gaactgtgac tcaaagacgt taagtaacca    13080
gctttggtca cacaactgtt aaatgttggt acgtggaggt gaatccactt cggttacact    13140
gggtcaataa gcccaggcga atcctcccaa tgctcaccca attctgtatt tctgtgtcct    13200
cagaggggga acaactagga gaggttctgt ttcctgagta caggttgtta ataattaaat    13260
atactagctc taaggcctgc ctgtgattta attagcattc aataaaaatt catgttgaat    13320
ttttctttag tacttctttc ttaatataat acatcttctt gaccaagtcc aagaggaacc    13380
tgcgttggac agttttcata tgagatcaaa ttctgagaga gcaagattta accctttttg    13440
gttccacttc tgatcctccc ctaaggaggt atacatgaaa tatttattac tcctgcctga    13500
acttctttca ttgaatatgc aattttgcag catgcagatt ctggatttaa attctgagtc    13560
ttaacttact ggctgaggga ccttggatag gctccttatc cctcagtttc ctcatctcta    13620
aaatggggat ggcacctgcc ccgtgggttg ttggaaggac ttacagaggt gcagaatgta    13680
cgttgtacat agcaggtttc agcaaatgtt agctccctct ttccccacat ccattcaaat    13740
ctgttccttc tccaaaggat gtgtcaagga ggaaatggac ctggctggga aaccctcaga    13800
atactgggat gatgctgagc ttggctcata cctgtgcttt gctttcaggc cagtacggaa    13860
ttcccaggcc ctggtatttt ccttgcacca agtcctactg gtttggcgag gaaagtgatg    13920
agaagagcca ccctggttcc aaccagaaga gaatgtcaga aagtaagtgc tgttgacctc    13980
ctgctctttc tttaacctag tgctgctgcc tctgctaact gttgggggca agcgatgtct    14040
cctgcctttc taaagactg tgaaaccact ccaggggcag agaaatcaca tgcagtgtcc    14100
ctttccaaat cctcccatgc catttatgtc caatgctgtt gacctattgg gagttcacgg    14160
tctcgatccc tgagggacat tttctttgtt gtcttggctt ctagaagagt atcttttact    14220
tgcccctcc caaacacaca tttcatggtc tcctaacaag ctagaagaaa gaggtaaaga    14280
caagcgtgat tgtggaacca tagcctcgct gcctgctgt gacatggtga cctgtgtatc    14340
agcctgtgtg ggctgagacc aagtggctac cacagagctc agcctatgct tcataatgta    14400
atcattaccc agatccctaa tcctctcttg gctcttaact gcagacagag atgtccacag    14460
ctcatcaaag gctctgcttc tgggttcttt gtgcttagag tggcttccta aatatttaat    14520
aggtcccttt tctgccagtc tcttctgtgc ccatcccctg attgcccttg gtaaaagtat    14580
```

```
gatgcccctt agtgtagcac gcttgcctgc tgttcctaat catcttctcc tacctcctct   14640
ttacacctag ctcctgtttc agtcacctag aaatgctcac agtcgctgga atatgtcatg   14700
ttcttccaca cctccatgcc tttgtaggta ctgtttgctc tcacaggaga actttctctc   14760
taacttgcct atcttctcaa ctcctccttt ctctccaaga tctagttccg gatcccctcc   14820
cctgagcatc cctccttggt tctcaggtag tcagtcactc tctgccctga acttccatgg   14880
cacgtgaaag aaaatctttt tattttaaaa caattacaga ctcacaagaa gtaatacaaa   14940
ttacatgagg gggttccctt aaacctttca tccagtttcc ccaatggtag cagcatgtgt   15000
aactgtagaa tagtatcaaa accatgaaat tgacataggt acaattcaca aaccttcttc   15060
agatttcact agctttatgt gcgctcattt gtgtgtgtgt gtgcgtattt agttctatgc   15120
aattttatca tgtgtgaatt catgtaatta ctagctcagt caagctgcag aaatatctca   15180
ttgtcacaaa gctccttcat gctaccccct aatggccaca gccacctccc ttcttcctca   15240
gttcctgaca cctgtcaacc actaatgcgt tcctcgtttt tacagttta ttatttctag   15300
aatgttacat aaatggaacc atacagtagg tatccttttg atactggctt ttttttttt    15360
ttcactcagc agtattccct tagatctatc caagttgtgt gtgtcaacag ttcattcctc   15420
ttcactgctg agtagtgttc cctgggaggg gtgtatcaca gttccatggc attttttagat   15480
gtatttttta aacagctttc agcatcctct attttaattg ttcatcaagt cctttttccc   15540
aatagactct gaatgctcct ttatcatcgt attcccatca ccaacatcag tacccaaata   15600
ggccctaaat aaacatttat agcctcctgc ctgcctgaga aaccagggtg gacatggaga   15660
gaaggcactt ctgaaagttc aagcgcagtg csctgtgtcc ttacactcca ctcctcagtg   15720
ctttctgtgg gttcatttct gtcttctctc ctgtcacagt ctgcatggag gaggaaccca   15780
cccacttgaa gctgggcgtg tccattcaga acctggtaaa agtctaccga gatgggatga   15840
aggtggctgt cgatggcctg gcactgaatt tttatgaggg ccagatcacc tccttcctgg   15900
gccacaatgg agcggggaag acgaccacca tgtaagaaga gggtgtggtt cccgcagaat   15960
cagccacagg agggttctgc agtagagtta gaaatttata ccttaggaaa ccatgctgat   16020
ccctgggcca agggaaggag cacatgagga gttgccgaat gtgaacatgt tatctaatca   16080
tgagtgtctt tccacgtgct agtttgctag atgttatttc ttcagcctaa aacaagctgg   16140
ggcctcagat gacctttccc atgtagttca cagaattctg cagtggtctt ggaacctgca   16200
gccacgaaaa gatagattac atatgttgga gggagttggt aattcccagg aactctgtct   16260
ctaagcagat gtgagaagca cctgtgagac gcaatcaagc tgggcagctg gcttgattgc   16320
cttccctgcg acctcaagga ccttacagtg ggtagtatca ggaggggtca ggggctgtaa   16380
agcaccagcg ttagcctcag tggcttccag cacgattcct caaccattct aaccattcca   16440
aagggtatat ctttggggg tgacattctt ttcctgtttt cttttaatc tttttttaaa   16500
acatagaatt aatatattat gagctttca gaagattttt aaaaggcagt cagaaatcct   16560
actacctaac acaaaaattg ttttatctt tgaataatat gttcttgttt gtccatttc    16620
catgcatgcg atgttaggca tacaaaatac atttttaaa gaatactttc attgcaaatt    16680
ggaaacttcg tttaaaaaat gctcatacta aaattggcat ttctaaccca taggcccact   16740
tgtagttatt taccgaagca aaaggacagc tttgctttgt gtgggtctgg tagggttcat   16800
tagaaaggaa tgggggcggt gggaggggttg gtgttctgtt ctctctgcag actgaatgga   16860
gcatctagag ttaagggtag gtcaaccctg acttctgtac ttctaaattt ttgtcctcag   16920
```

```
gtcaatcctg accgggttgt tccccccgac ctcgggcacc gcctacatcc tgggaaaaga    16980
cattcgctct gagatgagca ccatccggca gaacctgggg gtctgtcccc agcataacgt    17040
gctgtttgac atgtgagtac cagcagcacg ttaagaatag gccttttctg gatgtgtgtg    17100
tgtcatgcca tcatgggagg agtgggactt aagcatttta ctttgctgtg tttttgtttt    17160
ttctttttt cttttttatt ttttttgagat ggagtctcgc tctgtagcca ggctggactg    17220
tagtggcgcg atctcggctc actgcaacct tggcctccca ggttcaagcg attctcctgc    17280
ctcagcctcc cgagtagctg ggactctagg cacacaccac catgcccagc taattttgt     17340
gttttttagta gagacggggt ttcaccatgt tggccaggat ggtctcaatg tcttgacctc    17400
gtgatccgcc cacctcggtc tcccaaagtg ctgggaacac aggcatgagc cactgtgtct    17460
ggccacattt tactttcttt gaatatggca ggctcacctc cgtgaacacc ttgagaccta    17520
gttgttcttt gattttagga gaagtgggag gtgaatggtt gagctgtaga ggtgacatca    17580
gcccagccag tggatggggg cttgggaaac attgcttccc attattgtca tgctggaggg    17640
cccttagcc catcctctcc ccccgccacc ctccttattg aggcctggag cagacttccc     17700
agacctggta gtgcttcagg gccctggtat gatggaccta tatttgctgc ttaagacatt    17760
tgctcccact caggttgtcc catcagccat aaggccccca gggagcccgt gtgatggagc    17820
agagagagac ctgagctctg caatcttggg caaggctttt cccttatgtt tcttcttatc    17880
taaagtgaac agctggggct catgtgctcc ctcctcatct aaagtgaaca catggggctc    17940
atgtgcaggg tcctccccgc tttcagagcc tgaggtcccc tgaggctcag gaaggctgct    18000
ccaggtgagt gccgagctga cttcttggtg gacgtgctgt ggggacagcc cattaaagac    18060
cacatcttgg ggccctgaaa ttgaaagttg taactgcctg gtgcatggtg gccaggcctg    18120
ctggaaacag gttggaagcg atctgtcacc tttcactttg atttcctgag cagctcatgt    18180
ggttgctcac tgttgttcta ccttgaatct tgaagattat ttttcagaaa ttgataaagt    18240
tattttaaaa agcacgggga gagaaaaata tgcccattct catctgttct gggccagggg    18300
acactgtatt ctggggtatc cagtagggcc cagagctgac ctgcctccct gtccccaggc    18360
tgactgtcga agaacacatc tggttctatg cccgcttgaa agggctctct gagaagcacg    18420
tgaaggcgga gatggagcag atggccctgg atgttggttt gccatcaagc aagctgaaaa    18480
gcaaaacaag ccagctgtca ggtgcggccc agagctacct tccctatccc tctcccctcc    18540
tcctccggct acacacatgc ggaggaaaat cagcactgcc ccagggtccc aggctgggtg    18600
cggttggtaa cagaaacttg tccctggctg tgccctagg tcctctgcct tcactcactg     18660
tctggggctg gtcctggagt ttgtcttgct ctgtttttt gtaggtggaa tgcagagaaa     18720
gctatctgtg gccttggcct ttgtcggggg atctaaggtt gtcattctgg atgaacccac    18780
agctggtgtg gacccttact cccgcagggg aatatgggag ctgctgctga aataccgaca    18840
aggtgcctga tgtgtattta ttctgagtaa atggactgag agagagcggg gggcttttga   18900
gaagtgtggc tgtatctcat ggctaggctt ctgtgaagcc atgggatact cttctgttak    18960
cacagaaagag ataaagggca ttgagactga gattcctgag aggagatgct gtgtcttat    19020
tcatcttttt gtccccaaca tggtgcacta aatttatggt tagttgaaag ggtggatgct    19080
taaatgaatg gaagcggaga ggggcaggaa gacgattggg ctctctggtt agagatctga    19140
tgtggtacag tatgaggagc acaggcaggc ttggagccaa ctctggcttg gccctgagac    19200
attgggaaag tcacaacttg cctcaccttc tttgccgata taatagtgg tgcgttacct     19260
catagaggat taaattaaat gagaatgcac acaaaccacc tagcacaatg cctggcatat    19320
```

```
agcaagttcc caaataaaat gcgtactgtt cttacctctg tgaggatgtg gtacctatat    19380
atacaaagct ttgccattct aggggtcata gccatacagg gtgaaaggtg gcttccaggt    19440
ctcttccagt gcttacccct gctaatatct ctctagtccc tgtcactgtg acaaatcaga    19500
actgagaggc ctcacctgtc ccacatcctt gtgtttgtgc ctggcaggcc gcaccattat    19560
tctctctaca caccacatgg atgaagcgga cgtcctgggg gacaggattg ccatcatctc    19620
ccatgggaag ctgtgctgtg tgggctcctc cctgtttctg aagaaccagc tgggaacagg    19680
ctactacctg accttggtca agaaagatgt ggaatcctcc ctcagttcct gcagaaacag    19740
tagtagcact gtgtcatacc tgaaaaaggt gagctgcagt cttggagctg ggctggtgtt    19800
gggtctgggc agccaggact tgctggctgt gaatgatttc tccatctcca ccccttttgc    19860
catgttgaaa ccaccatctc cctgctctgt tgccccttg aaatcatatc atacttaagg     19920
catggaaagc taaggggccc tctgctccca ttgtgctagt tctgttgaat ccgttttcc     19980 ttttcctatg aggcacanag agtgatggag aaggtcctta gaggacatta ttatgtcaaa    20040
gaaaagagac ttgtcaagag gtaagagcct tggctacaaa tgacctggtc gttcctgctc    20100
attacttttc aatctcattg accttaactt ttaaactata aaacagccaa tatttattag    20160
gcactgattt catgccagag acactctggg cattgaaaga agtaatgat aatagttaat     20220 tttatatagc gttgttacca tttcaacctt tttttttttt taacctctat catctcaatt    20280
aaag                                                                 20284

<210> SEQ ID NO 22
<211> LENGTH: 7052
<212> TYPE: DNA
<213> ORGANISM: Homo sapiens

<400> SEQUENCE: 22
gtgaacacac attaaagcat gagaagcatg aactagacat gtagccaggt aaaggccttg      60
ctgagatggt tggcaaaggc ctcattgcag cattcattgg caggccacag ttcttttggc     120
agctctgctt cctgaccttt caccctcagg aagcgaggct gttcacacgg cacacacatg     180
ccagacaggg tcctctgaag ccacggctgc cagtgcatgt gtcccaggga aagcttttc      240 ctttagttct cacacaacag agcttcttgg aagccctccc cggcgaaggt gctggtggct     300
ctgccttgct ccgtccctga cccgttctca cctccttctt tgccatcagg aggacagtgt     360
ttctcagagc agttctgatg ctggcctggg cagcgaccat gagagtgaca cgctgaccat     420
cggtaaggac tctggggttt cttattcagg tggtgcctga gcttccccca gctgggcaga     480
gtggaggcag aggaggagag gtgcagaggc tggtggcgct gactcaaggt ttgctgctgg     540
gctggggctg ggtggctgcg ggggtgggag cagcttggtg gcgggttggc ctaatgcttg     600
ctggggtgcc tggggctcgg tttgggagct agcaggcag tgtcccagag agctgagatg      660
attggggttt ggggaatccc ttaggggagt ggacactgaa taccagggat gaggagctga    720
gggccaagcc aggagggtgg gatttgagct tagtacataa gaagagtgag agcccaggag    780
atgaggaaca gccttccaga ttttcttgg gtagcgtgtg taggaggcca gtgtcaccag     840
tagcatatgt ggaacagaag tcttgaccct tgctatctct gcctagtcct aatggctggc    900
ttttcccagg aaggcttctg cttccatgga ctgttagatt aacccttat ttaggtaaat     960 gagggaacct actttataag cataggaaag ggtgaagaat cttttaagat tcctttactc    1020
aagttttctt ttgaagaatc ccagagctta ggcaatagac accagacttt gagcctcagt    1080
```

```
tatccattca cccatccacc cacccaccca cccatccttc catcctccca tcctcccatt    1140
cacccatcca cccatccagc tgtccaccca ttctacactg agtacctata atgtgcctgg    1200
ctttggtgat acaaaggtga ataagacata gtcctttcct ttgccccaa ccctcagacc     1260 agagatgaac atgtggaatg acctaaacac ctggaacagg tgtggtgtat gagcggcagg    1320
cctctgatga gagggtgggg gatggccagc cctcactccg aagcccctct gagttgattg    1380
agccatcttt gcattctggt cctgcagatg tctctgctat ctccaacctc atcaggaagc    1440
atgtgtctga agcccggctg gtggaagaca tagggcatga gctgacctat gtgctgccat    1500
atgaagctgc taaggaggga gcctttgtgg aactctttca tgagattgat gaccggctct    1560
cagacctggg catttctagt tatggcatct cagagacgac cctggaagaa gtaagttaag    1620
tggctgactg tcggaatata tagcaaggcc aaatgtccta aggccagacc agtagcctgc    1680
attgggagca ggattatcat ggagttagtc attgagtttt taggtcatcg acatctgatt    1740
aatgttggcc ccagtgagcc atttaagatg gtagtgggag atagcaggaa agaagtgttt    1800
tcctctgtac cacagtacat gcctgagatt tgtgtgttga accagtggt acctaacaca     1860 tttcatccc aaccttaaac tcctatgcac ttatttaccc tttaatgagc ctctttactt     1920
aagtacagtg kgaggaacag cggcatcagg atcacttggg aacttgttag aaattcagca    1980
acttgggccc agctcagacc tactgaatca gaatcaggag caattctctg gtgtgactgt    2040
gtcacagcca ggtatcaact ggattctcat acataggaaa tgacaaacgt ttatggatgg    2100
atagtctact tgtgccaggt gctgagattt gttttttgtt ttttgatttt ttttaatca     2160 ctgtgacctc atttaattct caaaaaaga tgaaaaaatg aacactcagg aatgctgaca     2220
tgagattcag aatcagggt ttggggcttc aaagtccatc ctctctttat ccatgtaatg     2280
cctcccctta gagatacaac atcacagacc ttgaaggctg aaggggatat aaaagctgtc    2340
tggccaagtg gtctccaagc ttgacagtgc agcagaatca cctggggata ttattaaaaa    2400
taaacatact aaggtttggc ttcagggcct gtgaatcaga atttctggag gtgaggcctt    2460
gaagtctgta tttctattgc atactttgga cacagtggtc tatagactag agtttggaaa    2520
tgattgcgct cattcagatt ctcttctgat gtttgaattg ctgccatcat atttctagtg    2580
ctctatttcc tcctgctcat tctgtcttgg ataacttatc atagtactag cctactcaaa    2640
gatttagagc cacagtcctg aaagaagcca cttgactcat tccctgtagg ttcagaataa    2700
atttcttctg cgcagtgtct gtcatagctt ttttaaatt tttttttatt tttgatgaga    2760
ctggagtttt gctcttattg cccaagctgg agtgcagtgg tgcgattttg gctcactgca    2820
acctccacct cccaggttca agcgattctc ctgcctcagc ctcccaagta gctgagatta    2880
caagcatgtg ctaccacgcc cagctaattt tgtattttta gtagagatgg gttttatcca    2940
tgttggtcag gctggtctcg agctccagac ctcaggtgat ctgcccgcct cggcctccca    3000
aagtgctggg attataggcc tgagccacag cgctcagcca taactttaat ttgaaaatga    3060
ttgtctagct tgatagctct caccactgag gaaatgttct ctggcaaaaa cggcttctct    3120
cccaggtaac tctgagaaag tgttattaag aaatgtggct tctactttct ctgtcttacg    3180
gggctaacat gccactcagt aatataataa tcgtggcagt ggtgactact ctcgtaatgt    3240
tggtgcttat aatgttctca tctctctcat tttccagata ttcctcaagg tggccgaaga    3300
gagtggggtg gatgctgaga cctcaggtaa ctgccttgag ggagaatggc acacttaaga    3360
tagtgccttc tgctggcttt ctcagtgcac gagtattgtt cctttccctt tgaattgttc    3420
tattgcattc tcatttgtag agtgtaggtt tgttgcagat ggggaaggtt tgttttgttg    3480
```

```
taaataaaat aaagtatggg attctttcct tgtgccttca gatggtacct tgccagcaag    3540
acgaaacagg cgggccttcg gggacaagca gagctgtctt cgcccgttca ctgaagatga    3600
tgctgctgat ccaaatgatt ctgacataga cccaggtctg ttagggcaag atcaaacagt    3660
gtcctactgt ttgaatgtga aattctctct catgctctca cctgttttct ttggatggcc    3720
tttagccaag gtgatagatc cctacagagt ccaaagagaa gtgaggaaat ggtaaaagcc    3780
acttgttctt tgcagcatcg tgcatgtgat caaacctgaa agagcctatc catatcactt    3840
cctttaaaga cataaagatg gtgcctcaat cctctgaacc catgtattta ttatcttttc    3900
tgcggggtcc tagtttcttg tatacattag gtgtttaatt gttgaacaaa tattcattcg    3960
agtagatgag tgattttgaa agagtcagaa aggggaattt gctgttagag ttaattgtac    4020
cctaagactt agatatttga ggctgggcat ggtggctcat gccagtaatc ccagcgcttt    4080
gagaggctga ggtgggtaga tcacctgagg tcaggagttt gagaccagtc tgaccaacaa    4140
ggtgaaaccc cgtctctact aaatacaaaa aattagccga gtgtggtggc acatgcctgt    4200
catcccagct acttgggagg ctgaggcagg agaatcgctt gaacccagga ggcagaggtt    4260
gcagtcagcc acggttgcgc cattgcactc cagactgggc aacaagagtg aaaactccat    4320
ctcaaaaaag aaaaaaaaag aattagatat tttggatgag tgtgtctttg tgtgtttaac    4380
tgagatggag aggagagcta agacatcaaa caaatattgt taagatgtaa aagcacatca    4440
gttaggtatc attagtttag gacaaggatt tctagaaaat ttttaggaac agaaaacttt    4500
ccagttctct caccectgct caaagagtgt atggctctta cattatatat aactgcctga    4560
cttcatacag tatcagtact tagatcattt gaaatgtgtc cacgttttac caaaatataa    4620
tagggtgaga agctgagatg ctaattgcca ttgtgtattc tcaaatatgt caagctacgt    4680
acatggcctg tttcatagag tagtctataa gaaattgatg acttgattca tccgaatggc    4740
tggctgtaac acctggttac gcatgaacac ctcttttcag ttgtctcaag acacctttct    4800
tttctgtact tatcagacaa ggactgaaag gcagagactg ctactgttag acattttgag    4860
tcaagctttt ccttggacat agctttgtca tgaaagccct ttacttctga gaaacttcta    4920
gcttcagaca catgccttca agatagttgt tgaagacacc agaagaagga gcatggcaat    4980
gccgaaaaca cctaagataa taggtgacct tcagtgttgg cttcttgcag aatccagaga    5040
gacagacttg ctcagtggga tggatggcaa agggtcctac caggtgaaag gctggaaact    5100
tacacagcaa cagtttgtgg ccctttttgtg gaagagactg ctaattgcca gacggagtcg    5160
gaaaggattt tttgctcagg tgagacgtgc tgttttcgcc agagactctg gcttcatggg    5220
tgggctgcag gctctgtgac cagtgaaggc aggatagcat cctggtcaag atatggatgc    5280
cggagccaga tttatctgta tttcaatccc agttctattc cttgccagtt gtgtatccgc    5340
tggcaagtta cttctctatg cctcaatctc ctcatctgta aaatggggat aataatatta    5400
cctgcaatac agggttgtta cgaaaataaa aatgaatagg tgcttagaat ggggcctgac    5460
attagtaagt gcttagtttt gtgtgtgtat atgttatttt tattttggag agaacataa     5520
aaaggacaaa gtgtagaaaa actggttggg tgtattcagc tgtcataaca tgagagttgt    5580
tatgcccaga tgcacttgac atgtgaattt attagaaaca tgattttct ctgagttgat     5640
gtttaactca aactgataga aaagataggt cagaatatag ttggccaaca gagaagactt    5700
gttagactat tgtctgcatg tcagtgtttg catgctaact tgcttagtta gaaaggttaa    5760
attttttcac tctataaaat caagaaatat agagaaaagg tctgcagaga gtctttcatt    5820
```

```
tgatgatgtg gatattgtta agagcgggag tttggagcat acagagctca agttgaatcc      5880
tgactttgct acttattggc tatatgacct tgggcaagct gcttagtctc tctgatcctc      5940
agttaccttt gtttgttgat gatgaccatt gataacacaa ccataaataa tgacaacata      6000
gagatagttc tcattatagt agttgttata cagaattatt cactcaatgt taattttctg      6060
cattgaaatc ccagaacatt agaattgggg gcattatttg aatctttaag gttataagga      6120
atacatttct cagcaataaa tggaaggagt tttgggttaa cttataaagt atacccaagt      6180
catttttttt cagagaagat atggtagaaa gtcttaggag gttgaagaag gaattggata      6240
tttattcttt ctgagactat catgggagat aatgactatg gttgtccatg attggagccg      6300
ttgctgtaga gttggtttta ttatagtgta ggatttgaat gggccatgtg ttctcagacc      6360
tcagaataaa aagagaaaac tgaggccagt ggggagcgtg acttcacatg ggtacacttg      6420
tgctagagac agaaccagga ttcaggactt ctggctcctg gtcctgggtt catggcccaa      6480
tgtagtcttt ctcagtcttc aggaggagga agggcaggac ccagtgttct gagtcaccct      6540
gaatgtgagc actatttact tcgtgaactt cttggcttag tgcctctgcc aggtggccat      6600
aacctctggc cttgtgttgc cagagaaaag gtttagtttt caggctccat tgcttcccag      6660
ctgccaagaa tgccttggtg cagcacagtc ataggccctg cattcctcat tgccgtgctg      6720
gttggtcggg gaggtgggct ggactcgtag ggatttgccc cttggccttg tttctaacac      6780
ttgccgtttc ctgctgtccc cctgcccccct ccactgcctg ggtaaagatt gtcttgccag      6840
ctgtgtttgt ctgcattgcc cttgtgttca gcctgatcgt gccaccctttt ggcaagtacc      6900 ccagcctgga acttcagccc tggatgtaca acgaacagta cacatttgtc aggtatgttt      6960
gtcttctaca tcccaggagg gggtaagatt cgagcagacc aaagatgttt acgagggcca      7020
agggaatgga cttcagaatt acacggtgga at                                    7052

<210> SEQ ID NO 23
<211> LENGTH: 2534
<212> TYPE: DNA
<213> ORGANISM: Homo sapiens

<400> SEQUENCE: 23
gggaagcatt taaaaaaaaa aaagtatata tatatatata tatatatata tgtaatgtga        60
attggcctct ttttctctaa gcccacattt tcttcttaca tagttcaggt ttactttatt       120
ttttcctttc cggctgctga ccctgtattg cccgtagttg tggaacatag catgtgtttg       180
tgacctgtgc ctgttatttt tgtgcttttct agttgtgcat gcaaagagta caaagttttc       240
ttgccctttc ttggaaaatc ctgcttgtct gtgccaaagg gataattgtg aaagcacttt       300
tgaaatactt aatgagttga ttttcttcaa attaaaaaaa atatataaat gtatatgtgt       360
atgtacatgt gtgtacacat acacaccttt atacatacag cccatttaaa acaagctcca       420
ctttggagtg ctctacgtca ccctgatgcc gaatacaggg ccagagtctg agatccttct       480
gggtggtttc tgtgttttgt tcatttctgt tttaagagcc tgtcacagag aaatgcttcc       540
taaaatgttt aatttataaa acattttta tctctcgatt actggtttta atgaattact       600
aagctggctg cctctcatgt acccacagca atgatgctcc tgaggacacg ggaaccctgg       660
aactcttaaa cgccctcacc aaagaccctg gcttcgggac ccgctgtatg gaaggaaacc       720
caatcccgtg agtgccactt tagccataag cagggcttct tgtgcttgtt gcctggtttg       780
atttctaata tgctgcattt atcaactgca tgccacattg tgaccgccag catttgccct       840
ttgaattatt attatgtttt atttacaaaa agcgaaggta gtaaccgaac taaattatct       900
```

| | |
|---|---|
| aggaacaaac gtttggagag tcttctaaca ccgyscaaag cacgtcatta cagacatttg | 960 |
| tttactgatt tagaacctta atatttaatt taaatacgca ctttacactt actgatgaaa | 1020 |
| tgcttttcct ttctttctct cccagcccct gtacttaagt gcttcaatag gctctcatta | 1080 |
| tatatgattt ttaggttttg cttatcagct tcttcgcttt tataatctga aaagatggca | 1140 |
| tatgaatttt tataaaaagg gacactttct tcttctcaaa ttgtatattt ttattgtact | 1200 |
| ttccttcaaa acccccttt aaaagtaag cagtggataa ataaattcag tgaagcatcc | 1260 |
| atatgaccct taagtgagtg taggggaagg gaggtcacca gatcactgtg agtgaagatg | 1320 |
| gtggagaggt gaggatctta tgaggccgtg ctcaaggctg gtagaggtgg gttagtgttt | 1380 |
| ccaggtttag gcagaatctc agctgaggtc atgaaacaac agtgatctct gaaaaattat | 1440 |
| ggcaaggtgg gaaggtgctg gagaattgga gaggggcaa acttgacttt caagtttcaa | 1500 |
| tgggaagata ggtgactctg cacaccacag aacagtgagc atgataacct gtttatacaa | 1560 |
| ggttctagag cagatttcta aatggatagc tactgtgtgc ttgtttgttc ttaattagta | 1620 |
| ttggatagtt actaaatact tgttagtact tagtacataa tgggtggtaa atcctagcag | 1680 |
| ctaatattgg ttcccaaata accagatgac aaggatagag aaggacacag acacggccta | 1740 |
| tctggatttc atggtgcctt tgattttcca catgaaggtt gtgtagggaa gatagaagca | 1800 |
| tgagatgaga tgataatata gttatctgga ttcatcactg gccagctgaa ccatatgaac | 1860 |
| tcatggattg atgctagctt aggaaggctc tgtaggagcc agaactgggc tgagagccag | 1920 |
| cccatagaga caaaagaggc ccggccctga catcagaggg ttcaaacatg atgtctgagc | 1980 |
| cccacctaca gtctgccgga ggtggttgga aggaagagcc tttatcctta caattcttac | 2040 |
| tgaaattcaa atttttaggt tttgcaaaaa aatggtggac ctgaaggaaa tttgacagga | 2100 |
| gcatgtctca gctgtattta aatttgtctc agccaatccc cttttgaatg ttcagagtgt | 2160 |
| aagcttcagg agggcagcgc gtcttagtgt gacttttctg gtcagttcag gtgctttaag | 2220 |
| gagacaatta gagatcaatc tggaaaactt catttgaatt tttaatacat aagaaaacaa | 2280 |
| taagaaaatag ttaaaaatat atatttatat aatatatata tgtgtgtgtg tgtgtgtgtg | 2340 |
| tgtgtgtgtg tatatatata tatattttat ttatttattt tttttttgaga tggagtctcg | 2400 |
| ctctgttgcc caggctggag tgcagtggct caatcttggc tcactgccac ctctgcctcc | 2460 |
| caggttcaag tgattctcct acctcagcct cctgagtagc tgggattaca agcatgtgcc | 2520 |
| accacactgg ctaa | 2534 |

<210> SEQ ID NO 24
<211> LENGTH: 2841
<212> TYPE: DNA
<213> ORGANISM: Homo sapiens

<400> SEQUENCE: 24

| | |
|---|---|
| tcttgccagt ctctactcat ttttcagcac atcgagcata agatccagac tctttcccag | 60 |
| gcctctctca tctggctcct ctcctcctcc tttatcatta ctcttcttcg tagcttatcc | 120 |
| tactccagcc atgctgtctt cctattattc ctaaaaarta gaaatgcatt tcttcctagg | 180 |
| gcctttgtac ctgcacttgc catcgctttt gctcagaatg ttcttttgc caagcttttg | 240 |
| cccagcttgt tctccatcat tgttatgttt ggctgaaat gtcttctctt agtaggttca | 300 |
| ttctccccag tcactgtctt tttatttgc tttattttgg gccatctaag gttatcttat | 360 |
| tagtgtattt gttgttcgtc tcctccatgg gcatacacct ccatgaaggc aggtattttc | 420 |

-continued

```
accttaggcc ctcgaatata ctggacagca tctggcacgt agtagatgct caacgaatgt      480
ttgttgtgtg agcaaatggt tggttgattg gattgaactg agttcagtat gtaaatattt      540
agggcctctt tgcattctat tttacttatg tataaaatga tacataatga tgatataaat      600
gatgtcacag tgtacaaggc tgttgtggga tcaagcaatc aaatgagatc atgcttgtct      660
tttccaaatg gtgagggaat agatgcatgt ttgtggttgt tacggaatga tcctgtgctc      720
ctgaggcaac agaaaggcca ggccatctct ggtaatccta ctcttgctgt cttccctttg      780
cagagacacg ccctgccagg caggggagga agagtggacc actgcccag ttccccagac      840 catcatggac ctcttccaga atgggaactg gacaatgcag aacccttcac ctgcatgcca      900
gtgtagcagc gacaaaatca agaagatgct gcctgtgtgt cccccagggg caggggggct      960
gcctcctcca caagtgagtc actttcaggg ggtgattggg cagaaggggt gcaggatggg     1020
ctggtagctt ccgcttggaa gcaggaatga gtgagatatc atgttgggag gtctgtttc      1080 agtctttttt gtttttttgtt ttttttttctg aggcggagtc ttgctctgtc gcccaggctg     1140
gagtgctgtg gcatgatctt gcctcactgc aacctccacc tcccaggttc aagcgattct      1200
cctgcctcag cctcctgagt agctgggatt acaggcacgc accaccatgt ctggctaatt      1260
tttgtgtttt tagtagagat agggtttcgc cgtgttggct aggctggtct ggaattcctg      1320
acctcaggtg atccacccgc ctcggcctcc caaagtgctg ggattacagg cgtgagccac      1380
tacgcccagc cctgtttcag tctttaactc gcttcttgtc ataagaaaaa gcatgtgagt      1440
tttgagggga gaaggtttgg accacactgt gcccatgcct gtcccacagc agtaaagtca      1500
caggacagac tgtggcaggc ctggcttcca atcttggctc tgcaacaaat gagctggtag      1560
cctttgacag gcctgggcct gtttcttcac ctctgaatta gggaggctgg accagaaaac      1620
tcctgtggat cttgtcaact ctggtattct tagagactct gtttgggaag gagtcctgag      1680 ccatttttttt tttcttgaga atttcaggaa gaggagtgct tatgatagct ctctgctgct      1740
tttatcagca accaaattgc aggatgagga caagcaattc taaatgagta caggaactaa      1800
aagaaggctt ggttaccact cttgaaaata atagctagtc caggtgcggg gtggctcaca      1860
cctgtaatct cagtattttg ggatgccgag gtggactgat cacctaaggt caggagttcg      1920
aaaccagctt ggccaatgtg gcgaaaccct gtctctacta aaaattcaaa aattagccag      1980
gcatggtggc acatgcctgt aatcccagtt acttgggagg ctgaagcagg agaattgctt      2040
gaacctggga ggtggaggtc gcagggagcc aaaattgcgc cactgtactc cagcctgagc      2100
aacacagcaa aactccatat caaaaaataa aatgaataaa ataacagcta atctagtcat      2160
cagtataact ccagtgaaca gaagatttat taggcatagt gaatgatggt gcttcctaaa      2220
aatctcttga ctacaaagaa tctcatttca atgtttattg tttagatgtt cagaataaat      2280
tcttgggaaa gaccttggct tggtgtaagt gaattaccag tgccgagggc agggtgaacc      2340
aagtctcagt gctggttgac tgagggcagt gtctgggacc tgtagtcagg tttccggtca      2400
cactgtggac atggtcactg ttgtccttga tttgtttttct gtttcaattc ttgtctataa      2460
agacccgtat gcttggtttt catgtgatga cagagaaaac aaaacactgc agatatcctt      2520
caggacctga caggaagaaa catttcggat tatctggtga agacgtatgt gcagatcata      2580
gccaaaaggt gactttttac taaacttggc ccctgcctta ttattactaa ttagaggaat      2640
taaagaccta caaataacag actgaaacag tgggggaaat gccagattat ggcctgattc      2700
tgtctattgg aagtttagga tattatccca aactagaaaa gatgacgaga gggactgtga      2760
acattcagtt gtcagcttca aggctgaggc agcctggtct agaatgaaaa tagaaatgga      2820
```
ttcaacgtca aattttgcca c                                         2841

<210> SEQ ID NO 25
<211> LENGTH: 852
<212> TYPE: DNA
<213> ORGANISM: Homo sapiens

<400> SEQUENCE: 25
gcatgctgga gtgatagtga ccatgagttt ctaagaaaga agcataattt ctccatatgt    60
catccacaat tgaaatatta ttgttaattg aaaaagcttc taggccaggc acggtggctc   120
atgcctgtaa tcccagcact taggagcca aggcgggtgg atcacttgag gtcaggagtt    180
tgagaccagc ctggccaaca tggggaaacc ctgtctctac taaaaataca aataagctg    240
ggcgtggtgg tgcgtgcctg taatcccagc tacttgggag gctgaggcag gagaactgct   300
tgaatctggg aggcggaggt tgcagtgagc tgagttcatg ccattgcatt ccagcctggg   360
caacaagagc gaaaccatct cccaaaagaa aaaaaaaga aagaaaaagc ttctagtttg    420
gttacatctt ggtctataag gtggtttgta aattggttta acccaaggcc tggttctcat    480
ataagtaata gggtatttat gatggagaga aggctgaag aggcctgaac acaggcttct    540
tttctctagc acaaccctac aaggccagct gattctaggg ttatttctgt ccgttcctta   600
tatcctcagg tggatattta ctccttttgc atcattagga ataggctcag tgctttcttt   660
gaactgattt tttgtttctt tgtctctgca gcttaaagaa caagatctgg gtgaatgagt   720
ttaggtaagt tgctgtcttt ctggcacgtt tagctcaggg ggaggatggt gttgtaggtg    780
tgcttggatt gaagaaagcc ttggggattg tttgtcactc acacacttgt gggtgccatc   840
tcactgtgag ga                                                     852

<210> SEQ ID NO 26
<211> LENGTH: 6289
<212> TYPE: DNA
<213> ORGANISM: Homo sapiens

<400> SEQUENCE: 26
gctttataga gtttctgcct agagcatcat ggctcagtgc ccagcagccc ctccagaggc    60
ctctgaatat tgatatact gatttccttg aggagaatca gaaatctcct gcaggtgtct   120
agggatttca gtaagtagt gttgtgaggg gaatacctac ttgtactttc cccccaaacc    180
agattcccga ggcttcttaa ggactcaagg acaatttcta ggcatttagc acgggactaa    240
aaaggtctta gaggaaataa gaagcgccaa aaccatctct ttgcactgta tttcaaccca    300
tttgtccttc tgggttttga aggaacaggg gggactgggg acagaagagt tcttgaagcc    360
agtttgtcca tcatggaaaa tgagataggt gatgtggcta cgtcaggggg cccgaaggct    420
ccttgttact gatttccgtc ttttctctct gccttttccc caagggccag gacccctgga    480
tctctgggca gagcagacgc aggcccctat aatagccctc atgctagaaa ggagccggag    540
cctgtgtata aggccagcgc agcctactct ggacagtgca gggttcccac tctcccaact    600
ccccatctgc ttgcctccag acccacattc acacacgagc cactgggttg gaggagcatc    660
tgtgagatga aacaccattc tttcctcaat gtctcagcta tctaactgtg tgtgtaatca    720
ggccaggtcc tccctgctgg gcagaaacca tgggagttaa gagattgcca acatttatta    780
gaggaagctg acgtgtaact tctgaggcaa aatttagccc tcctttgaac aggaatttga    840
ctcagtgaac cttgtacaca ctcgcactga gtctgctgct gatgatactg tgcaccccac    900

```
tgtctgggtt ttaatgtcag gctgttcttt taggtatggc ggcttttccc tgggtgtcag      960
taatactcaa gcacttcctc cgagtcaaga agttaatgat gccatcaaac aaatgaagaa     1020
acacctaaag ctggccaagg taaaatatct atcgtaagat gtatcagaaa atgggcatg     1080
tagctgctgg gatataggag tagttggcag gttaaacgga tcacctggca gctcattgtt     1140
ctgaatatgt tggcatacag agccgtcttt ggcatttagc gatttgagcc agacaaaact     1200
gaattactta gttgtacgtt taaaagtgta ggtcaaaaac aaatccagag gccaggagct     1260
gtggctcatg cctgtaatcc tagcactttg ggaggctgaa gcgggtggat cacttgaggt     1320
caggagttcg agaccagcct ggcctacatg acaaaacccc gtatctacta aaaatacaaa     1380
aaaattagct gggcttggtg gcacacacct gtaatcccag ctacttggga ggctgaggca     1440
ggagaattgc ttgaaccctg taggaagagg ttgtagtgag ccaagatcgc accgttgcac     1500
tccagcctgg gcaacaagag caaaactcca tctcaaaaaa caaattaaat ccagagattt     1560
aaaagctctc agaggctggg cgcggtggct tacacctgtt atcccagcat tttgggatgc     1620
cgaggcgggc aaagcacaag gtcaggagtt tgagaccagc ctggccaaca tagtgaaacc     1680
ctgtctctgc taaaaacata gaaaaattag ccgggcatgg tggcgtgcgc ctgtaatccc     1740
agctactcgg gaggctgagg tgagagaatt rcttgaaccc gggaggcgga ggttgcagtg     1800
agcccagatt gcaccactgc actccagcct gggcgacaga gcaagactcc atctcaaaaa     1860
aagctctcag aacaaccagg tttacaaatt tggtcagttg gtaaataaac tgggtttcaa     1920
acatactttg ctgaaayaat cactgactaa ataggaaatg aatcttttt ttttttttt     1980
taagctggca agctggtctg taggacctga taagtactca cttcatttct ctgtgtctca     2040
ggtttcccat ttttaggtga gaattaaggg gctctgataa aacagaccct aggattgtgg     2100
acagcagtga tagtcctaga gtccacaagt ctgcttttga gtgatgggcc catgtatctg     2160
gcacatctgc aggcagagcg tggttctggc tcttcagatg atgccggtgg agcactttga     2220
ggagtcctca ccccaccgtg ataaccagac attaaaatct tggggctttg catcccagga     2280
tttctctgtg attccttcta gacttgtggc atcatggcag catcactgct gtagatttct     2340
agtcacttgg ttctcaggag ccgtttattt aatggcttca catttaattt cagtgaacaa     2400
ggtagtggca ttgctcttca cagggccgtc ctgttgtcca caggttccag attgactgtt     2460
gccccttatc tatgtgaaca gtcacaactg aggcaggttt ctgttgttta caggacagtt     2520
ctgcagatcg atttctcaac agcttgggaa gatttatgac aggactggac accagaaata     2580
atgtcaaggt aaaccgctgt ctttgttcta gtagcttttt gatgaacaat aatccttatg     2640
tttcctggag tactttcaac tcatggtaaa gttggcaggg gcattcacaa cagaaaagag     2700
caaactatta actttaccag tgaggcagta cggtgtagtg tagtgattca gagaatttgc     2760
tttgccacca gacataccag gtaaccttga ctaagttact taacctatct aaacctcagt     2820
tycctcatct gtgaaatgga gacagtaatc atagctattt ccaaactgtt gtgagaattc     2880
aatgagttaa aggtataagg tcctcaccac agcgcctgcc cacatagtca gtgatcacta     2940
tgtcctgaac actgtaatta cttcgccata ttctctgatc atagtgtttt gccttggtat     3000
gtgactagaa tttctttctg aggtttatgg gcatggttgg tgggtatgca cctgcctgca     3060
ggagcccggt tgggggcat taccttgtac ctggtatgtt ttctttcagg gtgtggttcaa     3120
taacaagggc tggcatgcaa tcagctcttt cctgaatgtc atcaacaatg ccattctccg     3180
ggccaacctg caaaagggag agaacctag ccattatgga attactgctt tcaatcatcc     3240
cctgaatctc accaagcagc agctctcaga ggtggctctg taagtgtggc tgtgtctgta     3300
```

```
tagatggagt ggggcaaggg agagggttat ggagaagggg agaaaaatgt gaatctcatt    3360
gtagggaac  agctgcagag accgttatat tatgataaat ctggattgat ccaggctctg    3420
ggcagaagtg ataagtttac gaattggctg gttgggcttc ttgaactgca gaagagaaaa    3480
tgacactgat atgtaaaaat cgtaacattt agtgaattca tataaagtga gttcaaaaat    3540
tgttaattaa attataattt aattataagt gtttaatcag tttgatttgt ttaaaaacca    3600
ctgttttaaa tttggtggaa tatgttttta ttagcttgta tctttaattc ctaaattaag    3660
ctgtgtgtgt gtgtgtgtgt gtgtgtgtgt gtgtgtgtgt gtgtgtgtgt gaagtttaaa    3720
gccaggatga gctagtttaa agtatgcagc ctttggagtc atacagatct gggtttgaat    3780
ctggtctcta aactttatag atgtatgata ttaaatgagg cagttcatgt aaattgccaa    3840
gcccagcact cagcacagag ttgatatttc acacacatta gatacctttc ctgtatgtgg    3900
agcatggcag ttcctgtttc tgctttactc ctacaggata ctaatatagg acactaggat    3960
ctttatacca agaccccatg taatgggctt atgagaccat tcttcttata aaaatctgac    4020
agaattttg  tatgtgttag atcaataggc tgcatactgt tattttcaag ttgatttaca    4080
gccagaaata ttaatttatt tgagtagtta cagagtaata tttctgctct catttagttt    4140
tcaagcccca ctagtccttt gtgtgtgaaa atttacaact tactgctctt acaaggtcat    4200
gaacagtgga ccaaagtgaa tgccattaac cactctgact tccttcatta gttttattgt    4260
gacagtggac tcttttgacc tcagtaatac cagtttggca tttacattgt catattttta    4320
gacttaaaaa tgatcatctt aaccctgaat aaaatgtgtc tggtgaacag atgttttcc    4380
ttggctgtgc ctcagatatc tctgtgtgtg tgtacgtgtg tgtttgtctg tgtgtccatg    4440
tcctcactga ttgagcccta actgcatcaa agacccctca gattttcaca cgcttttct    4500
ctccaggatg accacatcag tggatgtcct tgtgtccatc tgtgtcatct ttgcaatgtc    4560
cttcgtccca gccagctttg tcgtattcct gatccaggag cgggtcagca agcaaaaca    4620
cctgcagttc atcagtggag tgaagcctgt catctactgg ctctctaatt ttgtctggga    4680
tatggtaagg acacaggcct gctgtatctt tctgatgtct gtcagggcca tggattgata    4740
tggataagaa agaaagagct ctggctatca tcaggaaatg ttccagctac tctaaagatg    4800
tatgaaaaag aaatagccag aggcaggtga tcactttcat gacaccaaac acagcattgg    4860
gtaccagagt tcatgtcaca ccagagggaa aattctgtac acaatgatga aaattaatac    4920
cactaccact taagttccta tgtgacaact ttcccaagaa tcagagagat acaagtcaaa    4980
actccaagtc aatgcctcta acttctctga tgggttttaa cctccagagt cagaatgttc    5040
tttgccttac taggaaagcc atctgtcatt tagaaaactc tgtacatttt atcagcagct    5100
tatccatcca ttgcaaatat tgttttttgtg ccasccacaa tatattgctt ctatttggac    5160
caatatgggg gatttgaagg aattctgaag ttctaattat atttcaactc tactttacaa    5220
tatctccctg aaatatatct ccctgtaact tctattaatt ataagctaca cagagcaaat    5280
ctaattcttc tcccaccgaa caagtccctg gatatttaaa aataactctc atactctcat    5340
ttaacctgag tattacccag ataagatgat atatgagaat acaccttgta acctccgaag    5400
cactgtacaa atgtgagcaa tgatggtgga gatgatgatg agatctttgc tgtttatacc    5460
aagccccta  gactgtgtca ctcttctgat ccggttgtcc ttgtatggcc atgctgtata    5520
ttgtgaatgt cccgttttca aaagcaaagc caagaattaa ccttgtgttc aggctgtggt    5580
ctgaatggtt atgggtccag agggagttga tctttagctc acacttctat tactgcagca    5640
```

| | |
|---|---:|
| caaagatttt gcattttgga aggagcaccg tcttactggc aacttagtgg taaaccaaaa | 5700 |
| cctccatttc acacaaatga ttgtgaaatt cgggtctcct tcattctata caaattcatt | 5760 |
| tgatttttt gaaactaaac tttatattta tccatattaa attacatggg ttttattttt | 5820 |
| gttttatctt gattcagtaa ttactccttt cagtaaacac agactgagtg ctgtgtgtct | 5880 |
| gacttatgcc aggcataggt gattcagaga tgaaaggtca agtccctgaa cccatctctt | 5940 |
| gtcttcctgg gtattatctg tccctccctg ctttagagct cctgaaattt gctagaagca | 6000 |
| tgtcttcatc taagttgttg ataaacacat caagtaggat tggactgagg cagagccctg | 6060 |
| tagtctgaag ctgcagttct tctagcggct gacaagcccc actatcactt ccctgctggt | 6120 |
| gctttgctct gccagctgtg aattctcata attgtcctat cgtcaagtct ttatttctgc | 6180 |
| attttactgc ttgatacact gtcaggacag actttaaaat tattctcagt gcgatgaaac | 6240 |
| aattctgaca ttcatgttat gagcagttac ctcataaata gattacatg | 6289 |

<210> SEQ ID NO 27
<211> LENGTH: 4244
<212> TYPE: DNA
<213> ORGANISM: Homo sapiens

<400> SEQUENCE: 27

| | |
|---|---:|
| aaattactct gactgggaat ccatcgttca gtaagtttac tgagtgtgac accttggctt | 60 |
| gactgttgga aagacagaaa gggcatgtag tttataaaat cagccaaggg gaaaatgctt | 120 |
| gtcaaaatgt attgtcgggt attttgatta atagtttatg tggcttcatt aattcagagt | 180 |
| tactctccaa tatgtttatc tgccctttct tgtctgataa tggtgaaaac ttgtgtgatg | 240 |
| cattgtatat ttgatttagg ggtgaactgg atgtctttgt tttcactttt agtgcaatta | 300 |
| cgttgtccct gccacactgg tcattatcat cttcatctgc ttccagcaga agtcctatgt | 360 |
| gtcctccacc aatctgcctg tgctagccct tctacttttg ctgtatgggt aagtcacctc | 420 |
| tgagtgaggg agctgcacag tggataaggc atttggtgcc cagtgtcaga aggagggcag | 480 |
| ggactctcag tagacactta tctttttgtg tctcaacagg tggtcaatca cacctctcat | 540 |
| gtacccagcc tcctttgtgt tcaagatccc cagcacagcc tatgtggtgc tcaccagcgt | 600 |
| gaacctcttc attggcatta atggcagcgt ggccaccttt gtgctggagc tgttcaccga | 660 |
| caatgtgagt catgcagaga gaacactcct gctgggatga gcatctctgg gagccagagg | 720 |
| acagtgttta attgtgatct tattccactt gtcagtggta ttgacactgc tgactgcctt | 780 |
| gtcctgtctt cagagtctgt cttccctgag aaggcaaagc acctttcttt cttgctgtgc | 840 |
| cttacatttt gctggtcaag cctttcagtt tcttttgaca gttttttta cttctttctt | 900 |
| ttttcaatgt tgctccttacc aagagtagct cctctgcctt ccactttaca catgagagct | 960 |
| gggcgacgca ttcagtccta aggcttttac catcacctct cttggtgttt ttattgtcat | 1020 |
| ctctaagatc aatgccttta gccttgatca taaccttgaa ctctaatctc aaattctcac | 1080 |
| ttgcctagtg gattgctcca tttagatagt atatagatac cccaacctgg atatgtccta | 1140 |
| gttttctttc cccttggaac ttaatgcttt tcttgccatc cctgtcacac tcagtggcac | 1200 |
| taccatccac tcggttgccc aagctggctc ttagagttat cctagatgct gctttgctg | 1260 |
| ttgcagattt cccacattca actggttatg ttgtcagttc ttccaggtat ggacctctaa | 1320 |
| aataaggctt cctctccatt ccggttgtca ttgcctttgt ccaaacacag cacacaaggc | 1380 |
| cttttacagt tgcacaactc ttcctgtcca tacccaccac acccttccc agctgtaagc | 1440 |
| ttcagatgag ttgcctccaa ccaccatgct cctgtaggcc tggcttgaaa tgcccttctt | 1500 |

```
ctgtcacagg gtctggtagt atatcccttg cccttcaaga tttagctaaa atgtgaagct   1560
ttccttacct gctgggaggt gttctctctt ttctctgtgc tctcagagtc cttagtccat   1620
gcctccagta caacgtacat ccacttacat ggtaatttcc tgtttacata cttttcctac   1680
tcggagtgga gtctgtttct taataatttt gcctctccca tgccctagca cagtgcatcc   1740
agcgtatagc cccttattca gttggtagat atttggccac tgttgccttg tgggatcata   1800
agttctgatg tatttgagaa gaatttctaa aattctgaca aaatcctgaa actcaaatat   1860
tgacccagac atgagcaatt tgcttttcaa atgctaaggg attttttaatg gatttgcttt   1920
aattaaatct agcctgtttc taagctttat tcattatttc tccatactca gagcatttct   1980
ccagattttc taaagaatag aattttattg ctacatatca tcagctatgc ctgctgctat   2040
ttaattggta tctgaattaa aaggtctggt ttgtccctag agaatcaaat ttttcttca   2100
ctcccatatt tcagaacttg atacattttt aggataaacc atgaatgaca cccgtttctt   2160
ctccctcacc ctcccttccc tcccattttt tttttttttt tttttagaa gctgaataat   2220
atcaatgata tcctgaagtc cgtgttcttg atcttcccac attttgcct gggacgaggg   2280
ctcatcgaca tggtgaaaaa ccaggcaatg gctgatgccc tggaaaggtt tggtgagtga   2340
agcagtggct gtaggatgct ttaatggaga tggcactctg cataggcctt ggtaccctga   2400
actttgtttt ggaagaagc aggtgactaa gcacaggatg ttccccccacc cccatgccca   2460
gtgacagggc tcatgccaac acagctggtt gtggcatggg ttttgtgaca caaccatttg   2520
tctgtgtctc tgatagcatt gagaaaagtg aaagggcagt tttgaaggta aggaaaatag   2580
tgttatttgc ttggatccac tggctcatgc cactgtctgg gttggttaga agcactggaa   2640
aagtcaaacc ataactttga gaattaggtg atcaggaat cagaaggaaa gatgcaaact   2700
ttggctcttt taggcgaatc atgtgcctgc agatgaggtc atttattatc ttttacacag   2760
tctataaaat tataatgtat tacatctttt tctacctta gaatggttaa aaatatttct   2820
ccggtagcca tatgattatt attcatccat tagataatat agtcaaatgg gccatgttat   2880
ttactgttca tagaagaggg gcttttttgca acttgggcta caaggagat atgtaaggaa   2940
tttaaggaat ggttacatgg aactagattt aattgaatct agtggtttaa ttgattcact   3000
aggatatatg ctactgaaag gggaatctgc ttaaagtgct ttctgatatt tattattact   3060
aaaacttaga atttattaaa aatactgact gtgaaaatta cttgggtcgt ttgcctttt   3120
aaaaggattt ttggcatgtc tcattaaaaa agaaatact agatatcttc agtgaagtta   3180
caaatcgaat acacattggc tctgaaattc tgattgatac tgggtcataa aaagttttcc   3240
caaatcagac ttggaaagtg atcactctct tgttactctt ttttccttgt catgggtgat   3300
agccatttgt gtttattgga agatcggtga attttaagga acataggccc aaatttgagg   3360
aagggccatg gttttttgatc cctccattct gaccggatct ctgcattgtg tctactaggg   3420
gagaatcgct ttgtgtcacc attatcttgg gacttggtgg gacgaaacct cttcgccatg   3480
gccgtggaag gggtggtgtt cttcctcatt actgttctga tccagtacag attcttcatc   3540
aggcccaggt gagcttttc ttagaacccg tggagcacct ggttgagggt cacagaggag   3600
gcgcacaggg aaaacactcac caatgggggt tgcattgaac tgaactcaaa atatgtgata   3660
aaactgattt tcctgatgtg ggcatcccgc agcccctcc ctgcccatcc tggagactgt   3720
ggcaagtagg ttttataata ctacgttaga gactgaatct ttgtcctgaa aaatagtttg   3780
aaaggttcat ttttcttgtt ttttccccca agacctgtaa atgcaaagct atctcctctg   3840
```

| | |
|---|---:|
| aatgatgaag atgaagatgt gaggcgggaa agacagagaa ttcttgatgg tggaggccag | 3900 |
| aatgacatct tagaaatcaa ggagttgacg aaggtgagag agtacaggtt acaatagctc | 3960 |
| atcttcagtt ttttttcagct ttatgtgctg taacccagca gtttgctgac ttgcttaata | 4020 |
| aaagggcatg tgttcccaaa atgtacatct ataccaaggt tctgtcaatt ttattttaaa | 4080 |
| aacaccatgg agacttctta aagaattctt actgagaatt cttttgtgat atgaattccc | 4140 |
| attctcgaat actttggttt tatatgctta catttatgtg ttagttatta aaacatacta | 4200 |
| atattgtata tctagtcaaa ctgagtagag agataatggt gatt | 4244 |

<210> SEQ ID NO 28
<211> LENGTH: 5023
<212> TYPE: DNA
<213> ORGANISM: Homo sapiens

<400> SEQUENCE: 28

| | |
|---|---:|
| ttttaaaata cctgcaatac atatatatgt tgaatagatg aaaaattatg tagatgataa | 60 |
| tgaatgatac ggttctaaaa agacaggtta aaagtaagt tcacttttat tttgagcttc | 120 |
| agaatcattc agaagccagt cgccacaaac gcagaccaag gctcttggca catcaaatat | 180 |
| gcctatggct tagggttatt gacaagtctt atgttgcagt gtatgtggtt tatagtcctg | 240 |
| ccttccacag ttgcttggga gagctgtgag tcactgaggc ttatgaatgt ttacattttg | 300 |
| tttgttgcag atatatagaa ggaagcggaa gcctgctgtt gacaggattt gcgtgggcat | 360 |
| tcctcctggt gaggtaaaga cactttgtct atattgcgtt tgtccctatt agttcagact | 420 |
| atctctaccc aatcaagcaa cgatgctcgt taagaggtaa aagtggattt taaaggcttc | 480 |
| tgtatttatg ccaggatgga gcaattagtc atcgagaaga gagggacccct gtatgtcaag | 540 |
| agaatgattt cagagaatcc aatacaattt aagaaaaagc atgggctgg gcgcagtgat | 600 |
| tcactcctgt aatcccagca ctttgggagg ccgaggtggg cggactcacg aggtcaggag | 660 |
| attgagacca tcctggccaa catggtgaaa ccccatctct actataaata caaaaattag | 720 |
| ctgggcatag tagtgcattc ctgtagtccc agctactcgg gaggctgagg caggagaatt | 780 |
| gcttgaacct aggaggggga ggttgcccag attgcgctgc tgcactccag cctggtgaca | 840 |
| gagtgagact catgtcaaca acaaaaaacag aaaaagcacg cacatctaaa acatgctttt | 900 |
| gtgatccatt tgggatggtg atgacattca aatagttttt taaaaataga ttttctcctt | 960 |
| tctggtttcc gtttgtgttc ttttatgccc ttttgccaga gtaggtggtg caatttggct | 1020 |
| agctggcttt cattactgtt tttcacacat taactttggc ctcaacttga caactcaaat | 1080 |
| aatatttata aatacagcca cacttaaaat ggtcccatta tgaaatacat atttaaatat | 1140 |
| ctatacgatg tgttaaaacc aagaaaatat ttgattcttc tctgatatt aagaattgaa | 1200 |
| ggtttgaggt agttacgtgt taggggcatt tatattcatg tttttagagt ttgcttatac | 1260 |
| aacttaatct ttccttttca gtgctttggg ctcctgggag ttaatgggc tggaaaatca | 1320 |
| tcaactttca agatgttaac aggagatacc actgttacca gaggagatgc tttccttaac | 1380 |
| aaaaataggt gagaaaagaa gtggcttgta ttttgctgca aagactttgt ttttaattta | 1440 |
| tttaaagaaa taggttgtta ttttttgatta cagtggtatt tttagagttc ataaaaatgt | 1500 |
| tgaaatatag taaagggtaa agaagcacat aaaatcatcc atgatttcaa tatctagaga | 1560 |
| taatcacaat ttacattttcc tttcagtctc attctcttct tttaacagct ttattcaggt | 1620 |
| ataatttaca tacaatataa tttgcttgtt ttttaagagt ataatttagt gattttttggt | 1680 |
| aaattgagag ttttgcaacc atcaccacaa tccagttta gaacttttcc atcaccccac | 1740 |

```
atctgtctta tatacacata taaatgtgcc atacaattga gatcatactg tatgtagaat    1800
ttaaaattag tttttattgt taatgagtgt attatgaata tttcccagtg ggttacattt    1860
cctaagatgt ggaattttac attgctacat aaaatccccc tatgtacatg tacctataat    1920
ttatttaata aattccttat aaatgttgga cacattagtt tccatttttc actatgtaaa    1980
tatgtccctg tatacatctt ttattatttc ctcaggaaca attcctacaa agtaaattgc    2040
cctctctaaa gagcatacaa attgactgag ccaccgttag gccatttttct gagactgcac    2100 aggtcacaaa gcaatctgat ctttgggaat acagctacat tttataggct tcttagataa    2160
tgttactcta agtactttaa atatgtgggg cttctctggg cttttttttt tttgagacgg    2220
agtttcactc ttactgccca ggctggagag caatggcgcg accttggctc actgcaacct    2280
ccgcctccca ggttcaagcg attctcctgc ctcagcctcc tgagtagctg agattacagg    2340
tgcccgccac aatgcctgcc taattttttt gtattttcag tagagatggg gtttcaccat    2400
gttggccaga ctggtctcga gctcctgacc tcaggtgatc cacctgcctc agcctcccaa    2460
agttctggga ttacaggcat gagccactgc gcccggcttc tctggactta ttatgtggag    2520
agatagtaca aggcagtggc tttcagagtt ttttgaccat gaccgttgtg ggaaatacat    2580
tttatatctc aacctagtat gtacacacag acatgtagac acatgtataa cctaaagttt    2640
cataaagcag tacctactgt tactaattgt agtgcactct gctatttctt attctacctt    2700
atactgcgtc attaaaaaag tgctggtcat gacccactaa atttatttcc caaaccacta    2760
atgaacaatg actcacaatt tgaacacact ggacaggggg atagccaata aaattgaaaa    2820
gagcaaggaa attaatgtat tcatgatctc ctctcctgtc tcttacattt ttgcagtagc    2880
aatgtaaagg aatcctaaga gaacagacat tctgggaata gcaggcctag cgctgcacaa    2940
ctgctttcct aggcttgctc ctagtaccaa gctcctgacg catatagcag tggcagtaat    3000
aaccagccca tagtaaggtt tgtcacaggg actggttgta agaactgatt tgrttggtat    3060
agctgtgagg gcctggcacg gtgtccacgt gtgcctcaat cctaattctg aaaaaggctg    3120
accctggggg tgctaattag atacacagag aggaatgaat gctgccagaa ggccaagttc    3180
atggcaatgc cgctgtggct gaggtgcagt catcagtctg gaacgtgaac actgaacttc    3240
tctcacatgt gattcttcac ttgactggct tcatagaacc ccaaagccac cccaccacca    3300
cataaattgt gtctctaggt tctgtgttgc tcacactcaa aatttctggg ccttctcatt    3360
tggtgcatgt gaatggtgca tatgagtgaa gtctaggatg gggccttagc gttaaagccc    3420
tggggtagtg tgactgagat tgttggtaaa gaatgtgcag tggttggcat gacctcagaa    3480
attctgaaat gggactgcac ctgcagactg aagtgttcag agagccaggg aggtgcaagg    3540
actggggagg gtagaggcag gaaccctgcc tgccaggaag agctagcatc ctgggggcag    3600
aaaggctgtg ctttcaagta gcagcagatg tattggtatc tttgtaatgg agaagcatac    3660
tttacaggaa cattaggcca gattgtctaa ccagagtatc tctacctgct taaaatctaa    3720
gtagttttct tgtcctttgc agtatcttat caaacatcca tgaagtacat cagaacatgg    3780
gctactgccc tcagtttgat gccatcacag agctgttgac tgggagagaa cacgtggagt    3840
tctttgccct tttgagagga gtcccagaga aagaagttgg caaggtactg tgggcacctg    3900
aaagccagcc tgtctccttt ggcatcctga caatatatac cttatggctt ttccacacgc    3960
attgacttca ggctgttttt cctcatgaat gcagcagcac aaaatgctgg ttctttgtat    4020
ctgctttcag ggtggaaacc tgtaacggtg gtggggcagg gctgggtggg cagagaggga    4080
```

-continued

```
gtgctgctcc caccacacga gtcccttctc cctgctttgg ctcctcacca gttgtcaggt    4140
tatgattata gaatctagtc ctactcagtg aaagaacttt catacatgta tgtgtaggac    4200
agcatgataa aattcccaag ccagaccaaa gtcaaggtgc tttttatcac tgtaggttgg    4260
tgagtgggcg attcggaaac tgggcctcgt gaagtatgga gaaaaatatg ctggtaacta    4320
tagtggaggc aacaaacgca agctctctac agccatggct ttgatcggcg ggcctcctgt    4380
ggtgtttctg gtgagtataa ctgtggatgg aaaactgttg ttctggcctg agtggaaaac    4440
atgactgttc aaaagtccta tatgtccagg gctgttgtat gattggcttg tcttccccca    4500
gggacagcag agcaaccttg gaaaagcaga gggaagcttc tcccttggca cacactgggg    4560
tggctgtacc atgcctgcag atgctcccaa atagaggcac tccaagcact ttgtttctta    4620
gcgtgattga ggctggatat gtgatttgat ctttctctgg aacattcttt ctaatcatct    4680
ttgtgttcat tccctgaaaa tgaagagtgt ggacacagct ttaaaatccc caaggtagca    4740
actaggtcat agttccttac acacggatag atgaaaaaca gatcagactg ggaagtggcc    4800
cttgaccttt tttcttctgt agataagagc attgatgtta ttacgggaag aagcctttga    4860
ggcttttatg tattccacct cggtctggaa tttgtttctg taaggctaac agttgcaata    4920
tactagggta atctgagtga gctggaatta aaaaaaaaaa ggaatttcac cccaatctta    4980
tactgacttc aatagaggtt tcagacaaaa agttgttttg tat                     5023
```

<210> SEQ ID NO 29
<211> LENGTH: 5138
<212> TYPE: DNA
<213> ORGANISM: Homo sapiens
<220> FEATURE:
<221> NAME/KEY: misc_feature
<222> LOCATION: (1)...(5138)
<223> OTHER INFORMATION: n = a, t, c, or g

<400> SEQUENCE: 29

```
ngccnngttn aaaangaaaa tttnnnnnaa attnaanntt annggngnnn tttccccaga      60
aaaaacnaaa angatttccn cccnggggggg nccccccnant cnaaaaggcc ccncttnttt    120
gnggngaggg aaagntttttt ttggaattttt taattttttgg tccccccaaaa cctattattg   180 agaatttaat tacataaaaa agtactcaga atatttgagt ttcctgcatc aataagacat     240
ttataataat gaccttgttt acaaatgaat ttgaaagtta ctctaattct ttgattcatc     300
aagaaataac tagaatggca agttaaaatt taagctgttt caaagatgct tctgcattta    360
aaaacaaatt tatctttgat ttttttttccc cccagcaaat aagacttatt ttattctaat    420
tacaggatga acccaccaca ggcatggatc ccaaagcccg gcggttcttg tggaattgtg    480
ccctaagtgt tgtcaaggag gggagatcag tagtgcttac atctcatagg tccgtagtaa    540
agtcttgggt tcctcactgt gggatgtttt aactttccaa gtagaatatg cgatcatttt    600
gtaaaaatta gaaaatacag aaaagcaaag agtaaaacaa ttattacctg aaattatata   660
tgcatattct tacaaaaatg caagcccagt ataaatactg ctcttttttca cttaatatat    720 tgtaaacatt attccaagtc agtgcattta ggtgtcattt cttatagctg atagtattc      780 cattaggata tactcttatt taactattcc cccttttgta gacatttgga ttatttccaa    840
cttgttcaca attgtaaaca ccactacact gaacagcatc atccctatat ccacatgtac    900 tgtaacaga atacaattcc ctaggaagct ggaatgctgg aagtcatggt gatgttctca      960
tggttacaga gaatctctct aaaactaaaa cctctttctg ttttaccgca gtatggaaga   1020
atgtgaagct ctttgcacta ggatggcaat catggtcaat ggaaggttca ggtgccttgg   1080
```

```
cagtgtccag catctaaaaa ataggtaata aagataattt ctttgggata gtgcctagtg    1140
agaaggcttg atatttattc ttttgtgagt atataaatgg tgcctctaaa ataaagggaa    1200
ataaaactga gcaaaacagt atagtggaaa gaatgagggc tttgaagtcc gaactgcatt    1260
caaattctgt ctttaccatt tactggttct gtgactcttg ggcaagttac ttaactactg    1320
taagagttag tttccctgga agatctacct cctagctttg tgctatagat gaaatgaaaa    1380
aaatttacat gtgccagtac tggtgagagc gcaagctttg gagtcaaaca caaatgggtt    1440
tgcatcctgg ccctaccaat tatgagctct gagccatggg caagtgacta actccctggg    1500
cctcagtttc tctgtaacat ctgtcagact tcatgggtcc aggtgaggat taaaggagat    1560
catgtattta cagcacatgg catggtgctt cacataaaat aagtatttag taaatgataa    1620
ctggttcctt ctctcagaaa cttatttctg ggcctgccag gggccgccct ttttcatggc    1680
acaagttggg ttcccagggt tcagtattct tttaaatagt tttctggaga tcctccattt    1740
gggtatttttt tcctgctttc aggtttggag atggttatac aatagttgta cgaatagcag    1800
ggtccaaccc ggacctgaag cctgtccagg atttctttgg acttgcattt cctggaagtg    1860
ttcyaaaaga gaaacaccgg aacatgctac aataccagct tccatcttca ttatcttctc    1920
tggccaggat attcagcatc ctctcccaga gcaaaaagcg actccacata gaagactact    1980
ctgtttctca gacaacactt gaccaagtaa gctttgagtg tcaaaacaga tttacttctc    2040
agggtgtgga ttcctgcccc gacactcccg cccataggtc caagagcagt ttgtatcttg    2100
aattggtgct tgaattcctg atctactatt cctagctatg cttttttacta aacctctctg    2160
aacctgaaaa gggagatgat gcctatgtac tctataggat tattgtgaga atttactgta    2220
ataataacca taaaaactac catttagtga gcacctacca tgggccaggc attttacttg    2280
gtgcctaatc ctatttaaat tagataaaaa agtaccaaat aggtcctgac acttaagaag    2340
tactcagtaa atatttttctt ccctcttccc tttaatcaag accgtatgtg ccaaagtaaa    2400
tggatgactg agcagttggt gatgtagggg tgggggcga tatagaaagt cagttttttgg    2460
ccgggcgtgg tggctcatgc ctgtaatccc agcactttgg gaggctgagg agcaggcaga    2520
tcatgaggtc aggagatcca gataatcctg gccaacaggg tgaaaccccg tctctactaa    2580
aaatacaaaa attagctggg catggtggtg cgcacttgta gtcccagcta cttgcgaggc    2640
tgaggcagga gaattgctcg aacccaggag gtggaggtta cagtgagcca aggtctcgcc    2700
actgcactcc agcctgggga cagagcaaga ccccatttca aggggggaaa aaaagtctat    2760
ttttaagttg ttattgcttt tttcaagtat tcttccctcc ttcacacaca gttttctagt    2820
taatccattt atgtaattct gtatgctcct acttgaccta atttcaacat ctggaaaaat    2880
agaactagaa taaagaatga gcaagttgag tggtatttat aaaggtccat cttaatcttt    2940
taacaggtat ttgtgaactt tgccaaggac caaagtgatg atgaccactt aaaagacctc    3000
tcattacaca aaaaccagac agtagtggac gttgcagttc tcacatcttt tctacaggat    3060
gagaaagtga aagaaagcta tgtatgaaga atcctgttca tacggggtgg ctgaaagtaa    3120
agaggaacta gactttcctt tgcaccatgt gaagtgttgt ggagaaaaga gccagaagtt    3180
gatgtgggaa gaagtaaact ggatactgta ctgatactat tcaatgcaat gcaattcaat    3240
gcaatgaaaa caaaattcca ttacagggggc agtgcctttg tagcctatgt cttgtatggc    3300
tctcaagtga aagacttgaa tttagttttt tacctatacc tatgtgaaac tctattatgg    3360
aacccaatgg acatatgggt ttgaactcac acttttttttt ttttttttgt tcctgtgtat    3420
```

-continued

```
tctcattggg gttgcaacaa taattcatca agtaatcatg ccagcgatt attgatcaaa      3480 atcaaaaggt aatgcacatc ctcattcact aagccatgcc atgcccagga gactggtttc      3540
ccggtgacac atccattgct ggcaatgagt gtgccagagt tattagtgcc aagttttcca      3600
gaaagtttga agcaccatgg tgtgtcatgc tcacttttgt gaaagctgct ctgctcagag      3660
tctatcaaca ttgaatatca gttgacagaa tggtgccatg cgtggctaac atcctgcttt      3720
gattccctct gataagctgt tctggtggca gtaacatgca acaaaaatgt gggtgtctcc      3780
aggcacggga aacttggttc cattgttata ttgtcctatg cttcgagcca tgggtctaca      3840
gggtcatcct tatgagactc ttaaatatac ttagatcctg gtaagaggca aagaatcaac      3900
agccaaactg ctgggctgc aactgctgaa gccagggcat gggattaaag agattgtgcg      3960
ttcaaaccta gggaagcctg tgcccatttg tcctgactgt ctgctaacat ggtacactgc      4020
atctcaagat gtttatctga cacaagtgta ttatttctgg cttttttgaat taatctagaa      4080 aatgaaaaga tggagttgta ttttgacaaa aatgtttgta cttttttaatg ttatttggaa      4140 ttttaagttc tatcagtgac ttctgaatcc ttagaatggc ctctttgtag aaccctgtgg      4200
tatagaggag tatggccact gcccactatt tttatttttct tatgtaagtt tgcatatcag      4260
tcatgactag tgcctagaaa gcaatgtgat ggtcaggatc tcatgacatt atatttgagt      4320
ttctttcaga tcatttagga tactcttaat ctcacttcat caatcaaata ttttttgagt      4380
gtatgctgta gctgaaagag tatgtacgta cgtataagac tagagagata ttaagtctca      4440
gtacacttcc tgtgccatgt tattcagctc actggtttac aaatataggt tgtcttgtgg      4500
ttgtaggagc ccactgtaac aatactgggc agccttttt ttttttttt taattgcaac      4560 aatgcaaaag ccaagaaagt ttaagggtca caagtctaaa caatgaattc ttcaacaggg      4620
aaaacagcta gcttgaaaac ttgctgaaaa acacaacttg tgtttatggc atttagtacc      4680
ttcaaataat tggctttgca gatattggat accccattaa atctgacagt ctcaaatttt      4740
tcatctcttc aatcactagt caagaaaaaa tataaaaaca acaaatactt ccatatggag      4800
catttttcag agttttctaa cccagtctta tttttctagt cagtaaacat ttgtaaaaat      4860
actgtttcac taatacttac tgttaactgt cttgagagaa aagaaaaata tgagagaact      4920
attgtttggg gaagttcaag tgatctttca atatcattac taacttcttc cacttttcc      4980 agaatttgaa tattaacgct aaaggtgtaa gacttcagat ttcaaattaa tctttctata      5040
ttttttaaat ttacagaata ttatataacc cactgctgaa aaagaaacaa atgattgttt      5100
tagaagttaa aggtcaatat tgattttaaa atattaag                            5138
```

<210> SEQ ID NO 30
<211> LENGTH: 20
<212> TYPE: DNA
<213> ORGANISM: Homo sapiens

<400> SEQUENCE: 30

```
gtgttcctgc agagggcatg                                                    20
```

<210> SEQ ID NO 31
<211> LENGTH: 20
<212> TYPE: DNA
<213> ORGANISM: Homo sapiens

<400> SEQUENCE: 31

```
cacttccagt aacagctgac                                                    20
```

```
<210> SEQ ID NO 32
<211> LENGTH: 21
<212> TYPE: DNA
<213> ORGANISM: Homo sapiens

<400> SEQUENCE: 32
ctttgcgcat gtccttcatg c                                             21

<210> SEQ ID NO 33
<211> LENGTH: 21
<212> TYPE: DNA
<213> ORGANISM: Homo sapiens

<400> SEQUENCE: 33
gacatcagcc ctcagcatct t                                             21

<210> SEQ ID NO 34
<211> LENGTH: 19
<212> TYPE: DNA
<213> ORGANISM: Homo sapiens

<400> SEQUENCE: 34
caacaagcca tgttccctc                                                19

<210> SEQ ID NO 35
<211> LENGTH: 18
<212> TYPE: DNA
<213> ORGANISM: Homo sapiens

<400> SEQUENCE: 35
catgttccct cagccagc                                                 18

<210> SEQ ID NO 36
<211> LENGTH: 19
<212> TYPE: DNA
<213> ORGANISM: Homo sapiens

<400> SEQUENCE: 36
cagagctcac agcagggac                                                19

<210> SEQ ID NO 37
<211> LENGTH: 21
<212> TYPE: PRT
<213> ORGANISM: Homo sapiens

<400> SEQUENCE: 37

Cys Ser Val Arg Leu Ser Tyr Pro Pro Tyr Glu Gln His Glu Cys His
 1               5                  10                  15

Phe Pro Asn Lys Ala
            20

<210> SEQ ID NO 38
<211> LENGTH: 14
<212> TYPE: DNA
<213> ORGANISM: Homo sapiens

<400> SEQUENCE: 38
gcctgtgtgt cccc                                                     14

<210> SEQ ID NO 39
<211> LENGTH: 14
<212> TYPE: DNA
<213> ORGANISM: Homo sapiens
<220> FEATURE:
```

```
<221> NAME/KEY: misc_feature
<222> LOCATION: (1)...(14)
<223> OTHER INFORMATION: n = t or c

<400> SEQUENCE: 39
gcctgtgngt cccc                                                         14

<210> SEQ ID NO 40
<211> LENGTH: 45
<212> TYPE: DNA
<213> ORGANISM: Homo sapiens

<400> SEQUENCE: 40
aagaagatgc tgcctgtgtg tcccccaggg gcagggggc tgcct                        45

<210> SEQ ID NO 41
<211> LENGTH: 15
<212> TYPE: PRT
<213> ORGANISM: Homo sapiens

<400> SEQUENCE: 41
```

Lys Lys Met Leu Pro Val Cys Pro Pro Gly Ala Gly Gly Leu Pro
 1               5                  10                  15

```
<210> SEQ ID NO 42
<211> LENGTH: 15
<212> TYPE: PRT
<213> ORGANISM: Mus musculus

<400> SEQUENCE: 42
```

Lys Lys Met Leu Pro Val Cys Pro Pro Gly Ala Gly Gly Leu Pro
 1               5                  10                  15

```
<210> SEQ ID NO 43
<211> LENGTH: 15
<212> TYPE: PRT
<213> ORGANISM: Homo sapiens

<400> SEQUENCE: 43
```

Lys Lys Met Leu Pro Val Arg Pro Pro Gly Ala Gly Gly Leu Pro
 1               5                  10                  15

```
<210> SEQ ID NO 44
<211> LENGTH: 5
<212> TYPE: PRT
<213> ORGANISM: Caenorhabditis elegans

<400> SEQUENCE: 44
```

Leu Leu Gly Gly Ser
 1               5

```
<210> SEQ ID NO 45
<211> LENGTH: 45
<212> TYPE: DNA
<213> ORGANISM: Homo sapiens

<400> SEQUENCE: 45
aagaagatgc tgcctgtgcg tcccccaggg gcagggggc tgcct                        45

<210> SEQ ID NO 46
<211> LENGTH: 14
<212> TYPE: DNA
<213> ORGANISM: Homo sapiens

<400> SEQUENCE: 46
```

```
gcctacttgc agga                                                         14

<210> SEQ ID NO 47
<211> LENGTH: 14
<212> TYPE: DNA
<213> ORGANISM: Homo sapiens

<400> SEQUENCE: 47
gcctacttgc ggga                                                         14

<210> SEQ ID NO 48
<211> LENGTH: 45
<212> TYPE: DNA
<213> ORGANISM: Homo sapiens

<400> SEQUENCE: 48
tgggggggct cgcctactt gcaggatgtg gtggagcagg caatc                        45

<210> SEQ ID NO 49
<211> LENGTH: 15
<212> TYPE: PRT
<213> ORGANISM: Homo sapiens

<400> SEQUENCE: 49

Trp Gly Gly Phe Ala Tyr Leu Gln Asp Val Val Glu Gln Ala Ile
 1               5                  10                  15

<210> SEQ ID NO 50
<211> LENGTH: 15
<212> TYPE: PRT
<213> ORGANISM: Mus musculus

<400> SEQUENCE: 50

Trp Gly Gly Phe Ala Tyr Leu Gln Asp Val Val Glu Gln Ala Ile
 1               5                  10                  15

<210> SEQ ID NO 51
<211> LENGTH: 15
<212> TYPE: PRT
<213> ORGANISM: Homo sapiens

<400> SEQUENCE: 51

Trp Gly Gly Phe Ala Tyr Leu Arg Asp Val Val Glu Gln Ala Ile
 1               5                  10                  15

<210> SEQ ID NO 52
<211> LENGTH: 12
<212> TYPE: PRT
<213> ORGANISM: Caenorhabditis elegans

<400> SEQUENCE: 52

Phe Met Thr Val Gln Arg Ala Val Asp Val Ala Ile
 1               5                  10

<210> SEQ ID NO 53
<211> LENGTH: 45
<212> TYPE: DNA
<213> ORGANISM: Homo sapiens

<400> SEQUENCE: 53
tgggggggct cgcctactt gcgggatgtg gtggagcagg caatc                        45

<210> SEQ ID NO 54
```

```
<211> LENGTH: 25
<212> TYPE: DNA
<213> ORGANISM: Homo sapiens
<220> FEATURE:
<221> NAME/KEY: misc_feature
<222> LOCATION: (1)...(25)
<223> OTHER INFORMATION: n is a, t, c, or g.

<400> SEQUENCE: 54
tcattcctct tgtnngcncn gnncn                                            25

<210> SEQ ID NO 55
<211> LENGTH: 45
<212> TYPE: DNA
<213> ORGANISM: Homo sapiens

<400> SEQUENCE: 55
agtagcctca ttcctcttct tgtgagcgct ggcctgctag tggtc                      45

<210> SEQ ID NO 56
<211> LENGTH: 15
<212> TYPE: PRT
<213> ORGANISM: Homo sapiens

<400> SEQUENCE: 56

Ser Ser Leu Ile Pro Leu Leu Val Ser Ala Gly Leu Leu Val Val
 1               5                  10                  15

<210> SEQ ID NO 57
<211> LENGTH: 15
<212> TYPE: PRT
<213> ORGANISM: Mus musculus

<400> SEQUENCE: 57

Ser Ser Leu Ile Pro Leu Leu Val Ser Ala Gly Leu Leu Val Val
 1               5                  10                  15

<210> SEQ ID NO 58
<211> LENGTH: 14
<212> TYPE: PRT
<213> ORGANISM: Homo sapiens

<400> SEQUENCE: 58

Ser Ser Leu Ile Pro Leu Val Ser Ala Gly Leu Leu Val Val
 1               5                  10

<210> SEQ ID NO 59
<211> LENGTH: 15
<212> TYPE: PRT
<213> ORGANISM: Caenorhabditis elegans

<400> SEQUENCE: 59

Ile Asn Tyr Ala Lys Leu Thr Phe Ala Val Ile Val Leu Thr Ile
 1               5                  10                  15

<210> SEQ ID NO 60
<211> LENGTH: 42
<212> TYPE: DNA
<213> ORGANISM: Homo sapiens

<400> SEQUENCE: 60
agtagcctca ttcctcttgt gagcgctggc ctgctagtgg tc                         42

<210> SEQ ID NO 61
<211> LENGTH: 25
```

```
<212> TYPE: DNA
<213> ORGANISM: Homo sapiens
<220> FEATURE:
<221> NAME/KEY: misc_feature
<222> LOCATION: (1)...(25)
<223> OTHER INFORMATION: n is a, t, c, or g.

<400> SEQUENCE: 61
tgatgaagat gananncngn ngcga                                          25

<210> SEQ ID NO 62
<211> LENGTH: 36
<212> TYPE: DNA
<213> ORGANISM: Homo sapiens

<400> SEQUENCE: 62
aatgatgaag atgaagatgt gaggcgggaa agacag                              36

<210> SEQ ID NO 63
<211> LENGTH: 12
<212> TYPE: PRT
<213> ORGANISM: Homo sapiens

<400> SEQUENCE: 63

Asn Asp Glu Asp Glu Asp Val Arg Arg Glu Arg Gln
 1               5                  10

<210> SEQ ID NO 64
<211> LENGTH: 12
<212> TYPE: PRT
<213> ORGANISM: Mus musculus

<400> SEQUENCE: 64

Asn Asp Glu Asp Glu Asp Val Arg Arg Glu Arg Gln
 1               5                  10

<210> SEQ ID NO 65
<211> LENGTH: 10
<212> TYPE: PRT
<213> ORGANISM: Homo sapiens

<400> SEQUENCE: 65

Asn Asp Glu Asp Val Arg Arg Glu Arg Gln
 1               5                  10

<210> SEQ ID NO 66
<211> LENGTH: 15
<212> TYPE: PRT
<213> ORGANISM: Caenorhabditis elegans

<400> SEQUENCE: 66

Asp Glu Arg Asp Val Glu Asp Ser Asp Val Ile Ala Glu Lys Ser
 1               5                  10                  15

<210> SEQ ID NO 67
<211> LENGTH: 30
<212> TYPE: DNA
<213> ORGANISM: Homo sapiens

<400> SEQUENCE: 67
aatgatgaag atgtgaggcg ggaaagacag                                     30

<210> SEQ ID NO 68
<211> LENGTH: 14
<212> TYPE: DNA
```

```
<213> ORGANISM: Homo sapiens

<400> SEQUENCE: 68
agttgtacga atag                                                        14

<210> SEQ ID NO 69
<211> LENGTH: 14
<212> TYPE: DNA
<213> ORGANISM: Homo sapiens
<220> FEATURE:
<221> NAME/KEY: misc_feature
<222> LOCATION: (1)...(14)
<223> OTHER INFORMATION: n is t or c.

<400> SEQUENCE: 69
agttgtanga atag                                                        14

<210> SEQ ID NO 70
<211> LENGTH: 20
<212> TYPE: DNA
<213> ORGANISM: Homo sapiens

<400> SEQUENCE: 70
ggctggatta gcagtcctca                                                  20

<210> SEQ ID NO 71
<211> LENGTH: 20
<212> TYPE: DNA
<213> ORGANISM: Homo sapiens

<400> SEQUENCE: 71
ggatttccca gatcccagtg                                                  20

<210> SEQ ID NO 72
<211> LENGTH: 20
<212> TYPE: DNA
<213> ORGANISM: Homo sapiens

<400> SEQUENCE: 72
gacagacttg gcatgaagca                                                  20

<210> SEQ ID NO 73
<211> LENGTH: 20
<212> TYPE: DNA
<213> ORGANISM: Homo sapiens

<400> SEQUENCE: 73
gcacttggca gtcacttctg                                                  20

<210> SEQ ID NO 74
<211> LENGTH: 20
<212> TYPE: DNA
<213> ORGANISM: Homo sapiens

<400> SEQUENCE: 74
cgtttctcca ctgtcccatt                                                  20

<210> SEQ ID NO 75
<211> LENGTH: 20
<212> TYPE: DNA
<213> ORGANISM: Homo sapiens

<400> SEQUENCE: 75
acttcaagga cccagcttcc                                                  20
```

```
<210> SEQ ID NO 76
<211> LENGTH: 24
<212> TYPE: DNA
<213> ORGANISM: Homo sapiens

<400> SEQUENCE: 76
tcggtttctt gtttgttaaa ctca                                              24

<210> SEQ ID NO 77
<211> LENGTH: 20
<212> TYPE: DNA
<213> ORGANISM: Homo sapiens

<400> SEQUENCE: 77
tcccaaggct ttgagatgac                                                   20

<210> SEQ ID NO 78
<211> LENGTH: 19
<212> TYPE: DNA
<213> ORGANISM: Homo sapiens

<400> SEQUENCE: 78
ggctccaaag cccttgtaa                                                    19

<210> SEQ ID NO 79
<211> LENGTH: 20
<212> TYPE: DNA
<213> ORGANISM: Homo sapiens

<400> SEQUENCE: 79
gctgctgtga tggggtatct                                                   20

<210> SEQ ID NO 80
<211> LENGTH: 25
<212> TYPE: DNA
<213> ORGANISM: Homo sapiens

<400> SEQUENCE: 80
tttgtaaatt ttgtagtgct cctca                                             25

<210> SEQ ID NO 81
<211> LENGTH: 20
<212> TYPE: DNA
<213> ORGANISM: Homo sapiens

<400> SEQUENCE: 81
tagtcagccc ttgcctccta                                                   20

<210> SEQ ID NO 82
<211> LENGTH: 20
<212> TYPE: DNA
<213> ORGANISM: Homo sapiens

<400> SEQUENCE: 82 aaagggctt ggtaagggta                                                    20

<210> SEQ ID NO 83
<211> LENGTH: 20
<212> TYPE: DNA
<213> ORGANISM: Homo sapiens

<400> SEQUENCE: 83
```

-continued

```
gatgtggtgc tccctctagc                                         20

<210> SEQ ID NO 84
<211> LENGTH: 20
<212> TYPE: DNA
<213> ORGANISM: Homo sapiens

<400> SEQUENCE: 84
caagtgagtg cttgggattg                                         20

<210> SEQ ID NO 85
<211> LENGTH: 21
<212> TYPE: DNA
<213> ORGANISM: Homo sapiens

<400> SEQUENCE: 85
gcaaattcaa atttctccag g                                       21

<210> SEQ ID NO 86
<211> LENGTH: 20
<212> TYPE: DNA
<213> ORGANISM: Homo sapiens

<400> SEQUENCE: 86
tcaaggagga aatggacctg                                         20

<210> SEQ ID NO 87
<211> LENGTH: 20
<212> TYPE: DNA
<213> ORGANISM: Homo sapiens

<400> SEQUENCE: 87
ctgaaagttc aagcgcagtg                                         20

<210> SEQ ID NO 88
<211> LENGTH: 20
<212> TYPE: DNA
<213> ORGANISM: Homo sapiens

<400> SEQUENCE: 88
tgcagactga atggagcatc                                         20

<210> SEQ ID NO 89
<211> LENGTH: 20
<212> TYPE: DNA
<213> ORGANISM: Homo sapiens

<400> SEQUENCE: 89
gccaggggac actgtattct                                         20

<210> SEQ ID NO 90
<211> LENGTH: 20
<212> TYPE: DNA
<213> ORGANISM: Homo sapiens

<400> SEQUENCE: 90
aggtcctctg ccttcactca                                         20

<210> SEQ ID NO 91
<211> LENGTH: 20
<212> TYPE: DNA
<213> ORGANISM: Homo sapiens

<400> SEQUENCE: 91
```

```
ccagtgctta cccctgctaa                                              20

<210> SEQ ID NO 92
<211> LENGTH: 21
<212> TYPE: DNA
<213> ORGANISM: Homo sapiens

<400> SEQUENCE: 92
cacacaacag agcttcttgg a                                            21

<210> SEQ ID NO 93
<211> LENGTH: 20
<212> TYPE: DNA
<213> ORGANISM: Homo sapiens

<400> SEQUENCE: 93
acctggaaca ggtgtggtgt                                              20

<210> SEQ ID NO 94
<211> LENGTH: 21
<212> TYPE: DNA
<213> ORGANISM: Homo sapiens

<400> SEQUENCE: 94
gggctaacat gccactcagt a                                            21

<210> SEQ ID NO 95
<211> LENGTH: 20
<212> TYPE: DNA
<213> ORGANISM: Homo sapiens

<400> SEQUENCE: 95
gtttgttgca gatggggaag                                              20

<210> SEQ ID NO 96
<211> LENGTH: 20
<212> TYPE: DNA
<213> ORGANISM: Homo sapiens

<400> SEQUENCE: 96
caccagaaga aggagcatgg                                              20

<210> SEQ ID NO 97
<211> LENGTH: 20
<212> TYPE: DNA
<213> ORGANISM: Homo sapiens

<400> SEQUENCE: 97
ctggactcgt agggatttgc                                              20

<210> SEQ ID NO 98
<211> LENGTH: 21
<212> TYPE: DNA
<213> ORGANISM: Homo sapiens

<400> SEQUENCE: 98
gcctgtcaca gagaaatgct t                                            21

<210> SEQ ID NO 99
<211> LENGTH: 21
<212> TYPE: DNA
<213> ORGANISM: Homo sapiens
```

```
<400> SEQUENCE: 99
ttacggaatg atcctgtgct c                                          21

<210> SEQ ID NO 100
<211> LENGTH: 20
<212> TYPE: DNA
<213> ORGANISM: Homo sapiens

<400> SEQUENCE: 100
agtcaggttt ccggtcacac                                            20

<210> SEQ ID NO 101
<211> LENGTH: 22
<212> TYPE: DNA
<213> ORGANISM: Homo sapiens

<400> SEQUENCE: 101
ccgttcctta tatcctcagg tg                                         22

<210> SEQ ID NO 102
<211> LENGTH: 21
<212> TYPE: DNA
<213> ORGANISM: Homo sapiens

<400> SEQUENCE: 102
ccttgtacac actcgcactg a                                          21

<210> SEQ ID NO 103
<211> LENGTH: 20
<212> TYPE: DNA
<213> ORGANISM: Homo sapiens

<400> SEQUENCE: 103
tgttgtccac aggttccaga                                            20

<210> SEQ ID NO 104
<211> LENGTH: 20
<212> TYPE: DNA
<213> ORGANISM: Homo sapiens

<400> SEQUENCE: 104
tgaggtttat gggcatggtt                                            20

<210> SEQ ID NO 105
<211> LENGTH: 20
<212> TYPE: DNA
<213> ORGANISM: Homo sapiens

<400> SEQUENCE: 105
atgtttttcc ttggctgtgc                                            20

<210> SEQ ID NO 106
<211> LENGTH: 20
<212> TYPE: DNA
<213> ORGANISM: Homo sapiens

<400> SEQUENCE: 106
atctgccctt tcttgtctga                                            20

<210> SEQ ID NO 107
<211> LENGTH: 20
<212> TYPE: DNA
<213> ORGANISM: Homo sapiens
```

<400> SEQUENCE: 107
agggagctgc acagtggata					20

<210> SEQ ID NO 108
<211> LENGTH: 24
<212> TYPE: DNA
<213> ORGANISM: Homo sapiens

<400> SEQUENCE: 108
tcactcccat atttcagaac ttga				24

<210> SEQ ID NO 109
<211> LENGTH: 22
<212> TYPE: DNA
<213> ORGANISM: Homo sapiens

<400> SEQUENCE: 109
tgtttattgg aagatcggtg aa				22

<210> SEQ ID NO 110
<211> LENGTH: 25
<212> TYPE: DNA
<213> ORGANISM: Homo sapiens

<400> SEQUENCE: 110
cgttagagac tgaatctttg tcctg				25

<210> SEQ ID NO 111
<211> LENGTH: 20
<212> TYPE: DNA
<213> ORGANISM: Homo sapiens

<400> SEQUENCE: 111
agtcctgcct tccacagttg					20

<210> SEQ ID NO 112
<211> LENGTH: 21
<212> TYPE: DNA
<213> ORGANISM: Homo sapiens

<400> SEQUENCE: 112
ggtagttacg tgttaggggc a					21

<210> SEQ ID NO 113
<211> LENGTH: 21
<212> TYPE: DNA
<213> ORGANISM: Homo sapiens

<400> SEQUENCE: 113
caggaacatt aggccagatt g					21

<210> SEQ ID NO 114
<211> LENGTH: 23
<212> TYPE: DNA
<213> ORGANISM: Homo sapiens

<400> SEQUENCE: 114
catgtatgtg taggacagca tga				23

<210> SEQ ID NO 115
<211> LENGTH: 21
<212> TYPE: DNA

<213> ORGANISM: Homo sapiens

<400> SEQUENCE: 115
ctgtttcaaa gatgcttctg c                                             21

<210> SEQ ID NO 116
<211> LENGTH: 20
<212> TYPE: DNA
<213> ORGANISM: Homo sapiens

<400> SEQUENCE: 116
cctaggaagc tggaatgctg                                               20

<210> SEQ ID NO 117
<211> LENGTH: 20
<212> TYPE: DNA
<213> ORGANISM: Homo sapiens

<400> SEQUENCE: 117
gggttcccag ggttcagtat                                               20

<210> SEQ ID NO 118
<211> LENGTH: 23
<212> TYPE: DNA
<213> ORGANISM: Homo sapiens

<400> SEQUENCE: 118
cttgacctaa tttcaacatc tgg                                           23

<210> SEQ ID NO 119
<211> LENGTH: 20
<212> TYPE: DNA
<213> ORGANISM: Homo sapiens

<400> SEQUENCE: 119
atccccaact caaaaccaca                                               20

<210> SEQ ID NO 120
<211> LENGTH: 21
<212> TYPE: DNA
<213> ORGANISM: Homo sapiens

<400> SEQUENCE: 120
aagtccaatt tagcccacgt t                                             21

<210> SEQ ID NO 121
<211> LENGTH: 20
<212> TYPE: DNA
<213> ORGANISM: Homo sapiens

<400> SEQUENCE: 121
ccagccattc aaaattctcc                                               20

<210> SEQ ID NO 122
<211> LENGTH: 20
<212> TYPE: DNA
<213> ORGANISM: Homo sapiens

<400> SEQUENCE: 122
ggtgcaggtc aatttccaat                                               20

<210> SEQ ID NO 123
<211> LENGTH: 20

```
<212> TYPE: DNA
<213> ORGANISM: Homo sapiens

<400> SEQUENCE: 123 cccctttcacc accattacaa                                              20

<210> SEQ ID NO 124
<211> LENGTH: 20
<212> TYPE: DNA
<213> ORGANISM: Homo sapiens

<400> SEQUENCE: 124
tgtccaagga aaagcctcac                                               20

<210> SEQ ID NO 125
<211> LENGTH: 20
<212> TYPE: DNA
<213> ORGANISM: Homo sapiens

<400> SEQUENCE: 125
aggacctctt gccagactca                                               20

<210> SEQ ID NO 126
<211> LENGTH: 20
<212> TYPE: DNA
<213> ORGANISM: Homo sapiens

<400> SEQUENCE: 126
aggagatgac acaggccaag                                               20

<210> SEQ ID NO 127
<211> LENGTH: 20
<212> TYPE: DNA
<213> ORGANISM: Homo sapiens

<400> SEQUENCE: 127
cgcacacctc tgaagctacc                                               20

<210> SEQ ID NO 128
<211> LENGTH: 20
<212> TYPE: DNA
<213> ORGANISM: Homo sapiens

<400> SEQUENCE: 128
acctcactca cacctgggaa                                               20

<210> SEQ ID NO 129
<211> LENGTH: 20
<212> TYPE: DNA
<213> ORGANISM: Homo sapiens

<400> SEQUENCE: 129
gcctcctgcc tgaaccttat                                               20

<210> SEQ ID NO 130
<211> LENGTH: 23
<212> TYPE: DNA
<213> ORGANISM: Homo sapiens

<400> SEQUENCE: 130
caaaatcatg acaccaagtt gag                                           23

<210> SEQ ID NO 131
```

```
<211> LENGTH: 20
<212> TYPE: DNA
<213> ORGANISM: Homo sapiens

<400> SEQUENCE: 131
catgcacatg cacacacata                                                   20

<210> SEQ ID NO 132
<211> LENGTH: 20
<212> TYPE: DNA
<213> ORGANISM: Homo sapiens

<400> SEQUENCE: 132
ccttagcccg tgttgagcta                                                   20

<210> SEQ ID NO 133
<211> LENGTH: 21
<212> TYPE: DNA
<213> ORGANISM: Homo sapiens

<400> SEQUENCE: 133
tgcttttatt cagggactcc a                                                 21

<210> SEQ ID NO 134
<211> LENGTH: 20
<212> TYPE: DNA
<213> ORGANISM: Homo sapiens

<400> SEQUENCE: 134
cccatgcact gcagagattc                                                   20

<210> SEQ ID NO 135
<211> LENGTH: 19
<212> TYPE: DNA
<213> ORGANISM: Homo sapiens

<400> SEQUENCE: 135
aaggcaggag acatcgctt                                                    19

<210> SEQ ID NO 136
<211> LENGTH: 20
<212> TYPE: DNA
<213> ORGANISM: Homo sapiens

<400> SEQUENCE: 136
gggatcagca tggtttccta                                                   20

<210> SEQ ID NO 137
<211> LENGTH: 20
<212> TYPE: DNA
<213> ORGANISM: Homo sapiens

<400> SEQUENCE: 137
gcttaagtcc cactcctccc                                                   20

<210> SEQ ID NO 138
<211> LENGTH: 20
<212> TYPE: DNA
<213> ORGANISM: Homo sapiens

<400> SEQUENCE: 138
attttcctcc gcatgtgtgt                                                   20
```

```
<210> SEQ ID NO 139
<211> LENGTH: 20
<212> TYPE: DNA
<213> ORGANISM: Homo sapiens

<400> SEQUENCE: 139
tcacagaagc ctagccatga                                        20

<210> SEQ ID NO 140
<211> LENGTH: 20
<212> TYPE: DNA
<213> ORGANISM: Homo sapiens

<400> SEQUENCE: 140
aacagagcag ggagatggtg                                        20

<210> SEQ ID NO 141
<211> LENGTH: 20
<212> TYPE: DNA
<213> ORGANISM: Homo sapiens

<400> SEQUENCE: 141
tctgcacctc tcctcctctg                                        20

<210> SEQ ID NO 142
<211> LENGTH: 20
<212> TYPE: DNA
<213> ORGANISM: Homo sapiens

<400> SEQUENCE: 142
actggggcca acattaatca                                        20

<210> SEQ ID NO 143
<211> LENGTH: 20
<212> TYPE: DNA
<213> ORGANISM: Homo sapiens

<400> SEQUENCE: 143
cttccccatc tgcaacaaac                                        20

<210> SEQ ID NO 144
<211> LENGTH: 20
<212> TYPE: DNA
<213> ORGANISM: Homo sapiens

<400> SEQUENCE: 144
gctaaaggcc atccaaagaa                                        20

<210> SEQ ID NO 145
<211> LENGTH: 20
<212> TYPE: DNA
<213> ORGANISM: Homo sapiens

<400> SEQUENCE: 145
tcaagtgcat ctgggcataa                                        20

<210> SEQ ID NO 146
<211> LENGTH: 20
<212> TYPE: DNA
<213> ORGANISM: Homo sapiens

<400> SEQUENCE: 146
tctgaagtcc attcccttgg                                        20
```

```
<210> SEQ ID NO 147
<211> LENGTH: 20
<212> TYPE: DNA
<213> ORGANISM: Homo sapiens

<400> SEQUENCE: 147
caatgtggca tgcagttgat                                               20

<210> SEQ ID NO 148
<211> LENGTH: 19
<212> TYPE: DNA
<213> ORGANISM: Homo sapiens

<400> SEQUENCE: 148
gaagctacca gcccatcct                                                19

<210> SEQ ID NO 149
<211> LENGTH: 20
<212> TYPE: DNA
<213> ORGANISM: Homo sapiens

<400> SEQUENCE: 149
catttccccc actgtttcag                                               20

<210> SEQ ID NO 150
<211> LENGTH: 20
<212> TYPE: DNA
<213> ORGANISM: Homo sapiens

<400> SEQUENCE: 150
ccaaggcttt cttcaatcca                                               20

<210> SEQ ID NO 151
<211> LENGTH: 20
<212> TYPE: DNA
<213> ORGANISM: Homo sapiens

<400> SEQUENCE: 151
gatccgttta acctgccaac                                               20

<210> SEQ ID NO 152
<211> LENGTH: 19
<212> TYPE: DNA
<213> ORGANISM: Homo sapiens

<400> SEQUENCE: 152
atgcccctgc caactttac                                                19

<210> SEQ ID NO 153
<211> LENGTH: 20
<212> TYPE: DNA
<213> ORGANISM: Homo sapiens

<400> SEQUENCE: 153
ctctgcagct gttcccctac                                               20

<210> SEQ ID NO 154
<211> LENGTH: 20
<212> TYPE: DNA
<213> ORGANISM: Homo sapiens

<400> SEQUENCE: 154
tatcaatcca tggccctgac                                               20
```

<210> SEQ ID NO 155
<211> LENGTH: 20
<212> TYPE: DNA
<213> ORGANISM: Homo sapiens

<400> SEQUENCE: 155
agagtccctg ccctccttct                                               20

<210> SEQ ID NO 156
<211> LENGTH: 20
<212> TYPE: DNA
<213> ORGANISM: Homo sapiens

<400> SEQUENCE: 156
aaggcagtca gcagtgtcaa                                               20

<210> SEQ ID NO 157
<211> LENGTH: 20
<212> TYPE: DNA
<213> ORGANISM: Homo sapiens

<400> SEQUENCE: 157
ggggaacatc ctgtgcttag                                               20

<210> SEQ ID NO 158
<211> LENGTH: 20
<212> TYPE: DNA
<213> ORGANISM: Homo sapiens

<400> SEQUENCE: 158
ccattggtga gtgtttccct                                               20

<210> SEQ ID NO 159
<211> LENGTH: 20
<212> TYPE: DNA
<213> ORGANISM: Homo sapiens

<400> SEQUENCE: 159
agtcagcaaa ctgctgggtt                                               20

<210> SEQ ID NO 160
<211> LENGTH: 20
<212> TYPE: DNA
<213> ORGANISM: Homo sapiens

<400> SEQUENCE: 160
attgctccat cctggcataa                                               20

<210> SEQ ID NO 161
<211> LENGTH: 23
<212> TYPE: DNA
<213> ORGANISM: Homo sapiens

<400> SEQUENCE: 161
tcatggatga ttttatgtgc ttc                                           23

<210> SEQ ID NO 162
<211> LENGTH: 20
<212> TYPE: DNA
<213> ORGANISM: Homo sapiens

<400> SEQUENCE: 162

-continued gcgtgtggaa aagccataag 20

<210> SEQ ID NO 163
<211> LENGTH: 20
<212> TYPE: DNA
<213> ORGANISM: Homo sapiens

<400> SEQUENCE: 163
gccaatcata caacagccct 20

<210> SEQ ID NO 164
<211> LENGTH: 23
<212> TYPE: DNA
<213> ORGANISM: Homo sapiens

<400> SEQUENCE: 164
tgatcgcata ttctacttgg aaa 23

<210> SEQ ID NO 165
<211> LENGTH: 22
<212> TYPE: DNA
<213> ORGANISM: Homo sapiens

<400> SEQUENCE: 165
tccctttatt ttagaggcac ca 22

<210> SEQ ID NO 166
<211> LENGTH: 21
<212> TYPE: DNA
<213> ORGANISM: Homo sapiens

<400> SEQUENCE: 166
gatcaggaat tcaagcacca a 21

<210> SEQ ID NO 167
<211> LENGTH: 24
<212> TYPE: DNA
<213> ORGANISM: Homo sapiens

<400> SEQUENCE: 167
tgggttccat aatagagttt caca 24

<210> SEQ ID NO 168
<211> LENGTH: 22
<212> TYPE: DNA
<213> ORGANISM: Homo sapiens

<400> SEQUENCE: 168
tgtcagctgt tactggaagt gg 22

<210> SEQ ID NO 169
<211> LENGTH: 22
<212> TYPE: DNA
<213> ORGANISM: Homo sapiens

<400> SEQUENCE: 169
tgtcagctgc tgctggaagt gg 22

<210> SEQ ID NO 170
<211> LENGTH: 21
<212> TYPE: DNA
<213> ORGANISM: Homo sapiens

<400> SEQUENCE: 170
aggagctggc cgaagccaca a                              21

<210> SEQ ID NO 171
<211> LENGTH: 21
<212> TYPE: DNA
<213> ORGANISM: Homo sapiens

<400> SEQUENCE: 171
aggagctggc tgaagccaca a                              21

<210> SEQ ID NO 172
<211> LENGTH: 21
<212> TYPE: DNA
<213> ORGANISM: Homo sapiens

<400> SEQUENCE: 172
aatgatgcca ccaaacaaat g                              21

<210> SEQ ID NO 173
<211> LENGTH: 21
<212> TYPE: DNA
<213> ORGANISM: Homo sapiens

<400> SEQUENCE: 173
aatgatgcca tcaaacaaat g                              21

<210> SEQ ID NO 174
<211> LENGTH: 21
<212> TYPE: DNA
<213> ORGANISM: Homo sapiens

<400> SEQUENCE: 174
gaggtggctc cgatgaccac a                              21

<210> SEQ ID NO 175
<211> LENGTH: 21
<212> TYPE: DNA
<213> ORGANISM: Homo sapiens

<400> SEQUENCE: 175
gaggtggctc tgatgaccac a                              21

<210> SEQ ID NO 176
<211> LENGTH: 21
<212> TYPE: DNA
<213> ORGANISM: Homo sapiens

<400> SEQUENCE: 176
ttccttaaca gaaatagtat c                              21

<210> SEQ ID NO 177
<211> LENGTH: 21
<212> TYPE: DNA
<213> ORGANISM: Homo sapiens

<400> SEQUENCE: 177
ttccttaaca aaaatagtat c                              21

<210> SEQ ID NO 178
<211> LENGTH: 21
<212> TYPE: DNA
<213> ORGANISM: Homo sapiens

```
<400> SEQUENCE: 178
ggaagtgttc caaaagagaa a                                              21

<210> SEQ ID NO 179
<211> LENGTH: 21
<212> TYPE: DNA
<213> ORGANISM: Homo sapiens

<400> SEQUENCE: 179
ggaagtgttc taaaagagaa a                                              21

<210> SEQ ID NO 180
<211> LENGTH: 21
<212> TYPE: DNA
<213> ORGANISM: Homo sapiens

<400> SEQUENCE: 180
agtaaagagg gactagactt t                                              21

<210> SEQ ID NO 181
<211> LENGTH: 21
<212> TYPE: DNA
<213> ORGANISM: Homo sapiens

<400> SEQUENCE: 181
agtaaagagg aactagactt t                                              21

<210> SEQ ID NO 182
<211> LENGTH: 21
<212> TYPE: DNA
<213> ORGANISM: Homo sapiens

<400> SEQUENCE: 182
gcctacttgc aggatgtggt g                                              21

<210> SEQ ID NO 183
<211> LENGTH: 21
<212> TYPE: DNA
<213> ORGANISM: Homo sapiens

<400> SEQUENCE: 183
gcctacttgc gggatgtggt g                                              21

<210> SEQ ID NO 184
<211> LENGTH: 23
<212> TYPE: DNA
<213> ORGANISM: Homo sapiens

<400> SEQUENCE: 184
cctcattcct cttcttgtga gcg                                            23

<210> SEQ ID NO 185
<211> LENGTH: 20
<212> TYPE: DNA
<213> ORGANISM: Homo sapiens

<400> SEQUENCE: 185
cctcattcct cttgtgagcg                                                20

<210> SEQ ID NO 186
<211> LENGTH: 21
<212> TYPE: DNA
<213> ORGANISM: Homo sapiens
```

```
<400> SEQUENCE: 186
gcaggactac gtgggcttca c                                              21

<210> SEQ ID NO 187
<211> LENGTH: 21
<212> TYPE: DNA
<213> ORGANISM: Homo sapiens

<400> SEQUENCE: 187
gcaggactac atgggcttca c                                              21

<210> SEQ ID NO 188
<211> LENGTH: 21
<212> TYPE: DNA
<213> ORGANISM: Homo sapiens

<400> SEQUENCE: 188
aaaagtctac cgagatggga t                                              21

<210> SEQ ID NO 189
<211> LENGTH: 21
<212> TYPE: DNA
<213> ORGANISM: Homo sapiens

<400> SEQUENCE: 189
aaaagtctac tgagatggga t                                              21

<210> SEQ ID NO 190
<211> LENGTH: 21
<212> TYPE: DNA
<213> ORGANISM: Homo sapiens

<400> SEQUENCE: 190
ggccagatca cctccttcct g                                              21

<210> SEQ ID NO 191
<211> LENGTH: 21
<212> TYPE: DNA
<213> ORGANISM: Homo sapiens

<400> SEQUENCE: 191
ggccagatca tctccttcct g                                              21

<210> SEQ ID NO 192
<211> LENGTH: 21
<212> TYPE: DNA
<213> ORGANISM: Homo sapiens

<400> SEQUENCE: 192
acacaccaca tggatgaagc g                                              21

<210> SEQ ID NO 193
<211> LENGTH: 21
<212> TYPE: DNA
<213> ORGANISM: Homo sapiens

<400> SEQUENCE: 193
acacaccaca cggatgaagc g                                              21

<210> SEQ ID NO 194
<211> LENGTH: 21
<212> TYPE: DNA
```

```
<213> ORGANISM: Homo sapiens

<400> SEQUENCE: 194
cctggaagaa gtaagttaag t                                    21

<210> SEQ ID NO 195
<211> LENGTH: 21
<212> TYPE: DNA
<213> ORGANISM: Homo sapiens

<400> SEQUENCE: 195
cctggaagaa ctaagttaag t                                    21

<210> SEQ ID NO 196
<211> LENGTH: 21
<212> TYPE: DNA
<213> ORGANISM: Homo sapiens

<400> SEQUENCE: 196
gctgcctgtg tgtcccccag g                                    21

<210> SEQ ID NO 197
<211> LENGTH: 21
<212> TYPE: DNA
<213> ORGANISM: Homo sapiens

<400> SEQUENCE: 197
gctgcctgtg cgtcccccag g                                    21

<210> SEQ ID NO 198
<211> LENGTH: 22
<212> TYPE: DNA
<213> ORGANISM: Homo sapiens

<400> SEQUENCE: 198
tagccattat ggaattactg ct                                   22

<210> SEQ ID NO 199
<211> LENGTH: 21
<212> TYPE: DNA
<213> ORGANISM: Homo sapiens

<400> SEQUENCE: 199
tagccattat caattactgc t                                    21

<210> SEQ ID NO 200
<211> LENGTH: 26
<212> TYPE: DNA
<213> ORGANISM: Homo sapiens

<400> SEQUENCE: 200
gatgaagatg aagatgtgag gcggga                               26

<210> SEQ ID NO 201
<211> LENGTH: 20
<212> TYPE: DNA
<213> ORGANISM: Homo sapiens

<400> SEQUENCE: 201
gatgaagatg tgaggcggga                                      20

<210> SEQ ID NO 202
<211> LENGTH: 21
```

<212> TYPE: DNA
<213> ORGANISM: Homo sapiens

<400> SEQUENCE: 202
aatagttgta cgaatagcag g                                          21

<210> SEQ ID NO 203
<211> LENGTH: 21
<212> TYPE: DNA
<213> ORGANISM: Homo sapiens

<400> SEQUENCE: 203
aatagttgta tgaatagcag g                                          21

<210> SEQ ID NO 204
<211> LENGTH: 21
<212> TYPE: DNA
<213> ORGANISM: Homo sapiens

<400> SEQUENCE: 204
acacgctggg ggtgctggct g                                          21

<210> SEQ ID NO 205
<211> LENGTH: 21
<212> TYPE: DNA
<213> ORGANISM: Homo sapiens

<400> SEQUENCE: 205
acacgctggg cgtgctggct g                                          21

<210> SEQ ID NO 206
<211> LENGTH: 20
<212> TYPE: DNA
<213> ORGANISM: Homo sapiens

<400> SEQUENCE: 206
gaccagccac ggcgtccctg                                            20

<210> SEQ ID NO 207
<211> LENGTH: 21
<212> TYPE: DNA
<213> ORGANISM: Homo sapiens

<400> SEQUENCE: 207
gaccagccac gggcgtccct g                                          21

<210> SEQ ID NO 208
<211> LENGTH: 22
<212> TYPE: DNA
<213> ORGANISM: Homo sapiens

<400> SEQUENCE: 208
cattttctta gaaaagagag gt                                         22

<210> SEQ ID NO 209
<211> LENGTH: 22
<212> TYPE: DNA
<213> ORGANISM: Homo sapiens

<400> SEQUENCE: 209
cattttctta gagaagagag gt                                         22

<210> SEQ ID NO 210

```
<211> LENGTH: 21
<212> TYPE: DNA
<213> ORGANISM: Homo sapiens

<400> SEQUENCE: 210
gaaaattagt atgtaaggaa g                                              21

<210> SEQ ID NO 211
<211> LENGTH: 21
<212> TYPE: DNA
<213> ORGANISM: Homo sapiens

<400> SEQUENCE: 211
gaaaattagt ctgtaaggaa g                                              21

<210> SEQ ID NO 212
<211> LENGTH: 25
<212> TYPE: DNA
<213> ORGANISM: Homo sapiens

<400> SEQUENCE: 212
cctccgcctg ccaggttcag cgatt                                          25

<210> SEQ ID NO 213
<211> LENGTH: 25
<212> TYPE: DNA
<213> ORGANISM: Homo sapiens

<400> SEQUENCE: 213
cctccgcctg ccgggttcag cgatt                                          25

<210> SEQ ID NO 214
<211> LENGTH: 25
<212> TYPE: DNA
<213> ORGANISM: Homo sapiens

<400> SEQUENCE: 214
tatgtgctga ccatgggagc ttgtt                                          25

<210> SEQ ID NO 215
<211> LENGTH: 25
<212> TYPE: DNA
<213> ORGANISM: Homo sapiens

<400> SEQUENCE: 215
tatgtgctga ccgtgggagc ttgtt                                          25

<210> SEQ ID NO 216
<211> LENGTH: 21
<212> TYPE: DNA
<213> ORGANISM: Homo sapiens

<400> SEQUENCE: 216
gtgacaccca acggagtagg g                                              21

<210> SEQ ID NO 217
<211> LENGTH: 21
<212> TYPE: DNA
<213> ORGANISM: Homo sapiens

<400> SEQUENCE: 217
gtgacaccca gcggagtagg g                                              21
```

```
<210> SEQ ID NO 218
<211> LENGTH: 21
<212> TYPE: DNA
<213> ORGANISM: Homo sapiens

<400> SEQUENCE: 218
agtatccctt gttcacgaga a                                        21

<210> SEQ ID NO 219
<211> LENGTH: 25
<212> TYPE: DNA
<213> ORGANISM: Homo sapiens

<400> SEQUENCE: 219
agtatccctc ccttgttcac gagaa                                    25

<210> SEQ ID NO 220
<211> LENGTH: 21
<212> TYPE: DNA
<213> ORGANISM: Homo sapiens

<400> SEQUENCE: 220
ctgggttcct gtatcacaac c                                        21

<210> SEQ ID NO 221
<211> LENGTH: 21
<212> TYPE: DNA
<213> ORGANISM: Homo sapiens

<400> SEQUENCE: 221
ctgggttcct atatcacaac c                                        21

<210> SEQ ID NO 222
<211> LENGTH: 21
<212> TYPE: DNA
<213> ORGANISM: Homo sapiens

<400> SEQUENCE: 222
ggcctaccaa gggagaaact g                                        21

<210> SEQ ID NO 223
<211> LENGTH: 21
<212> TYPE: DNA
<213> ORGANISM: Homo sapiens

<400> SEQUENCE: 223
ggcctaccaa aggagaaact g                                        21

<210> SEQ ID NO 224
<211> LENGTH: 20
<212> TYPE: DNA
<213> ORGANISM: Homo sapiens

<400> SEQUENCE: 224
tttaaagggg gtgattagga                                          20

<210> SEQ ID NO 225
<211> LENGTH: 20
<212> TYPE: DNA
<213> ORGANISM: Homo sapiens

<400> SEQUENCE: 225
tttaaagggg ttgattagga                                          20
```

```
<210> SEQ ID NO 226
<211> LENGTH: 22
<212> TYPE: DNA
<213> ORGANISM: Homo sapiens

<400> SEQUENCE: 226
gaagaaattt gtttttttga tt                                              22

<210> SEQ ID NO 227
<211> LENGTH: 22
<212> TYPE: DNA
<213> ORGANISM: Homo sapiens

<400> SEQUENCE: 227
gaagaaattt ttttttttga tt                                              22

<210> SEQ ID NO 228
<211> LENGTH: 21
<212> TYPE: DNA
<213> ORGANISM: Homo sapiens

<400> SEQUENCE: 228
gcgggcatcc cgagggaggg g                                               21

<210> SEQ ID NO 229
<211> LENGTH: 21
<212> TYPE: DNA
<213> ORGANISM: Homo sapiens

<400> SEQUENCE: 229
gcgggcatcc tgagggaggg g                                               21

<210> SEQ ID NO 230
<211> LENGTH: 21
<212> TYPE: DNA
<213> ORGANISM: Homo sapiens

<400> SEQUENCE: 230
agggaggggg gctgaagatc a                                               21

<210> SEQ ID NO 231
<211> LENGTH: 21
<212> TYPE: DNA
<213> ORGANISM: Homo sapiens

<400> SEQUENCE: 231
agggaggggg actgaagatc a                                               21

<210> SEQ ID NO 232
<211> LENGTH: 20
<212> TYPE: DNA
<213> ORGANISM: Homo sapiens

<400> SEQUENCE: 232
aggagccaaa cgctcattgt                                                 20

<210> SEQ ID NO 233
<211> LENGTH: 21
<212> TYPE: DNA
<213> ORGANISM: Homo sapiens

<400> SEQUENCE: 233
aggagccaaa gcgctcattg t                                               21
```

<210> SEQ ID NO 234
<211> LENGTH: 21
<212> TYPE: DNA
<213> ORGANISM: Homo sapiens

<400> SEQUENCE: 234
aagccactgt ttttaaccag t                                              21

<210> SEQ ID NO 235
<211> LENGTH: 21
<212> TYPE: DNA
<213> ORGANISM: Homo sapiens

<400> SEQUENCE: 235
aagccactgt atttaaccag t                                              21

<210> SEQ ID NO 236
<211> LENGTH: 21
<212> TYPE: DNA
<213> ORGANISM: Homo sapiens

<400> SEQUENCE: 236
cgtgggcttc acactcaaga t                                              21

<210> SEQ ID NO 237
<211> LENGTH: 21
<212> TYPE: DNA
<213> ORGANISM: Homo sapiens

<400> SEQUENCE: 237
cgtgggcttc ccactcaaga t                                              21

<210> SEQ ID NO 238
<211> LENGTH: 21
<212> TYPE: DNA
<213> ORGANISM: Homo sapiens

<400> SEQUENCE: 238
tcacactcaa gatcttcgct g                                              21

<210> SEQ ID NO 239
<211> LENGTH: 21
<212> TYPE: DNA
<213> ORGANISM: Homo sapiens

<400> SEQUENCE: 239
tcacactcaa catcttcgct g                                              21

<210> SEQ ID NO 240
<211> LENGTH: 21
<212> TYPE: DNA
<213> ORGANISM: Homo sapiens

<400> SEQUENCE: 240
gcagcctcac ccgctcttcc c                                              21

<210> SEQ ID NO 241
<211> LENGTH: 21
<212> TYPE: DNA
<213> ORGANISM: Homo sapiens

<400> SEQUENCE: 241

-continued

| | |
|---|---|
| gcagcctcac tcgctcttcc c | 21 |

<210> SEQ ID NO 242
<211> LENGTH: 21
<212> TYPE: DNA
<213> ORGANISM: Homo sapiens

<400> SEQUENCE: 242

| | |
|---|---|
| agaagagaat atcagaaatc t | 21 |

<210> SEQ ID NO 243
<211> LENGTH: 21
<212> TYPE: DNA
<213> ORGANISM: Homo sapiens

<400> SEQUENCE: 243

| | |
|---|---|
| agaagagaat gtcagaaatc t | 21 |

<210> SEQ ID NO 244
<211> LENGTH: 21
<212> TYPE: DNA
<213> ORGANISM: Homo sapiens

<400> SEQUENCE: 244

| | |
|---|---|
| gcgcagtgcc ctgtgtcctt a | 21 |

<210> SEQ ID NO 245
<211> LENGTH: 21
<212> TYPE: DNA
<213> ORGANISM: Homo sapiens

<400> SEQUENCE: 245

| | |
|---|---|
| gcgcagtgcg ctgtgtcctt a | 21 |

<210> SEQ ID NO 246
<211> LENGTH: 21
<212> TYPE: DNA
<213> ORGANISM: Homo sapiens

<400> SEQUENCE: 246

| | |
|---|---|
| gatctaaggt tgtcattctg g | 21 |

<210> SEQ ID NO 247
<211> LENGTH: 21
<212> TYPE: DNA
<213> ORGANISM: Homo sapiens

<400> SEQUENCE: 247

| | |
|---|---|
| gatctaaggt ggtcattctg g | 21 |

<210> SEQ ID NO 248
<211> LENGTH: 23
<212> TYPE: DNA
<213> ORGANISM: Homo sapiens

<400> SEQUENCE: 248

| | |
|---|---|
| ctcttctgtt agcacagaag aga | 23 |

<210> SEQ ID NO 249
<211> LENGTH: 23
<212> TYPE: DNA
<213> ORGANISM: Homo sapiens

<400> SEQUENCE: 249

```
ctcttctgtt atcacagaag aga                                    23

<210> SEQ ID NO 250
<211> LENGTH: 21
<212> TYPE: DNA
<213> ORGANISM: Homo sapiens

<400> SEQUENCE: 250
cattctaggg atcatagcca t                                      21

<210> SEQ ID NO 251
<211> LENGTH: 21
<212> TYPE: DNA
<213> ORGANISM: Homo sapiens

<400> SEQUENCE: 251
cattctaggg gtcatagcca t                                      21

<210> SEQ ID NO 252
<211> LENGTH: 22
<212> TYPE: DNA
<213> ORGANISM: Homo sapiens

<400> SEQUENCE: 252
aagtacagtg ggaggaacag cg                                     22

<210> SEQ ID NO 253
<211> LENGTH: 22
<212> TYPE: DNA
<213> ORGANISM: Homo sapiens

<400> SEQUENCE: 253
aagtacagtg tgaggaacag cg                                     22

<210> SEQ ID NO 254
<211> LENGTH: 22
<212> TYPE: DNA
<213> ORGANISM: Homo sapiens

<400> SEQUENCE: 254
attcctaaaa aatagaaatg ca                                     22

<210> SEQ ID NO 255
<211> LENGTH: 22
<212> TYPE: DNA
<213> ORGANISM: Homo sapiens

<400> SEQUENCE: 255
attcctaaaa agtagaaatg ca                                     22

<210> SEQ ID NO 256
<211> LENGTH: 21
<212> TYPE: DNA
<213> ORGANISM: Homo sapiens

<400> SEQUENCE: 256
ggcccctgcc ttattattac t                                      21

<210> SEQ ID NO 257
<211> LENGTH: 21
<212> TYPE: DNA
<213> ORGANISM: Homo sapiens
```

```
<400> SEQUENCE: 257
ggcccctgcc gtattattac t                                              21

<210> SEQ ID NO 258
<211> LENGTH: 22
<212> TYPE: DNA
<213> ORGANISM: Homo sapiens

<400> SEQUENCE: 258
tgagagaatt acttgaaccc gg                                             22

<210> SEQ ID NO 259
<211> LENGTH: 22
<212> TYPE: DNA
<213> ORGANISM: Homo sapiens

<400> SEQUENCE: 259
tgagagaatt gcttgaaccc gg                                             22

<210> SEQ ID NO 260
<211> LENGTH: 21
<212> TYPE: DNA
<213> ORGANISM: Homo sapiens

<400> SEQUENCE: 260
tttgctgaaa caatcactga c                                              21

<210> SEQ ID NO 261
<211> LENGTH: 21
<212> TYPE: DNA
<213> ORGANISM: Homo sapiens

<400> SEQUENCE: 261
tttgctgaaa taatcactga c                                              21

<210> SEQ ID NO 262
<211> LENGTH: 22
<212> TYPE: DNA
<213> ORGANISM: Homo sapiens

<400> SEQUENCE: 262
aacctcagtt ccctcatctg tg                                             22

<210> SEQ ID NO 263
<211> LENGTH: 22
<212> TYPE: DNA
<213> ORGANISM: Homo sapiens

<400> SEQUENCE: 263
aacctcagtt tcctcatctg tg                                             22

<210> SEQ ID NO 264
<211> LENGTH: 21
<212> TYPE: DNA
<213> ORGANISM: Homo sapiens

<400> SEQUENCE: 264
ctggacacca gaataatgt c                                               21

<210> SEQ ID NO 265
<211> LENGTH: 21
<212> TYPE: DNA
<213> ORGANISM: Homo sapiens
```

<400> SEQUENCE: 265
ctggacacca aaaataatgt c                                                    21

<210> SEQ ID NO 266
<211> LENGTH: 21
<212> TYPE: DNA
<213> ORGANISM: Homo sapiens

<400> SEQUENCE: 266
tcctatgtgt cctccaccaa t                                                    21

<210> SEQ ID NO 267
<211> LENGTH: 21
<212> TYPE: DNA
<213> ORGANISM: Homo sapiens

<400> SEQUENCE: 267
tcctatgtgt gctccaccaa t                                                    21

<210> SEQ ID NO 268
<211> LENGTH: 21
<212> TYPE: DNA
<213> ORGANISM: Homo sapiens

<400> SEQUENCE: 268
aagaagtggc ttgtattttg c                                                    21

<210> SEQ ID NO 269
<211> LENGTH: 21
<212> TYPE: DNA
<213> ORGANISM: Homo sapiens

<400> SEQUENCE: 269
aagaagtggc ctgtattttg c                                                    21

<210> SEQ ID NO 270
<211> LENGTH: 23
<212> TYPE: DNA
<213> ORGANISM: Homo sapiens

<400> SEQUENCE: 270
aactgatttg attggtatag ctg                                                  23

<210> SEQ ID NO 271
<211> LENGTH: 23
<212> TYPE: DNA
<213> ORGANISM: Homo sapiens

<400> SEQUENCE: 271
aactgatttg gttggtatag ctg                                                  23

<210> SEQ ID NO 272
<211> LENGTH: 21
<212> TYPE: DNA
<213> ORGANISM: Homo sapiens

<400> SEQUENCE: 272
cagggtccaa cccggacctg a                                                    21

<210> SEQ ID NO 273
<211> LENGTH: 21
<212> TYPE: DNA

<213> ORGANISM: Homo sapiens

<400> SEQUENCE: 273
cagggtccaa tccggacctg a                                           21

<210> SEQ ID NO 274
<211> LENGTH: 22
<212> TYPE: DNA
<213> ORGANISM: Homo sapiens

<400> SEQUENCE: 274
ttgggaggct aaggcaggag aa                                          22

<210> SEQ ID NO 275
<211> LENGTH: 22
<212> TYPE: DNA
<213> ORGANISM: Homo sapiens

<400> SEQUENCE: 275
ttgggaggct gaggcaggag aa                                          22

<210> SEQ ID NO 276
<211> LENGTH: 15
<212> TYPE: DNA
<213> ORGANISM: Gallus gallus

<400> SEQUENCE: 276
accaggggaa tctcc                                                  15

<210> SEQ ID NO 277
<211> LENGTH: 15
<212> TYPE: DNA
<213> ORGANISM: Gallus gallus

<400> SEQUENCE: 277
accagggaaa tctcc                                                  15

<210> SEQ ID NO 278
<211> LENGTH: 45
<212> TYPE: DNA
<213> ORGANISM: Gallus gallus

<400> SEQUENCE: 278
cgctacccaa caccagggga atctcctggt attgttggaa acttc                 45

<210> SEQ ID NO 279
<211> LENGTH: 15
<212> TYPE: PRT
<213> ORGANISM: Homo sapiens

<400> SEQUENCE: 279

Arg Tyr Pro Thr Pro Gly Glu Ala Pro Gly Val Val Gly Asn Phe
 1               5                  10                  15

<210> SEQ ID NO 280
<211> LENGTH: 15
<212> TYPE: PRT
<213> ORGANISM: Mus musculus

```
<400> SEQUENCE: 280

Arg Tyr Pro Thr Pro Gly Glu Ala Pro Gly Val Val Gly Asn Phe
 1               5                  10                  15

<210> SEQ ID NO 281
<211> LENGTH: 15
<212> TYPE: PRT
<213> ORGANISM: Gallus gallus

<400> SEQUENCE: 281

Arg Tyr Pro Thr Pro Gly Glu Ser Pro Gly Ile Val Gly Asn Phe
 1               5                  10                  15

<210> SEQ ID NO 282
<211> LENGTH: 15
<212> TYPE: PRT
<213> ORGANISM: Gallus gallus

<400> SEQUENCE: 282

Arg Tyr Pro Thr Pro Gly Lys Ser Pro Gly Ile Val Gly Asn Phe
 1               5                  10                  15

<210> SEQ ID NO 283
<211> LENGTH: 45
<212> TYPE: DNA
<213> ORGANISM: Gallus gallus

<400> SEQUENCE: 283
cgctacccaa caccagggaa atctcctggt attgttggaa acttc              45

<210> SEQ ID NO 284
<211> LENGTH: 19
<212> TYPE: DNA
<213> ORGANISM: Homo sapiens

<400> SEQUENCE: 284
gcgtcaggga tggggacag                                           19

<210> SEQ ID NO 285
<211> LENGTH: 20
<212> TYPE: DNA
<213> ORGANISM: Homo sapiens

<400> SEQUENCE: 285
gcgtcaggga ttggggacag                                          20

<210> SEQ ID NO 286
<211> LENGTH: 17
<212> TYPE: DNA
<213> ORGANISM: Homo sapiens

<400> SEQUENCE: 286
ccacttcggt ctccatg                                             17

<210> SEQ ID NO 287
<211> LENGTH: 17
<212> TYPE: DNA
<213> ORGANISM: Homo sapiens

<400> SEQUENCE: 287
ccacttcgat ctccatg                                             17
```

METHODS AND REAGENTS FOR MODULATING CHOLESTEROL LEVELS

This application is a continuation of and claims priority of Ser. No. 10/617,334, filed 10 Jul. 2003, now abandoned and Ser. No. 10/452,510, filed 2 Jun. 2003, both of which are continuing applications of Ser. No. 09/526,193, filed 15 Mar. 2000, now U.S. Pat. No. 6,617,122, which claims priority from U.S. Provisional Application No. 60/124,702, filed Mar. 15, 1999, U.S. Provisional Application No. 60/138,048, filed Jun. 8, 1999, U.S. Provisional Application No. 60/139,600, filed Jun. 17, 1999, and U.S. Provisional Application No. 60/151,977, filed Sep. 1, 1999, the disclosures of all of which are hereby incorporated by reference in their entirety.

BACKGROUND OF THE INVENTION

Low HDL cholesterol (HDL-C), or hypoalphalipoproteinemia, is a blood lipid abnormality which correlates with a high risk of cardiovascular disease (CVD), in particular coronary artery disease (CAD), but also cerebrovascular disease, coronary restenosis, and peripheral vascular disease. HDL, or 'good cholesterol' levels are influenced by both environmental and genetic factors.

Epidemiological studies have consistently demonstrated that plasma HDL-C) concentration is inversely related to the incidence of CAD. HDL-C levels are a strong graded and independent cardiovascular risk factor. Protective effects of an elevated HDL-C persist until 80 years of age. A low HDL-C is associated with an increased CAD risk even with normal (<5.2 mmol/l) total plasma cholesterol levels. Coronary disease risk is increased by 2% in men and 3% in women for every 1 mg/dL (0.026 mmol/l) reduction in HDL-C and in the majority of studies this relationship is statistically significant even after adjustment for other lipid and non-lipid risk factors. Decreased HDL-C levels are the most common lipoprotein abnormality seen in patients with premature CAD. Four percent of patients with premature CAD with have an isolated form of decreased HDL-C levels with no other lipoprotein abnormalities while 25% have low HDL levels with accompanying hypertriglyceridemia.

Even in the face of other dyslipidemias or secondary factors, HDL-C levels are important predictors of CAD. In a cohort of diabetics, those with isolated low HDL cholesterol had a 65% increased death rate compared to diabetics with normal HDL cholesterol levels (>0.9 mmol/l). Furthermore, it has been shown that even within high risk populations, such as those with familial hypercholesterolemia, HDL cholesterol level is an important predictor of CAD. Low HDL cholesterol levels thus constitute a major, independent, risk for CAD.

These findings have led to increased attention to HDL cholesterol levels as a focus for treatment, following the recommendations of the National Cholesterol Education Program. These guidelines suggest that HDL cholesterol values below 0.9 mmol/l confer a significant risk for men and women. As such, nearly half of patients with CAD would have low HDL cholesterol. It is therefore crucial that we obtain a better understanding of factors which contribute to this phenotype. In view of the fact that pharmacological intervention of low HDL cholesterol levels has so far proven unsatisfactory, it is also important to understand the factors that regulate these levels in the circulation as this understanding may reveal new therapeutic targets.

Absolute levels of HDL cholesterol may not always predict risk of CAD. In the case of CETP deficiency, individuals display an increased risk of developing CAD, despite increased HDL cholesterol levels. What seems to be important in this case is the functional activity of the reverse cholesterol transport pathway, the process by which intracellular cholesterol is trafficked out of the cell to acceptor proteins such as ApoAI or HDL. Other important genetic determinants of HDL cholesterol levels, and its inverse relation with CAD, may reside in the processes leading to HDL formation and intracellular cholesterol trafficking and efflux. To date, this process is poorly understood, however, and clearly not all of the components of this pathway have been identified. Thus, defects preventing proper HDL-mediated cholesterol efflux may be important predictors of CAD. Therefore it is critical to identify and understand novel genes involved in the intracellular cholesterol trafficking and efflux pathways.

HDL particles are central to the process of reverse cholesterol transport and thus to the maintenance of tissue cholesterol homeostasis. This process has multiple steps which include the binding of HDL to cell surface components, the acquisition of cholesterol by passive absorption, the esterification of this cholesterol by LCAT and the subsequent transfer of esterified cholesterol by CETP, to VLDL and chylomicron remnants for liver uptake. Each of these steps is known to impact the plasma concentration of HDL.

Changes in genes for ApoAI-CIII, lipoprotein lipase, CETP, hepatic lipase, and LCAT all contribute to determination of HDL-C levels in humans. One rare form of genetic HDL deficiency is Tangier disease (TD), diagnosed in approximately 40 patients world-wide, and associated with almost complete absence of HDL cholesterol (HDL-C) levels (listed in OMIM as an autosomal recessive trait (OMIM 205400)). These patients have very low HDL cholesterol and ApoAI levels, which have been ascribed to hypercatabolism of nascent HDL and ApoAI, due to a delayed acquisition of lipid and resulting failure of conversion to mature HDL. TD patients accumulate cholesterol esters in several tissues, resulting in characteristic features, such as enlarged yellow tonsils, hepatosplenomegaly, peripheral neuropathy, and cholesterol ester deposition in the rectal mucosa. Defective removal of cellular cholesterol and phospholipids by ApoAI as well as a marked deficiency in HDL mediated efflux of intracellular cholesterol has been demonstrated in TD fibroblasts. Even though this is a rare disorder, defining its molecular basis could identify pathways relevant for cholesterol regulation in the general population. The decreased availability of free cholesterol for efflux in the surface membranes of cells in Tangier Disease patients appears to be due to a defect in cellular lipid metabolism or trafficking. Approximately 45% of Tangier patients have signs of premature CAD, suggesting a strong link between decreased cholesterol efflux, low HDL cholesterol and CAD. As increased cholesterol is observed in the rectal mucosa of persons with TD, the molecular mechanism responsible for TD may also regulate cholesterol adsorption from the gastrointestinal (GI) tract.

A more common form of genetic HDL deficiency occurs in patients who have low plasma HDL cholesterol usually below the 5th percentile for age and sex (OMIM 10768), but an absence of clinical manifestations specific to Tangier disease (Marcil et al., Arterioscler. Thromb. Vasc. Biol. 19:159-169, 1999; Marcil et al., Arterioscler. Thromb. Vasc. Biol. 15:1015-1024, 1995). These patients have no obvious environmental factors associated with this lipid phenotype, and do not have severe hypertriglyceridemia nor have known causes of severe HDL deficiency (mutations in ApoAI, LCAT, or LPL deficiency) and are not diabetic. The pattern of inheritance of this condition is most consistent with a Mendelian dominant trait (OMIM 10768).

The development of drugs that regulate cholesterol metabolism has so far progressed slowly. Thus, there is a need for a better understanding of the genetic components of the cholesterol efflux pathway. Newly-discovered components can then serve as targets for drug design.

Low HDL levels are likely to be due to multiple genetic factors. The use of pharmacogenomics in the aid of designing treatment tailored to the patient makes it desirable to identify polymorphisms in components of the cholesterol efflux pathway. An understanding of the effect of these polymorphisms on protein function would allow for the design of a therapy that is optimal for the patient.

SUMMARY OF THE INVENTION

In a first aspect, the invention features a substantially pure ABC1 polypeptide having ABC1 biological activity. Preferably, the ABC1 polypeptide is human ABC1 (e.g., one that includes amino acids 1 to 60 or amino acids 61 to 2261 of SEQ ID NO: 1). In one preferred embodiment, the ABC1 polypeptide includes amino acids 1 to 2261 of SEQ ID NO: 1.

Specifically excluded from the polypeptides of the invention are the polypeptide having the exact amino acid sequence as GenBank accession number CAA10005.1 and the nucleic acid having the exact sequence as AJ012376.1. Also excluded is protein having the exact amino acid sequence as GenBank accession number X75926.

In a related aspect, the invention features a substantially pure ABC1 polypeptide that includes amino acids 1 to 2261 of SEQ ID NO: 1.

In another aspect, the invention features a substantially pure nucleic acid molecule encoding an ABC1 polypeptide having ABC1 biological activity (e.g., a nucleic acid molecule that includes nucleotides 75 to 254 or nucleotides 255 to 6858 of SEQ ID NO: 2). In one preferred embodiment, the nucleic acid molecule includes nucleotides 75 to 6858 of SEQ ID NO: 2.

In a related aspect, the invention features an expression vector, a cell, or a non-human mammal that includes the nucleic acid molecule of the invention.

In yet another aspect, the invention features a substantially pure nucleic acid molecule that includes nucleotides 75 to 254 of SEQ ID NO: 2, nucleotides 255 to 6858 of SEQ ID NO: 2, or nucleotides 75 to 6858 of SEQ ID NO: 2.

In still another aspect, the invention features a substantially pure nucleic acid molecule that includes at least fifteen nucleotides corresponding to the 5' or 3' untranslated region from a human ABC1 gene. Preferably, the 3' untranslated region includes nucleotides 7015-7860 of SEQ ID NO: 2.

In a related aspect, the invention features a substantially pure nucleic acid molecule that hybridizes at high stringency to a probe comprising nucleotides 7015-7860 of SEQ ID NO: 2.

In another aspect, the invention features a method of treating a human having low HDL cholesterol or a cardiovascular disease, including administering to the human an ABC1 polypeptide, or cholesterol-regulating fragment thereof, or a nucleic acid molecule encoding an ABC1 polypeptide, or cholesterol-regulating fragment thereof. In a preferred embodiment, the human has a low HDL cholesterol level relative to normal. Preferably, the ABC1 polypeptide is wild-type ABC1, or has a mutation that increases its stability or its biological activity. A preferred biological activity is regulation of cholesterol.

In a related aspect, the invention features a method of preventing or treating cardiovascular disease, including introducing into a human an expression vector comprising an ABC1 nucleic acid molecule operably linked to a promoter and encoding an ABC1 polypeptide having ABC1 biological activity.

In another related aspect, the invention features a method of preventing or ameliorating the effects of a disease-causing mutation in an ABC1 gene, including introducing into a human an expression vector comprising an ABC1 nucleic acid molecule operably linked to a promoter and encoding an ABC1 polypeptide having ABC1 biological activity.

In still another aspect, the invention features a method of treating or preventing cardiovascular disease, including administering to an animal (e.g., a human) a compound that mimes the activity of wild-type ABC1 or modulates the biological activity of ABC1.

One preferred cardiovascular disease that can be treated using the methods of the invention is coronary artery disease. Others include cerebrovascular disease and peripheral vascular disease.

The discovery that the ABC1 gene and protein are involved in cholesterol transport that affects serum HDL levels allows the ABC1 protein and gene to be used in a variety of diagnostic tests and assays for identification of HDL-increasing or CVD-inhibiting drugs. In one family of such assays, the ability of domains of the ABC1 protein to bind ATP is utilized; compounds that enhance this binding are potential HDL-increasing drugs. Similarly, the anion transport capabilities and membrane pore-forming functions in cell membranes can be used for drug screening.

ABC1 expression can also serve as a diagnostic tool for low HDL or CVD; determination of the genetic subtyping of the ABC1 gene sequence can be used to subtype low HDL individuals or families to determine whether the low HDL phenotype is related to ABC1 function. This diagnostic process can lead to the tailoring of drug treatments according to patient genotype (referred to as pharmacogenomics), including prediction of the patient's response (e.g., increased or decreased efficacy or undesired side effects upon administration of a compound or drug.

Antibodies to an ABC1 polypeptide can be used both as therapeutics and diagnostics. Antibodies are produced by immunologically challenging a B-cell-containing biological system, e.g., an animal such as a mouse, with an ABC1 polypeptide to stimulate production of anti-ABC1 protein by the B-cells, followed by isolation of the antibody from the biological system. Such antibodies can be used to measure ABC1 polypeptide in a biological sample such as serum, by contacting the sample with the antibody and then measuring immune complexes as a measure of the ABC1 polypeptide in the sample. Antibodies to ABC1 can also be used as therapeutics for the modulation of ABC1 biological activity.

Thus, in another aspect, the invention features a purified antibody that specifically binds to ABC1.

In yet another aspect, the invention features a method for determining whether a candidate compound modulates ABC1 biological activity, comprising: (a) providing an ABC1 polypeptide; (b) contacting the ABC1 polypeptide with the candidate compound; and (c) measuring ABC1 biological activity, wherein altered ABC1 biological activity, relative to an ABC1 polypeptide not contacted with the compound, indicates that the candidate compound modulates ABC1 biological activity. Preferably, the ABC1 polypeptide is in a cell or is in a cell-free assay system.

In still another aspect, the invention features a method for determining whether a candidate compound modulates ABC1 expression. The method includes (a) providing a nucleic acid molecule comprising an ABC1 promoter operably linked to a reporter gene; (b) contacting the nucleic acid molecule with the candidate compound; and (c) measuring reporter gene expression, wherein altered reporter gene expression, relative to a nucleic acid molecule not contacted with the compound, indicates that the candidate compound modulates ABC1 expression.

In another aspect, the invention features a method for determining whether candidate compound is useful for modulating cholesterol levels, the method including the steps of: (a) providing an ABC1 polypeptide; (b) contacting the polypeptide with the candidate compound; and (c) measuring binding of the ABC1 polypeptide, wherein binding of the ABC1 polypeptide indicates that the candidate compound is useful for modulating cholesterol levels.

In a related aspect, the invention features method for determining whether a candidate compound mimics ABC1 biological activity. The method includes (a) providing a cell that is not expressing an ABC1 polypeptide; (b) contacting the cell with the candidate compound; and (c) measuring ABC1 biological activity of the cell, wherein altered ABC1 biological activity, relative to a cell not contacted with the compound, indicates that the candidate compound modulates ABC1 biological activity. Preferably, the cell has an ABC1 null mutation. In one preferred embodiment, the cell is in a mouse or a chicken (e.g., a WHAM chicken) in which its ABC1 gene has been mutated.

In still another aspect, the invention features a method for determining whether a candidate compound is useful for the treatment of low HDL cholesterol. The method includes (a) providing an ABC transporter (e.g., ABC1); (b) contacting the transporter with the candidate compound; and (c) measuring ABC transporter biological activity, wherein increased ABC transporter biological activity, relative to a transporter not contacted with the compound, indicates that the candidate compound is useful for the treatment of low HDL cholesterol. Preferably the ABC transporter is in a cell or a cell free assay system.

In yet another aspect, the invention features a method for determining whether candidate compound is useful for modulating cholesterol levels. The method includes (a) providing a nucleic acid molecule comprising an ABC transporter promoter operably linked to a reporter gene; (b) contacting the nucleic acid molecule with the candidate compound; and (c) measuring expression of the reporter gene, wherein increased expression of the reporter gene, relative to a nucleic acid molecule not contacted with the compound, indicates that the candidate compound is useful for modulating cholesterol levels.

In still another aspect, the invention features a method for determining whether a candidate compound increases the stability or decreases the regulated catabolism of an ABC transporter polypeptide. The method includes (a) providing an ABC transporter polypeptide; (b) contacting the transporter with the candidate compound; and (c) measuring the half-life of the ABC transporter polypeptide, wherein an increase in the half-life, relative to a transporter not contacted with the compound, indicates that the candidate compound increases the stability or decreases the regulated catabolism of an ABC transporter polypeptide. Preferably the ABC transporter is in a cell or a cell free assay system.

In a preferred embodiment of the screening methods of the present invention, the cell is in an animal. The preferred ABC transporters are ABC1, ABC2, ABCR, and ABC8, and the preferred biological activity is transport of cholesterol (e.g., HDL cholesterol or LDL cholesterol) or interleukin-1, or is binding or hydrolysis of ATP by the ABC1 polypeptide.

Preferably, the ABC1 polypeptide used in the screening methods includes amino acids 1-60 of SEQ ID NO: 1. Alternatively, the ABC1 polypeptide can include a region encoded by a nucleotide sequence that hybridizes under high stringency conditions to nucleotides 75 to 254 of SEQ ID NO: 2.

In another aspect, the invention features a method for determining whether a patient has an increased risk for cardiovascular disease. The method includes determining whether an ABC1 gene of the patient has a mutation, wherein a mutation indicates that the patient has an increased risk for cardiovascular disease.

In related aspect, the invention features a method for determining whether a patient has an increased risk for cardiovascular disease. The method includes determining whether an ABC1 gene of the patient has a polymorphism, wherein a polymorphism indicates that the patient has an increased risk for cardiovascular disease.

In another aspect, the invention features a method for determining whether a patient has an increased risk for cardiovascular disease. The method includes measuring ABC1 biological activity in the patient, wherein increased or decreased levels in the ABC1 biological activity, relative to normal levels, indicates that the patient has an increased risk for cardiovascular disease.

In still another aspect, the invention features a method for determining whether a patient has an increased risk for cardiovascular disease. The method includes measuring ABC1 expression in the patient, wherein decreased levels in the ABC1 expression relative to normal levels, indicates that the patient has an increased risk for cardiovascular disease. Preferably, the ABC1 expression is determined by measuring levels of ABC1 polypeptide or ABC1 RNA.

In another aspect, the invention features a non-human mammal having a transgene comprising a nucleic acid molecule encoding a mutated ABC1 polypeptide. In one embodiment, the mutation is a dominant-negative mutation.

In a related aspect, the invention features a non-human mammal, having a transgene that includes a nucleic acid molecule encoding an ABC1 polypeptide having ABC1 biological activity.

In another related aspect, the invention features a cell from a non-human mammal having a transgene that includes a nucleic acid molecule encoding an ABC1 polypeptide having ABC1 biological activity.

In still another aspect, the invention features a method for determining whether a candidate compound decreases the inhibition of a dominant-negative ABC1 polypeptide. The method includes (a) providing a cell expressing a dominant-negative ABC1 polypeptide; (b) contacting the cell with the candidate compound; and (c) measuring ABC1 biological activity of the cell, wherein an increase in the ABC1 biological activity, relative to a cell not contacted with the compound, indicates that the candidate compound decreases the inhibition of a dominant-negative ABC1 polypeptide.

By "polypeptide" is meant any chain of more than two amino acids, regardless of post-translational modification such as glycosylation or phosphorylation.

By "substantially identical" is meant a polypeptide or nucleic acid exhibiting at least 50%, preferably 85%, more preferably 90%, and most preferably 95% identity to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "high stringency conditions" is meant hybridization in 2×SSC at 40_C with a DNA probe length of at least 40 nucleotides. For other definitions of high stringency conditions, see F. Ausubel et al., *Current Protocols in Molecular Biology*, pp. 6.3.1-6.3.6, John Wiley & Sons, New York, N.Y., 1994, hereby incorporated by reference.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is an ABC1 polypeptide that is at least 75%, more preferably at least 90%, and most preferably at least 99%, by weight, pure. A substantially pure ABC1 polypeptide may be obtained, for example, by extraction from a natural source (e.g., a pancreatic cell), by expression of a recombinant nucleic acid encoding a ABC1 polypeptide, or by chemically synthesizing the protein. Purity can be measured by any appropriate method, e.g., by column chromatography, polyacrylamide gel electrophoresis, or HPLC analysis.

A polypeptide is substantially free of naturally associated components when it is separated from those contaminants that accompany it in its natural state. Thus, a polypeptide which is chemically synthesized or produced in a cellular system different from the cell from which it naturally originates will be substantially free from its naturally associated components. Accordingly, substantially pure polypeptides include those which naturally occur in eukaryotic organisms but are synthesized in *E. coli* or other prokaryotes.

By "substantially pure nucleic acid" is meant nucleic acid that is free of the genes which, in the naturally-occurring genome of the organism from which the nucleic acid of the invention is derived, flank the nucleic acid. The term therefore includes, for example, a recombinant nucleic acid that is incorporated into a vector; into an autonomously replicating plasmid or virus; into the genomic nucleic acid of a prokaryote or a eukaryote cell; or that exists as a separate molecule (e.g., a cDNA or a genomic or cDNA fragment produced by PCR or restriction endonuclease digestion) independent of other sequences. It also includes a recombinant nucleic acid that is part of a hybrid gene encoding additional polypeptide sequence.

By "modulates" is meant increase or decrease. Preferably, a compound that modulates cholesterol levels (e.g., HDL-cholesterol levels, LDL-cholesterol levels, or total cholesterol levels), or ABC1 biological activity, expression, stability, or degradation does so by at least 10%, more preferably by at least 25%, and most preferably by at least 50%.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody. A purified antibody may be obtained, for example, by affinity chromatography using recombinantly-produced protein or conserved motif peptides and standard techniques.

By "specifically binds" is meant an antibody that recognizes and binds to, for example, a human ABC1 polypeptide but does not substantially recognize and bind to other non-ABC1 molecules in a sample, e.g., a biological sample, that naturally includes protein. A preferred antibody binds to the ABC1 polypeptide sequence of FIG. 9A (SEQ ID NO: 1).

By "polymorphism" is meant that a nucleotide or nucleotide region is characterized as occurring in several different forms. A "mutation" is a form of a polymorphism in which the expression level, stability, function, or biological activity of the encoded protein is substantially altered.

By "ABC transporter" or "ABC polypeptide" is meant any transporter that hydrolyzes ATP and transports a substance across a membrane. Preferably, an ABC transporter polypeptide includes an ATP Binding Cassette and a transmembrane region. Examples of ABC transporters include, but are not limited to, ABC1, ABC2, ABCR, and ABC8.

By "ABC1 polypeptide" is meant a polypeptide having substantial identity to an ABC1 polypeptide having the amino acid sequence of SEQ ID NO: 1.

By "ABC biological activity" or "ABC1 biological activity" is meant hydrolysis or binding of ATP, transport of a compound (e.g., cholesterol, interleukin-1) or ion across a membrane, or regulation of cholesterol or phospholipid levels (e.g., either by increasing or decreasing HDL-cholesterol or LDL-cholesterol levels).

The invention provides screening procedures for identifying therapeutic compounds (cholesterol-modulating or anti-CVD pharmaceuticals) which can be used in human patients. Compounds that modulate ABC biological activity (e.g., ABC1 biological activity) are considered useful in the invention, as are compounds that modulate ABC concentration, protein stability, regulated catabolism, or its ability to bind other proteins or factors. In general, the screening methods of the invention involve screening any number of compounds for therapeutically active agents by employing any number of in vitro or in vivo experimental systems. Exemplary methods useful for the identification of such compounds are detailed below.

The methods of the invention simplify the evaluation, identification and development of active agents for the treatment and prevention of low HDL and CVD. In general, the screening methods provide a facile means for selecting natural product extracts or compounds of interest from a large population which are further evaluated and condensed to a few active and selective materials. Constitutes of this pool are then purified and evaluated in the methods of the invention to determine their HDL-raising or anti-CVD activities or both.

Other features and advantages of the invention will be apparent from the following description of the preferred embodiments thereof, and from the claims.

Figure 3:
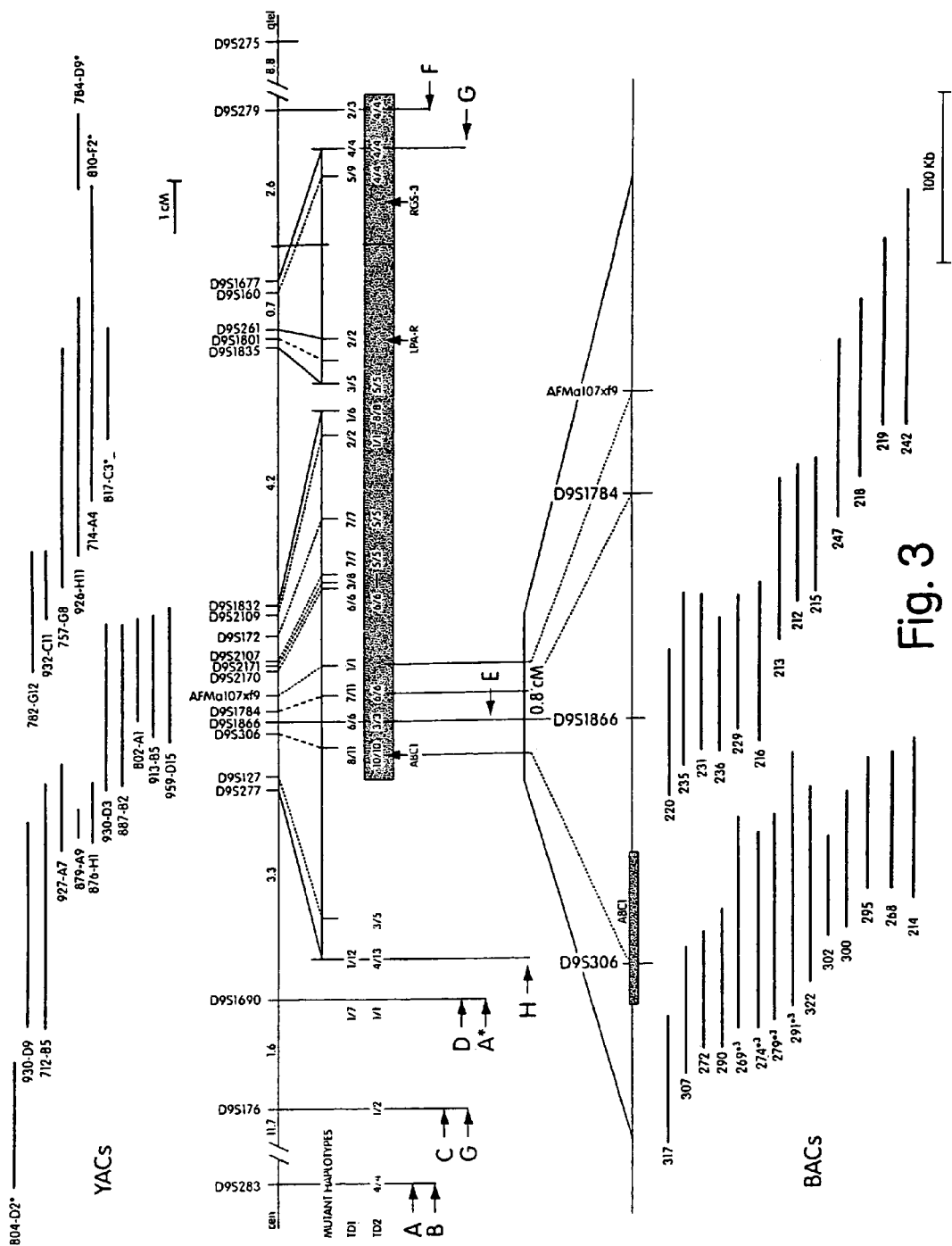

Each individual's ID number, age at the time of lipid measurement, triglyceride level and HDL cholesterol level followed by their percentile ranking for age and sex are listed below the pedigree symbol. Markers spanning the 9q31.1 region are displayed to the left of the pedigree. The affected allele is represented by the darkened bars which illustrate the mapping of the limits of the shared haplotype region as seen in FIG. 3. Parentheses connote inferred marker data, questions marks indicate unknown genotypes, and large arrows show the probands.

Figure 1B:
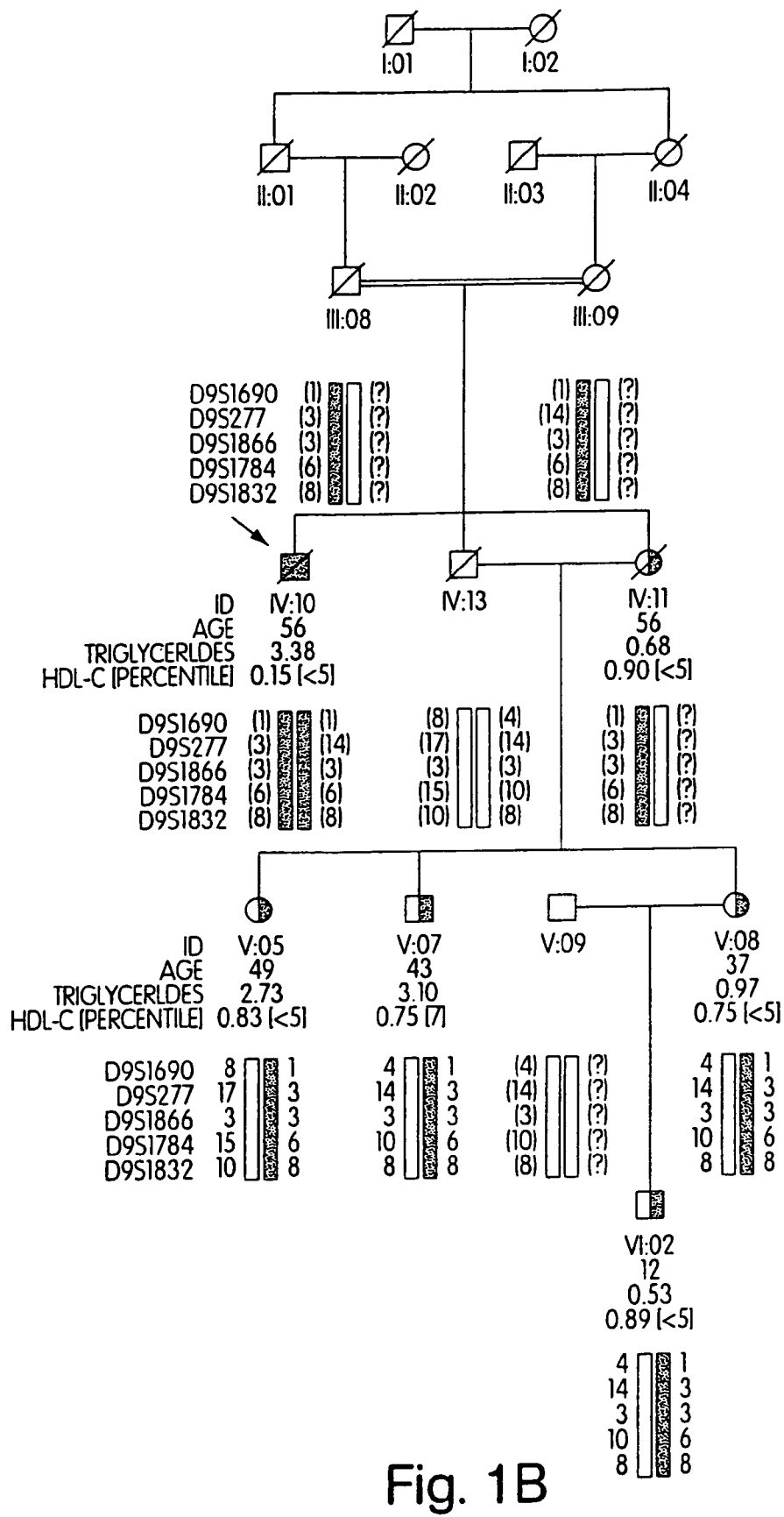
FIGS. 1A and 1B are schematic illustrations showing two pedigrees with Tangier Disease, (TD-1 and TD-2). Square and circle symbols represent males and females, respectively. Diagonal lines are placed through the symbols of all deceased individuals. A shaded symbol on both alleles indicates the probands with Tangier Disease. Individuals with half shaded symbols have HDL-C levels at or below the 10th percentile for age and sex, while those with quarter shaded symbols have HDL-C between the 11th and 20th percentiles.
Figure 1C:
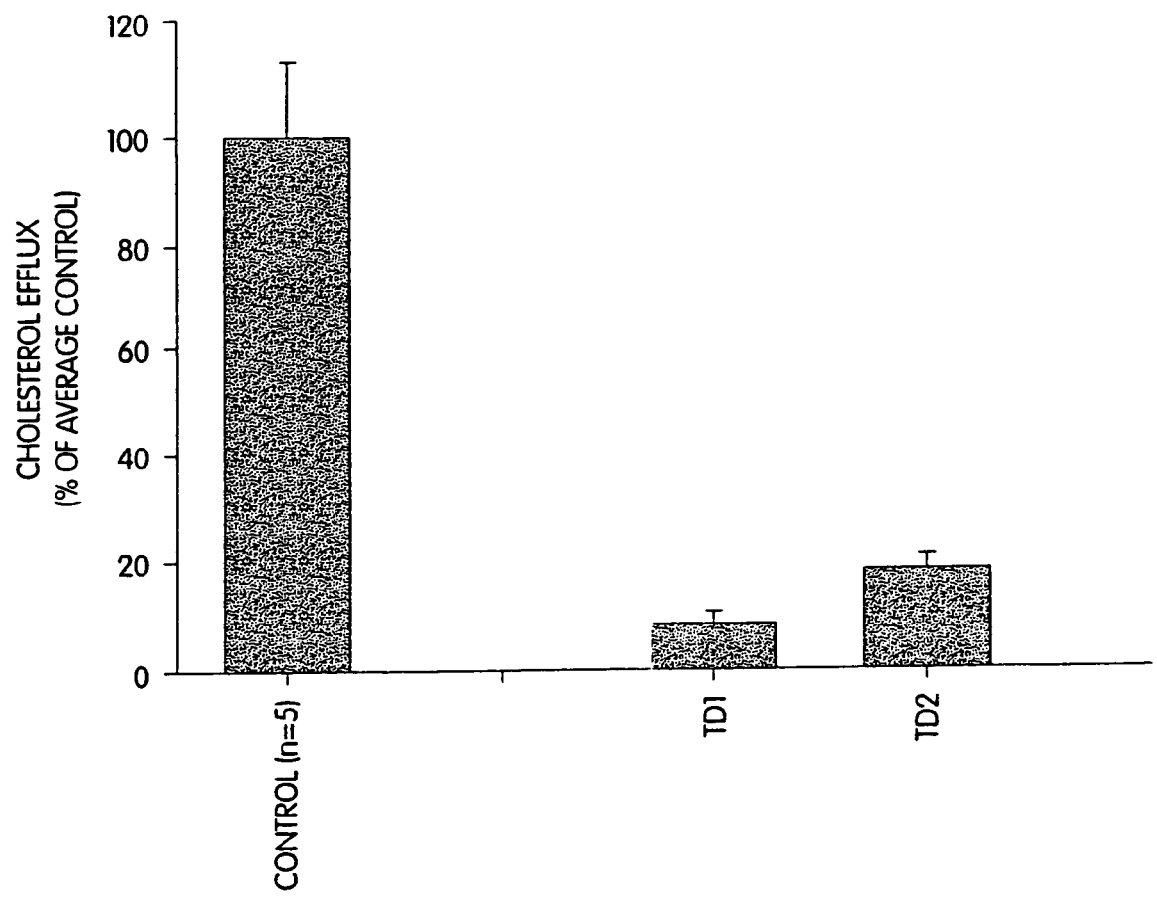
Figure 2C:
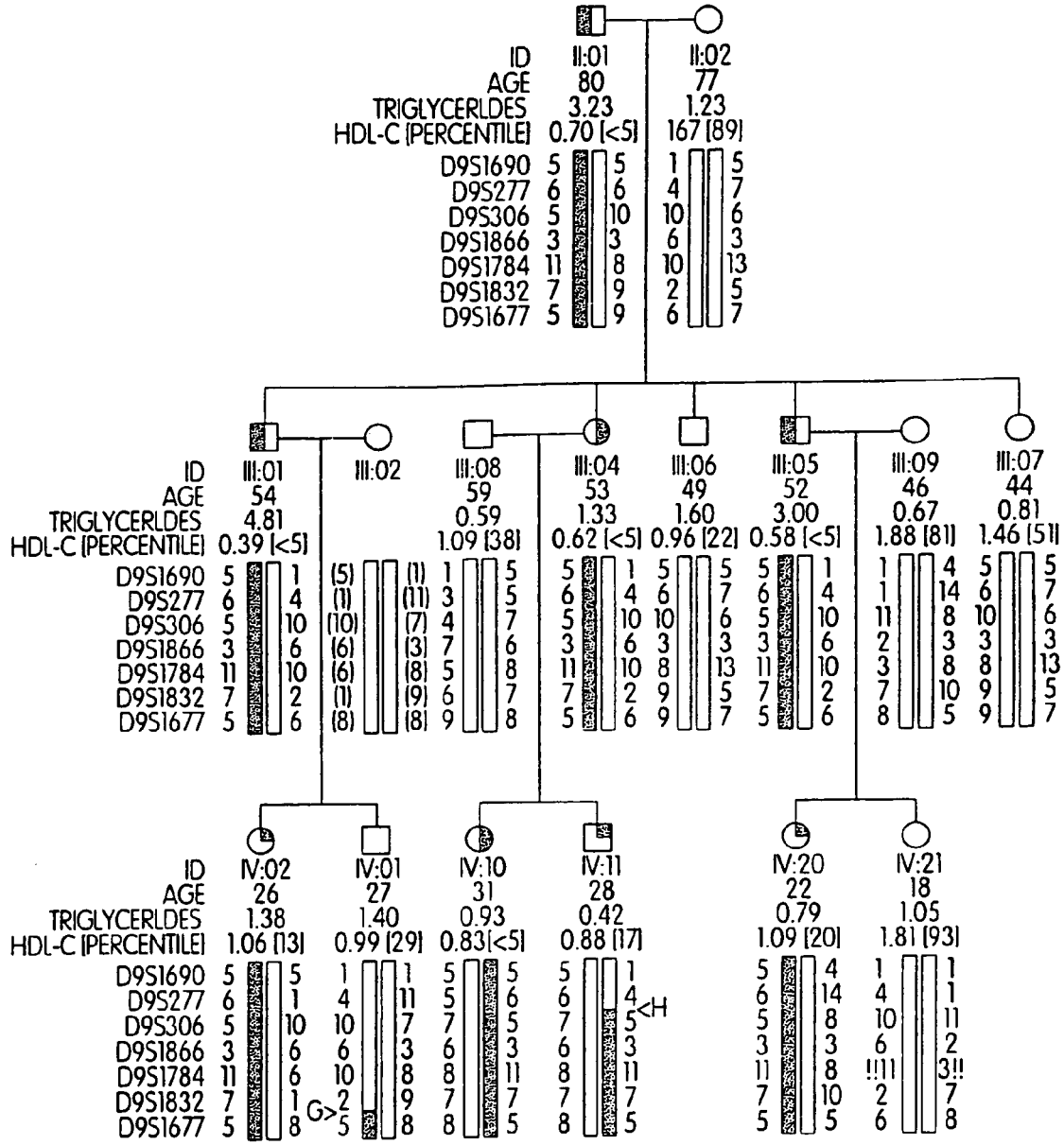
Figure 2D:
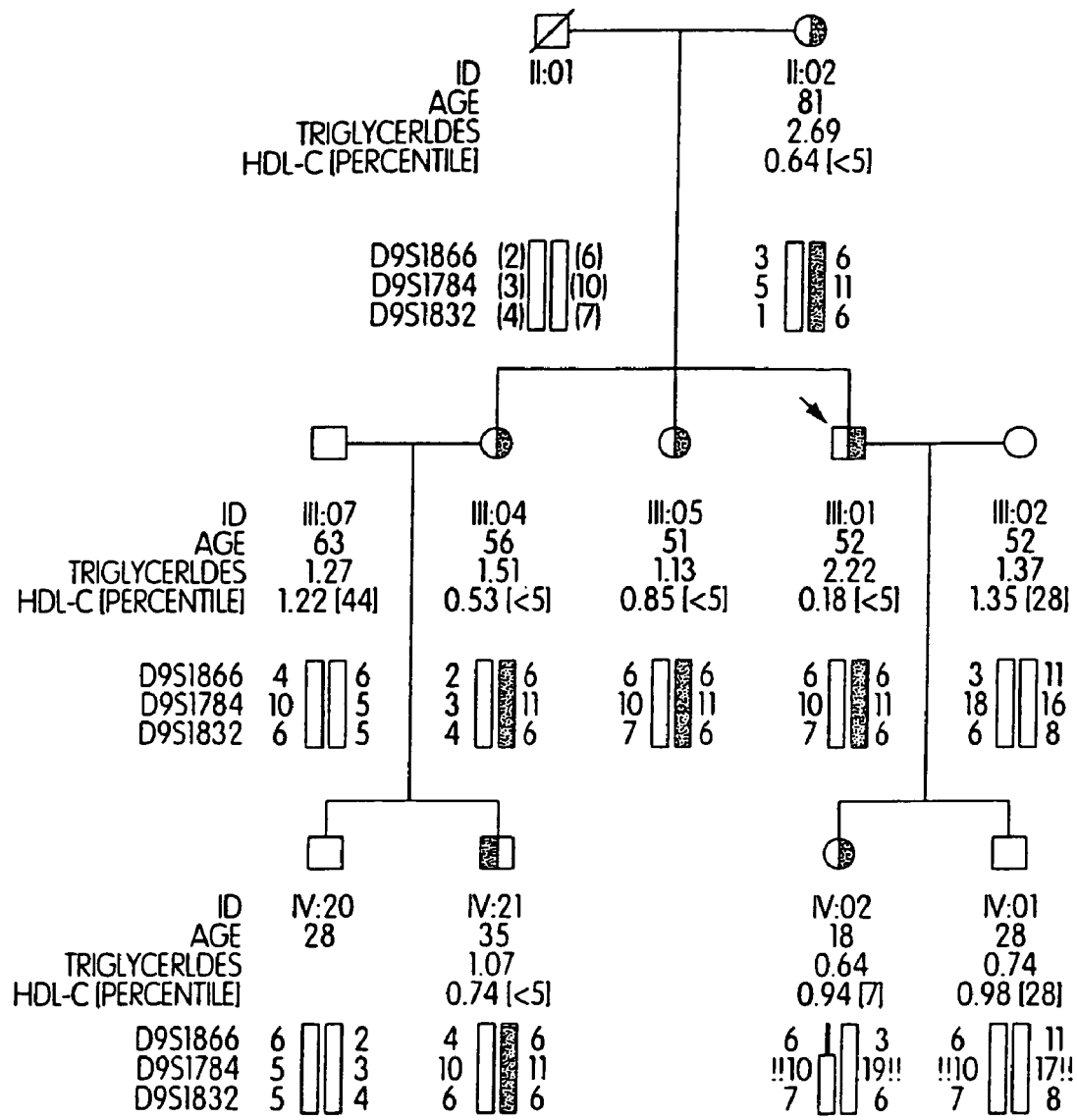

FIG. 1C shows ApoAI (10 µg/mL)-mediated cellular cholesterol efflux in control fibroblasts (n=5, normalized to 100%) and two subjects with Tangier disease (TD). Cells were $^3$H-cholesterol (0.2 µCi/mL) labeled during growth and cholesterol (20 µg/mL) loaded in growth arrest. Cholesterol efflux is determined as $^3$H medium/(3H cell+$^3$H medium).

FIG. 2A-2D are schematic illustrations showing four French Canadian pedigrees with FHA (FHA-1 to -4). The notations are as in FIG. 1. Exclamation points on either side of a genotype (as noted in Families FHA-3 and FHA-4) are used when the marker data appears to be inconsistent due to potential microsatellite repeat expansions. A bar that becomes a single thin line suggests that the haplotype is indeterminate at that marker.

FIG. 3 provides a schematic illustration showing a genetic and physical map of 9q31 spanning 35 cM. At the top is shown YACs from the region of 9q22-34 were identified and a YAC contig spanning this region was constructed. Below that is shown a total of 22 polymorphic CA microsatellite markers were mapped to the contig and used in haplotype analysis in TD-1 and TD-2. The figure then shows mutant haplotypes for probands in TD-1 and -2 indicate a significant region of homozygosity in TD-2, while the proband in TD-1 has 2 different mutant haplotypes. The candidate region can be narrowed to the region of homozygosity for CA markers in proband 2. A critical crossover at D9S1690 in TD-1 (A)* also provides a centromeric boundary for the region containing the gene. Three candidate genes in this region (ABC1, LPA-R and RGS-3) are shown. FIG. 3D: Meiotic The figure then shows recombinations in the FHA families (A-H) refine the minimal critical region to 1.2 cM between D9S277 and D9S1866. The heterozygosity of the TD-2 proband at D9S127, which ends a continuous region of homozygosity in TD-2, further refines the region to less than 1 cM. This is the region to which ABC1 has been mapped. Also shown are isolated YAC DNA and selected markers from the region were used to probe high-density BAC grid filters, selecting BACs which via STS-content mapping produced an 800 Kb contig. Four BACs containing ABC1 were sequenced using high-throughput methods.

FIG. 4A shows sequence of one mutation in family TD-1. Patient III-01 is heterozygous for a T to C transition at nucleotide 4503 of the cDNA; the control is homozygous for T at this position. This mutation corresponds to a cysteine to arginine substitution in the ABC1 protein (C1477R).

FIG. 4B shows the amino acid sequence conservation of residue 1477 in mouse and human, but not a related *C. elegans* gene. A change from cysteine to arginine likely has an important effect on the protein secondary and tertiary structure, as noted by its negative scores in most substitution matrices (Schuler et al., A Practical Guide to the Analysis of Genes and Proteins, eds. Baxevanis, A. D. & Ouellette, B. F. F. 145:171, 1998). The DNA sequences of the normal and mutant genes are shown above and below the amino acid sequences, respectively.

Figure 4C:
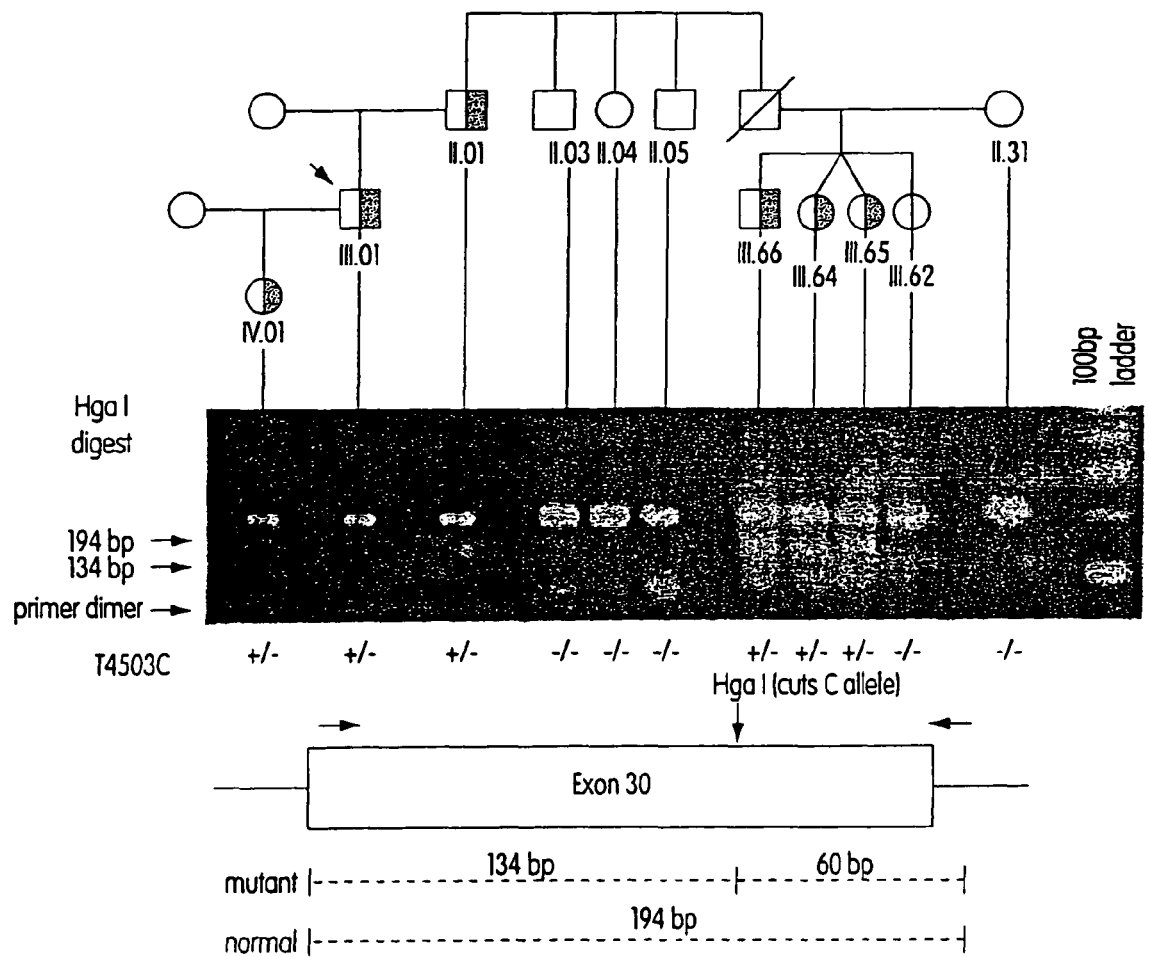

FIG. 4C shows the segregation of the T4503C mutation in TD-1. The presence of the T4503C mutation (+) was assayed by restriction enzyme digestion with HgaI, which cuts only the mutant (C) allele (Õ). Thus, in the absence of the mutation, only the 194 bp PCR product (amplified between ø and Ø) is observed, while in its presence the PCR product is cleaved into fragments of 134 bp and 60 bp. The proband (individual III.01) was observed to be heterozygous for this mutation (as indicated by both the 194 bp and 134 bp bands), as were his daughter, father, and three paternal cousins. A fourth cousin and three of the father's siblings were not carriers of this mutation.

Figure 4D:
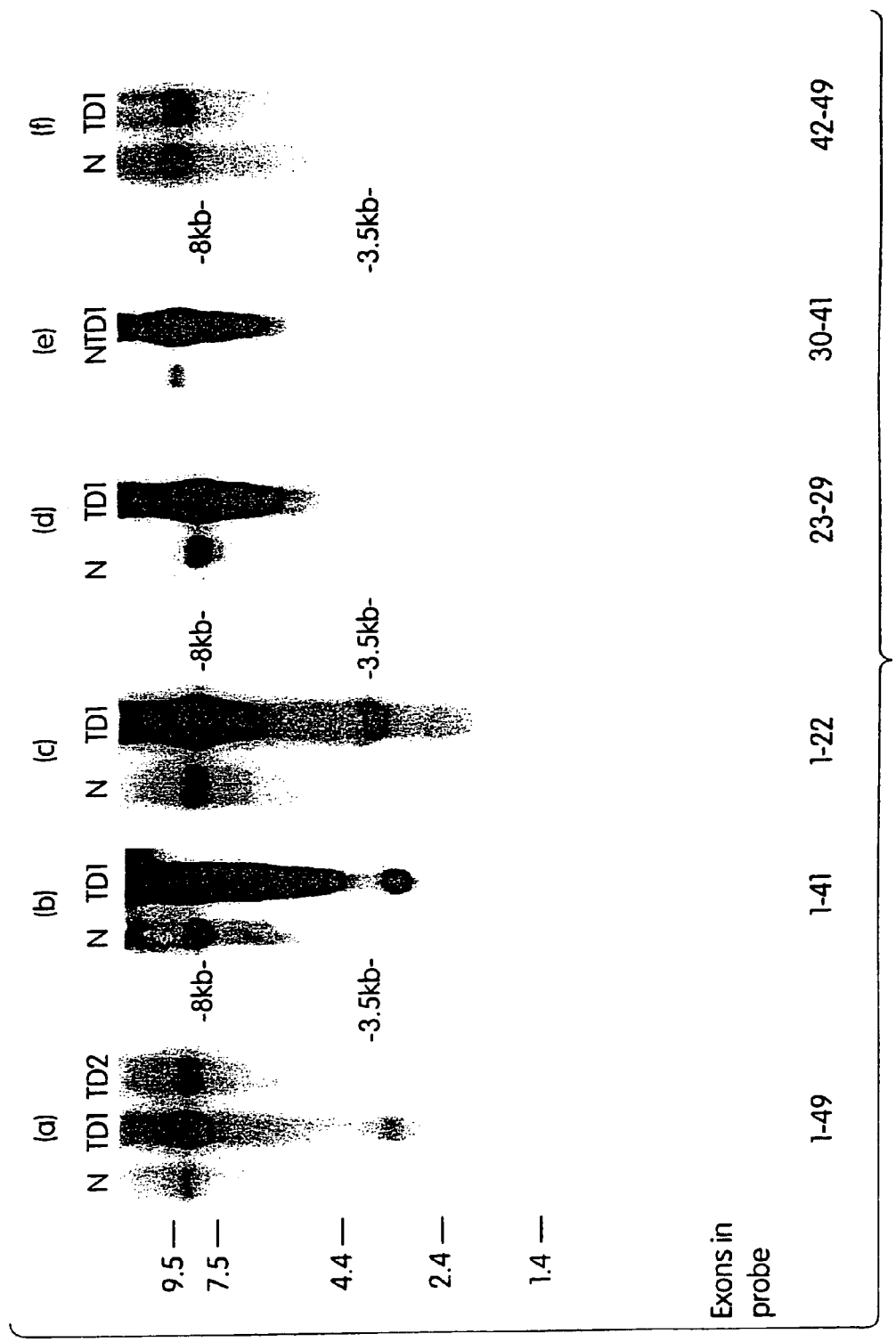

FIG. 4D shows Northern blot analysis with probes spanning the complete ABC1 gene reveal the expected ~8 Kb transcript and, in addition, a ~3.5 kb truncated transcript only seen in the proband TD-1 and not in TD-2 or control. This was detected by probes spanning exons 1-49 (a), 1-41 (b), 1-22 (c), and 23-29 (d), but not with probes spanning exons 30-41 (e) or 42-49 (f).

Figure 5A:
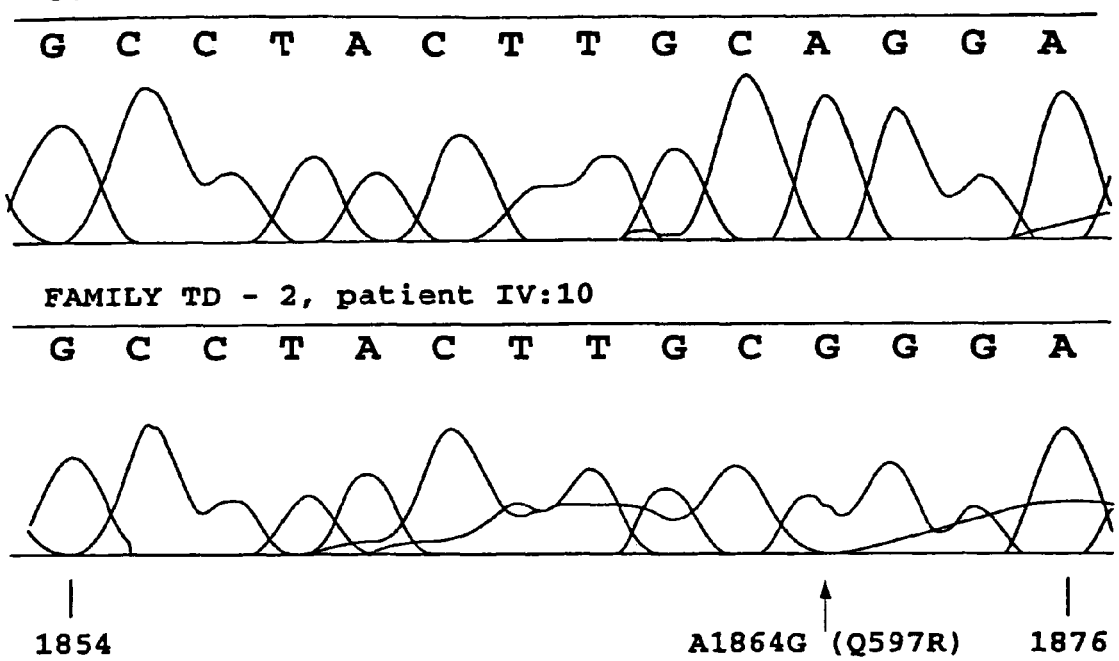

FIG. 5A shows the sequence of the mutation in family TD-2. Patient IV-10 is homozygous for an A to G transition at nucleotide 1864 of the cDNA (SEQ ID NO: 2); the control is homozygous for A at this position. This mutation corresponds to a glutamine to arginine substitution in the ABC1 protein (Q597R).

FIG. 5B shows that the glutamine amino acid, which is mutated in the TD-2 proband, is conserved in human and mouse ABC1 as well as in an ABC orthologue from *C. elegans*, revealing the specific importance of this residue in the structure/function of this ABC protein in both worms and mammals. The DNA sequences of the normal and mutant proteins are shown above and below the amino acid sequences, respectively.

Figure 5C:
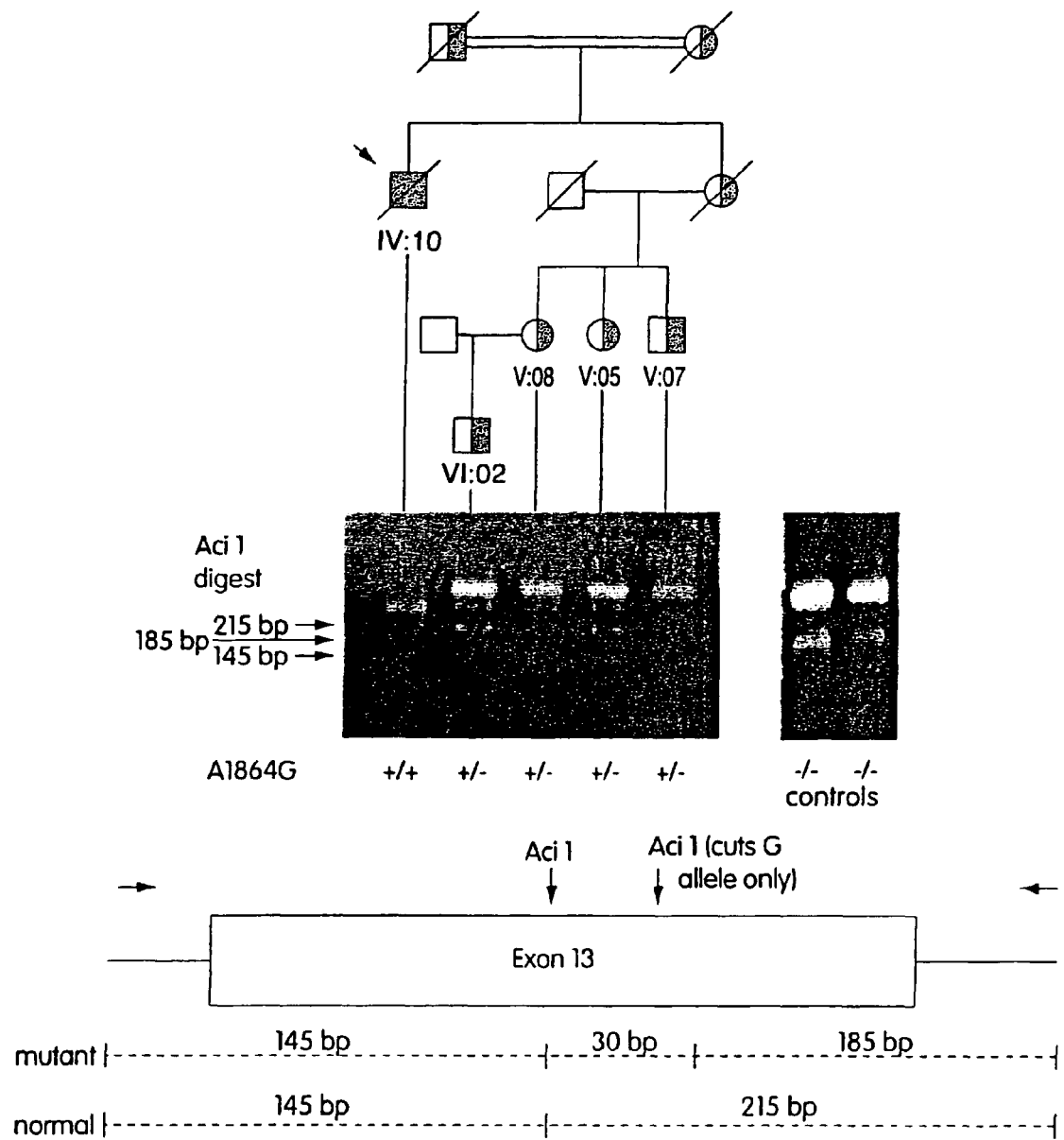

FIG. 5C shows the segregation of the A1864G mutation in TD-2. The presence of the A1864G mutation (indicated by +) was assayed by restriction enzyme digestion with AciI. The 360 bp PCR product has one invariant AciI recognition site (Õ), and a second one is created by the A1864G mutation. The wild-type allele is thus cleaved to fragments of 215 bp and 145 bp, while the mutant allele (G-allele) is cleaved to fragments of 185 bp, 145 bp and 30 bp. The proband (individual IV-10), the product of a consanguineous mating, was homozygous for the A1864G mutation (+/+), as evidenced by the presence of only the 185 bp and 145 bp bands, while four other family members for whom DNA was tested are heterozygous carriers of this mutation (both the 215 bp and 185 bp fragments were present). Two unaffected individuals (−/−), with only the 215 bp and 145 bp bands are shown for comparison.

Figure 6A:
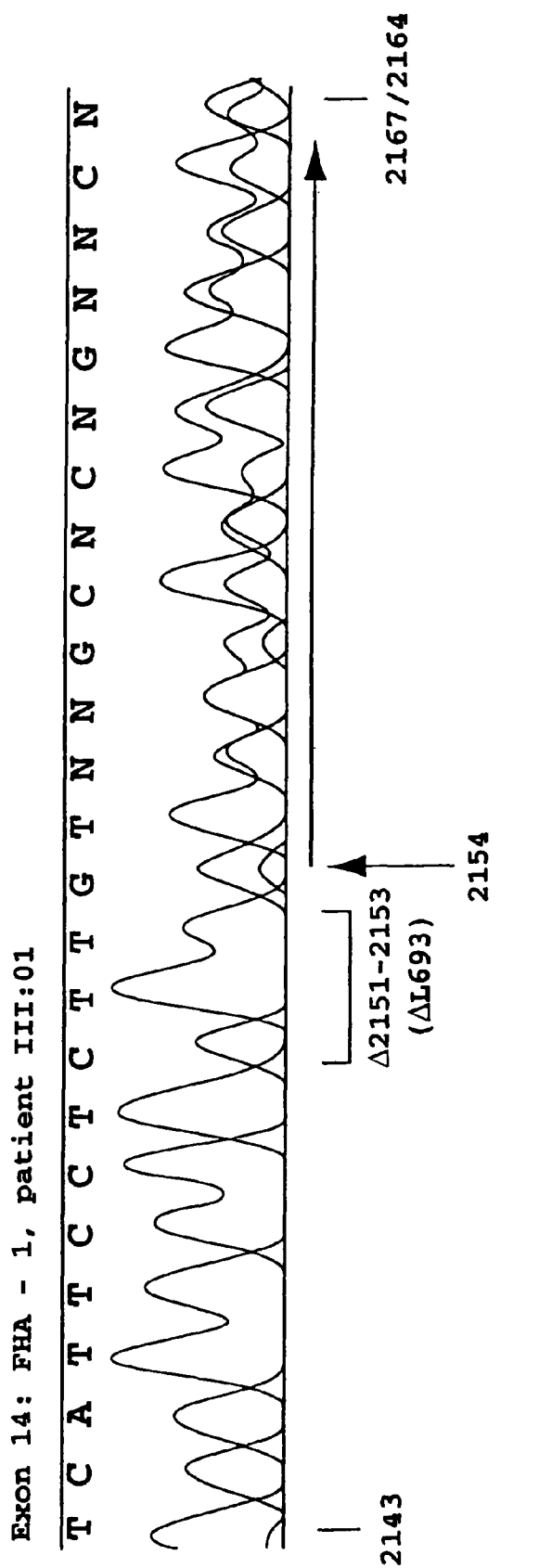

FIG. 6A shows a sequence of the mutation in family FHA-1. Patient III-01 is heterozygous for a deletion of nucleotides 2151-2153 of the cDNA (SEQ ID NO: 2). This deletion was detected as a superimposed sequence starting at the first nucleotide after the deletion. This corresponds to deletion of leucine 693 in the ABC1 protein (SEQ ID NO: 1).

FIG. 6B is an alignment of the human and mouse wild-type amino acid sequences, showing that the human and mouse sequences are identical in the vicinity of L693. L693 is also conserved in *C. elegans*. This highly conserved residue lies within a predicted transmembrane domain. The DNA sequences of the normal and mutant proteins are shown above and below the amino acid sequences, respectively.

Figure 6C:
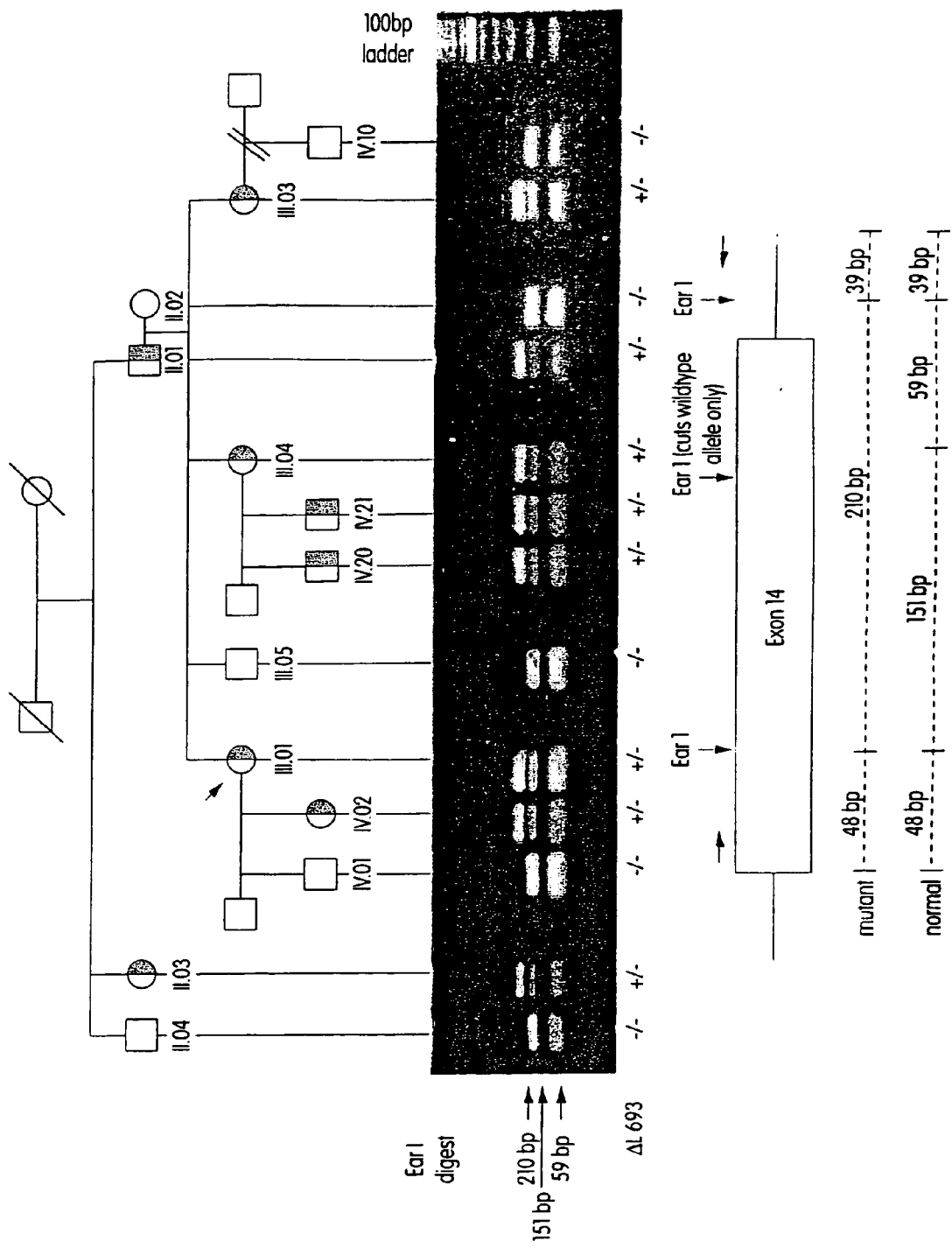

FIG. 6C shows segregation of the L693 mutation in FHA-1, as assayed by EarI restriction digestion. Two invariant EarI restriction sites (indicated by Õ) are present within the 297 bp PCR product located between the horizontal arrows (øØ) while a third site is present in the wild-type allele only. The presence of the mutant allele is thus distinguished by the presence of a 210 bp fragment (+), while the normal allele produces a 151 bp fragment (−). The proband of this family (III.01) is heterozygous for this mutation, as indicated by the presence of both the 210 and 151 bp bands.

Figure 6D:
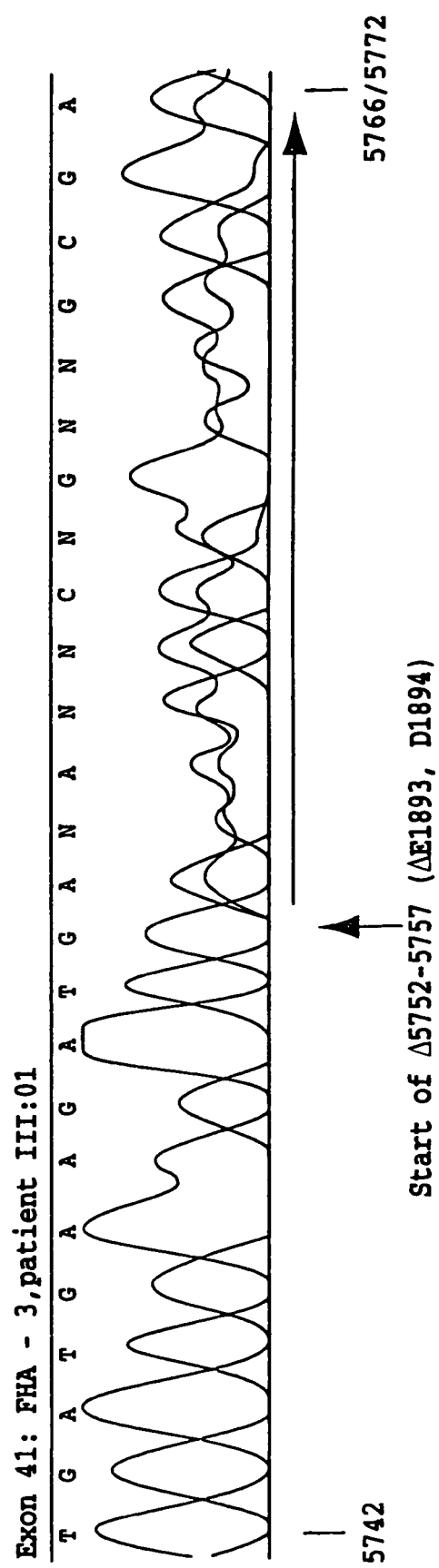

FIG. 6D shows a sequence of the mutation in family FHA-3. Patient III-01 is heterozygous for a deletion of nucleotides 5752-5757 of the cDNA (SEQ ID NO: 2). This deletion was detected as a superimposed sequence starting at the first nucleotide after the deletion. This corresponds to deletion of glutamic acid 1893 and aspartic acid 1894 in the ABC1 protein (SEQ ID NO: 1).

Figure 6E:
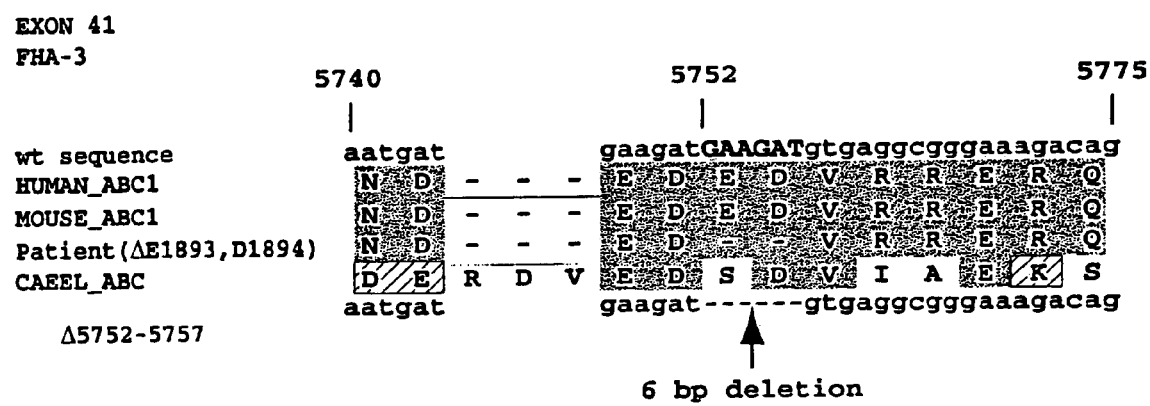

FIG. 6E is an alignment of the human and mouse wild-type amino acid sequences, showing that the human and mouse sequences are identical in the vicinity of 5752-5757. This region is highly conserved in *C. elegans*. The DNA sequences of the normal and mutant proteins are shown above and below the amino acid sequences, respectively.

FIG. 6F shows a sequence of the mutation in family FHA-2. Patient III-01 is heterozygous for a for a C to T transition at nucleotide 6504 of the cDNA (SEQ ID NO: 2). This alteration converts an arginine at position 2144 of SEQ ID NO: 1 to a STOP codon, causing truncation of the last 118 amino acids of the ABC1 protein.

Figure 7A:
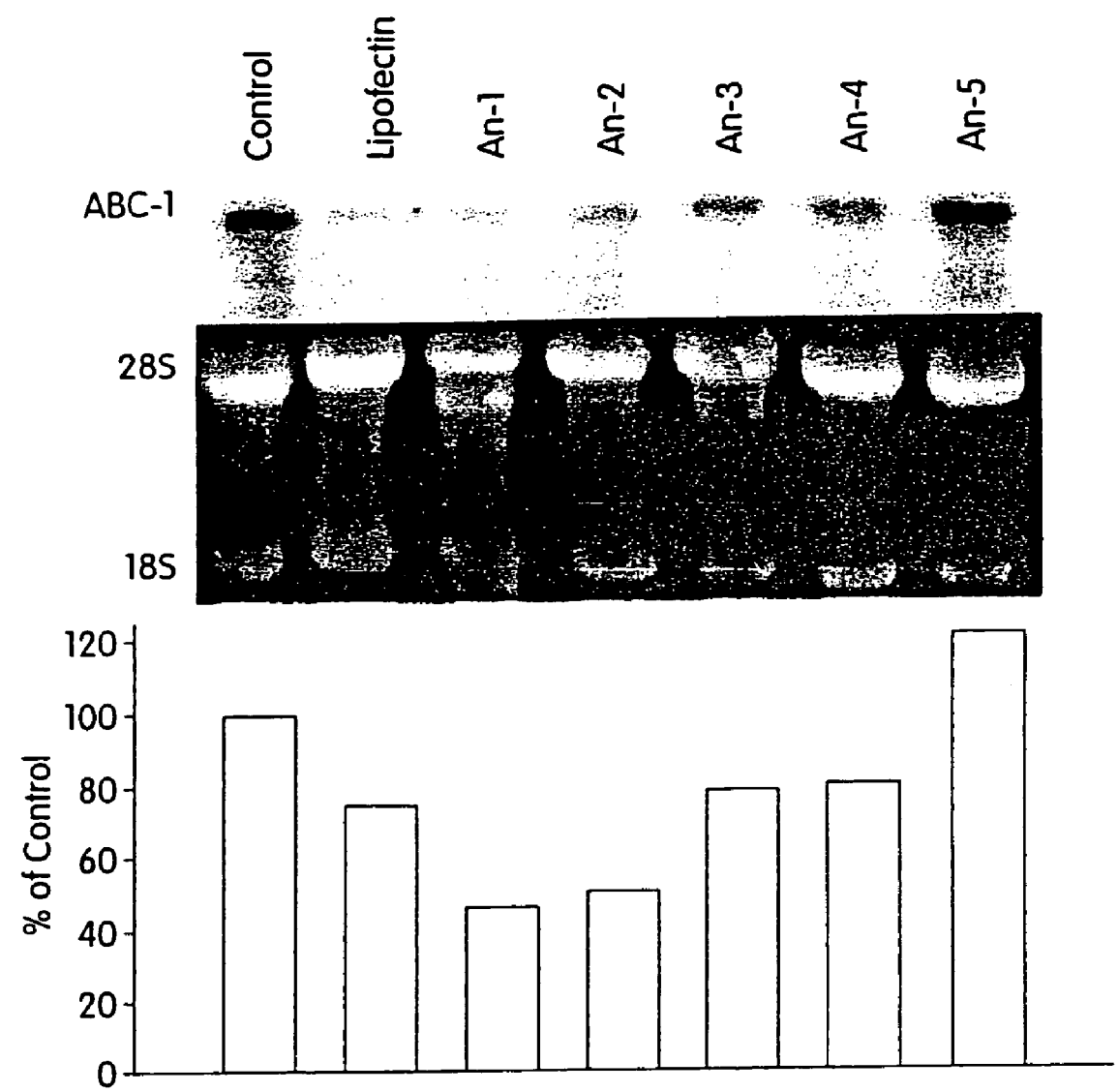
Figure 7B:
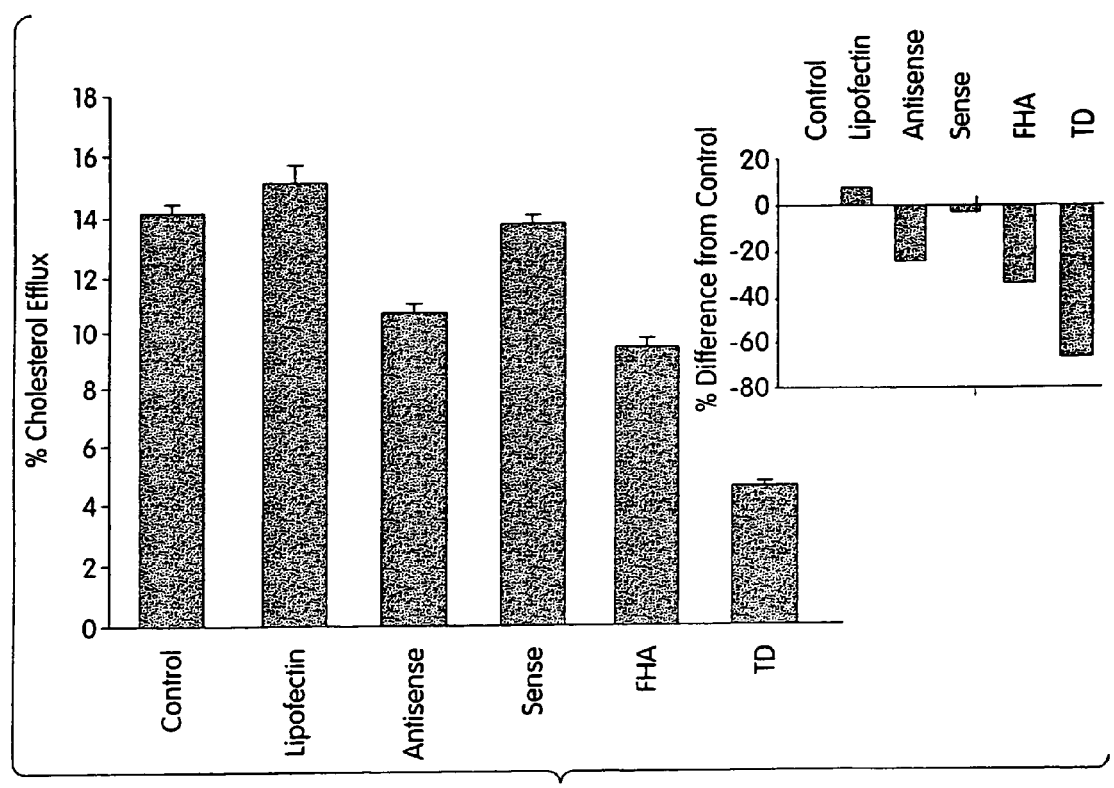

FIGS. 7A and 7B show cholesterol efflux from human skin fibroblasts treated with ABC1 antisense oligonucleotides. Fibroblasts from a control subject were labeled with $^3$H cholesterol (0.2 µCi/mL) during growth for 48 hours and transfected with 500 nM ABC1 antisense AN-1 (5'-GCA GAG GGC ATG GCT TTA TTT G-3'; SEQ ID NO: 3) with 7.5 µg lipofectin for 4 hours. Following transfection, cells were cholesterol loaded (20 µg/mL) for 12 hours and allowed to equilibrate for 6 hours. Cells were either then harvested for total RNA and 10 µg was used for Northern blot analysis. Cholesterol efflux experiments were carried out as described herein. FIG. 7A: AN-1 was the oligonucleotide that resulted in a predictable decrease in ABC1 RNA transcript levels. FIG. 7B: A double antisense transfection method was used. In this method, cells were labeled and transfected with AN-1 as above, allowed to recover for 20 hours, cholesterol loaded for 24 hours, and then re-transfected with AN-1. Twenty hours after the second transfection, the cholesterol efflux as measured. A ~50% decrease in ABC1 transcript levels was associated with a significant decrease in cholesterol efflux intermediate between that seen in wild-type and TD fibroblasts.

Figure 7C:
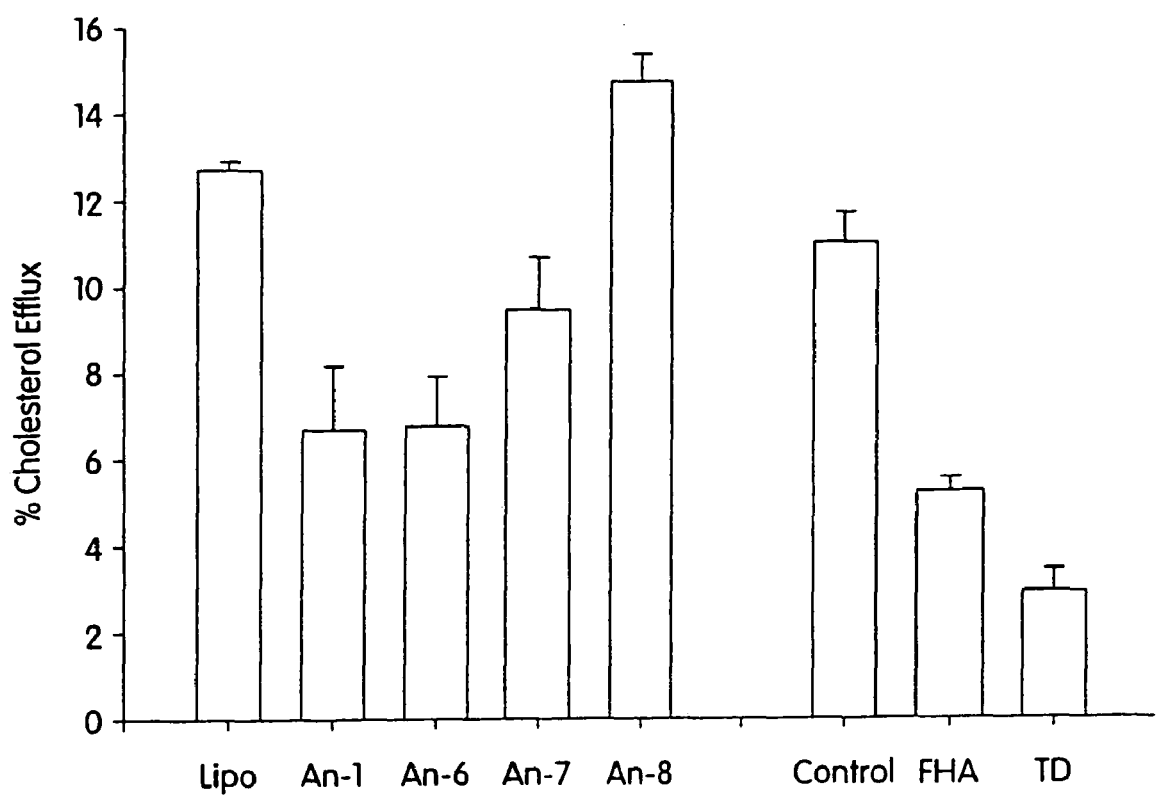

FIG. 7C shows show cholesterol efflux from human skin fibroblasts treated with antisense oligonucleotides directed to the region encoding the amino-terminal 60 amino acids. Note that the antisense oligonucleotide AN-6, which is directed to the previously unrecognized translation start site, produces a substantial decrease in cellular cholesterol efflux.

Figure 8:
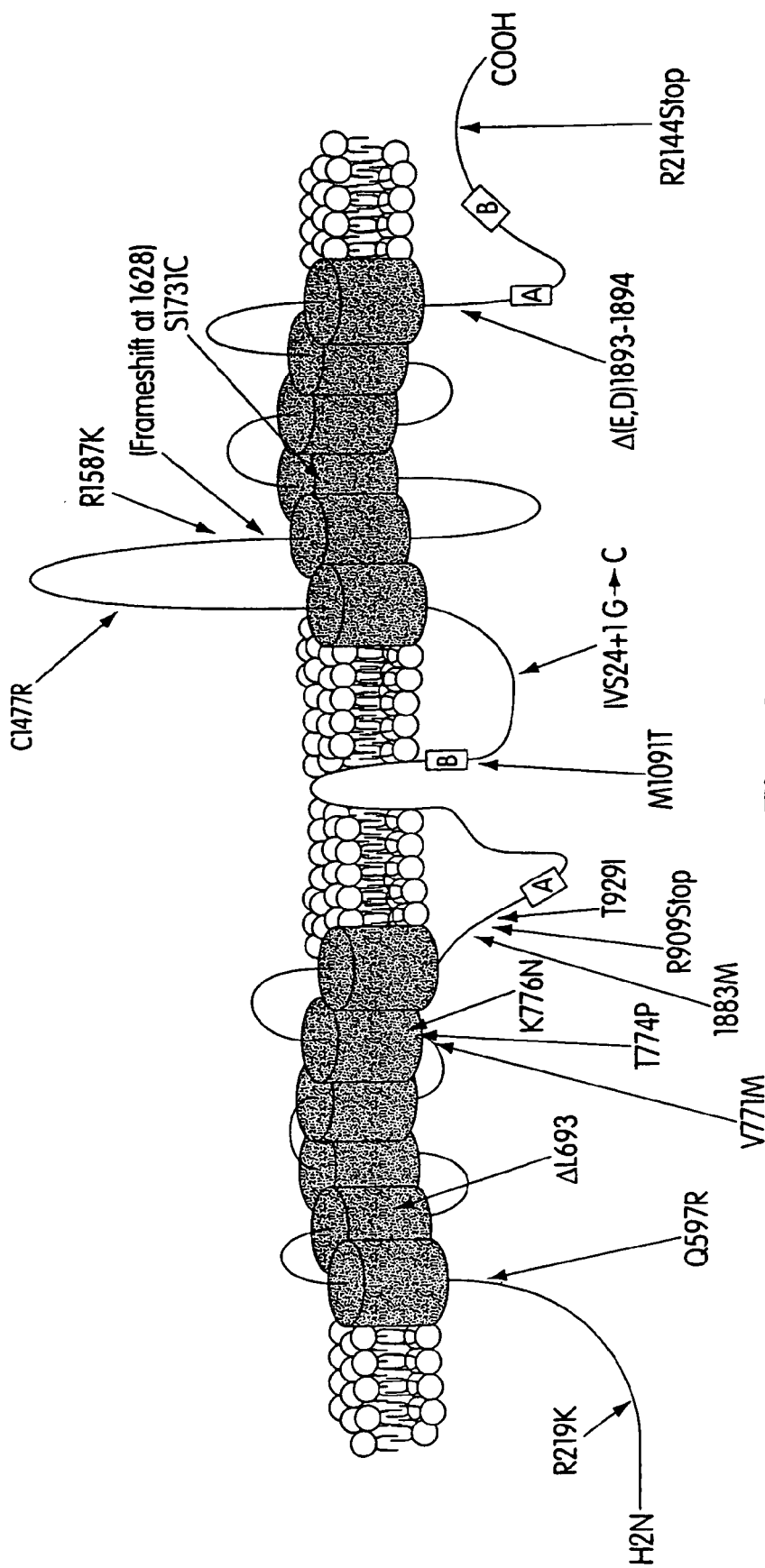

FIG. 8 is a schematic illustration showing predicted topology, mutations, and polymorphisms of ABC1 in Tangier disease and FHA. The two transmembrane and ATP binding domains are indicated. The locations of mutations are indicated by the arrows with the amino acid changes, which are predicted from the human ABC1 cDNA sequence. These mutations occur in different regions of the ABC1 protein.

FIG. 9A shows the amino acid sequence of the human ABC1 protein (SEQ ID NO: 1).

FIGS. 9B-9E show the nucleotide sequence of the human ABC1 cDNA (SEQ ID NO: 2).

Figure 10B:
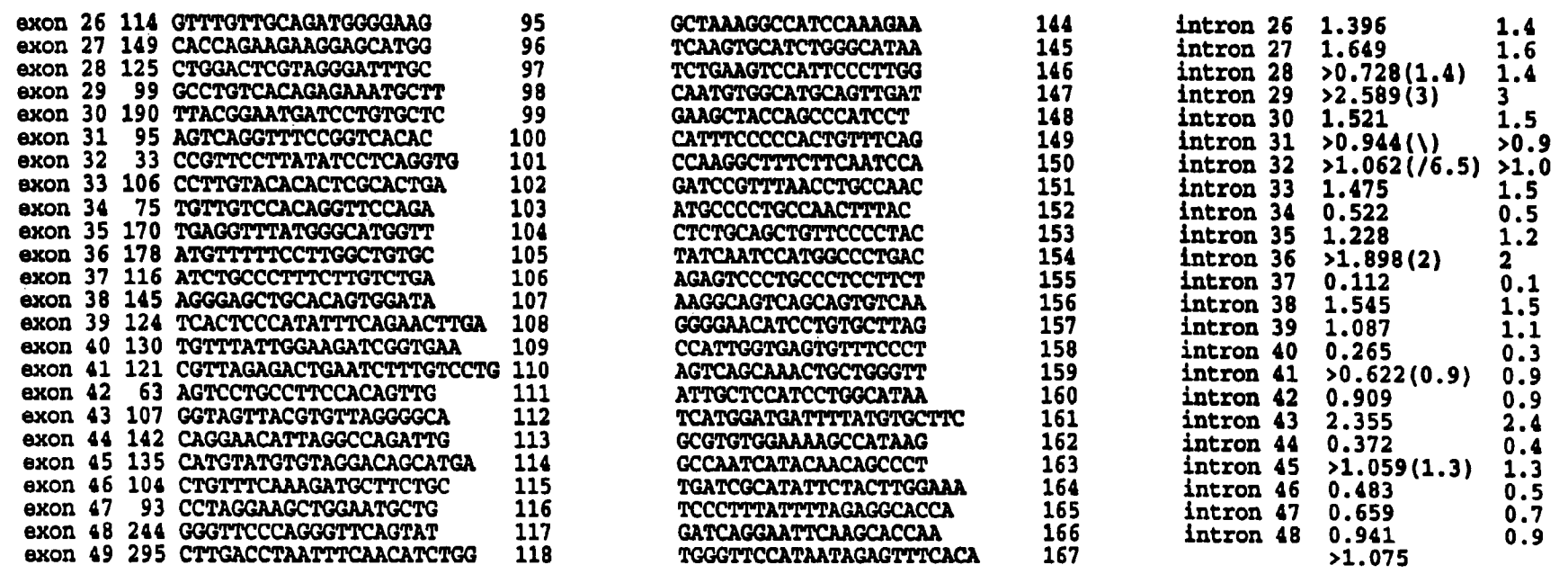

FIG. 10 shows the 5' and 3' nucleotide sequences suitable for use as 5' and 3' PCR primers, respectively, for the amplification of the indicated ABC1 exon.

FIG. 11 shows a summary of alterations found in ABC1, including sequencing errors, mutations, and polymorphisms.

FIG. 12 shows a series of genomic contigs (SEQ ID NOS. 14-29) containing the ABC1 promoter (SEQ ID NO: 14), as well as exons 1-49 (and flanking intronic sequence) of ABC1.

The exons (capitalized letters) are found in the contigs as follows: SEQ ID NO: 14—exon 1; SEQ ID NO: 15—exon 2; SEQ ID NO: 16—exon 3; SEQ ID NO: 17—exon 4; SEQ ID NO: 18—exon 5; SEQ ID NO: 19—exon 6; SEQ ID NO: 20—exons 7 and 8; SEQ ID NO: 21—exons 9 through 22; SEQ ID NO: 22—exons 23 through 28; SEQ ID NO: 23—exon 29; SEQ ID NO: 24—exons 30 and 31; SEQ ID NO: 25—exon 32; SEQ ID NO: 26—exons 33 through 36; SEQ ID NO: 27—exons 37 through 41; SEQ ID NO: 28—exons 42-45; SEQ ID NO: 29—exons 46-49.

Figure 13:
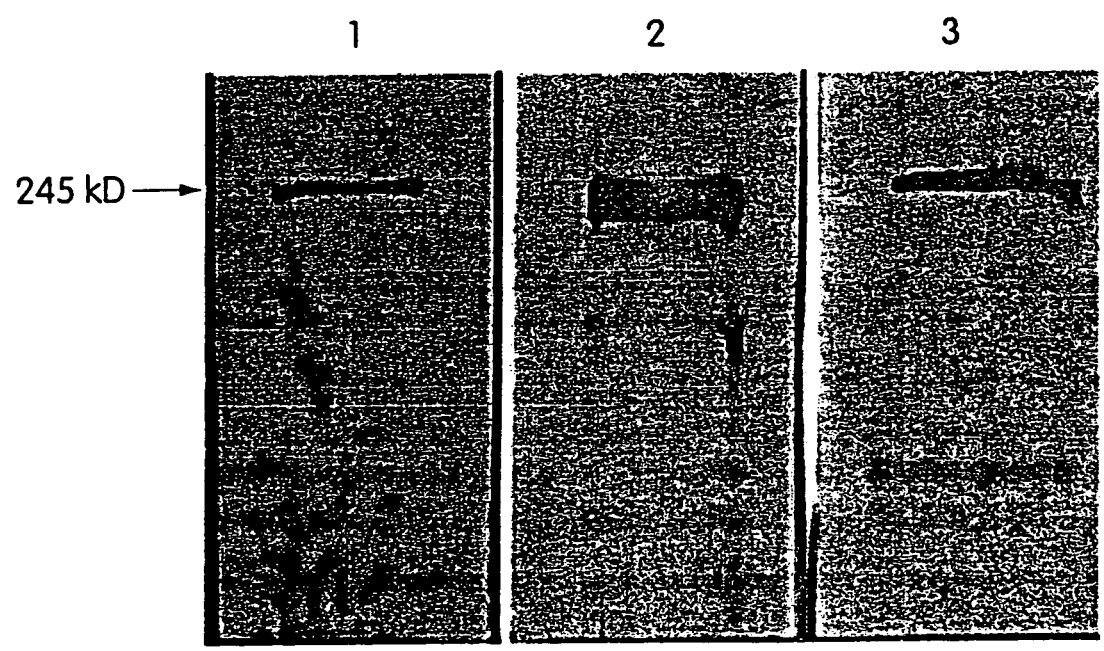

FIG. 13 is a series of illustrations showing that the aminoterminal 60 amino acid region of ABC1 is protein-coding. Lysates of normal human fibroblasts were immunoblotted in parallel with a rabbit polyclonal antibody to amino acids 1-20 of human ABC1 (1); a rabbit polyclonal antibody to amino acids 1430-1449 of human ABC1 (2); and a mouse monoclonal antibody to amino acids 2236-2259 of human ABC1. The additional bands detected in lane 2 may be due to a lack of specificity of that antibody or the presence of degradation products of ABC1.

Figure 14:
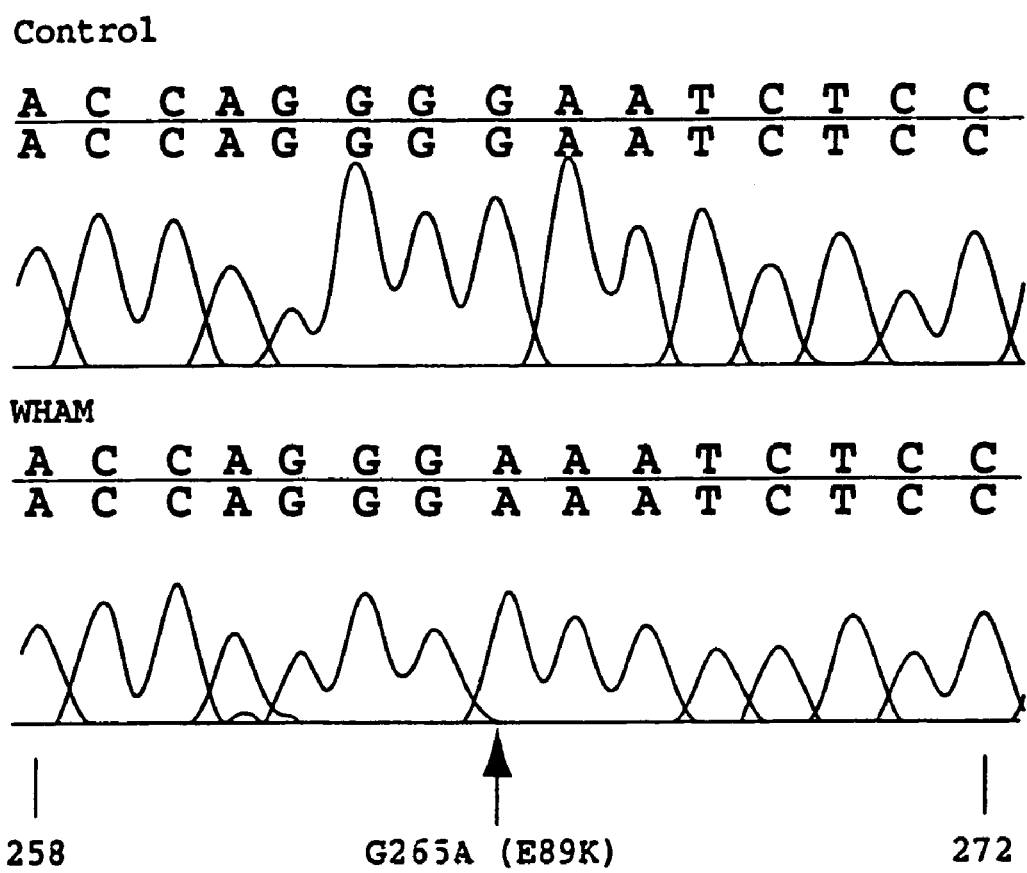

FIG. 14 is a schematic illustration showing that the WHAM chicken contains a non-conservative substitution (G265A) resulting in an amino acid change (E89K).

Figure 15:
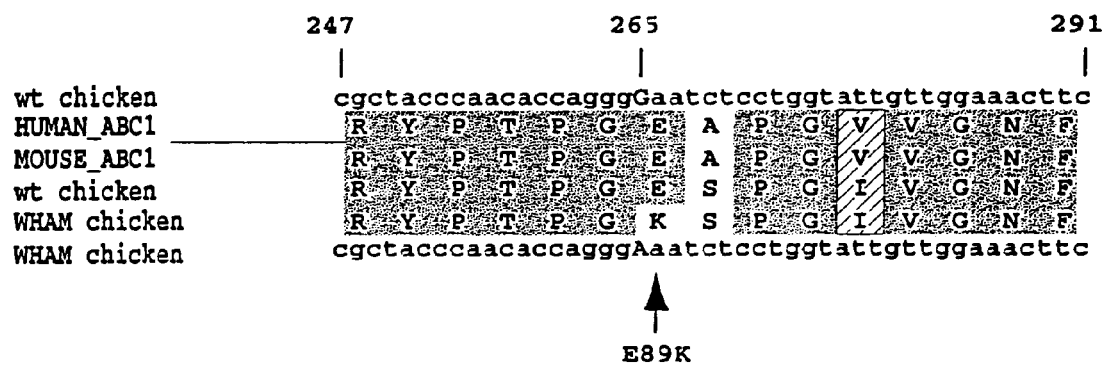

FIG. 15 is a schematic illustration showing that the mutation in the WHAM chicken is at an amino acid that is conserved among human, mouse, and chicken.

FIG. 16 show a summary of locations of consensus transcription factor binding sites in the human ABC1 promoter (nucleotides 1-8238 of SEQ ID NO: 14). The abbreviations are as follows: PPRE=peroxisome proliferator-activated receptor. SRE=steroid response element-binding protein site. ROR=RAR-related orphan receptor.

DETAILED DESCRIPTION

Genes play a significant role influencing HDL levels. Tangier disease (TD) was the first reported genetic HDL deficiency. The molecular basis for TD is unknown, but has been mapped to 9q31 in three families. We have identified two additional probands and their families, and confirmed linkage and refined the locus to a limited genomic region. Mutations in the ABC1 gene accounting for all four alleles in these two families were detected. A more frequent cause of low HDL levels is a distinct disorder, familial HDL deficiency (FHA). On the basis of independent linkage, meiotic recombinants and disease associated haplotypes, FHA was localized to a small genomic region encompassing the ABC1 gene. A mutation in a conserved residue in ABC1 segregated with FHA. Antisense reduction of the ABC1 transcript in fibroblasts was associated with a significant decrease in cholesterol efflux.

Cholesterol is normally assembled with intracellular lipids and secreted, but in TD the process is diverted and cholesterol is degraded in lysosomes. This disturbance in intracellular trafficking of cholesterol results in an increase in intracellular cholesterol ester accumulation associated with morphological changes of lysosomes and the Golgi apparatus and cholesteryl ester storage in histiocytes, Schwann cells, smooth muscle cells, mast cells and fibroblasts.

The clinical and biochemical heterogeneity in patients with TD has led to the possibility that genetic heterogeneity may also underlie this disorder. Considering this, we initially performed linkage analysis on these two families of different ancestries (TD-1 is Dutch, TD-2 is British; Frohlich et al., Clin. Invest. Med. 10:377-382, 1987) and confirmed that the genetic mutations underlying TD in these families were localized to the same 9q31 region, to which a large family with TD had been assigned (Rust et al., Nature Genetics 20:96-98, 1998). Detailed haplotype analysis, together with the construction of a physical map, refined the localization of this gene. Mutations in the ABC1 gene were found in TD.

FHA is much more common than TD, although its precise frequency is not known. While TD has been described to date in only 40 families, we have identified more than 40 FHA families in the Netherlands and Quebec alone. After initial suggestions of linkage to 9q31, thirteen polymorphic markers spanning approximately 10 cM in this region were typed and demonstrated the highest LOD score at D9S277. Analysis of the homozygosity of markers in the TD-2 proband, who was expected to be homozygous for markers close to TD due to his parents' consanguinity, placed the TD gene distal to D9S127. Combined genetic data from TD and FHA families pointed to the same genomic segment spanning approximately 1,000 kb between D9S127 and D9S1866. The ABC1 transporter gene was contained within the minimal genomic region. RT-PCR analysis in one family demonstrated a deletion of leucine at residue 693 (Δ693) in the first transmembrane domain of ABC1, which segregated with the phenotype of HDL deficiency in this family.

ABC1 is part of the ATP-binding cassette (ABC transporter) superfamily, which is involved in energy-dependent transport of a wide variety of substrates across membranes (Dean et al., Curr. Opin. Gen. Dev. 5:779-785, 1995). These proteins have characteristic motifs conserved throughout evolution which distinguish this class of proteins from other ATP binding proteins. In humans these genes essentially encode two ATP binding segments and two transmembrane domains (Dean et al., Curr. Opin. Gen. Dev. 5:779-785, 1995). We have now shown that the ABC1 transporter is crucial for intracellular cholesterol transport.

We have demonstrated that reduction of the ABC1 transcript using oligonucleotide antisense approaches results in decreased efflux, clearly demonstrating the link between alterations in this gene and its functional effects. TD and FHA now join the growing list of genetic diseases due to defects in the ABC group of proteins including cystic fibrosis (Zielenski, et al., Annu. Rev. Genet. 29:777-807, 1995), adrenoleukodystrophy (Mosser et al., Nature 361: 726-730, 1993), Zellweger syndrome (Gärtner et al., Nat. Genet. 1:23, 1992), progressive familial intrahepatic cholestatis (Bull et al., Nat. Genet. 18:219-224, 1998), and different eye disorders including Stargardt disease (Allikmets et al., Nat. Genet. 15:236-246, 1997), autosomal recessive retinitis pigmentosa (Allikmets et al., Science 277:1805-1807, 1997), and cone-rod dystrophy (Cremers et al., Hum. Mol. Genet. 7:355-362, 1998).

Patients with TD have been distinguished from patients with FHA on the basis that Tangier disease was an autosomal recessive disorder (OMIM 20540) while FHA is inherited as an autosomal dominant trait (OMIM 10768). Furthermore, patients with TD have obvious evidence for intracellular cholesterol accumulation which is not seen in FHA patients. It is now evident that heterozygotes for TD do have reduced HDL levels and that the same mechanisms underlie the HDL deficiency and cholesterol efflux defects seen in heterozygotes for TD as well as FHA. Furthermore, the more severe phenotype in TD represents loss of function from both alleles of the ABC1 gene.

ABC1 is activated by protein kinases, presumably via phosphorylation, which also provides one explanation for the essential role of activation of protein kinase C in promoting cholesterol efflux (Drobnick et al., Arterioscler. Thromb. Vasc. Biol. 15: 1369-1377, 1995). Brefeldin, which inhibits trafficking between the endoplasmic reticulum and the Golgi, significantly inhibits cholesterol efflux, essentially reproducing the effect of mutations in ABC1, presumably through the inhibition of ABC1 biological activity. This finding has significance for the understanding of mechanisms leading to premature atherosclerosis. TD homozygotes develop premature coronary artery disease, as seen in the proband of TD-1 (III-01) who had evidence for coronary artery disease at 38 years. This is particular noteworthy as TD patients, in addition to exhibiting significantly reduced HDL, also have low LDL cholesterol, and yet they develop atherosclerosis despite this. This highlights the importance of HDL intracellular transport as an important mechanism in atherogenesis. There is significant evidence that heterozygotes for TD are also at increased risk for premature vascular disease (Schaefer et al., Ann. Int. Med. 93:261-266, 1980; Serfaty-Lacrosniere et al., Atherosclerosis 107:85-98, 1994). There is also preliminary evidence for premature atherosclerosis in some probands with FHA (FIG. 2B), e.g., the proband in FHA-2 (III-01) had a coronary artery bypass graft at 46 years while the proband in FHA-3 (FIG. 2C) had evidence for CAD around 50 years of age. The TD-1 proband had more severe efflux deficiency than the TD-2 proband (FIG. 1C). Interestingly, the TD-2 proband had no evidence for CAD by 62 when he died of unrelated causes, providing preliminary evidence for a relationship between the degree of cholesterol efflux (mediated in part by the nature of the mutation) and the likelihood of atherosclerosis.

The ABC1 gene plays a crucial role in cholesterol transport and, in particular, intracellular cholesterol trafficking in monocytes and fibroblasts. It also appears to play a significant role in other tissues such as the nervous system, GI tract, and the cornea. Completely defective intracellular cholesterol transport results in peripheral neuropathy, corneal opacities, and deposition of cholesterol esters in the rectal mucosa.

HDL deficiency is heterogeneous in nature. The delineation of the genetic basis of TD and FHA underlies the importance of this particular pathway in intracellular cholesterol transport, and its role in the pathogenesis of atherosclerosis. Unraveling of the molecular basis for TD and FHA defines a key step in a poorly defined pathway of cholesterol efflux from cells and could lead to new approaches to treatment of patients with HDL deficiency in the general population.

HDL has been implicated in numerous other biological processes, including but not limited to: prevention of lipoprotein oxidation; absorption of endotoxins; protection against *Trypanosoma brucei* infection; modulation of endothelial cells; and prevention of platelet aggregation (see Genest et al., J. Invest. Med. 47: 31-42, 1999, hereby incorporated by reference). Any compound that modulates HDL levels may be useful in modulating one or more of the foregoing processes. The present discovery that ABC1 functions to regulate HDL levels links, for the first time, ABC1 with the foregoing processes.

The following examples are to illustrate the invention. They are not meant to limit the invention in any way.

Analysis of TD Families

Studies of Cholesterol Efflux

Both probands had evidence of marked deficiency of cholesterol efflux similar to that previously demonstrated in TD patients (FIG. 1C). TD-1 is of Dutch descent while TD-2 is of British descent.

Linkage Analysis and Establishment of a Physical Map

Multiple DNA markers were genotyped in the region of 9q31 to which linkage to TD had been described (Rust et al., Nat. Genet. 20, 96-98, 1998). Two point linkage analysis gave a maximal peak LOD score of 6.49 at D9S1832 (Table 1) with significant evidence of linkage to all markers in a ~10 cM interval. Recombination with the most proximal marker, D9S1690 was seen in II-09 in Family TD-1 (A* in FIG. 3D) providing a centromeric boundary for the disease gene. Multipoint linkage analysis of these data did not increase the precision of the positioning of the disease trait locus.

A physical map spanning approximately 10 cM in this region was established with the development of a YAC contig (FIG. 3A). In addition, 22 other polymorphic multi-allelic markers which spanned this particular region were mapped to the contig (FIG. 3B) and a subset of these were used in construction of a haplotype for further analysis (FIGS. 1A and 1B; Table 2). The condensed haplotype in these families is shown in FIGS. 1A and 1B.

While the family of Dutch decent did not demonstrate any consanguinity, the proband in TD-2 was the offspring of a first-cousin consanguineous marriage (FIG. 1B). We postulated, therefore, that it was most likely that this proband would be homozygous for the mutation while the proband in the Dutch family was likely to be a compound heterozygote. The Dutch proband shows completely different mutation bearing haplotypes, supporting this hypothesis (FIG. 3C).

The TD-2 proband was homozygous for all markers tested (FIG. 1B) distal to D9S127 but was heterozygous at D9S127 and DNA markers centromeric to it (FIG. 3C). This suggested that the gene for TD was likely located to the genomic region telomeric of D9S127 and encompassed by the markers demonstrating homozygosity (FIG. 3B).

TABLE 1

Two Point Linkage Analysis of TD-1 and TD-2

| Marker Locus | LOD Score at recombination fraction | | | | | | |
|---|---|---|---|---|---|---|---|
| | 0 | 0.01 | 0.05 | 0.10 | 0.20 | 0.30 | 0.40 |
| D9S1690 | -infini | 4.25 | 4.52 | 4.26 | 3.39 | 2.30 | 1.07 |
| D9S277 | 6.22 | 6.11 | 5.67 | 5.10 | 3.90 | 2.60 | 1.17 |
| D9S1866 | 4.97 | 4.87 | 4.49 | 4.00 | 2.96 | 1.85 | 0.70 |
| D9S1784 | 5.50 | 5.40 | 5.00 | 4.47 | 3.36 | 2.17 | 0.92 |
| D9S1832 | 6.49 | 6.37 | 5.91 | 5.31 | 4.05 | 2.69 | 1.21 |
| D9S1677 | 4.60 | 4.51 | 4.18 | 3.76 | 2.88 | 1.93 | 0.93 |

Results of pairwise linkage analysis using MLINK. Values correspond to LOD score for linkage between the disease locus and a marker locus for specified values of the recombination fraction.

TABLE 2

Microsatellite markers used in this study

| Genetic Markers | Type | Heterozygocity | Number of alleles | Allele fraquency[r] size.bp (proportion |
|---|---|---|---|---|
| D9S283 | CA | 0.80 | 10 | 179(0.04); 181(0.34); 183(0.19); 185(0.20); 189(0.05); 193(0.04); 197(0.07); 199(0.02); 201(0.04); 203(0.04) |
| D9S176 | CA | 0.82 | 9 | 129(0.03); 131(0.06); 133(0.26); 135(0.12); 137(0.25); 139(0.03); 141(0.01); 145(0.05); 147(0.05) |
| D9S1690 | CA | 0.79 | 8 | 225(0.38); 227(0.14); 229(0.04); 231(0.12); 233(0.05); 235(0.16); 237(0.05); 239(0.05) |
| D9S277 | CA | 0.89 | 15 | 167(0.07); 171(0.02); 173(0.15); 175(0.11); 177(0.07); 179(0.04); 181(0.17); 183(0.06); 185(0.02); 187(0.02); 189(0.13); 191(0.13); 193(0.02); 197(0.00); 199(0.00) |
| D9S127 | CA | 0.72 | 6 | 149(0.11); 151(0.07); 153(0.25); 155(0.03); 157(0.45); 159(0.06) |
| D9S306 | CA | 0.87 | 13 | 102(0.06); 104(0.01); 110(0.03); 112(0.08); 114(0.16); 116(0.15); 118(0.11); 120(0.23); 122(0.06); 124(0.06); 126(0.03); 134(0.02); 136(0.01) |
| D9S1866 | CA | 0.62 | 11 | 248(0.06); 252(0.04); 254(0.01); 256(58); 258(0.03); 260(0.06); 262(0.02); 264(0.12); 266(0.06); 268(0.03); 270(0.01) |
| D9S1784 | CA | 0.86 | 15 | 174(0.10); 176(0.02); 178(0.00); 180(0.08); 182(0.11); 184(0.22); 136(0.15); 158(0.06); 190(0.04); 192(0.07); 194(0.08); 196(0.07); 198(0.01); 200(0.01); 202(0.01) |
| AFMa107xf9 | CA | n.a. | n.a. | n.a. |
| D9S2170 | CA | n.a. | n.a. | n.a. |
| D9S2171 | CA | n.a. | n.a. | n.a. |
| D9S2107 | CA | 0.63 | 5 | n.a. |
| D9S172 | CA | 0.54 | 5 | 291(0.00); 297(0.05); 299(0.32); 303(0.62); 305(0.02) |
| D9S2109 | CA | 0.51 | 3 | 1(0.42); 2(0.56); 3(0.02) |
| D9S1832 | CA | 0.88 | 12 | 161(0.04); 163(0.02); 167(0.02); 169(0.04); 171(0.10); 173(0.09); 175(0.15); 177(0.28); 179(0.19); 181(0.04); 183(0.01); 185(0.01) |
| D9S1835 | CA | 0.48 | 4 | 110(0.02); 112(0.23); 116(0.68); 118(0.07); |
| D9S1801 | CA | 0.77 | 10 | 166(0.10); 172(0.04); 174(0.02); 182(0.02); 184(0.19); 186(0.40); 188(0.15); 190(0.04); 192(0.02); 194(0.02) |
| D9S261 | CA | 0.63 | 7 | 90(0.02); 92(0.52); 94(0.02); 98(0.02); 100(0.10); 102(0.04); 104(0.08) |
| D9S160 | CA | 0.62 | 6 | 136(0.25); 138(0.53); 140(0.01); 142(0.12); 144(0.00); 146(0.07) |

TABLE 2-continued

Microsatellite markers used in this study

| Genetic Markers | Type | Heterozygocity | Number of alleles | Allele fraquency[f] size.bp (proportion |
|---|---|---|---|---|
| D9S1677 | CA | 0.81 | 10 | 251(0.27); 257(0.27); 259(0.07); 261(0.09); 263(0.27); 265(0.14); 267(0.02); 267(0.02); 271(0.04); 273(0.02) |
| D9S279 | CA | 0.78 | 6 | 244(0.09); 246(0.18); 248(0.29); 250(0.29); 252(0.07); 254(0.09) |
| D9S275 | CA | 0.62 | 4 | 190(0.31); 196(0.07); 198(0.52); 200(0.09); |

[f]In a Caucasian population of French Canadian or French descent (J. Weissenbach, Personal Communication 1993).
n.a. = not assessed
These polymorphic microsatellite markers were used for DNA typing in the region of 9q31 seen in FIG. 3. The majority come from the last version of the Genethon human linkage map. The frquency of heterozygosity, the number of alleles as well as the allele frequency of each marker are presented.

Mutation Detection

Based on the defect in intracellular cholesterol transport in patients with TD, we reviewed the EST database for genes in this region which might be relevant to playing a role in this process. One gene that we reviewed as a candidate was the lysophosphatidic acid (LPA) receptor (EDG2) which mapped near D9S1801 (FIG. 3C). This receptor binds LPA and stimulates phospholipase-C (PLC), and is expressed in fibroblasts. It has previously been shown that the coordinate regulation of PLC that is necessary for normal HDL3 mediated cholesterol efflux is impaired in TD (Walter et al., J. Clin. Invest. 98:2315-2323, 1996). Therefore this gene represented an excellent candidate for the TD gene. Detailed assessment of this gene, using Northern blot and RT-PCR and sequencing analysis, revealed no changes segregating with the mutant phenotype in this family, in all likelihood excluding this gene as the cause for TD. Polymorphisms were detected, however, in the RT-PCR product, indicating expression of transcripts from both alleles.

The second candidate gene (RGS3) encodes a member of a family regulating G protein signaling which could also be involved in influencing cholesterol efflux (Mendez et al., Trans. Assoc. Amer. Phys. 104:48-53, 1991). This gene mapped 0.7 cM telomeric to the LPA-receptor (FIG. 3C), and is expressed in fibroblasts. It was assessed by exon-specific amplification, as its genomic organization was published (Chatterjee et al., Genomics 45:429-433, 1997). No significant sequence changes were detected.

The ABC1 transporter gene had previously been mapped to 9q31, but its precise physical location had not been determined (Luciani et al., Genomics 21:150-159, 1994). The ABC1 gene is a member of the ATP binding cassette transporters which represents a super family of highly conserved proteins involved in membrane transport of diverse substrates including amino acids, peptides, vitamins and steroid hormones (Luciani et al., Genomics 21:150-159, 1994; Dean et al., Curr. Opin. Gen. Dev. 5:779-785, 1995). Primers to the 3' UTR of this gene mapped to YACs spanning D9S306 (887-B2 and 930-D3) compatible with it being a strong candidate for TD. We initiated large scale genomic sequencing of BACs spanning approximately 800 kb around marker D9S306 (BACs 269, 274, 279 and 291) (FIG. 3E). The ABC1 gene was revealed encompassing 49 exons and a minimum of 75 Kb of genomic sequence. In view of the potential function of a gene in this family as a cholesterol transporter, its expression in fibroblasts and localization to the minimal genomic segment underlying TD, we formally assessed ABC1 as a candidate.

Patient and control total fibroblast RNA was used in Northern blot analysis and RT-PCR and sequence analyses. RT-PCR and sequence analysis of TD-1 revealed a heterozygous T to C substitution (FIG. 4A) in the TD-1 proband, which would result in a substitution of arginine for cysteine at a conserved residue between mouse and man (FIG. 4B). This mutation, confirmed by sequencing exon 30 of the ABC1 gene, exhibited complete segregation with the phenotype on one side of this family (FIG. 4C). This substitution creates a HgaI site, allowing for RFLP analysis of amplified genomic DNA and confirmation of the mutation (FIG. 4C). The point mutation in exon 30 was not seen on over 200 normal chromosomes from unaffected persons of Dutch decent, and 250 chromosomes of Western European decent, indicating it is unlikely to be a polymorphism. Northern blot analysis of fibroblast RNA from this patient, using a cDNA encompassing exons 1 to 49 of the gene, revealed a normal sized ~8 Kb transcript and a truncated mutant transcript which was not visible in control RNA or in RNA from other patients with HDL deficiency (FIG. 4D). Additionally, Northern blot analysis using clones encompassing discrete regions of the cDNA revealed that the mutant transcript was detected with a cDNA compassing exons 1 to 49 (a), 1 to 41 (b), 1 to 22 (c), much more faintly with a probe spanning exon 23 to 29 (d) and not seen with probes encompassing exons 30 to 42 (e), but not seen with cDNA fragment spanning exons 30 to 49 (f). This was repeated on multiple filters with control RNA, RNA from other patients with HDL deficiency and the other TD proband, and only in TD-1 was the truncated transcript observed. Sequence analysis of the coding region did not reveal an alteration in sequence that could account for this finding. Furthermore, DNA analysis by Southern blot did not reveal any major rearrangements. Completion of exon sequencing in genomic DNA showed that this mutation was a G to C transversion at position (+1) of intron 24, (FIG. 11) affecting a splice donor site and causing aberrant splicing.

RT-PCR analysis of fibroblast RNA encoding the ABC1 gene from the proband in TD-2 (FIG. 1B) revealed a homozygous nucleotide change of A to G at nucleotide 1864 of SEQ ID NO: 2 in exon 13 (FIG. 5A), resulting in a substitution of arginine for glutamine at residue 597 of SEQ ID NO: 1 (FIG. 5B), occurring just proximal to the first predicted transmembrane domain of ABC1 (FIG. 8) at a residue conserved in mouse and as well as a C. elegans homolog. This mutation creates a second AciI site within exon 13. Segregation analysis of the mutation in this family revealed complete concordance between the mutation and the low HDL phenotype as predicted (FIG. 5C). The proband in TD-2 is homozygous for this mutation, consistent with our expectation of a disease causing mutation in this consanguineous family.

Analysis of FHA Families

Linkage Analysis and Refinement of the Minimal Genomic Region Containing the Gene for FHA Data from microsatellite typing of individual family members from the four pedigrees of French Canadian origin were analyzed (FIG. 2). A maximum LOD score of 9.67 at a recombination fraction of 0.0 was detected at D9S277 on chromosome 9q31 (FIG. 3; Table 3). Thereafter, 22 markers were typed in a region spanning 10 cM around this locus in these families (FIGS. 2 and 3). The frequency for these markers were estimated from a sample of unrelated and unaffected subjects of French ancestry (Table 2).

TABLE 3

Two Point Linkage Analysis of FHA

| Marker Locus | LOD Score at recombination fraction | | | | | | |
|---|---|---|---|---|---|---|---|
| | 0 | 0.01 | 0.05 | 0.10 | 0.20 | 0.30 | 0.40 |
| D9S283 | -infini | -2.57 | 0.51 | 1.48 | 1.84 | 1.48 | 0.76 |
| D9S176 | -infini | 1.42 | 3.07 | 3.39 | 3.05 | 2.22 | 1.12 |
| D9S1690 | -infini | 3.11 | 4.04 | 4.04 | 3.33 | 2.24 | 0.96 |
| D9S277 | 9.67 | 9.51 | 8.89 | 8.06 | 6.29 | 4.30 | 2.10 |
| D9S306 | 5.60 | 5.51 | 5.13 | 4.62 | 3.55 | 2.36 | 1.11 |
| D9S1866 | -infini | 7.24 | 7.35 | 6.87 | 5.50 | 3.82 | 1.91 |
| D9S1784 | -infini | 8.85 | 7.76 | 9.03 | 7.09 | 4.78 | 2.25 |
| D9S172 | -infini | 2.63 | 3.00 | 2.87 | 2.26 | 1.50 | 0.67 |
| D9S1832 | -infini | 5.20 | 5.97 | 5.75 | 4.59 | 3.02 | 1.30 |
| D9S1801 | 0.14 | 0.13 | 0.11 | 0.09 | 0.06 | 0.03 | 0.01 |
| D9S1677 | -infini | 7.83 | 7.90 | 7.38 | 5.90 | 4.08 | 2.01 |
| D9S279 | -infini | 3.43 | 3.80 | 3.66 | 3.01 | 2.12 | 1.05 |
| D9S275 | -infini | 2.57 | 2.98 | 2.91 | 2.41 | 1.69 | 0.81 |

Results of pairwise linkage analysis using MLINK. Values correspond to LOD score for linkage between the disease locus and a marker locus for specified values of the recombination fraction.

TD and FHA have thus far been deemed distinct with separate clinical and biochemical characteristics. Even though the genes for these disorders mapped to the same region, it was uncertain whether FHA and TD were due to mutations in the same gene or, alternatively, due to mutations in genes in a similar region.

Refinement of the region containing the gene for FHA was possible by examining haplotype sharing and identification of critical recombination events (FIG. 2). Seven separate meiotic recombination events were seen in these families ("A" through "G" in FIGS. 2 and 3), clearly indicating that the minimal genomic region containing the potential disease gene was a region of approximately 4.4 cM genomic DNA spanned by marker D9S1690 and D9S1866 (FIGS. 2 and 3). This region is consistent with the results of two point linkage analysis which revealed maximal LOD scores with markers D9S277 and D9S306 and essentially excluded the region centromeric to D9S1690 or telomeric to D9S1866. An 8$^{th}$ meiotic recombination event ("H" in FIG. 3) further refined the FHA region to distal to D9S277.

As described herein, the ABC1 gene mapped within this interval. The overlapping genetic data strongly suggested that FHA may in fact be allelic to TD. Utilization of sets of genetic data from FHA and TD provided a telomeric boundary at D9S1866 (meiotic recombinant) (FIG. 3D) and a centromeric marker at D9S127 based on the homozygosity data of TD-2. This refined the locus to approximately 1 Mb between D9S127 and D9S1866. The ABC1 gene mapped within this minimal region (FIG. 3E).

Mutation Detection in FHA

Mutation assessment of the ABC1 gene was undertaken in FHA-1 (FIG. 2A). Using primers that spanned overlapping segments of the mRNA we performed RT-PCR analysis and subjected these fragments to mutational analysis. A deletion of three nucleotides is evident in the RT-PCR sequence of FHA-1 III.01 (FIG. 6A), resulting in a loss of nucleotides 2151-2153 of SEQ ID NO: 2 and deletion of a leucine (L693) at amino acid position 693 of SEQ ID NO: 1 (FIG. 6A). This leucine is conserved in mouse and C. elegans (FIG. 6B). The alteration was detected in the RT-PCR products as well as in genomic sequence from exon 14 specific amplification. This mutation results in a loss of an EarI restriction site. Analysis of genomic DNA from the family indicated that the mutation segregated completely with the phenotype of HDL deficiency. The loss of the EarI site results in a larger fragment being remaining in persons heterozygous for this mutation (FIG. 6C). This mutation maps to the first putative transmembrane domain of ABC1 (FIG. 8) and was not seen in 130 chromosomes from persons of French Canadian descent nor seen in over 400 chromosomes from persons of other Western European ancestry.

A mutation has also been found in patient genomic DNA in pedigree FHA-3 from Quebec. The alteration, a 6 bp deletion of nucleotides 5752-5757 of SEQ ID NO: 2 within exon 41, results in a deletion of amino acids 1893 (Glu) and 1894 (Asp) of SEQ ID NO: 1. The deletion was detected as a double, superimposed, sequence starting from the point of the deletion (FIG. 6D), and was detected in sequence reads in both directions. The deletion can be detected on 3% agarose or 10% polyacrylamide gels, and segregates with disease in FHA-3. It was not seen in 128 normal chromosomes of French-Canadian origin or in 434 other control chromosomes. Amino acids 1893 and 1894 are in a region of the ABC1 protein that is conserved between human, mouse, and C. elegans (FIG. 6E), implying that it is of functional importance.

An additional mutation has been found in patient genomic DNA in pedigree FHA-2 from Quebec (FIG. 6F). The alteration, a C to T transition at position 6504 of SEQ ID NO: 2, converts an arginine at position 2144 of SEQ ID NO: 1 to a STOP codon, causing truncation of the last 118 amino acids of the ABC1 protein. This alteration segregates with disease in family FHA-2.

A summary of all mutations and polymorphisms found in ABC1 is shown in FIG. 11. Each variant indicated as a mutation segregates with low HDL in its family, and was not seen in several hundred control chromosomes.

Functional Relationship Between Changes in ABC1 Transcript Levels and Cholesterol Efflux Antisense approaches were undertaken to decrease the ABC1 transcript and assess the effect of alteration of the transcript on intracellular cholesterol transport. The use of antisense primers to the 5' end of ABC1 clearly resulted in a decrease to approximately 50% of normal RNA levels (FIG. 7A). This would be expected to mimic in part the loss of function due to mutations on one allele, similar to that seen in heterozygotes for TD and patients with FHA. Importantly, reduction in the mRNA for the ABC1 gene resulted in a significant reduction in cellular cholesterol efflux (FIG. 7B), further establishing the role of this protein in reverse cholesterol transport and providing evidence that the mutations detected are likely to constitute loss of function mutations. Furthermore, these data support the functional importance of the first 60 amino acids of the protein. Antisense oligonucleotide AN-6 is directed to the novel start codon 5' to the one indicated in AJ012376.1; this antisense oligonucleotide effectively suppresses efflux.

The above-described results were obtained using the following materials and methods.

Patient Selection

The probands in TD families had previously been diagnosed as suffering from TD based on clinical and biochemical data. Study subjects with FHA were selected from the Cardiology Clinic of the Clinical Research Institute of Montreal. The main criterion was an HDL-C level <5th percentile for age and gender, with a plasma concentration of triglycerides <95th percentile in the proband and a first-degree relative with the same lipid abnormality. In addition, the patients did not have diabetes.

Biochemical Studies

Blood was withdrawn in EDTA-containing tubes for plasma lipid, lipoprotein cholesterol, ApoAI, and triglyceride analyses, as well as storage at.

−80° C. Leukocytes were isolated from the buffy coat for DNA extraction.

Lipoprotein measurement was performed on fresh plasma as described elsewhere (Rogler et al., Arterioscler. Thromb. Vasc. Biol. 15:683-690, 1995). The laboratory participates and meets the criteria of the Lipid Research Program Standardization Program. Lipids, cholesterol and triglyceride levels were determined in total plasma and plasma at density d<1.006 g/mL (obtained after preparative ultracentrifugation) before and after precipitation with dextran manganese. Apolipoprotein measurement was performed by nephelometry for ApoB and ApoAI.

Linkage Analysis

Linkage between the trait locus and microsatellite loci was analyzed using the FASTLINK version (4.0 P). FASTLINK/MLINK was used for two-point linkage analysis assuming an autosomal dominant trait with complete penetrance. In FHA and TD heterozygotes, the phenotype was HDL deficiency <5th percentile for age and sex. The disease allele frequency was estimated to be 0.005. Marker allele frequencies were estimated from the genotypes of the founders in the pedigrees using NEWPREP. Multipoint linkage analysis was carried out using FASTLINK/LINKMAP.

Genomic Clone Assembly and Physical Map Construction of the 9q31 Region

Using the Whitehead Institute/MIT Center for Genome Research map as a reference, the genetic markers of interest at 9q31 were identified within YAC contigs. Additional markers that mapped to the approximate 9q31 interval from public databases and the literature were then assayed against the YAC clones by PCR and hybridization analysis. The order of markers was based on their presence or absence in the anchored YAC contigs and later in the BAC contig. Based on the haplotype analysis, the region between D9S277 and D9S306 was targeted for higher resolution physical mapping studies using bacterial artificial chromosomes (BACs). BACs within the region of interest were isolated by hybridization of DNA marker probes and whole YACs to high-density filters containing clones from the RPCI-11 human BAC library (FIG. 3).

Sequence Retrieval and Alignment

The human ABC1 mRNA sequence was retrieved from GenBank using the Entrez nucleotide query (Baxevanis et al., A Practical Guide to the Analysis of Genes and Proteins, eds. Baxevanis, A. D. & Ouellette, B. F. F. 98:120, 1998) as GenBank accession number AJ012376.1. The version of the protein sequence we used as wild-type (normal) was CAA10005.1.

We identified an additional 60 amino acids in-frame with the previously-believed start methionine (FIG. 9A). Bioinformatic analysis of the additional amino acids indicates the presence of a short stretch of basic amino acid residues, followed by a hydrophobic stretch, then several polar residues. This may represent a leader sequence, or another transmembrane or membrane-associated region of the ABC1 protein. In order to differentiate among the foregoing possibilities, antibodies directed to the region of amino acids 1-60 are raised against and used to determine the physical relationship of amino acids 1-60 in relation to the cell membrane. Other standard methods can also be employed, including, for example, expression of fusion proteins and cell fractionation.

We also identified six errors in the previously-reported nucleotide sequence (at positions 839, 4738, 5017, 5995, 6557, and 6899 of SEQ ID NO: 2; FIG. 11). Hence, the sequence of the ABC1 polypeptide of FIG. 9A differs from CAA10005.1 as follows: Thr_Ile at position 1554; Pro_Leu at position 1642; Arg_Lys at position 1973; and Pro_Leu at position 2167. We also identified 5' and 3' UTR sequence (FIGS. 9B-9E).

The mouse ABC1 sequence used has accession number X75926. It is very likely that this mouse sequence is incomplete, as it lacks the additional 60 amino acids described herein for human ABC1.

Version 1.7 of ClustalW was used for multiple sequence alignments with BOXSHADE for graphical enhancement (www.isrec.isb-sib.ch:8080/software/BOX_form.html) with the default parameter. A *Caenorhabditis elegans* ABC1 orthologue was identified with BLAST (version 2.08) using CAA1005.1 (see above) as a query, with the default parameter except for doing an organism filter for *C. elegans*. The selected protein sequence has accession version number AAC69223.1 with a score of 375, and an E value of 103.

Genomic DNA Sequencing

BAC DNA was extracted from bacterial cultures using NucleoBond Plasmid Maxi Kits (Clontech, Palo Alto, Calif.). For DNA sequencing, a sublibrary was first constructed from each of the BAC DNAs (Rowen et al., Automated DNA Sequencing and Analysis, eds. Adams, M. D., Fields, C. & Venter, J. C., 1994). In brief, the BAC DNA was isolated and randomly sheared by nebulization. The sheared DNA was then size fractionated by agarose gel electrophoresis and fragments above 2 kb were collected, treated with Mung Bean nuclease followed by T4 DNA polymerase and klenow enzyme to ensure blunt-ends, and cloned into SmaI-cut M13 mp19. Random clones were sequenced with an ABI373 or 377 sequencer and fluorescently labeled primers (Applied BioSystems, Foster City, Calif.). DNAStar software was used for gel trace analysis and contig assembly. All DNA sequences were examined against available public databases primarily using BLASTn with RepeatMasker (University of Washington).

Reverse Transcription (RT)-PCR Amplification and Sequence Analysis

Total RNA was isolated from the cultured fibroblasts of TD and FHA patients, and reverse transcribed with a CDS primer containing oligo d(T)18 using 250 units of SuperScript II reverse transcriptase (Life Technologies, Inc., Rockville, Md.) as described (Zhang et al., J. Biol. Chem. 27:1776-1783, 1996). cDNA was amplified with Taq DNA polymerase using primers derived from the published human ABC1 cDNA sequence (Luciani et al., Genomics 21:150-159, 1994). Six sets of primer pairs were designed to amplify each cDNA sample, generating six DNA fragments which are sequentially overlapped covering 135 to 7014 bp of the full-length human ABC1 cDNA. The nucleotides are numbered according to the order of the published human cDNA sequence (AJ012376.1). Primer pairs (1): 135-158 (f) and 1183-

1199 (r); (2): 1080-1107 (f) and 2247-2273 (r); (3): 2171-2197 (f) and 3376-3404 (r); (4): 3323-3353 (f) and 4587-4617 (r); (5) 4515-4539 (f) and 5782-5811 (r); (6): 5742-5769 (f) and 6985-7014 (r). RT-PCR products were purified by Qiagen spin columns. Sequencing was carried out in a Model 373A Automated DNA sequencer (Applied Biosystems) using Taq di-deoxy terminator cycle sequencing and Big Dye Kits according to the manufacturer's protocol.

Northern Blot Analysis

Northern transfer and hybridizations were performed essentially as described (Zhang et al., J. Biol. Chem. 27:1776-1783, 1996). Briefly, 20 µg of total fibroblast RNA samples were resolved by electrophoresis in a denaturing agarose (1.2%; w/v) gel in the presence of 7% formaldehyde, and transferred to nylon membranes. The filters were probed with $^{32}$P-labeled human ABC1 cDNA as indicated. Pre-hybridization and hybridizations were carried out in an ExpressHyb solution (ClonTech) at 68° C. according to the manufacturer's protocol.

Detection of the Mutations in TD

Genotyping for the T4503C and A1864G variants was performed by PCR amplification of exon 30 followed by restriction digestion with HgaI and amplification of exon 13 followed by digestion with AciI, respectively. PCR was carried out in a total volume of 50 µL with 1.5 mM MgCl$_2$, 187.5 nM of each dNTP, 2.5 U Taq polymerase and 15 pmol of each primer (forward primer in exon 30: 5'-CTG CCA GGC AGG GGA GGA AGA GTG-3' (SEQ ID NO: 4); reverse primer spanning the junction of exon 30 and intron 30: 5'-GAA AGT GAC TCA CTT GTG GAG GA-3' (SEQ ID NO: 5); forward primer in intron 12: 5'-AAA GGG GCT TGG TAA GGG TA-3' (SEQ ID NO: 6); reverse in intron 13: 5'-CAT GCA CAT GCA CAC ACA TA-3' (SEQ ID NO: 7)). Following an initial denaturation of 3 minutes at 95° C., 35 cycles consisting of 95° C. 10 seconds, 58° C. 30 seconds, 72° C. 30 seconds were performed, with a final extension of 10 minutes at 72° C. For detection of the T4503C mutation, 15 µL of exon 30 PCR product was incubated with 4 U HgaI in a total volume of 25 µL, for 2 hours at 37° C., and the resulting fragments were separated on a 1.5% agarose gel. The presence of the T4503C mutation creates a restriction site for HgaI, and thus the 194 bp PCR product will be cut into fragments of 134 and 60 bp in the presence of the T4503C variant, but not in its absence. For detection of the A1864G mutation, 15 µL of exon 13 PCR products were digested with 8 U AciI for three hours at 37° C. Products were separated on 2% agarose gels. The presence of the A1864G mutation creates a second AciI site within the PCR product. Thus, the 360 bp PCR product is cleaved into fragments of 215 bp and 145 bp on the wild-type allele, but 185 bp, 145 bp and 30 bp on the mutant allele.

Detection of Mutation in FHA

Genotyping for the 693 variant was performed by PCR amplification of exon 14 followed by restriction enzyme digestion with EarI. PCR was carried out in a total volume of 80 µL with 1.5 mM MgCl$_2$, 187.5 nM of each dNTP, 2.5 U Taq polymerase and 20 pmol of each primer (forward primer in exon 14: 5'-CTT TCT GCG GGT GAT GAG CCG GTC AAT-3' (SEQ ID NO: 8); reverse primer in intron 14: 5'-CCT TAG CCC GTG TTG AGC TA-3' (SEQ ID NO: 9)). Following an initial denaturation of 3 minutes at 95° C., 35 cycles consisting of 95° C. 10 seconds, 55° C. 30 seconds, 72° C. 30 seconds were performed, with a final extension of 10 minutes at 72° C. Twenty microliters of PCR product was incubated with 4 U EarI in a total volume of 25 µL, for two hours at 37° C., and the fragments were separated on a 2% agarose gel. The presence of the 693 mutation destroys a restriction site for EarI, and thus the 297 bp PCR product will be cut into fragments of 151 bp, 59 bp, 48 bp and 39 bp in the presence of a wild-type allele, but only fragments of 210 bp, 48 bp and 39 bp in the presence of the deletion.

A 6 bp deletion encompassing nucleotides 5752-5757 (inclusive), was detected in exon 41 in the proband of family FHA-3 by genomic sequencing using primers located within the introns flanking this exon. Genotyping of this mutation in family FHA-3 and controls was carried out by PCR with forward (5'-CCT GTA AAT GCA AAG CTA TCT CCT CT-3' (SEQ ID NO: 10)) and reverse primers (5'-CGT CAA CTC CTT GAT TTC TAA GAT GT (SEQ ID NO: 11)) located near the 5' and 3' ends of exon 41, respectively. Each PCR was carried out as for the genotyping of the 693 variant, but with annealing temperature of 58° C. Twenty microliters of PCR product was resolved on 3% agarose or 10% acrylamide gels. The wild type allele was detected as a 117 bp band and the mutant allele as a 111 bp band upon staining with ethidium bromide.

A C to T transition was detected at nucleotide 6504 in genomic DNA of the proband of family FHA-2. It was detectable as a double C and T peak in the genomic sequence of exon 48 of this individual, who is heterozygous for the alteration. This mutation, which creates a STOP codon that results in truncation of the last 118 amino acids of the ABC1 protein, also destroys an RsaI restriction site that is present in the wild type sequence. Genotyping of this mutation in family FHA-2 and controls was carried out by PCR with forward (5'-GGG TTC CCA GGG TTC AGT AT-3') (SEQ ID NO: 12)) and reverse (5'-GAT CAG GAA TTC AAG CAC CAA-3') (SEQ ID NO: 13)) primers directed to the intronic sequences flanking exon 48. PCR was done as for the 693 variant. Fifteen microliters of PCR product was digested with 5 Units of RsaI at 37° C. for two hours and the digestion products resolved on 1.5% agarose gels. The mutant allele is detected as an uncut 436 bp band. The normal sequence is cut by RsaI to produce 332 and 104 bp bands.

Cell Culture

Skin fibroblast cultures were established from 3.0 mm punch biopsies of the forearm of FHD patients and healthy control subjects as described (Marcil et al., Arterioscler. Thromb. Vasc. Biol. 19:159-169, 1999).

Cellular Cholesterol Labeling and Loading

The protocol for cellular cholesterol efflux experiments was described in detail elsewhere (Marcil et al., Arterioscler. Thromb. Vasc. Biol. 19:159-169, 1999). The cells were $^3$H-cholesterol labeled during growth and free cholesterol loaded in growth arrest.

Cholesterol Efflux Studies

Efflux studies were carried out from 0 to 24 hours in the presence of purified ApoAI (10 µg protein/mL medium). Efflux was determined as a percent of free cholesterol in the medium after the cells were incubated for specified periods of time. All experiments were performed in triplicate, in the presence of cells from one control subject and the cells from the study subjects to be examined. All results showing an efflux defect were confirmed at least three times.

Oligonucleotide Synthesis

Eight phosphorothioate deoxyoligonucleotides complementary to various regions of the human ABC1 cDNA sequence were obtained from GIBCO BRL. The oligonucleotides were purified by HPLC. The sequences of the antisense oligonucleotides and their location are listed. One skilled in the art will recognize that other ABC1 antisense sequences can also be produced and tested for their ability to decrease ABC1-mediated cholesterol regulation.

| Name | Sequence (5'-3') | | mRNA target | % control |
|---|---|---|---|---|
| AN-1 | GCAGAGGGCATGGCTTTATTTG | (SEQ ID NO: 3) | AUG codon | 46 |
| AN-2 | GTGTTCCTGCAGAGGGCATG | (SEQ ID NO: 30) | AUG codon | 50 |
| AN-3 | CACTTCCAGTAACAGCTGAC | (SEQ ID NO: 31) | 5'-Untranslated | 79 |
| AN-4 | CTTTGCGCATGTCCTTCATGC | (SEQ ID NO: 32) | Coding | 80 |
| AN-5 | GACATCAGCCCTCAGCATCTT | (SEQ ID NO: 33) | Coding | 120 |
| AN-6: | CAACAAGCCATGTTCCCTC | (SEQ ID NO: 34) | Coding | |
| AN-7: | CATGTTCCCTCAGCCAGC | (SEQ ID NO: 35) | Coding | |
| AN-8: | CAGAGCTCACAGCAGGGA C | (SEQ ID NO: 36) | Coding | |

Cell Transfection with Antisense Oligonucleotides

Cells were grown in 35 mm culture dishes until 80% confluent, then washed once with DMEM medium (serum and antibiotics free). One milliliter of DMEM (serum and antibiotics free) containing 500 nM antisense oligonucleotides and 5 µg/ml or 7.5 µg/ml of lipofectin (GIBCO BRL) were added to each well according to the manufacturer's protocol. The cells were incubated at 37° C. for 4 hours, and then the medium was replaced by DMEM containing 10% FCS. Twenty-four hours after the transfection, the total cell RNA was isolated. Ten micrograms of total RNA was resolved on a 1% of agarose-formaldehyde gel and transferred to nylon membrane. The blot was hybridized with $\gamma$-$^{32}$P dCTP labeled human ABC1 cDNA overnight at 68° C. The membrane was subsequently exposed to x-ray film. The hybridizing bands were scanned by optical densitometry and standard to 28S ribosome RNA.

Cholesterol Efflux with Anti-ABC1 Oligonucleotides

Human skin fibroblasts were plated in 6-well plates. The cells were labeled with $^3$H-cholesterol (0.2 µCi/ml) in DMEM with 10% FBS for two days when the cell reached 50% confluence. The cells were then transfected with the antisense ABC1 oligonucleotides at 500 nM in DMEM (serum and antibiotic free) with 7.5 µg/ml Lipofectin (GIBCO BRL) according to the manufacturer's protocol. Following the transfection, and the cells were loaded with nonlipoprotein (20 µg/ml) for 12 hours in DMEM containing 2 mg/ml BSA without serum. The cellular cholesterol pools were then allowed to equilibrate for 6 hours in DMEM-BSA. The cholesterol efflux mediated by ApoAI (10 µg/ml, in DMEM-BSA) were then carried out which is 48 hours after transfection.

Radiolabeled cholesterol released into the medium is expressed as a percentage of total $^3$H-cholesterol per well (medium+cell). Results are the mean+/−SD of triplicate dishes.

Determination of Genomic Structure of the ABC1 Gene

Most splice junction sequences were determined from genomic sequence generated from BAC clones spanning the ABC1 gene. More than 160 kb of genomic sequence were generated. Genomic sequences were aligned with cDNA sequences to identify intron/exon boundaries. In some cases, long distance PCR between adjacent exons was used to amplify intron/exon boundary sequences using amplification primers designed according to the cDNA sequence.

Functionality of the Newly-Discovered 60 Amino Acids at the N-Terminus

Antisense Experiments

Phosphorothioate antisense oligonucleotides were designed to be complementary to the regions of the cDNA near newly discovered translation start site. AN-6 and AN-7 both overlap the initiator methionine codon; this site is in the middle of oligonucleotide AN-6. AN-8 is complementary to the very 5' end of the ABC1 cDNA. Antisense oligonucleotide AN-1 is complementary to the region of the ABC1 cDNA corresponding to the site identified as the ABC1 initiator methionine in AJ012376. FIG. 7C shows that antisense oligonucleotide AN-6 interferes with cellular cholesterol efflux in normal fibroblasts to the same extent as does antisense oligonucleotide AN-1. Transfection with either of these antisense oligonucleotides results in a decrease in cellular cholesterol efflux almost as severe as that seen in FHA cells. In general, antisense oligonucleotides complementary to coding sequences, especially near the 5'end of a gene's coding sequence, are expected to be more effective in decreasing the effective amount of transcript than are oligonucleotides directed to more 3' sequences or to non-coding sequences. The observation that AN-6 depresses cellular cholesterol efflux as effectively as AN-1 implies that both of these oligonucleotides are complementary to ABC1 coding sequences, and that the amino terminal 60 amino acids are likely to be contained in ABC1 protein. In contrast, the ineffectiveness of AN-8 shows that it is likely to be outside the protein coding region of the transcript, as predicted by presence of an in-frame stop codon between the initiator methionine and the region targeted by AN-8.

Antibody Experiments

Polyclonal and monoclonal antibodies have been generated using peptides corresponding to discrete portions of the ABC1 amino acid sequence. One of these, 20-amino acid peptide #2 (Pep2: CSVRLSYPPYEQHECHFPNKA (SEQ ID NO: 37), in which the N-terminal cysteine was added to facilitate conjugation of the peptide) corresponds to a protein sequence within the 60 amino-terminal amino acids of the newly-discovered ABC1 protein sequence. The peptide was coupled to the KLH carrier protein and 300 µg injected at three intervals into two Balb/c mice over a four week period. The spleen was harvested from the mouse with the highest ELISA-determined immune response to free peptide, and the cells fused to NS-1 myeloma cells by standard monoclonal antibody generation methods. Positive hybridomas were selected first by ELISA and then further characterized by western blotting using cultured primary human fibroblasts.

Monoclonal cell lines producing a high antibody titre and specifically recognizing the 245 kD human ABC1 protein were saved. The same size ABC1 protein product was detected by antibodies directed to four other discrete regions of the same protein. The 245 kD band could be eliminated in competition experiments with appropriate free peptide, indicating that it represents ABC1 protein (FIG. 13).

The foregoing experiments indicate that ABC1 protein is detected not only by antibodies corresponding to amino acid sequences within the previously-described ABC1 amino acid sequence, but also by the Pep2 monoclonal antibody that recognizes an epitope within the newly-discovered N-terminal 60 amino acids. The N-terminal 60 amino acid region is therefore coding, and is part of the ABC1 protein.

The epitope recognized by the Pep2 monoclonal antibody is also conserved among human, mouse, and chicken. Liver tissues from these three species employed in a Western blot produced an ABC1 band of 245 kD when probed with the Pep2 monoclonal antibody. This indicates that the 60 amino acid N-terminal sequence is part of the ABC1 coding sequence in humans, mice, and chickens. Presence of this region is therefore evolutionarily conserved and likely to be of important functional significance for the ABC1 protein.

Bioinformatic Analyses of ABC1 Protein Sequences

Transmembrane prediction programs indicate 13 transmembrane (TM) regions, the first one being between amino acids 26 and 42 (psort.nibb.ac.jp:8800/psort/helpwww2.ealom). The tentative number of TM regions for the threshold 0.5 is 13. (INTEGRAL Likelihood=−7.75 Transmembrane 26-42). The other 12 TM range in value between −0.64 and −12 (full results below). It is therefore very likely that the newly-discovered 60 amino acids contain a TM domain, and that the amino end of ABC1 may be on the opposite side of the membrane than originally thought.

ALOM: TM region allocation
Init position for calculation: 1
Tentative number of TMs for the threshold 0.5: 13

INTEGRAL Likelihood = −7.75 Transmembrane 26-42
INTEGRAL Likelihood = −3.98 Transmembrane 640-656
INTEGRAL Likelihood = −8.70 Transmembrane 690-706
INTEGRAL Likelihood = −9.61 Transmembrane 717-733
INTEGRAL Likelihood = −1.44 Transmembrane 749-765
INTEGRAL Likelihood = −0.64 Transmembrane 771-787
INTEGRAL Likelihood = −1.28 Transmembrane 1041-1057
INTEGRAL Likelihood = −12.79 Transmembrane 1351-1367
INTEGRAL Likelihood = −8.60 Transmembrane 1661-1677
INTEGRAL Likelihood = −6.79 Transmembrane 1708-1724
INTEGRAL Likelihood = −3.40 Transmembrane 1737-1753
INTEGRAL Likelihood = −1.49 Transmembrane 1775-1791
INTEGRAL Likelihood = −8.39 Transmembrane 1854-1870
PERIPHERAL Likelihood = 0.69 (at 1643)

ALOM score: −12.79 (number of TMSs: 13)

There does not appear to be an obvious cleaved peptide, so this first 60 amino acid residues are not likely to be cleaved, and are therefore not specifically a signal/targeting sequence. No other signals (e.g., for targeting to specific organelles) are apparent.

Agonists and Antagonists

Useful therapeutic compounds include those which modulate the expression, activity, or stability of ABC1. To isolate such compounds, ABC1 expression, biological activity, or regulated catabolism is measured following the addition of candidate compounds to a culture medium of ABC1-expressing cells. Alternatively, the candidate compounds may be directly administered to animals (for example mice, pigs, or chickens) and used to screen for their effects on ABC1 expression.

In addition its role in the regulation of cholesterol, ABC1 also participates in other biological processes for which the development of ABC1 modulators would be useful. In one example, ABC1 transports interleukin-1β (IL-1β) across the cell membrane and out of cells. IL-1β is a precursor of the inflammatory response and, as such, inhibitors or antagonists of ABC1 expression or biological activity may be useful in the treatment of any inflammatory disorders, including but not limited to rheumatoid arthritis, systemic lupus erythematosis (SLE), hypo- or hyper-thyroidism, inflammatory bowel disease, and diabetes mellitus. In another example, ABC1 expressed in macrophages has been shown to be engaged in the engulfment and clearance of dead cells. The ability of macrophages to ingest these apoptotic bodies is impaired after antibody-mediated blockade of ABC1. Accordingly, compounds that modulate ABC1 expression, stability, or biological activity would be useful for the treatment of these disorders.

ABC1 expression is measured, for example, by standard Northern blot analysis using an ABC1 nucleic acid sequence (or fragment thereof as a hybridization probe, or by Western blot using an anti-ABC1 antibody and standard techniques. The level of ABC1 expression in the presence of the candidate molecule is compared to the level measured for the same cells, in the same culture medium, or in a parallel set of test animals, but in the absence of the candidate molecule. ABC1 activity can also be measured using the cholesterol efflux assay.

Transcriptional Regulation of ABC1 Expression

ABC1 mRNA is increased approximately 8-fold upon cholesterol loading. This increase is likely controlled at the transcriptional level. Using the promoter sequence described herein, one can identify transcription factors that bind to the promoter by performing, for example, gel shift assays, DNAse protection assays, or in vitro or in vivo reporter gene-based assays. The identified transcription factors are themselves drug targets. In the case of ABC1, drug compounds that act through modulation of transcription of ABC1 could be used for HDL modulation, atherosclerosis prevention, and the treatment of cardiovascular disease. For example, using a compound to inhibit a transcription factor that represses ABC1 would be expected to result in up-regulation of ABC1 and, therefore, HDL levels. In another example, a compound that increases transcription factor expression or activity would also increase ABC1 expression and HDL levels.

Transcription factors known to regulate other genes in the regulation of apolipoprotein genes or other cholesterol- or lipid-regulating genes are of particular relevance. Such factors include, but are not limited to, the steroid response element binding proteins (SREBP-1 and SREBP-2), the PPAR (peroxisomal proliferation-activated receptor) transcription factors. Several consensus sites for certain elements are present in the sequenced region 5' to the ABC1 gene (FIG. 16) and are likely to modulate ABC1 expression. For example, PPARs may alter transcription of ABC1 by mechanisms including heterodimerization with retinoid X receptors (RXRs) and then binding to specific proliferator response elements (PPREs). Examples of such PPARs include PPARα, β, γ and δ. These distinct PPARs have been shown to have transcriptional regulatory effects on different genes. PPARα is expressed mainly in liver, whereas PPARγ is expressed in predominantly in adipocytes. Both PPARα and PPARγ are found in coronary and carotid artery atherosclerotic plaques and in endothelial cells, smooth muscle cells, monocytes and monocyte-derived macrophages. Activation of PPARα results in altered lipoprotein metabolism through PPARα's effect on genes such as lipoprotein lipase (LPL), apolipoprotein CIII (apo CIII) and apolipoprotein AI (apo AI) and AII (apo AII). PPARα activation results in overexpression of LPL and apoA-I and apoA-II, but inhibits the expression of apo CIII. PPARα activation also inhibits inflammation, stimulates lipid oxidation and increases the hepatic uptake and esterification of free fatty acids (FFA's). PPARα and PPARγ activation may inhibit nitric oxide (NO) synthase in macrophages and prevent interleukin-1 (IL-1) induced expression of IL-6 and cyclo-oxygenase-2 (COX-2) and thrombin induced endothelin-1 expression secondary to negative transcriptional regulation of NF-KB and activation of protein-1 signaling pathway. It has also been shown that PPARα induces apoptosis in monocyte-derived macrophages through the inhibition of NF-KB activity.

Activation of PPARα can be achieved by compounds such as fibrates, β-estradiol, arachidonic acid derivatives, WY-14, 643 and LTB4 or 8(s)HETE. PPARγ activation can be achieved through compounds such as thiozolidinedione antidiabetic drugs, 9-HODE and 13-HODE. Additional compounds such as nicotinic acid or HMG CoA reductase inhibitors may also alter the activity of PPARs.

Compounds which alter activity of any of the PPARs (e.g., PPARα or PPARγ) may have an effect on ABC1 expression and thereby could affect HDL levels, atherosclerosis and risk of CAD. PPARs are also regulated by fatty acids (including modified fatty acids such as 3 thia fatty acids), leukotrienes such as leukotriene B4 and prostaglandin J2, which is a natural activator/ligand for PPARγ. Drugs that modulate PPARs may therefore have an important effect on modulating lipid levels (including HDL and triglyceride levels) and altering CAD risk. This effect could be achieved through the modulation of ABC1 gene expression. Drugs may also effect ABC1 gene expression and thereby HDL levels, by an indirect effect on PPARs via other transcriptional factors such as adipocyte differentiation and determination factor-1 (ADD-1) and sterol regulatory element binding protein-1 and 2 (SREBP-1 and 2). Drugs with combined PPARα and PPARγ agonist activity or PPARα and PPARγ agonists given in combination for example, may increase HDL levels even more.

A PPAR binding site (PPRE element) is found 5' to the ABC1 gene (nucleotides 2150 to 2169 of SEQ ID NO: 14). Like the PPRE elements found in the C-ACS, HD, CYP4A6 and ApoA-I genes, this PPRE site is a trimer related to the PPRE consensus sequence. Partly because of its similarity in the number and arrangement of repeats in this PPAR binding site, this element in particular is very likely to be of physiological relevance to the regulation of the ABC1 gene.

Additional transcription factors which may also have an effect in modulating ABC1 gene expression and thereby HDL levels, atherosclerosis and CAD risk include; REV-ERBα, SREBP-1 & 2, ADD-1, EBPα, CREB binding protein, P300, HNF 4, RAR, LXR, and RORα. Additional degenerate binding sites for these factors can be found through examination of the sequence in SEQ ID NO: 14.

Additional Utility of ABC1 Polypeptides, Nucleic Acids, and Modulators

ABC1 may act as a transporter of toxic proteins or protein fragments (e.g., APP) out of cells. Thus, ABC1 agonists/upregulators may be useful in the treatment of other disease areas, including Alzheimer's disease, Niemann-Pick disease, and Huntington's disease.

ABC transporters have been shown to increase the uptake of long chain fatty acids from the cytosol to peroxisomes and, moreover, to play a role in β-oxidation of very long chain fatty acids. Importantly, in x-linked adrenoleukodystrophy (ALD), fatty acid metabolism is abnormal, due to defects in the peroxisomal ABC transporter. Any agent that upregulates ABC transporter expression or biological activity may therefor be useful for the treatment of ALD or any other lipid disorder.

ABC1 is expressed in macrophages and is required for engulfment of cells undergoing programmed cell death. The apoptotic process itself, and its regulation, have important implications for disorders such as cancer, one mechanism of which is failure of cells to undergo cell death appropriately. ABC1 may facilitate apoptosis, and as such may represent an intervention point for cancer treatment. Increasing ABC1 expression or activity or otherwise up-regulating ABC1 by any method may constitute a treatment for cancer by increasing apoptosis and thus potentially decreasing the aberrant cellular proliferation characterized by this disease. Conversely, down-regulation of ABC1 by any method may provide opportunity for decreasing apoptosis and allowing increased proliferation of cells in conditions where cell growth is limited. Such disorders include but are not limited to neurodeficiencies and neurodegeneration, and growth disorders. ABC1 could, therefore, potentially be used as a method for identification of compounds for use in the treatment of cancer, or in the treatment of degenerative disorders.

Agents that have been shown to inhibit ABC1 include, for example, the anti-diabetic agents glibenclamide and glyburide, flufenamic acid, diphenylamine-2-carbonic acid, sulfobromophthalein, and DIDS.

Agents that upregulate ABC1 expression or biological activity include but are not limited to protein kinase A, protein kinase C, vanadate, okadaic acid, and IBMX1.

Those in the art will recognize that other compounds can also modulate ABC1 biological activity, and these compounds are also in the spirit of the invention.

Drug Screens Based on the ABC1 Gene or Protein

The ABC1 protein and gene can be used in screening assays for identification of compounds which modulate its activity and may be potential drugs to regulate cholesterol levels. Useful ABC1 proteins include wild-type and mutant ABC1 proteins or protein fragments, in a recombinant form or endogenously expressed. Drug screens to identify compounds acting on the ABC1 expression product may employ any functional feature of the protein. In one example, the phosphorylation state or other post-translational modification is monitored as a measure of ABC1 biological activity. ABC1 has ATP binding sites, and thus assays may wholly or in part test the ability of ABC1 to bind ATP or to exhibit ATPase activity. ABC1, by analogy to similar proteins, is thought to be able to form a channel-like structure; drug screening assays could be based upon assaying for the ability of the protein to form a channel, or upon the ability to transport cholesterol or another molecule, or based upon the ability of other proteins bound by or regulated by ABC1 to form a channel. Alternatively, phospholipid or lipid transport can also be used as measures of ABC1 biological activity.

There is evidence that, in addition to its role as a regulator of cholesterol levels, ABC1 also transports anions. Functional assays could be based upon this property, and could employ drug screening technology such as (but not limited to) the ability of various dyes to change color in response to changes in specific ion concentrations in such assays can be performed in vesicles such as liposomes, or adapted to use whole cells.

Drug screening assays can also be based upon the ability of ABC1 or other ABC transporters to interact with other proteins. Such interacting proteins can be identified by a variety of methods known in the art, including, for example, radioimmunoprecipitation, co-immunoprecipitation, co-purification, and yeast two-hybrid screening. Such interactions can be further assayed by means including but not limited to fluorescence polarization or scintillation proximity methods. Drug screens can also be based upon functions of the ABC1 protein deduced upon X-ray crystallography of the protein and comparison of its 3-D structure to that of proteins with known functions. Such a crystal structure has been determined for the prokaryotic ABC family member H is P, histidine permease. Drug screens can be based upon a function or feature apparent upon creation of a transgenic or knockout mouse, or upon overexpression of the protein or protein fragment in mammalian cells in vitro. Moreover, expression of mammalian (e.g., human) ABC1 in yeast or C. elegans allows for screening of candidate compounds in wild-type and mutant backgrounds, as well as screens for mutations that enhance or suppress an ABC1-dependent phenotype. Modifier screens can also be performed in ABC1 transgenic or knock-out mice.

Additionally, drug screening assays can also be based upon ABC1 functions deduced upon antisense interference with the gene function. Intracellular localization of ABC1, or effects which occur upon a change in intracellular localization of the protein, can also be used as an assay for drug screening. Immunocytochemical methods will be used to determine the exact location of the ABC1 protein.

Human and rodent ABC1 protein can be used as an antigen to raise antibodies, including monoclonal antibodies. Such antibodies will be useful for a wide variety of purposes, including but not limited to functional studies and the development of drug screening assays and diagnostics. Monitoring the influence of agents (e.g., drugs, compounds) on the expression or biological activity of ABC1 can be applied not only in basic drug screening, but also in clinical trials. For example, the effectiveness of an agent determined by a screening assay as described herein to increase ABC1 gene expression, protein levels, or biological activity can be monitored in clinical trails of subjects exhibiting altered ABC1 gene expression, protein levels, or biological activity. Alternatively, the effectiveness of an agent determined by a screening assay to modulate ABC1 gene expression, protein levels, or biological activity can be monitored in clinical trails of subjects exhibiting decreased altered gene expression, protein levels, or biological activity. In such clinical trials, the expression or activity of ABC1 and, preferably, other genes that have been implicated in, for example, cardiovascular disease can be used to ascertain the effectiveness of a particular drug.

For example, and not by way of limitation, genes, including ABC1, that are modulated in cells by treatment with an agent (e.g., compound, drug or small molecule) that modulates ABC1 biological activity (e.g., identified in a screening assay as described herein) can be identified. Thus, to study the effect of agents on cholesterol levels or cardiovascular disease, for example, in a clinical trial, cells can be isolated and RNA prepared and analyzed for the levels of expression of ABC1 and other genes implicated in the disorder. The levels of gene expression can be quantified by Northern blot analysis or RT-PCR, or, alternatively, by measuring the amount of protein produced, by one of a number of methods known in the art, or by measuring the levels of biological activity of ABC1 or other genes. In this way, the gene expression can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an ABC1 protein, mRNA, or genomic DNA in the preadministration sample; (iii) obtaining one or more post-administration samples from the subject; (iv) detecting the level of expression or activity of the ABC1 protein, mRNA, or genomic DNA in the post-administration samples; (v) comparing the level of expression or activity of the ABC1 protein, mRNA, or genomic DNA in the pre-administration sample with the ABC1 protein, mRNA, or genomic DNA in the post administration sample or samples; and (vi) altering the administration of the agent to the subject accordingly. For example, increased administration of the agent may be desirable to increase the expression or activity of ABC1 to higher levels than detected, i.e., to increase the effectiveness of the agent. Alternatively, decreased administration of the agent may be desirable to decrease expression or activity of ABC1 to lower levels than detected.

The ABC1 gene or a fragment thereof can be used as a tool to express the protein in an appropriate cell in vitro or in vivo (gene therapy), or can be cloned into expression vectors which can be used to produce large enough amounts of ABC1 protein to use in in vitro assays for drug screening. Expression systems which may be employed include baculovirus, herpes virus, adenovirus, adeno-associated virus, bacterial systems, and eucaryotic systems such as CHO cells. Naked DNA and DNA-liposome complexes can also be used.

Assays of ABC1 activity includes binding to intracellular interacting proteins; interaction with a protein that up-regulates ABC1 activity; interaction with HDL particles or constituents; interaction with other proteins which facilitate interaction with HDL or its constituents; and measurement of cholesterol efflux. Furthermore, assays may be based upon the molecular dynamics of macromolecules, metabolites and ions by means of fluorescent-protein biosensors. Alternatively, the effect of candidate modulators on expression or activity may be measured at the level of ABC1 protein production using the same general approach in combination with standard immunological detection techniques, such as Western blotting or immunoprecipitation with an ABC1-specific antibody. Again, useful cholesterol-regulating or anti-CVD therapeutic modulators are identified as those which produce an change in ABC1 polypeptide production. Agonists may also affect ABC1 activity without any effect on expression level.

Candidate modulators may be purified (or substantially purified) molecules or may be one component of a mixture of compounds (e.g., an extract or supernatant obtained from cells). In a mixed compound assay, ABC1 expression is tested against progressively smaller subsets of the candidate compound pool (e.g., produced by standard purification techniques, e.g., HPLC or FPLC; Ausubel et al.) until a single compound or minimal compound mixture is demonstrated to modulate ABC1 expression.

Agonists, antagonists, or mimetics found to be effective at modulating the level of cellular ABC1 expression or activity may be confirmed as useful in animal models (for example, mice, pigs, rabbits, or chickens). For example, the compound may ameliorate the low HDL levels of mouse or chicken hypoalphalipoproteinemias.

A compound that promotes an increase in ABC1 expression or activity is considered particularly useful in the invention; such a molecule may be used, for example, as a therapeutic to increase the level or activity of native, cellular ABC1 and thereby treat a low HDL condition in an animal (for example, a human).

One method for increasing ABC biological activity is to increase the stabilization of the ABC protein or to prevent its degradation. Thus, it would be useful to identify mutations in an ABC polypeptide (e.g., ABC1) that lead to increased protein stability. These mutations can be incorporated into any protein therapy or gene therapy undertaken for the treatment of low HDL-C or any other condition resulting from loss of ABC1 biological activity. Similarly, compounds that increase the stability of a wild-type ABC polypeptide or decrease its catabolism may also be useful for the treatment of low HDL-C or any other condition resulting from loss of ABC1 biological activity. Such mutations and compounds can be identified using the methods described herein.

In one example, cells expressing an ABC polypeptide having a mutation are transiently metabolically labeled during translation and the half-life of the ABC polypeptide is determined using standard techniques. Mutations that increase the half-life of an ABC polypeptide are ones that increase ABC protein stability. These mutations can then be assessed for ABC biological activity. They can also be used to identify proteins that affect the stability of ABC1 mRNA or protein. One can then assay for compounds that act on these factors or on the ability of these factors to bind ABC1.

In another example, cells expressing wild-type ABC polypeptide are transiently metabolically labeled during translation, contacted with a candidate compounds, and the half-life of the ABC polypeptide is determined using standard techniques. Compounds that increase the half-life of an ABC polypeptide are useful compounds in the present invention.

If desired, treatment with an agonist of the invention may be combined with any other HDL-raising or anti-CVD therapies.

It is understood that, while ABC1 is the preferred ABC transporter for the drug screens described herein, other ABC transporters can also be used. The replacement of ABC1 with another ABC transporter is possible because it is likely that ABC transporter family members, such as ABC2, ABCR, or ABC8 will have a similar mechanism of regulation.

Exemplary assays are described in greater detail below.

Protein-Based Assays

ABC1 polypeptide (purified or unpurified) can be used in an assay to determine its ability to bind another protein (including, but not limited to, proteins found to specifically interact with ABC1). The effect of a compound on that binding is then determined.

Protein Interaction Assays

ABC1 protein (or a polypeptide fragment thereof or an epitope-tagged form or fragment thereof) is harvested from a suitable source (e.g., from a prokaryotic expression system, eukaryotic cells, a cell-free system, or by immunoprecipitation from ABC1-expressing cells). The ABC1 polypeptide is then bound to a suitable support (e.g., nitrocellulose or an antibody or a metal agarose column in the case of, for example, a his-tagged form of ABC1). Binding to the support is preferably done under conditions that allow proteins associated with ABC1 polypeptide to remain associated with it. Such conditions may include use of buffers that minimize interference with protein-protein interactions. The binding step can be done in the presence and absence of compounds being tested for their ability to interfere with interactions between ABC1 and other molecules. If desired, other proteins (e.g., a cell lysate) are added, and allowed time to associate with the ABC polypeptide. The immobilized ABC1 polypeptide is then washed to remove proteins or other cell constituents that may be non-specifically associated with it and the polypeptide or the support. The immobilized ABC1 polypeptide is then dissociated from its support, and so that proteins bound to it are released (for example, by heating), or, alternatively, associated proteins are released from ABC1 without releasing the ABC1 polypeptide from the support. The released proteins and other cell constituents can be analyzed, for example, by SDS-PAGE gel electrophoresis, Western blotting and detection with specific antibodies, phospho-amino acid analysis, protease digestion, protein sequencing, or isoelectric focusing. Normal and mutant forms of ABC1 can be employed in these assays to gain additional information about which part of ABC1 a given factor is binding to. In addition, when incompletely purified polypeptide is employed, comparison of the normal and mutant forms of the protein can be used to help distinguish true binding proteins.

The foregoing assay can be performed using a purified or semipurified protein or other molecule that is known to interact with ABC1. This assay may include the following steps.

1. Harvest ABC1 protein and couple a suitable fluorescent label to it;

2. Label an interacting protein (or other molecule) with a second, different fluorescent label. Use dyes that will produce different quenching patterns when they are in close proximity to each other vs. when they are physically separate (i.e., dyes that quench each other when they are close together but fluoresce when they are not in close proximity);

3. Expose the interacting molecule to the immobilized ABC1 in the presence or absence of a compound being tested for its ability to interfere with an interaction between the two; and 4. Collect fluorescent readout data.

Another assay is includes Fluorescent Resonance Energy Transfer (FRET) assay. This assay can be performed as follows.

1. Provide ABC1 protein or a suitable polypeptide fragment thereof and couple a suitable FRET donor (e.g., nitrobenzoxadiazole (NBD)) to it;

2. Label an interacting protein (or other molecule) with a FRET acceptor (e.g., rhodamine);

3. Expose the acceptor-labeled interacting molecule to the donor-labeled ABC1 in the presence or absence of a compound being tested for its ability to interfere with an interaction between the two; and 4. Measure fluorescence resonance energy transfer.

Quenching and FRET assays are related. Either one can be applied in a given case, depending on which pair of fluorophores is used in the assay.

Membrane Permeability Assay

The ABC1 protein can also be tested for its effects on membrane permeability. For example, beyond its putative ability to translocate lipids, ABC1 might affect the permeability of membranes to ions. Other related membrane proteins, most notably the cystic fibrosis transmembrane conductance regulator and the sulfonylurea receptor, are associated with and regulate ion channels.

ABC1 or a fragment of ABC1 is incorporated into a synthetic vesicle, or, alternatively, is expressed in a cell and vesicles or other cell sub-structures containing ABC1 are isolated. The ABC1-containing vesicles or cells are loaded with a reporter molecule (such as a fluorescent ion indicator whose fluorescent properties change when it binds a particular ion) that can detect ions (to observe outward movement), or alternatively, the external medium is loaded with such a molecule (to observe inward movement). A molecule which exhibits differential properties when it is inside the vesicle compared to when it is outside the vesicle is preferred. For example, a molecule that has quenching properties when it is at high concentration but not when it is at another low concentration would be suitable. The movement of the charged molecule (either its ability to move or the kinetics of its movement) in the presence or absence of a compound being tested for its ability to affect this process can be determined.

In another assay, membrane permeability is determined electrophysiologically by measuring ionic influx or efflux mediated by or modulated by ABC1 by standard electrophysiological techniques. A suitable control (e.g., TD cells or a cell line with very low endogenous ABC1 expression) can be used as a control in the assay to determine if the effect observed is specific to cells expressing ABC1.

In still another assay, uptake of radioactive isotopes into or out of a vesicle can be measured. The vesicles are separated from the extravesicular medium and the radioactivity in the vesicles and in the medium is quantitated and compared.

Nucleic Acid-Based Assays

ABC1 nucleic acid may be used in an assay based on the binding of factors necessary for ABC1 gene transcription. The association between the ABC1 DNA and the binding factor may be assessed by means of any system that discriminates between protein-bound and non-protein-bound DNA (e.g., a gel retardation assay). The effect of a compound on the binding of a factor to ABC1 DNA is assessed by means of such an assay. In addition to in vitro binding assays, in vivo assays in which the regulatory regions of the ABC1 gene are linked to reporter genes can also be performed.

Assays Measuring ABC1 Stability

A cell-based or cell-free system can be used to screen for compounds based on their effect on the half-life of ABC1 mRNA or ABC1 protein. The assay may employ labeled mRNA or protein. Alternatively, ABC1 mRNA may be detected by means of specifically hybridizing probes or a quantitative PCR assay. Protein can be quantitated, for example, by fluorescent antibody-based methods.

In Vitro mRNA Stability Assay

1. Isolate or produce, by in vitro transcription, a suitable quantity of ABC1 mRNA;
2. Label the ABC1 mRNA;
3. Expose aliquots of the mRNA to a cell lysate in the presence or absence of a compound being tested for its ability to modulate ABC1 mRNA stability;
4. Assess intactness of the remaining mRNA at suitable time points.

In Vitro Protein Stability Assay

1. Express a suitable amount of ABC1 protein;
2. Label the protein;
3. Expose aliquots of the labeled protein to a cell lysate in the presence or absence of a compound being tested for its ability to modulate ABC1 protein stability;
4. Assess intactness of the remaining protein at suitable time points In Vivo mRNA or Protein Stability Assay 1. Incubate cells expressing ABC1 mRNA or protein with a tracer (radiolabeled ribonucleotide or radiolabeled amino acid, respectively) for a very brief time period (e.g., five minutes) in the presence or absence of a compound being tested for its effect on mRNA or protein stability;
2. Incubate with unlabeled ribonucleotide or amino acid; and
3. Quantitate the ABC1 mRNA or protein radioactivity at time intervals beginning with the start of step 2 and extending to the time when the radioactivity in ABC1 mRNA or protein has declined by approximately 80%. It is preferable to separate the intact or mostly intact mRNA or protein from its radioactive breakdown products by a means such as gel electrophoresis in order to quantitate the mRNA or protein.

Assays Measuring Inhibition of Dominant Negative Activity

Mutant ABC1 polypeptides are likely to have dominant negative activity (i.e., activity that interferes with wild-type ABC1 function). An assay for a compound that can interfere with such a mutant may be based on any method of quantitating normal ABC1 activity in the presence of the mutant. For example, normal ABC1 facilitates cholesterol efflux, and a dominant negative mutant would interfere with this effect. The ability of a compound to counteract the effect of a dominant negative mutant may be based on cellular cholesterol efflux, or on any other normal activity of the wild-type ABC1 that was inhibitable by the mutant.

Assays Measuring Phosphorylation

The effect of a compound on ABC1 phosphorylation can be assayed by methods that quantitate phosphates on proteins or that assess the phosphorylation state of a specific residue of a ABC1. Such methods include but are not limited to $^{32}P$ labelling and immunoprecipitation, detection with antiphosphoamino acid antibodies (e.g., antiphosphoserine antibodies), phosphoamino acid analysis on 2-dimensional TLC plates, and protease digestion fingerprinting of proteins followed by detection of $^{32}P$-labeled fragments.

Assays Measuring Other Post-Translational Modifications

The effect of a compound on the post-translational modification of ABC1 is based on any method capable of quantitating that particular modification. For example, effects of compounds on glycosylation may be assayed by treating ABC1 with glycosylase and quantitating the amount and nature of carbohydrate released.

Assays Measuring ATP Binding

The ability of ABC1 to bind ATP provides another assay to screen for compounds that affect ABC1. ATP binding can be quantitated as follows.

1. Provide ABC1 protein at an appropriate level of purity and reconstitute it in a lipid vesicle;
2. Expose the vesicle to a labeled but non-hydrolyzable ATP analog (such as gamma $^{35}S$-ATP) in the presence or absence of compounds being tested for their effect on ATP binding. Note that azido-ATP analogs can be used to allow covalent attachment of the azido-ATP to protein (by means of U.V. light), and permit easier quantitation of the amount of ATP bound to the protein.
3. Quantitate the amount of ATP analog associated with ABC1

Assays Measuring ATPase Activity

Quantitation of the ATPase activity of ABC1 can also be assayed for the effect of compounds on ABC1. This is preferably performed in a cell-free assay so as to separate ABC1 from the many other ATPases in the cell. An ATPase assay may be performed in the presence or absence of membranes, and with or without integration of ABC1 protein into a membrane. If performed in a vesicle-based assay, the ATP hydrolysis products produced or the ATP hydrolyzed may be measured within or outside of the vesicles, or both. Such an assay may be based on disappearance of ATP or appearance of ATP hydrolysis products.

For high-throughput screening, a coupled ATPase assay is preferable. For example, a reaction mixture containing pyruvate kinase and lactate dehydrogenase can be used. The mixture includes phosphoenolpyruvate (PEP), nicotinamide adenine dinucleotide (NAD+), and ATP. The ATPase activity of ABC1 generates ADP from ATP. The ADP is then converted back to ATP as part of the pyruvate kinase reaction. The product, pyruvate, is then converted to lactate. The latter reaction generates a colored quinone (NADH) from a colorless substrate (NAD+), and the entire reaction can be monitored by detection of the color change upon formation of NADH. Since ADP is limiting for the pyruvate kinase reaction, this coupled system precisely monitors the ATPase activity of ABC1.

Assays Measuring Cholesterol Efflux

A transport-based assay can be performed in vivo or in vitro. For example, the assay may be based on any part of the reverse cholesterol transport process that is readily re-created in culture, such as cholesterol or phospholipid efflux. Alternatively, the assay may be based on net cholesterol transport in a whole organism, as assessed by means of a labeled substance (such as cholesterol).

For high throughput, fluorescent lipids can be used to measure ABC1-catalyzed lipid efflux. For phospholipids, a fluorescent precursor, C6-NBD-phosphatidic acid, can be used. This lipid is taken up by cells and dephosphorylated by phosphatidic acid phosphohydrolase. The product, NBD-diglyceride, is then a precursor for synthesis of glycerophospholipids like phosphatidylcholine. The efflux of NBD-phosphatidylcholine can be monitored by detecting fluorescence resonance energy transfer (FRET) of the NBD to a suitable acceptor in the cell culture medium. This acceptor can be rhodamine-labeled phosphatidylethanolamine, a phospholipid that is not readily taken up by cells. The use of short-chain precursors obviates the requirement for the phospholipid transfer protein in the media. For cholesterol, NBD-cholesterol ester can be reconstituted into LDL. The LDL can efficiently deliver this lipid to cells via the LDL receptor pathway. The NBD-cholesterol esters are hydrolyzed in the lysosomes, resulting in NBD-cholesterol that can now be transported back to the plasma membrane and efflux from the cell. The efflux can be monitored by the aforementioned FRET assay in which NBD transfers its fluorescence resonance energy to the rhodamine-phosphatidylethanoline acceptor.

Animal Model Systems

Compounds identified as having activity in any of the above-described assays are subsequently screened in any available animal model system, including, but not limited to, pigs, rabbits, and WHAM chickens. Test compounds are administered to these animals according to standard methods. Test compounds may also be tested in mice bearing mutations in the ABC1 gene. Additionally, compounds may be screened for their ability to enhance an interaction between ABC1 and any HDL particle constituent such as ApoAI, ApoAII, or ApoE.

The Cholesterol Efflux Assay as a Drug Screen

The cholesterol efflux assay measures the ability of cells to transfer cholesterol to an extracellular acceptor molecule and is dependent on ABC1 function. In this procedure, cells are loaded with radiolabeled cholesterol by any of several biochemical pathways (Marcil et al., Arterioscler. Thromb. Vasc. Biol. 19:159-169, 1999). Cholesterol efflux is then measured after incubation for various times (typically 0 to 24 hours) in the presence of HDL3 or purified ApoAI. Cholesterol efflux is determined as the percentage of total cholesterol in the culture medium after various times of incubation. ABC1 expression levels and/or biological activity are associated with increased efflux while decreased levels of ABC1 are associated with decreased cholesterol efflux.

This assay can be readily adapted to the format used for drug screening, which may consist of a multi-well (e.g., 96-well) format. Modification of the assay to optimize it for drug screening would include scaling down and streamlining the procedure, modifying the labeling method, using a different cholesterol acceptor, altering the incubation time, and changing the method of calculating cholesterol efflux. In all these cases, the cholesterol efflux assay remains conceptually the same, though experimental modifications may be made. A transgenic mouse overexpressing ABC1 would be expected to have higher than normal HDL levels.

Knock-Out Mouse Model

An animal, such as a mouse, that has had one or both ABC1 alleles inactivated (e.g., by homologous recombination) is likely to have low HDL-C levels, and thus is a preferred animal model for screening for compounds that raise HDL-C levels. Such an animal can be produced using standard techniques. In addition to the initial screening of test compounds, the animals having mutant ABC1 genes are useful for further testing of efficacy and safety of drugs or agents first identified using one of the other screening methods described herein. Cells taken from the animal and placed in culture can also be exposed to test compounds. HDL-C levels can be measured using standard techniques, such as those described herein.

WHAM Chickens: an Animal Model for Low HDL Cholesterol

Wisconsin Hypo-Alpha Mutant (WHAM) chickens arose by spontaneous mutation in a closed flock. Mutant chickens came to attention through their a Z-linked white shank and white beak phenotype referred to as 'recessive white skin' (McGibbon, 1981) and were subsequently found to have a profound deficiency of HDL (Poernama et al., 1990).

This chicken low HDL locus (Y) is Z-linked, or sex-linked. (In birds, females are ZW and males are ZZ). Genetic mapping placed the Y locus on the long arm of the Z chromosome (Bitgood, 1985), proximal to the ID locus (Bitgood, 1988). Examination of current public mapping data for the chicken genome mapping project, ChickMap (maintained by the Roslin Institute) showed that a region of synteny with human chromosome 9 lies on the long arm of the chicken Z chromosome (Zq) proximal to the ID locus. Evidence for this region of synteny is the location of the chicken aldolase B locus (ALDOB) within this region. The human ALDOB locus maps to chromosome 9q22.3 (The Genome Database), not far from the location of human ABC1. This comparison of maps showed that the chicken Zq region near chicken ALDOB and the human 9q region near human ALDOB represent a region of synteny between human and chicken.

Since a low HDL locus maps to the 9q location in humans and to the Zq region in chickens, these low HDL loci are most probably located within the syntenic region. Thus we predicted that ABC1 is mutated in WHAM chickens. In support of this, we have identified an E_K mutation at a position that corresponds to amino acid 89 of human ABC1 (FIGS. 14 and 15). This non-conservative substitution is at a position that is conserved among human, mouse, and chicken, indicating that it is in a region of the protein likely to be of functional importance.

Discovery of the WHAM mutation in the amino-terminal portion of the ABC1 protein also establishes the importance of the amino-terminal region. This region may be critical because of association with other proteins required to carry out cholesterol efflux or related tasks. It may be an important regulatory region (there is a phosphorylation site for casein kinase near the mutated residue), or it may help to dictate a precise topological relationship with cellular membranes (the N-terminal 60 amino acid region contains a putative membrane-spanning or membrane-associated segment).

The amino-terminal region of the protein (up to the first 6-TM region at approximately amino acid 639) is an ideal tool for screening factors that affect ABC1 activity. It can be expressed as a truncated protein in ABC1 wild type cells in order to test for interference of the normal ABC1 function by the truncated protein. If the fragment acts in a dominant negative way, it could be used in immunoprecipitations to identify proteins that it may be competing away from the normal endogenous protein.

The C-terminus also lends itself to such experiments, as do the intracellular portions of the molecule, expressed as fragments or tagged or fusion proteins, in the absence of transmembrane regions.

Since it is possible that there are several genes in the human genome which affect cholesterol efflux, it is important to establish that any animal model to be used for a human genetic disease represents the homologous locus in that animal, and not a different locus with a similar function. The evidence above establishes that the chicken Y locus and the human chromosome 9 low HDL locus are homologous. WHAM chickens are therefore an important animal model for the identification of drugs that modulate cholesterol efflux.

The WHAM chickens' HDL deficiency syndrome is not, however, associated with an increased susceptibility to atherosclerosis in chickens. This probably reflects the shorter lifespan of the chicken rather than an inherent difference in the function of the chicken ABC1 gene compared to the human gene. We propose the WHAM chicken as a model for human low HDL for the development and testing of drugs to raise HDL in humans. Such a model could be employed in several forms, through the use of cells or other derivatives of these chickens, or by the use of the chickens themselves in tests of drug effectiveness, toxicity, and other drug development purposes.

Therapy

Compounds of the invention, including but not limited to, ABC1 polypeptides, ABC1 nucleic acids, other ABC transporters, and any therapeutic agent that modulates biological activity or expression of ABC1 identified using any of the methods disclosed herein, may be administered with a pharmaceutically-acceptable diluent, carrier, or excipient, in unit dosage form. Conventional pharmaceutical practice may be employed to provide suitable formulations or compositions to administer such compositions to patients. Although intravenous administration is preferred, any appropriate route of administration may be employed, for example, perenteral, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspension; for oral administration, formulations may be in the form of tablets or capsules; and for intranasal formulations, in the form of powders, nasal drops, or aerosols.

Methods well known in the art for making formulations are found in, for example, *Remington: The Science and Practice of Pharmacy*, (19th ed.) ed. A. R. Gennaro A R., 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the invention include ethylenevinyl acetate copolymer particles, osmotic pumps, implantable infusion systems, and liposomes. Formulations for inhalation may contain excipients, or example, lactose, or may be aqueous solutions containing, for example, polyoxyethylene-9-lauryl ether, glycocholate and deoxycholate, or may be oily solutions for administration in the form of nasal drops, or as a gel.

Compounds

In general, novel drugs for the treatment of aberrant cholesterol levels and/or CVD are identified from large libraries of both natural product or synthetic (or semi-synthetic) extracts or chemical libraries according to methods known in the art. Those skilled in the field or drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof or the elimination of replicates or repeats of materials already known for their HDL-raising and anti-CVD activities should be employed whenever possible.

When a crude extract is found to have cholesterol-modulating or anti-CVD activities or both, further fractionation of the positive lead extract is necessary to isolate chemical constituent responsible for the observed effect. Thus, the goal of the extraction, fractionation, and purification process is the careful characterization and identification of a chemical entity within the crude extract having cholesterol-modulating or anti-CVD activities. The same in vivo and in vitro assays described herein for the detection of activities in mixtures of compounds can be used to purify the active component and to test derivatives thereof. Methods of fractionation and purification of such heterogeneous extracts are known in the art. If desired, compounds shown to be useful agents for the treatment of pathogenicity are chemically modified according to methods known in the art. Compounds identified as being of therapeutic value are subsequently analyzed using any standard animal model of diabetes or obesity known in the art.

It is understood that compounds that modulate activity of proteins that modulate or are modulated by ABC1 are useful compounds for modulating cholesterol levels. Exemplary compounds are provided herein; others are known in the art.

Compounds that are structurally related to cholesterol, or that mimic ApoAI or a related apolipoprotein, and increase ABC1 biological activity are particularly useful compounds in the invention. Other compounds, known to act on the MDR protein, can also be used or derivatized and assayed for their ability to increase ABC1 biological activity. Exemplary MDR modulators are PSC833, bromocriptine, and cyclosporin A.

Screening Patients Having Low HDL-C

ABC1 expression, biological activity, and mutational analysis can each serve as a diagnostic tool for low HDL; thus determination of the genetic subtyping of the ABC1 gene sequence can be used to subtype low HDL individuals or families to determine whether the low HDL phenotype is related to ABC1 function. This diagnostic process can lead to the tailoring of drug treatments according to patient genotype, including prediction of side effects upon administration of HDL increasing drugs (referred to herein as pharmacogenomics). Pharmacogenomics allows for the selection of agents (e.g., drugs) for therapeutic or prophylactic treatment of an individual based on the genotype of the individual (e.g., the genotype of the individual is examined to determine the ability of the individual to respond to a particular agent).

Agents, or modulators which have a stimulatory or inhibitory effect on ABC1 biological activity or gene expression can be administered to individuals to treat disorders (e.g., cardiovascular disease or low HDL cholesterol) associated with aberrant ABC1 activity. In conjunction with such treatment, the pharmacogenomics (i.e., the study of the relationship between an individual's genotype and that individual's response to a foreign compound or drug) of the individual may be considered. Differences in efficacy of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of ABC1 protein, expression of ABC1 nucleic acid, or mutation content of ABC1 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons (Eichelbaum, M., Clin. Exp. Pharmacol. Physiol., 23:983-985, 1996; Linder, M. W., Clin. Chem., 43:254-266, 1997). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). Altered drug action may occur in a patient having a polymorphism (e.g., an single nucleotide polymorphism or SNP) in promoter, intronic, or exonic sequences of ABC1. Thus by determining the presence and prevalence of polymorphisms allow for prediction of a patient's response to a particular therapeutic agent. In particular, polymorphisms in the promoter region may be critical in determining the risk of HDL deficiency and CVD.

In addition to the mutations in the ABC1 gene described herein, we have detected polymorphisms in the human ABC1 gene (FIG. 11). These polymorphisms are located in promoter, intronic, and exonic sequence of ABC1. Using standard methods, such as direct sequencing, PCR, SSCP, or any other polymorphism-detection system, one could easily ascertain whether these polymorphisms are present in a patient prior to the establishment of a drug treatment regimen for a patient having low HDL, cardiovascular disease, or any other ABC1-mediated condition. It is possible that some these polymorphisms are, in fact, weak mutations. Individuals harboring such mutations may have an increased risk for cardiovascular disease; thus, these polymorphisms may also be useful in diagnostic assays.

Association Studies of ABC1 Gene Variants and HDL Levels or Cardiovascular Disease The following polymorphisms have been examined for their effect on cholesterol regulation and the predisposition for the development of cardiovascular disease.

Substitution of G for A at nucleotide −1045 [G(−1045)A]. This variant is in complete linkage disequilibrium with the variant at −738 in the individuals we have sequenced, and thus any potential phenotypic effects currently attributed to the variant at −738 may at least in part be due to changes at this site.

Substitution of G for A at nucleotide −738 [G(−738)A]. This variant has been found at very high frequencies in populations selected for low HDL cholesterol or premature coronary artery disease.

Insertion of a G nucleotide at position −4 [G ins (−4)]. This variant has been associated with less coronary artery disease in its carriers than in non-carriers.

Substitution of a C for G at nucleotide −57 [G(−57)C]. This variant is in complete linkage disequilibrium with the variant at −4 in the individuals we have sequenced, and thus the phenotypic effects currently attributed to the variant at −4 may at least in part be due to changes at this site.

Substitution of A for G at nucleotide 730 (R219K). We have found carriers to have significantly less cardiovascular disease.

Substitution of C for T at nucleotide 1270 (V399A). Within the French Canadian population, this variant has only been found in individuals from the low HDL population. It has also been seen in individuals with low HDL or premature coronary artery disease in individuals of Dutch ancestry.

Substitution of A for G at nucleotide 2385 (V771M). This variant has been found at an increased frequency in a Dutch population selected for low HDL and at an increased frequency in a population selected for premature coronary artery disease compared to a control Dutch population, indicating carriers of this variant may have reduced HDL and an increased susceptibility to coronary artery disease.

Substitution of C for A at nucleotide 2394 (T774P). This variant has been seen at lower frequencies in populations with coronary artery disease or low HDL than in individuals without.

Substitution of C for G at nucleotide 2402 (K776N). This variant has been found at a significantly lower frequency (0.56% vs. 2.91%, p=0.02) in a coronary artery disease population vs. a control population of similar Dutch background.

Substitution of C for G at nucleotide 3590 (E1172D). This variant is seen at lower frequencies in individuals with low HDL and in some populations with premature coronary artery disease.

Substitution of A for G at nucleotide 4384 (R1587K). This variant has been found at decreased frequencies in the ⅓ of individuals with the highest HDL levels in our large Dutch coronary artery disease population (p=0.036), at increased frequencies in those with HDL cholesterol <0.9 mmol/L (p<0.0001) and at decreased frequencies in the cohorts with HDL cholesterol >1.4 mmol/L in both this population (p=0.02) and the Dutch control population (p=0.003).

Substitution of G for C at nucleotide 5266 (S1731C). Two FHA individuals who have this variant on the other allele have much lower HDL cholesterol (0.155±0.025) than the FHA individuals in the family who do not have this variant on the other allele (0.64±0.14, p=0.0009). This variant has also been found in one general population French Canadian control with HDL at the 8th percentile (0.92) and one French Canadian individual from a population selected for low HDL and coronary disease (0.72).

Substitution of G for A at nucleotide −1113 [A(−1113)G]. This variant has been seen at varying frequencies in populations distinguished by their HDL levels.

Additional polymorphisms that may be associated with altered risk for cardiovascular disease or altered cholesterol levels are as follows:

Substitution of G for A at nucleotide 2723 (I883M). This variant has been seen at a much higher frequency in individuals of Dutch ancestry with premature coronary artery disease.

Insertion of 4 nucleotides (CCCT) at position −1181.

Substitution of C for A at nucleotide −479 (linkage disequilibrium with −518).

Substitution of G for A at nucleotide −380.

Other Embodiments

All publications mentioned in this specification are herein incorporated by reference to the same extent as if each independent publication was specifically and individually indicated to be incorporated by reference.

While the invention has been described in connection with specific embodiments thereof, it will be understood that it is capable of further modifications. This application is intended to cover any variations, uses, or adaptations following, in general, the principles of the invention and including such departures from the present disclosure within known or customary practice within the art to which the invention pertains and may be applied to the essential features hereinbefore set forth.

What is claimed is:

1. A method of increasing ATP Binding Cassette Transporter 1 (ABC1) lipid transport activity in a human, said method comprising administering intravenously to said human a nucleic acid molecule that encodes the amino acid sequence of SEQ ID NO: 1 and having ABC1 lipid transport activity thereby increasing ABC1 lipid transport activity in said human wherein said nucleic acid molecule is operably linked to a promoter and is provided in a delivery system selected from herpes virus, adenovirus, adeno-associated virus, and DNA-liposome complex.

2. The method of claim 1, wherein said human has a disease selected from the group consisting of Alzheimer's disease, Niemann-Pick disease, Huntington's disease, x-linked adrenoleukodystrophy disease and cancer.

3. The method of claim 1, wherein said human has a disease selected from the group consisting of cardiovascular disease, coronary artery disease, cerebrovascular disease, coronary restenosis, or peripheral vascular disease.

4. The method of claim 1, wherein said delivery system is adenovirus.

5. The method of claim 1, wherein said nucleic acid has the nucleotide sequence of SEQ ID NO: 2.

* * * * *